(12) United States Patent
Monk et al.

(10) Patent No.: US 9,315,575 B2
(45) Date of Patent: *Apr. 19, 2016

(54) METHODS OF TREATMENT USING HUMAN ANTIBODY MOLECULES FOR IL-13

(75) Inventors: Phillip David Monk, Cambridge (GB); Lutz Jermutus, Cambridge (GB); Celia Patricia Shorrock, Noyarey (FR); Ralph Raymond Minter, Cambridge (GB)

(73) Assignee: MEDIMMUNE LIMITED, Cambridge (GB)

( * ) Notice: Subject to any disclaimer, the term of this patent is extended or adjusted under 35 U.S.C. 154(b) by 1555 days.

This patent is subject to a terminal disclaimer.

(21) Appl. No.: 12/941,677

(22) Filed: Nov. 8, 2010

(65) Prior Publication Data

US 2012/0052060 A1     Mar. 1, 2012

Related U.S. Application Data

(62) Division of application No. 10/564,647, filed as application No. PCT/GB2004/003059 on Jul. 15, 2004, now Pat. No. 7,829,090.

(60) Provisional application No. 60/487,512, filed on Jul. 15, 2003, provisional application No. 60/558,216, filed on Mar. 31, 2004, provisional application No. 60/573,791, filed on May 24, 2004.

(30) Foreign Application Priority Data

Mar. 31, 2004 (GB) .................................. 0407315.1

(51) Int. Cl.
*A61K 39/395* (2006.01)
*C07K 16/24* (2006.01)
*A61K 39/00* (2006.01)

(52) U.S. Cl.
CPC ......... *C07K 16/244* (2013.01); *A61K 2039/505* (2013.01); *C07K 2317/21* (2013.01); *C07K 2317/565* (2013.01); *C07K 2317/622* (2013.01); *C07K 2317/73* (2013.01); *C07K 2317/76* (2013.01); *Y10S 514/826* (2013.01); *Y10S 514/883* (2013.01)

(58) Field of Classification Search
None
See application file for complete search history.

(56) References Cited

U.S. PATENT DOCUMENTS

| | | | |
|---|---|---|---|
| 5,859,205 | A | 1/1999 | Adair et al. |
| 5,959,085 | A | 9/1999 | Garrone et al. |
| 5,969,108 | A | 10/1999 | McCafferty et al. |
| 6,811,780 | B2 | 11/2004 | Furfine et al. |
| 7,935,343 | B2 | 5/2011 | Monk et al. |
| 7,947,273 | B2 | 5/2011 | Monk et al. |
| 2003/0235555 | A1 | 12/2003 | Shealey et al. |
| 2004/0234499 | A1 | 11/2004 | Shealy et al. |
| 2005/0065327 | A1 | 3/2005 | Monk et al. |
| 2007/0128192 | A1 | 6/2007 | Monk et al. |

FOREIGN PATENT DOCUMENTS

| | | |
|---|---|---|
| WO | WO94/04680 A1 | 3/1994 |
| WO | WO00/36103 A1 | 6/2000 |
| WO | WO00/64944 A1 | 11/2000 |
| WO | WO00/66631 A1 | 11/2000 |
| WO | WO01/62933 A2 | 8/2001 |
| WO | WO03/035847 A2 | 5/2003 |
| WO | WO03/086451 A1 | 10/2003 |
| WO | WO2005/062967 A2 | 7/2005 |
| WO | WO2006/003407 A2 | 1/2006 |
| WO | WO2006/055638 A2 | 5/2006 |

OTHER PUBLICATIONS

Tariq et al., Clinical and Experimental Allergy, 1999, vol. 29, pp. 1042-1048.*
Bergmann et al., Eur Respir J 1998; 12: Suppl. 27: 9s-12s.*
C.A. Stiller, European Journal of Cancer, vol. 34, No. 4, pp. 523-528, 1998.*
Mayes et al. (Environ Health Perspect. Oct. 1999;107 Suppl 5:743-8).*
Lentsch et al. Respiration Physiology 128 (2001) 17-22.*
Webb et al., J. Immunol. 2000;165;108-113.*
Matsukawa et al. (J. Immunol. 2000;164;2738-2744).*
Riechmann et al., Journal of Immunological Methods 231 (1999), pp. 25-38.*
Riccieri et al. (Clinical Rheumatology, May 10, 2003, vol. 22, Issue 2, pp. 102-106).*
Ahlers, J. D. et al., "A push-pull approach to maximize vaccine efficacy: abrogating suppression with an IL-13 inhibitor while augmenting help with granulocyte/macrophage colony-stimulating factor and CD40L," Proc Natl Acad Sci USA, vol. 99, Issue 20, pp. 13020-13025, Oct. 1, 2002.
Andrews, A.L. et al., "Kinetic analysis of the interleukin-13 receptor complex," J Biol Chem., vol. 277, Issue 8, pp. 46073-46078, Nov. 29, 2002.
Arima, K. et al., "Upregulation of IL-13 concentration in vivo by the IL13 variant associated with bronchial asthma," J Allergy Clin Immunol, vol. 109, Issue 6, pp. 980-987, Jun. 2002.
Bochner, B. S. et al., "IL-13 selectively induces vascular cell adhesion molecule-1 expression in human endothelial cells," J Immunol, vol. 154, Issue 2, pp. 799-803, Jan. 15, 1995.
Caput, D. et al., "Cloning and characterization of a specific interleukin (IL)-13 binding protein structurally related to the IL-5 receptor alpha chain," J. Biol. Chem., vol. 271, Issue 28, pp. 16921-16926, 1996.
Chiaramonte, M.G. et al., "An IL-13 inhibitor blocks the development of hepatic fibrosis during a T-helper type 2-dominated inflammatory response," J Clin Invest, vol. 104, Issue 6, pp. 777-785, Sep. 1999.
Chiaramonte, M.G. et al., "Regulation and function of the interleukin 13 receptor alpha 2 during a T helper cell type 2-dominant immune response," J Exp Med, vol. 197, Issue 6, pp. 687-701, Mar. 17, 2003.

(Continued)

*Primary Examiner* — Zachary Skelding

(57) ABSTRACT

Specific binding members, in particular human anti-IL-13 antibody molecules and especially those which neutralise IL-13 activity. Methods for using anti-IL-13 antibody molecules in diagnosis or treatment of IL-13 related disorders, including asthma, atopic dermatitis, allergic rhinitis, fibrosis, inflammatory bowel disease and Hodgkin's lymphoma.

72 Claims, 24 Drawing Sheets

(56) References Cited

OTHER PUBLICATIONS

Chiaramonte, M.G. et al., "Studies of murine schistosomiasis reveal interleukin-13 blockade as a treatment for established and progressive liver fibrosis," Hepatology, vol. 34, Issue 2, pp. 273-282, Aug. 2001.
Cohn, L. et al., "IL-4-independent induction of airway hyper-responsiveness by Th2, but not Th1, cells" J Immunol, vol. 161, Issue 8, pp. 3813-3816, Oct. 15, 1998.
Deshpande, D. et al., "Modulation of calcium signaling by interleukin-13 in human airway smooth muscle: role of CD38/cyclic adenosine diphosphate ribose pathway," American Journal of Respiratory Cell and Molecular Biology, vol. 31, Issue: 1, pp. 36-42, 2004.
Fallon, P. G. et al., "Schistosome infection of transgenic mice defines distinct and contrasting pathogenic roles for IL-4 and IL-13: IL-13 is a profibrotic agent," J Immunol, vol. 164, Issue 5, pp. 2585-2591, Mar. 1, 2000.
Fiumara, P. et al., "Interleukin-13 levels in serum from patients with Hodgkin disease and healthy volunteers," Blood, vol. 98, Issue 9, pp. 2877-2878, Nov. 1, 2001.
Graves, P.E. et al., "A cluster of seven tightly linked polymorphisms in the IL-13 gene is associated with total serum IgE levels in three populations of white children," J Allergy Clin Immunol, vol. 105, Issue 3, pp. 506-513, Mar. 2000.
Grunstein, M.M. et al., "IL-13-dependent autocrine signaling mediates altered responsiveness of IgE-sensitized airway smooth muscle," American journal of physiology Lung cellular and molecular physiology, vol. 282: p. L520-L528, 2002.
Hancock, A. et al., "Production of interleukin 13 by alveolar macrophages from normal and fibrotic lung," Am J Respir Cell Mol Biol, vol. 18, Issue 1, pp. 60-65, Jan. 1998.
Hasegawa, M. et al., "Elevated serum levels of interleukin 4 (IL-4), IL-10, and IL-13 in patients with systemic sclerosis," J Rheumatol, vol. 24, Issue 2, pp. 328-32, 1997.
Heller, F. Et al., "Oxazolone colitis, a Th2 colitis model resembling ulcerative colitis, is mediated by IL-13-producing NK-T cells," Immunity, vol. 17, Issue: 5, pp. 629-638, 2002.
Hilton, D.J. et al., "Cloning and characterization of a binding subunit of the interleukin 13 receptor that is also a component of the interleukin 4 receptor," Proc. Natl. Acad. Sci., USA, vol. 93, pp. 497-501, Jan. 1996.
Howard, T.D. et al., "Gene-gene interation in asthma: IL4RA and IL13 in a Dutch population with asthma," Am J Hum Genet, vol. 70, Issue 1, pp. 230-236, Jan. 2002.
Howard, T.D. et al., "Identification and association of polymorphisms in the interleukin-13 gene with asthma and atopy in a Dutch population," Am J Respir Cell Mol Biol, vol. 25, Issue 3, pp. 377-384, Sep. 2001.
Humbert, M. et al., "Elevated expression messenger ribonucleic acid encoding IL-13 in the bronchial mucosa of atopic and nonatopic subjects with asthma," J. Allergy Clin. Immunol., vol. 99,pp. 657-665, 1997.
Kapp, U. et al., "Interleukin 13 is secreted by and stimulates the growth of Hodgkin and Reed-Sternberg cells," J Exp Med, vol. 189, Issue 12, pp. 1939-1946, Jun. 21, 1999.
Kawakami, K. et al., "The interleukin-13 receptor alpha2 chain: an essential component for binding and internalization but not for interleukin-13-induced signal transduction through the STAT6 pathway," Blood, vol. 97, Issue 9, pp. 2673-2679, May 1, 2001.
Kotowicz, K. et al., "Biological activity of IL-4 and IL-13 on human endothelial cells: functional evidence that both cytokines act through the same receptor," International Immunology, vol. 8, Issue 12, pp. 1915-1925, 1996.
Kotsimbos, T.C. et al., "Interleukin-13 and interleukin-4 are coexpressed in atopic asthma," Proc Assoc Am Physicians, vol. 108, Issue 5, pp. 368-373, Sep. 1996.
Kroegel, C. et al., "Endobronchial secretion of interleukin-13 following local allergen challenge in atopic asthma: relationship to interleukin-4 and eosinophil counts," Eur Respir J, vol. 9, Issue 5, pp. 899-904, 1996.

Laporte, J.C. et al., "Direct Effects of Interleukin-13 on Signaling Pathways for Physiological Responses in Cultured Human Airway Smooth Muscle Cells," American Journal of Respiratory and Critical Care Medicine,vol. 164, Issue: 1, pp. 141-148, 2001.
Lee, C.G. et al., "Interleukin-13 induces tissue fibrosis by selectively stimulating and activating transforming growth factor beta(1)," J Exp Med, vol. 194, Issue 6, pp. 809-821, Sep. 17, 2001.
Lefort, S. et al., "IL-13 and IL-4 share signal transduction elements as well as receptor components in TF-1 cells," FEBS Lett, vol. 366, Issue 2-3, pp. 122-126, Jun. 12, 1995.
McDonough, J.E. et al., "TGF- beta Isoform and IL-13 Immunostaining on Lung Tissue from Patients with COPD," ATS 99th International Conference, 2003, Seattle.
Miloux, B. et al., "Cloning of the human IL-13R alphal chain and reconstitution with the IL4R alpha of a functional IL-41/IL-13 receptor complex," FEBS Lett., vol. 401, Issue 2-3, pp. 163-196, Jan. 20, 1997.
Morse, B. et al., "Effects of IL-13 on airway responses in the guinea pig," Am J Physiol Lung Cell Mol Physiol, vol. 282, Issue 1, pp. L44-L49, Jan. 2002.
Murata, T. et al., "Sharing of receptor subunits and signal transduction pathway between the IL-4 and IL-13 receptor system," Int J Hematol., vol. 69, Issue 1, pp. 13-20, Jan. 1999.
Naseer, T. et al., "Expression of IL-12 and IL-13 mRNA in asthma and their modulation in response to steroid therapy," Am J Respir Crit Care Med, vol. 155, Issue 3, pp. 845-851, Mar. 1997.
Obase, Y. et al., "Correlation between airway hyperresponsiveness and airway inflammation in a young adult population: eosinophil, ECP, and cytokine levels in induced sputum," Ann Allergy Asthma Immunol., vol. 86, Issue 3, pp. 304-310, Mar. 2001.
Ohshima, Y. et al., "Dysregulation of IL-13 production by cord blood CD4+ T cells is associated with the subsequent development of atopic disease in infants," Pediatr Res, vol. 51, Issue 2, pp. 195-200, Feb. 2002.
Punnonen, J. Et al., "Interleukin 13 induces interleukin 4-independent IgG4 and IgE synthesis and CD23 expression by human B cells," Proceedings of the National Academy of Sciences, vol. 90, Issue: 8, pp. 3730-3734, 1993.
Richter, A. et al., "The contribution of interleukin (IL)-4 and IL-13 to the epithelial-mesenchymal trophic unit in asthma," Am J Respir Cell Mol Biol, vol. 25, Issue 3, pp. 385-391, Sep. 2001.
Skinnider, B. F. et al., "The role of interleukin 13 in classical Hodgkin lymphoma," Leuk Lymphoma, vol. 43, Issue 6, pp. 1203-1210, Jun. 2002.
Taube, C. et al., "The role of IL-13 in established allergic airway disease," J Immunol, vol. 169, Issue 11, pp. 6482-6489, Dec. 1, 2002.
Terabe, M. et al., "NKT cell-mediated repression of tumor immunosurveillance by IL-13 and the IL-4R-STAT6 pathway," Nat Immunol, vol. 1, Issue 6 pp. 515-520, Dec. 2000.
Terada, N. Et al., "Interleukin-13 and tumour necrosis factor-alpha synergistically induce eotaxin production in human nasal fibroblasts," Clin. Exp. Allergy., vol. 30, Issue 9, pp. 348-355, Mar. 2000.
Tuba, O. et al., "IL-13 enhances agonist-evoked calcium signals and contractile responses in airway smooth muscle," British journal of pharmacology, vol. 140, Issue: 7, pp. 1159-1162, 2003.
Van Der Pouw Kraan, T.C. et al., "An IL-13 promoter polymorphism associated with increased risk of allergic asthma," Genes Immun, vol. 1, Issue 1, pp. 61-65, Sep. 1999.
Van Der Pouw Kraan, T.C. et al., "Chronic obstructive pulmonary disease is associated with the -1055 IL-13 promoter polymorphism," Genes Immun, vol. 3, Issue 7, pp. 436-439, Nov. 2002.
Venkayya, R. et al., "The Th2 lymphocyte products IL-4 and IL-13 rapidly induce airway hyperresponsiveness through direct effects on resident airway cells," Am J Respir Cell Mol Biol, vol. 26, Issue 2, pp. 202-208, Feb. 2002.
Walker, C. et al., "Activated T cells and cytokines in bronchoalveolar lavages from patients with various lung diseases associated with eosinophilia," Am J Respir Crit Care Med, vol. 150, Issue 4, pp. 1038-1048, 1994.
Walter, D.M. et al., "Critical role for IL-13 in the development of allergen-induced airway hyperreactivity," J Immunol, vol. 167, Issue 8, pp. 4668-4675, 2007.

(56) References Cited

OTHER PUBLICATIONS

Wenzel, S. E. et al., "TGF-beta and IL-13 synergistically increase eotaxin-1 production in human airway fibroblasts," J Immunol, vol. 169, Issue 8, pp. 4613-4619, Oct. 15, 2002.

Wood, N. et al., "Enhanced Interleukin (IL)-13 Responses in Mice Lacking IL-13 Receptor α 2," J. Exp. Med., vol. 197, Issue 6, pp. 703-709, Mar. 17, 2003.

Yang, M. et al., "Interleukin-13 mediates airways hyperreactivity through the IL-4 receptor-alpha chain and STAT-6 independently of IL-5 and eotaxin," American Journal of Respiratory Cell and Molecular Biology, vol. 25, Issue: 4, pp. 522-530, 2001.

Zhang, J.G. et al., "Identification, purification, and characterization of a soluble interleukin (IL)-13-binding protein. Evidence that it is distinct from the cloned IL-13 receptor and IL-4 receptor alpha-chains" J. Biol. Chem., vol. 272, No. 14, pp. 9474-9480, 1997.

Zheng, T. et al., "Inducible targeting of IL-13 to the adult lung causes matrix metalloproteinase- and cathepsin-dependent emphysema," J Clin Invest, vol. 106, Issue 9, pp. 1081-1093, Nov. 2000.

International Search Report from PCT/GB2004/003059 dated Jan. 4, 2005.

Extended European Search Report from EP10183949.6 dated Sep. 9, 2011.

Blease, K. et al., "Therapeutic effect of IL-13 immunoneutralization during chronic experimental fungal asthma," J Immunol, vol. 166, Issue 8, pp. 5219-5224, Apr. 15, 2001.

Brown, M. et al., "Tolerance of single, but not multiple, amino acid replacements in antibody VH CDR 2: a means of minimizing B cell wastage from somatic hypermutation?" J Immunol., vol. 156, Issue 9, pp. 3285-32891, May 1, 1996.

Catalog No. MAB213—"Monoclonal Anti-human IL-13 Antibody," R & D Systems (Oct. 14, 2002).

Catalog No. MAB2131—"Monoclonal Anti-human IL-13 Antibody," R & D Systems (Nov. 3, 2003).

Catalog No. MAB413—"Monoclonal Anti-mouse IL-13 Antibody," R & D Systems (Dec. 3, 2004).

Combined Search and Examination Report Under Sections 17 and 18(3), The UK Patent Office, Patents Act 1977,4 pages (2004).

Grunig G., et al., "Requirement for IL-13 independently of IL-4 in experimental asthma," Science, vol. 282, Issue 5397, pp. 2261-2263, Dec. 18, 1998.

Harlow et al., "Antibodies A Laboratory Manual", Cold Spring Harbor Press, pp. 72-77, 1988.

Heinrichs et al., "Universal cloning and direct sequencing of rearranged antibody V genes using C region primers, biotin-captured cDNA and one-side PCR", Journal of Immunological Methods 178 (1995), 241-51.

Heinzmann, A. et al., "Genetic variants of IL-13 signalling and human asthma and atopy," Hum Mol Genet, vol. 9, Issue 4, pp. 549-559, Mar. 1, 2000.

Huang, S.K. et al., "IL-13 expression at the sites of allergen challenge in patients with asthma," J Immunol, vol. 155, Issue 5, pp. 2688-2694, 1995.

Holt et al., "Domain antibodies: proteins for therapy", Trends in Biotechnology, Nov. 2003;21 (11):484-90.

Janeway et al., "Antigen Recognition by B-cell and T-cell Receptors", Immunobiology, 5th Ed., Garland Science, (2001),pp. 94-105.

Kuperman, D. et al., "Direct Effects of Interleukin-13 on Epithelial Cells Cause Airway Hyperreactivity and Mucus Overproduction in Asthma," Nature Medicine, vol. 8, No. 8, pp. 885-889 (2002).

Madhankumar et al., "Alanine-scanning Mutagenesis of a-Helix D Segment of Interleukin-13 Reveals New Functionally Important Residues of the Cytokine", J Bioi Chem. Nov. 8, 2002;277(45):43194-205. Epub Aug. 19, 2002.

Makitalo et al, "ELI Spot and ELISA analysis of spontaneous, mitogen-Induced and antigen-specific cytokine production in cynomolgus and rhesus macaques", Journal of Immunological Methods, vol. 270, Issue 1, Dec. 1, 2002, 85-97.

Mendez, M.J. et al., "Funtional transplant of megabase human immunoglobulin loci recapitulates human antibody response in mice," Nature Genetics, vol. 15, Issue: 2, pp: 146-156, 1967.

Minty, A. et al., "Interleukin-13 is a new human lymphokine regulating inflammatory and immune responses," Nature, vol. 362, Issue 6417, pp. 248-250, Mar. 18, 1993.

Monk et al., U.S. Appl. No. 10/564,647.

Monk et al., U.S. Appl. No. 10/891,972.

Monk et al., U.S. Appl. No. 11/821,880.

Padlan E., "Anatomy of the Antibody Molecule", Molecular Immunology, vol. 31, Issue 3, pp. 169-217, Feb. 1994.

International Search Report and Written Opinion for International Patent Application No. PCT/GB2004/003059 mailed on Mar. 15, 2005.

Portolano et al., "Lack of Promiscuity in Autoantigen-Specific H and L Chain Combinations as Revealed by Human Hand L Chain "Roulette"", J Immunol. Feb. 1, 1993; 150(3):880-7.

Punnonen et al., "The relative contribution of iL-4 and IL-13 to human IgE synthesis induced by activated CD4+ or CD3+ T cells," Journal of Allergy and Clinical Immunology, vol. 100, No. 6, Part 1, pp. 792-801 (1997).

Riechmann, L. et al., "Single domain antibodies: comparison of camel VH and camelised human VH domains," Journal of Immunological Methods, vol. 231,pp. 25-38, Dec. 10, 1999.

Robinson, D. S. et al., "Predominant TH2-like Bronchoalveolar T-Lymphocyte Population in Atopic Asthma," N. Engl J. Med, vol. 326, pp. 298-304.

Skinnider, B.F. et al., "Interleukin 13 and interleukin 13 receptor are frequently expressed by Hodgkin and Reed-Sternberg cells of Hodgkin lymphoma," Blood, vol. 97, Issue 1, pp. 250-255, Jan. 1, 2001.

Stahl et al., "Cytokine Traps: Heteromeric receptor based protein therapeutics that function as high affinity blockers ofcytokine action," FASJ;B Journal, vol. 13, No. 7, A1585, (1999).

Vajdos et al., "Comprehensive Functional Maps of the Antigen-binding Site of an Anti-ErbB2 Antibody Obtained with Shortgun Scanning Mutagenesis", J Mol Bioi. Jul. 5, 2002;320(2):415-28.

Van Den Beucken, T. et al., "Building novel binding ligands to B7.1 and B7.2 based on human antibody single variable light chain domains,"J Mol Biol., vol. 310, Issue 3, pp. 591-601, Jul. 13, 2001.

Wills-Karp, M., et al., "Interleukin-13: central mediator of allergic asthma," Science, vol. 282, Issue 5397, pp. 2258-2261, Dec. 18, 1998.

Zhu, Z. et al., "Pulmonary expression of interleukin-13 causes inflammation, mucus hypersecretion, subepithelial fibrosis, physiologic abnormalities, and eotaxin production," J Clin Invest, vol. 103, Issue 6, pp. 779-788, Mar. 1999.

\* cited by examiner

|  |  |
|---|---|
| | 10 20 30 40 |
| Human IL-13 | MALLLTTVIALTCLGGFASPGPVPPSTALPELIEELVNIT |
| Cynomolgus IL-13 | MALLLTTVIALTCLGGFASPSPVPPSTALLELIEELVNIT |
| | MALLLTTVIALTCLGGFASP PVPPSTAL ELIEELVNIT |

|  |  |
|---|---|
| | 50 60 70 80 |
| Human IL-13 | QNQKAPLCNGSMVWSINLTAGMYCAALESLINVSGCSAIE |
| Cynomolgus IL-13 | QNQKAPLCNGSMVWSINLTAGVYCAALESLINVSGCSAIE |
| | QNQKAPLCNGSMVWSINLTAG YCAALESLINVSGCSAIE |

|  |  |
|---|---|
| | 90 100 110 120 |
| Human IL-13 | KTQRMLSGFCPHKVSAGQFSSLHVRDTKIEVAQFVKDLLL |
| Cynomolgus IL-13 | KTQRMLNGFCPHKVSAGQFSSLRVRDTKIEVAQFVKDLLV |
| | KTQRML GFCPHKVSAGQFSSL VRDTKIEVAQFVKDLL |

|  |  |
|---|---|
| | 130 |
| Human IL-13 | HLKKLFREGRFN |
| Cynomolgus IL-13 | HLKKLFREGQFN |
| | HLKKLFREG FN |

Figure 20

Effect of a single 10mg/kg dose of BAK502G9 (IgG4) on serum IgE levels in allergic but non-challenged cynomolgus monkeys

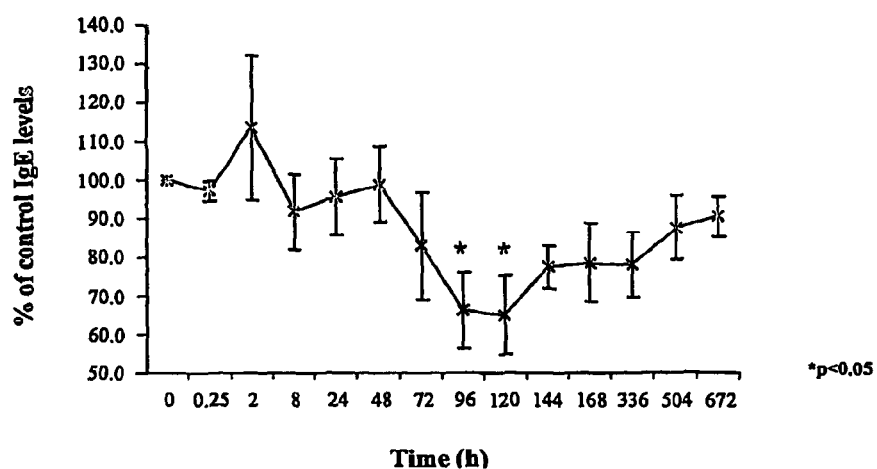

*p<0.05

Figure 21
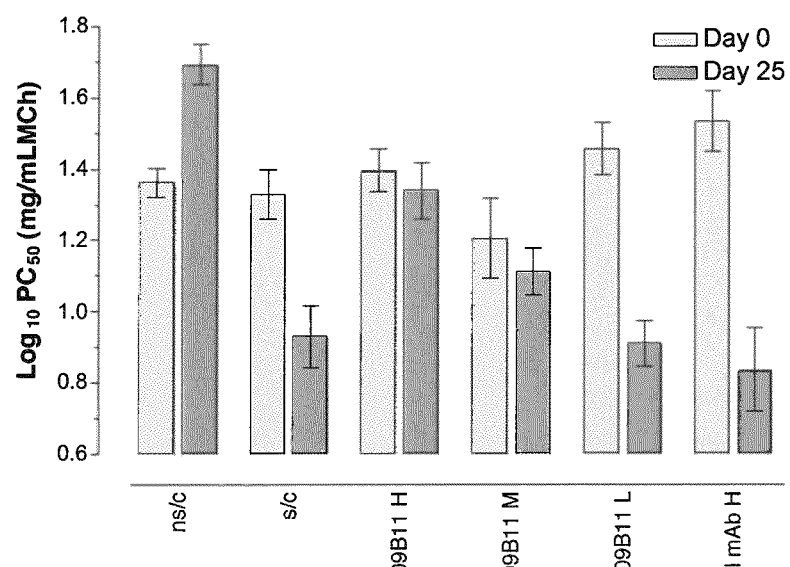
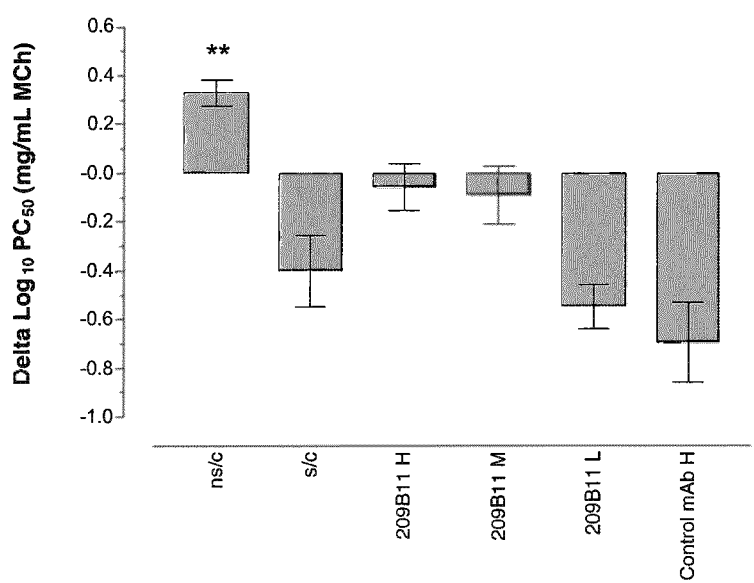
** $p<0.01$ vs s/c control; One-way ANOVA followed by Dunnett's multiple comparisons test

Figure 22
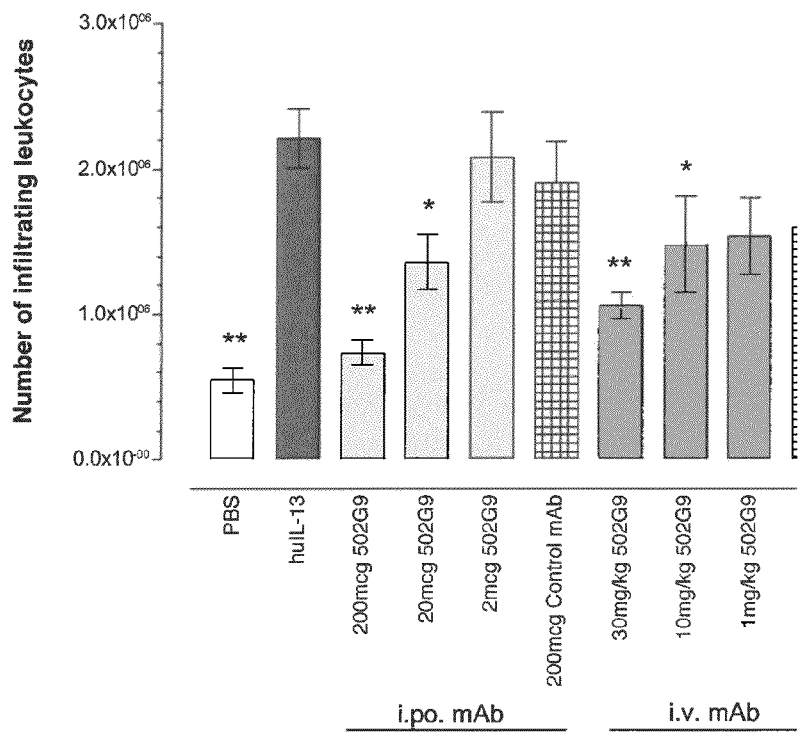
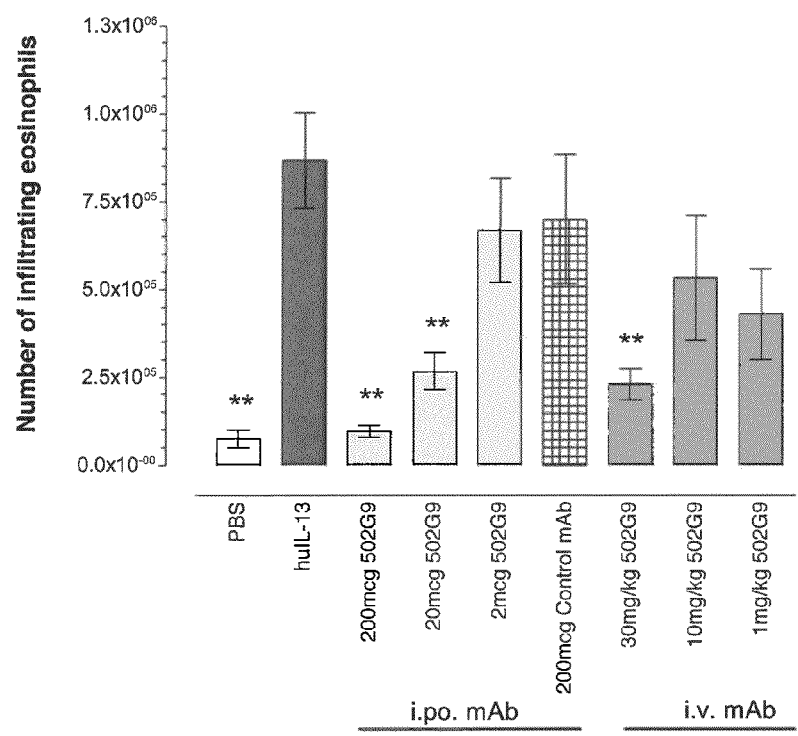

Figure 29A
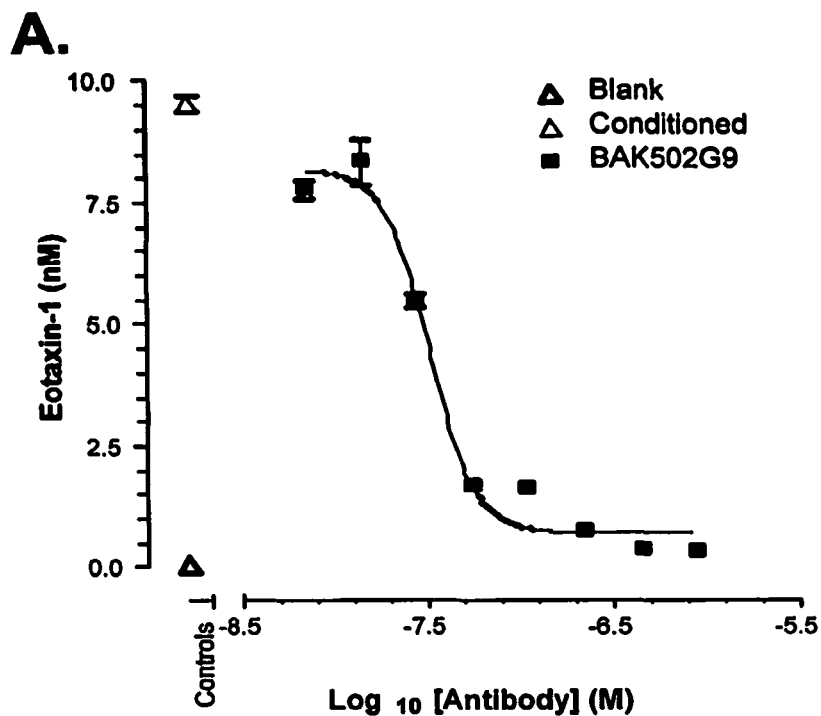
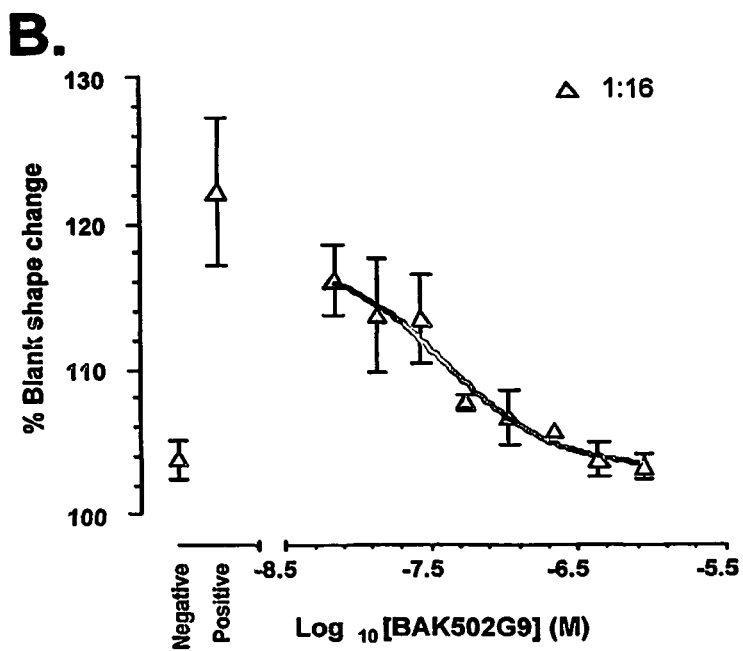
Figure 29B

```
                        10                  20                  30
human IL13P    M A L L L T T V I A L T C L G G F A S P G P V P P S T - - -
murine IL13P   M A L W V T A V L A L A C L G G L A A P G P V P R S V S L P
               M A L . T . V . A L . C L G G   A . P G P V P   S 40                  50                  60
human IL13P    - A L R E L I E E L V N I T Q N Q K A P L C N G S M V W S I
murine IL13P   L T L K E L I E E L S N I T Q D Q - T P L C N G S M V W S V
                 . L . E L I E E L   N I T Q   Q   . P L C N G S M V W S .

70                  80                  90
human IL13P    N L T A G M Y C A A L E S L I N V S G C S A I E K T Q R M L
murine IL13P   D L A A G G F C V A L D S L T N I S N C N A I Y R T Q R I L
                 L . A G   . C   A L . S L   N . S . C   A I   . T Q R . L 100                 110                 120
human IL13P    S G F C P H K V S A G Q F S S L H V R D T K I E V A Q F V K
murine IL13P   H G L C N R K A P T - T V S S L P - - D T K I E V A H F I T
                 G   C   . K   .       S S L     D T K I E V A . F .

130                 140                 150
human IL13P    D L L L H L K K L F R E G R F N
murine IL13P   K L L S Y T K Q L F R H G P F
                 L L     K . L F R   G   F
```

Figure 30

```
              10                  20                  30
human IL13P   MAL L LTTVIALTCLGG F AS PGPVP P S T - - -
murine IL13P  MAL W VTAVLALACLGG L AA PGPVP R S V S L P
              MAL . T . V . AL . CLGG   A . PGPVP   S 40                  50                  60
human IL13P   - A L R E L I E E L V N I T Q N Q K A P L C N G S M V W S I
murine IL13P  L T L K E L I E E L S N I T Q D Q - T P L C N G S M V W S V
              . L . E L I E E L   N I T Q   Q   . P L C N G S M V W S .

70                  80                  90
human IL13P   N L T A G M Y C A A L E S L I N V S G C S A I E K T Q R M L
murine IL13P  D L A A G F C V A L D S L T N I S N C N A I Y R T Q R I L
              . L . A G   . C   A L . S L   N . S . C   A I   . T Q R . L 100                 110                 120
human IL13P   S G F C P H K V S A G Q F S S L H V R D T K I E V A Q F V K
murine IL13P  H G L C N R K A P T - T V S S L P - - D T K I E V A H F I T
                G   C     K     .       S S L     D T K I E V A . F .

130                 140                 150
human IL13P   D L L H L K K L F R E G R F N
murine IL13P  K L L S Y T K Q L F R H G P F
                L L     K . L F R   G   F
```

Figure 31

```
        10         20         30         40         50
MALLLTTVIA LTCLGGFASP GPVPPSTALR ELIEELVNIT QNQKAPLCNG
        60         70         80         90        100
SMVWSINLTA GMYCAALESL INVSGCSAIEK TQRMLSGFCP HKVSAGQFS
       110        120        130
SLHVRDTKIE VAQFVKDLLL HLKKLFREGR FN
```

Figure 32

SEQUENCE LISTING

<160> NUMBER OF SEQ ID NOS: 249

<210> SEQ ID NO 1
<211> LENGTH: 5
<212> TYPE: PRT
<213> ORGANISM: Homo sapiens

<400> SEQUENCE: 1

Asn Tyr Gly Leu Ser
1               5

<210> SEQ ID NO 2
<211> LENGTH: 17
<212> TYPE: PRT
<213> ORGANISM: Homo sapiens

<400> SEQUENCE: 2

Trp Ile Ser Ala Asn Asn Gly Asp Thr Asn Tyr Gly Gln Glu Phe Gln Gly
1               5                   10                  15

<210> SEQ ID NO 3
<211> LENGTH: 13
<212> TYPE: PRT
<213> ORGANISM: Homo sapiens

<400> SEQUENCE: 3

Asp Ser Ser Ser Asn Trp Ala Arg Trp Phe Phe Asp Leu

```
1               5                   10

<210> SEQ ID NO 4
<211> LENGTH: 11
<212> TYPE: PRT
<213> ORGANISM: Homo sapiens

<400> SEQUENCE: 4

Gly Gly Asn Asn Ile Gly Ser Lys Leu Val His
1               5                   10

<210> SEQ ID NO 5
<211> LENGTH: 7
<212> TYPE: PRT
<213> ORGANISM: Homo sapiens

<400> SEQUENCE: 5

Asp Asp Gly Asp Arg Pro Ser
1               5

<210> SEQ ID NO 6
<211> LENGTH: 11
<212> TYPE: PRT
<213> ORGANISM: Homo sapiens

<400> SEQUENCE: 6

Gln Val Trp Asp Thr Gly Ser Asp Pro Val Val
1               5                   10

<210> SEQ ID NO 7
<211> LENGTH: 5
<212> TYPE: PRT
<213> ORGANISM: Homo sapiens

<400> SEQUENCE: 7

Asn Tyr Gly Leu Ser
1               5

<210> SEQ ID NO 8
<211> LENGTH: 17
<212> TYPE: PRT
<213> ORGANISM: Homo sapiens

<400> SEQUENCE: 8

Trp Ile Ser Ala Asn Asn Gly Asp Thr Asn Tyr Gly Gln Glu Phe Gln Gly
1               5                   10                  15

<210> SEQ ID NO 9
<211> LENGTH: 13
<212> TYPE: PRT
<213> ORGANISM: Homo sapiens

<400> SEQUENCE: 9

Asp Ser Ser Ser Ser Trp Ala Arg Trp Phe Phe Asp Leu
1               5                   10

<210> SEQ ID NO 10
<211> LENGTH: 11
<212> TYPE: PRT
<213> ORGANISM: Homo sapiens

<400> SEQUENCE: 10

Gly Gly Asn Ile Ile Gly Ser Lys Leu Val His
1               5                   10
```

<210> SEQ ID NO 11
<211> LENGTH: 7
<212> TYPE: PRT
<213> ORGANISM: Homo sapiens

<400> SEQUENCE: 11

Asp Asp Gly Asp Arg Pro Ser
1               5

<210> SEQ ID NO 12
<211> LENGTH: 11
<212> TYPE: PRT
<213> ORGANISM: Homo sapiens

<400> SEQUENCE: 12

Gln Val Trp Asp Thr Gly Ser Asp Pro Val Val
1               5                   10

<210> SEQ ID NO 13
<211> LENGTH: 122
<212> TYPE: PRT
<213> ORGANISM: Homo sapiens

<400> SEQUENCE: 13

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Arg Asn Tyr
            20                  25                  30

Gly Leu Ser Trp Val Arg Gln Ala Pro Gly Gln Gly Leu Glu Trp Met
        35                  40                  45

Gly Trp Ile Ser Ala Asn Asn Gly Asp Thr Asn Tyr Gly Gln Glu Phe
    50                  55                  60

Gln Gly Arg Ile Thr Met Thr Thr Glu Thr Ser Thr Asn Thr Ala His
65                  70                  75                  80

Met Glu Leu Arg Ser Leu Arg Ser Asp Asp Thr Ala Val Tyr Tyr Cys
                85                  90                  95

Val Arg Asp Ser Ser Ser Asn Trp Ala Arg Trp Phe Phe Asp Leu Trp
            100                 105                 110

Gly Lys Gly Thr Met Val Thr Val Ser Ser
        115                 120

<210> SEQ ID NO 14
<211> LENGTH: 108
<212> TYPE: PRT
<213> ORGANISM: Homo sapiens

<400> SEQUENCE: 14

Ser Tyr Val Leu Thr Gln Pro Pro Ser Val Ser Val Ala Pro Gly Gln
1               5                   10                  15

Thr Ala Arg Ile Pro Cys Gly Gly Asn Asn Ile Gly Ser Lys Leu Val
            20                  25                  30

His Trp Tyr Gln Gln Lys Pro Gly Gln Ala Pro Val Leu Val Val Tyr
        35                  40                  45

Asp Asp Gly Asp Arg Pro Ser Gly Ile Pro Glu Arg Phe Ser Gly Ser
    50                  55                  60

Asn Ser Gly Asn Thr Ala Thr Leu Thr Ile Ser Arg Ile Asp Ala Gly
65                  70                  75                  80

Asp Glu Ala Asp Tyr Tyr Cys Gln Val Trp Asp Thr Gly Ser Asp Pro
                85                  90                  95

```
Val Val Phe Gly Gly Gly Thr Lys Leu Thr Val Leu
            100                 105

<210> SEQ ID NO 15
<211> LENGTH: 122
<212> TYPE: PRT
<213> ORGANISM: Homo sapiens

<400> SEQUENCE: 15

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Gly Leu Ser Trp Val Arg Gln Ala Pro Gly Gln Gly Leu Glu Trp Met
        35                  40                  45

Gly Trp Ile Ser Ala Asn Asn Gly Asp Thr Asn Tyr Gly Gln Glu Phe
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Ser Ser Ser Trp Ala Arg Trp Phe Phe Asp Leu Trp
            100                 105                 110

Gly Arg Gly Thr Leu Val Thr Val Ser Ser
        115                 120

<210> SEQ ID NO 16
<211> LENGTH: 108
<212> TYPE: PRT
<213> ORGANISM: Homo sapiens

<400> SEQUENCE: 16

Ser Tyr Val Leu Thr Gln Pro Pro Ser Val Ser Val Ala Pro Gly Lys
1               5                   10                  15

Thr Ala Arg Ile Thr Cys Gly Gly Asn Ile Ile Gly Ser Lys Leu Val
            20                  25                  30

His Trp Tyr Gln Gln Lys Pro Gly Gln Ala Pro Val Leu Val Ile Tyr
        35                  40                  45

Asp Asp Gly Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Thr Gly Ser Asp Pro
                85                  90                  95

Val Val Phe Gly Gly Gly Thr Lys Leu Thr Val Leu
            100                 105

<210> SEQ ID NO 17
<211> LENGTH: 30
<212> TYPE: PRT
<213> ORGANISM: Homo sapiens

<400> SEQUENCE: 17

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Arg
            20                  25                  30
```

<210> SEQ ID NO 18
<211> LENGTH: 14
<212> TYPE: PRT
<213> ORGANISM: Homo sapiens

<400> SEQUENCE: 18

Trp Val Arg Gln Ala Pro Gly Gln Gly Leu Glu Trp Met Gly
1               5                   10

<210> SEQ ID NO 19
<211> LENGTH: 32
<212> TYPE: PRT
<213> ORGANISM: Homo sapiens

<400> SEQUENCE: 19

Arg Ile Thr Met Thr Thr Glu Thr Ser Thr Asn Thr Ala His Met Glu
1               5                   10                  15

Leu Arg Ser Leu Arg Ser Asp Asp Thr Ala Val Tyr Tyr Cys Val Arg
            20                  25                  30

<210> SEQ ID NO 20
<211> LENGTH: 22
<212> TYPE: PRT
<213> ORGANISM: Homo sapiens

<400> SEQUENCE: 20

Ser Tyr Val Leu Thr Gln Pro Pro Ser Val Ser Val Ala Pro Gly Gln
1               5                   10                  15

Thr Ala Arg Ile Pro Cys
            20

<210> SEQ ID NO 21
<211> LENGTH: 15
<212> TYPE: PRT
<213> ORGANISM: Homo sapiens

<400> SEQUENCE: 21

Trp Tyr Gln Gln Lys Pro Gly Gln Ala Pro Val Leu Val Val Tyr
1               5                   10                  15

<210> SEQ ID NO 22
<211> LENGTH: 32
<212> TYPE: PRT
<213> ORGANISM: Homo sapiens

<400> SEQUENCE: 22

Gly Ile Pro Glu Arg Phe Ser Gly Ser Asn Ser Gly Asn Thr Ala Thr
1               5                   10                  15

Leu Thr Ile Ser Arg Ile Asp Ala Gly Asp Glu Ala Asp Tyr Tyr Cys
            20                  25                  30

<210> SEQ ID NO 23
<211> LENGTH: 120
<212> TYPE: PRT
<213> ORGANISM: Homo sapiens

<400> SEQUENCE: 23

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val

```
                35                  40                  45
Ser Ala Ile Ser Gly Ser Gly Gly Ser Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Val Gly Ala Ala Gly Glu Gly Tyr Tyr Gly Tyr Trp Gly Arg
                100                 105                 110

Gly Thr Leu Val Thr Val Ser Ser
            115                 120

<210> SEQ ID NO 24
<211> LENGTH: 110
<212> TYPE: PRT
<213> ORGANISM: Homo sapiens

<400> SEQUENCE: 24

Asn Phe Met Leu Thr Gln Pro His Ser Val Ser Glu Ser Pro Gly Lys
 1               5                  10                  15

Thr Val Thr Ile Ser Cys Thr Arg Ser Ser Gly Ser Ile Ala Ser Asn
                20                  25                  30

Tyr Val Gln Trp Tyr Gln Gln Arg Pro Gly Ser Ala Pro Thr Thr Val
             35                  40                  45

Ile Tyr Asp Asp Asn Gln Arg Pro Ser Gly Val Pro Asp Arg Phe Ser
 50                  55                  60

Gly Ser Ile Asp Ser Ser Asn Ser Ala Ser Leu Thr Ile Ser Gly
 65                  70                  75                  80

Leu Lys Thr Glu Asp Glu Ala Asp Tyr Tyr Cys Gln Ser Tyr Asp Ser
                 85                  90                  95

Asn Asn Asp Val Phe Gly Gly Gly Thr Lys Val Thr Val Leu
                100                 105                 110

<210> SEQ ID NO 25
<211> LENGTH: 123
<212> TYPE: PRT
<213> ORGANISM: Homo sapiens

<400> SEQUENCE: 25

Gln Val Gln Leu Gln Glu Ser Gly Gly Gly Leu Val Gln Pro Gly Gly
 1               5                  10                  15

Gly Ser Leu Arg Leu Ser Cys Ala Ala Ser Gly Phe Thr Phe Ser Ser
                20                  25                  30

Tyr Gly Met Ser Trp Val Arg Gln Ala Pro Gly Lys Gly Leu Glu Trp
             35                  40                  45

Val Ser Ser Ile Ser Ala Ser Gly Asp Ser Thr Phe Tyr Ala Asp Ser
 50                  55                  60

Val Lys Gly Arg Phe Thr Ile Ser Arg Asp Asn Asn Lys Asn Met Val
 65                  70                  75                  80

Phe Leu Gln Val Asn Ser Leu Arg Ala Asp Asp Thr Ala Val Tyr Phe
                 85                  90                  95

Cys Ala Lys Asp Trp Ser Gln Trp Leu Val Gly Asp Ala Phe Asp Val
                100                 105                 110

Trp Gly Arg Gly Thr Thr Val Thr Val Ser Ser
            115                 120
```

```
<210> SEQ ID NO 26
<211> LENGTH: 108
<212> TYPE: PRT
<213> ORGANISM: Homo sapiens

<400> SEQUENCE: 26

Asp Ile Gln Leu Thr Gln Ser Pro Ser Thr Leu Ser Ala Ser Val Gly
1               5                   10                  15

Asp Arg Val Thr Ile Thr Cys Arg Ala Ser Gln Ser Val Ser Leu Trp
            20                  25                  30

Val Ala Trp Tyr Gln Gln Arg Pro Gly Lys Ala Pro Lys Leu Leu Ile
        35                  40                  45

Tyr Asp Gly Ser Thr Leu Gln Ser Gly Val Pro Ala Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Lys Thr Phe Ser Thr
                85                  90                  95

Phe Gly Gln Gly Thr Lys Val Glu Ile Lys Arg Ala
            100                 105

<210> SEQ ID NO 27
<211> LENGTH: 30
<212> TYPE: PRT
<213> ORGANISM: Homo sapiens

<400> SEQUENCE: 27

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr
            20                  25                  30

<210> SEQ ID NO 28
<211> LENGTH: 14
<212> TYPE: PRT
<213> ORGANISM: Homo sapiens

<400> SEQUENCE: 28

Trp Tyr Arg Gln Ala Pro Gly Gln Gly Leu Glu Trp Met Gly
1               5                   10

<210> SEQ ID NO 29
<211> LENGTH: 32
<212> TYPE: PRT
<213> ORGANISM: Homo sapiens

<400> SEQUENCE: 29

Arg Val Thr Met Thr Thr Asp Thr Ser Thr Ser Thr Ala Tyr Met Glu
1               5                   10                  15

Leu Arg Ser Leu Arg Ser Asp Asp Thr Ala Val Tyr Tyr Cys Ala Arg
            20                  25                  30

<210> SEQ ID NO 30
<211> LENGTH: 22
<212> TYPE: PRT
<213> ORGANISM: Homo sapiens

<400> SEQUENCE: 30

Ser Tyr Val Leu Thr Gln Pro Pro Ser Val Ser Val Ala Pro Gly Lys
1               5                   10                  15

Thr Ala Arg Ile Thr Cys
```

```
<210> SEQ ID NO 31
<211> LENGTH: 15
<212> TYPE: PRT
<213> ORGANISM: Homo sapiens

<400> SEQUENCE: 31

Trp Tyr Gln Gln Lys Pro Gly Gln Ala Pro Val Leu Val Ile Tyr
1               5                   10                  15

<210> SEQ ID NO 32
<211> LENGTH: 32
<212> TYPE: PRT
<213> ORGANISM: Homo sapiens

<400> SEQUENCE: 32

Gly Ile Pro Glu Arg Phe Ser Gly Ser Asn Ser Gly Asn Thr Ala Thr
1               5                   10                  15

Leu Thr Ile Ser Arg Val Glu Ala Gly Asp Glu Ala Asp Tyr Tyr Cys
            20                  25                  30

<210> SEQ ID NO 33
<211> LENGTH: 122
<212> TYPE: PRT
<213> ORGANISM: Homo sapiens

<400> SEQUENCE: 33

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Gly Lys Ala Thr Glu Glu Tyr Tyr Gly Tyr Trp
            100                 105                 110

Gly Arg Gly Thr Leu Val Thr Val Ser Ser
        115                 120

<210> SEQ ID NO 34
<211> LENGTH: 110
<212> TYPE: PRT
<213> ORGANISM: Homo sapiens

<400> SEQUENCE: 34

Asn Phe Met Leu Thr Gln Pro His Ser Val Ser Glu Ser Pro Gly Lys
1               5                   10                  15

Thr Val Thr Ile Ser Cys Thr Arg Ser Ser Gly Ser Ile Ala Ser Asn
            20                  25                  30

Tyr Val Gln Trp Tyr Gln Gln Arg Pro Gly Ser Ala Pro Thr Thr Val
        35                  40                  45

Ile Tyr Asp Asp Asn Gln Arg Pro Ser Gly Val Pro Ser Arg Phe Ser
    50                  55                  60
```

```
Gly Ser Ile Asp Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Asp Ser
                85                  90                  95

Asn Asn Asp Val Phe Gly Gly Gly Thr Lys Val Thr Val Leu
            100                 105                 110

<210> SEQ ID NO 35
<211> LENGTH: 122
<212> TYPE: PRT
<213> ORGANISM: Homo sapiens

<400> SEQUENCE: 35

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Glu Gln Thr
            20                  25                  30

Gly Val Ser Trp Val Arg Gln Ala Pro Gly Gln Gly Leu Glu Trp Met
        35                  40                  45

Gly Trp Ile Ser Ala Asn Asn Gly Asp Thr Asn Tyr Gly Gln Glu Phe
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Ser Ser Ser Ser Trp Ala Arg Trp Phe Phe Asp Leu Trp
            100                 105                 110

Gly Arg Gly Thr Leu Val Thr Val Ser Ser
        115                 120

<210> SEQ ID NO 36
<211> LENGTH: 108
<212> TYPE: PRT
<213> ORGANISM: Homo sapiens

<400> SEQUENCE: 36

Ser Tyr Val Leu Thr Gln Pro Pro Ser Val Ser Val Ala Pro Gly Lys
1               5                   10                  15

Thr Ala Arg Ile Thr Cys Gly Gly Asn Ile Ile Gly Ser Lys Leu Val
            20                  25                  30

His Trp Tyr Gln Gln Lys Pro Gly Gln Ala Pro Val Leu Val Ile Tyr
        35                  40                  45

Asp Asp Gly Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Thr Gly Ser Asp Pro
                85                  90                  95

Val Val Phe Gly Gly Gly Thr Lys Leu Thr Val Leu
            100                 105

<210> SEQ ID NO 37
<211> LENGTH: 122
<212> TYPE: PRT
<213> ORGANISM: Homo sapiens

<400> SEQUENCE: 37

Gln Val Gln Leu Val Gln Ser Gly Ala Glu Val Lys Lys Pro Gly Ala
```

```
            1               5                  10                 15
         Ser Val Lys Val Ser Cys Lys Ala Ser Gly Tyr Thr Phe Thr Asn Tyr
                         20                  25                  30

Gly Leu Ser Trp Val Arg Gln Ala Pro Gly Gln Gly Leu Glu Trp Met
                         35                  40                  45

Gly Trp Ile Asn Tyr Asp Gly Asn Thr Gln Tyr Gly Gln Glu Phe
                 50                  55                      60

Gln Gly Arg Val Thr Met Thr Thr Asp Thr Ser Thr Ser Thr Ala Tyr
         65                  70                  75                  80

Met Glu Leu Arg Ser Leu Arg Ser Asp Asp Thr Ala Val Tyr Tyr Cys
                         85                  90                  95

Ala Arg Asp Ser Ser Ser Trp Ala Arg Trp Phe Phe Asp Leu Trp
                         100                 105                 110

Gly Arg Gly Thr Leu Val Thr Val Ser Ser
                         115                 120

<210> SEQ ID NO 38
<211> LENGTH: 108
<212> TYPE: PRT
<213> ORGANISM: Homo sapiens

<400> SEQUENCE: 38

Ser Tyr Val Leu Thr Gln Pro Pro Ser Val Ser Val Ala Pro Gly Lys
         1               5                  10                  15

Thr Ala Arg Ile Thr Cys Gly Gly Asn Ile Ile Gly Ser Lys Leu Val
                         20                  25                  30

His Trp Tyr Gln Gln Lys Pro Gly Gln Ala Pro Val Leu Val Ile Tyr
                         35                  40                  45

Asp Asp Gly Asp Arg Pro Ser Gly Ile Pro Glu Arg Phe Ser Gly Ser
                 50                  55                      60

Asn Ser Gly Asn Thr Ala Thr Leu Thr Ile Ser Arg Val Glu Ala Gly
         65                  70                  75                  80

Asp Glu Ala Asp Tyr Tyr Cys Gln Val Trp Asp Thr Gly Ser Asp Pro
                         85                  90                  95

Val Val Phe Gly Gly Gly Thr Lys Leu Thr Val Leu
                         100                 105

<210> SEQ ID NO 39
<211> LENGTH: 122
<212> TYPE: PRT
<213> ORGANISM: Homo sapiens

<400> SEQUENCE: 39

Gln Val Gln Leu Val Gln Ser Gly Ala Glu Val Lys Lys Pro Gly Ala
         1               5                  10                  15

Ser Val Lys Val Ser Cys Lys Ala Ser Gly Tyr Thr Phe Thr Asn Tyr
                         20                  25                  30

Gly Leu Ser Trp Val Arg Gln Ala Pro Gly Gln Gly Leu Glu Trp Met
                         35                  40                  45

Gly Trp Ile Ser Gly Leu Asn Gly Glu Thr Leu Tyr Gly Gln Glu Phe
                 50                  55                      60

Gln Gly Arg Val Thr Met Thr Thr Asp Thr Ser Thr Ser Thr Ala Tyr
         65                  70                  75                  80

Met Glu Leu Arg Ser Leu Arg Ser Asp Asp Thr Ala Val Tyr Tyr Cys
                         85                  90                  95

Ala Arg Asp Ser Ser Ser Ser Trp Ala Arg Trp Phe Phe Asp Leu Trp
```

<210> SEQ ID NO 40
<211> LENGTH: 108
<212> TYPE: PRT
<213> ORGANISM: Homo sapiens

<400> SEQUENCE: 40

Ser Tyr Val Leu Thr Gln Pro Pro Ser Val Ser Val Ala Pro Gly Lys
1               5                   10                  15

Thr Ala Arg Ile Thr Cys Gly Gly Asn Ile Ile Gly Ser Lys Leu Val
            20                  25                  30

His Trp Tyr Gln Gln Lys Pro Gly Gln Ala Pro Val Leu Val Ile Tyr
        35                  40                  45

Asp Asp Gly Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Thr Gly Ser Asp Pro
                85                  90                  95

Val Val Phe Gly Gly Gly Thr Lys Leu Thr Val Leu
            100                 105

<210> SEQ ID NO 41
<211> LENGTH: 122
<212> TYPE: PRT
<213> ORGANISM: Homo sapiens

<400> SEQUENCE: 41

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Gly Leu Ser Trp Val Arg Gln Ala Pro Gly Gln Gly Leu Glu Trp Met
        35                  40                  45

Gly Trp Ile Ala Thr Pro Asp Gly Gln Thr Tyr Gly Gln Glu Phe
    50                  55                  60

Gln Gly Arg Val Thr Met Thr Thr Asp Thr Ser Thr Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Ser Asn Ser Ser Trp Ala Arg Trp Phe Phe Asp Leu Trp
            100                 105                 110

Gly Arg Gly Thr Leu Val Thr Val Ser Ser
        115                 120

<210> SEQ ID NO 42
<211> LENGTH: 108
<212> TYPE: PRT
<213> ORGANISM: Homo sapiens

<400> SEQUENCE: 42

Ser Tyr Val Leu Thr Gln Pro Pro Ser Val Ser Val Ala Pro Gly Lys
1               5                   10                  15

Thr Ala Arg Ile Thr Cys Gly Gly Asn Ile Ile Gly Ser Lys Leu Val
            20                  25                  30

```
His Trp Tyr Gln Gln Lys Pro Gly Gln Ala Pro Val Leu Val Ile Tyr
            35                  40                  45

Asp Asp Gly Asp Arg Pro Ser Gly Ile Pro Glu Arg Phe Ser Gly Ser
 50                  55                  60

Asn Ser Gly Asn Thr Ala Thr Leu Thr Ile Ser Arg Val Glu Ala Gly
 65                  70                  75                  80

Asp Glu Ala Asp Tyr Tyr Cys Gln Val Trp Asp Thr Gly Ser Asp Pro
                 85                  90                  95

Val Val Phe Gly Gly Gly Thr Lys Leu Thr Val Leu
                100                 105

<210> SEQ ID NO 43
<211> LENGTH: 122
<212> TYPE: PRT
<213> ORGANISM: Homo sapiens

<400> SEQUENCE: 43

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Ile Asp Thr
                20                  25                  30

Gly Val Ser Trp Val Arg Gln Ala Pro Gly Gln Gly Leu Glu Trp Met
            35                  40                  45

Gly Trp Ile Ser Ala Asn Asn Gly Asp Thr Asn Tyr Gln Gln Glu Phe
         50                  55                  60

Gln Gly Arg Val Thr Met Thr Thr Asp Thr Ser Thr Ser Thr Ala Tyr
 65                  70                  75                  80

Met Glu Leu Arg Ser Leu Arg Ser Asp Asp Thr Ala Val Tyr Tyr Cys
                 85                  90                  95

Ala Arg Asp Ser Ser Ser Trp Ala Arg Trp Phe Phe Asp Leu Trp
                100                 105                 110

Gly Arg Gly Thr Leu Val Thr Val Ser Ser
            115                 120

<210> SEQ ID NO 44
<211> LENGTH: 108
<212> TYPE: PRT
<213> ORGANISM: Homo sapiens

<400> SEQUENCE: 44

Ser Tyr Val Leu Thr Gln Pro Pro Ser Val Ser Val Ala Pro Gly Lys
 1               5                  10                  15

Thr Ala Arg Ile Thr Cys Gly Gly Asn Ile Ile Gly Ser Lys Leu Val
                20                  25                  30

His Trp Tyr Gln Gln Lys Pro Gly Gln Ala Pro Val Leu Val Ile Tyr
            35                  40                  45

Asp Asp Gly Asp Arg Pro Ser Gly Ile Pro Glu Arg Phe Ser Gly Ser
 50                  55                  60

Asn Ser Gly Asn Thr Ala Thr Leu Thr Ile Ser Arg Val Glu Ala Gly
 65                  70                  75                  80

Asp Glu Ala Asp Tyr Tyr Cys Gln Val Trp Asp Thr Gly Ser Asp Pro
                 85                  90                  95

Val Val Phe Gly Gly Gly Thr Lys Leu Thr Val Leu
                100                 105

<210> SEQ ID NO 45
```

-continued

```
<211> LENGTH: 122
<212> TYPE: PRT
<213> ORGANISM: Homo sapiens

<400> SEQUENCE: 45

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
                20                  25                  30

Gly Leu Ser Trp Val Arg Gln Ala Pro Gly Gln Gly Leu Glu Trp Met
            35                  40                  45

Gly Trp Ile Ser Gly Ser Asn Gly Tyr Thr Ser Tyr Gly Gln Glu Phe
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Ser Ser Ser Ser Trp Ala Arg Trp Phe Phe Asp Leu Trp
                100                 105                 110

Gly Arg Gly Thr Leu Val Thr Val Ser Ser
            115                 120

<210> SEQ ID NO 46
<211> LENGTH: 108
<212> TYPE: PRT
<213> ORGANISM: Homo sapiens

<400> SEQUENCE: 46

Ser Tyr Val Leu Thr Gln Pro Pro Ser Val Ser Val Ala Pro Gly Lys
1               5                   10                  15

Thr Ala Arg Ile Thr Cys Gly Gly Asn Ile Ile Gly Ser Lys Leu Val
                20                  25                  30

His Trp Tyr Gln Gln Lys Pro Gly Gln Ala Pro Val Leu Val Ile Tyr
            35                  40                  45

Asp Asp Gly Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Thr Gly Ser Asp Pro
                85                  90                  95

Val Val Phe Gly Gly Gly Thr Lys Leu Thr Val Leu
                100                 105

<210> SEQ ID NO 47
<211> LENGTH: 122
<212> TYPE: PRT
<213> ORGANISM: Homo sapiens

<400> SEQUENCE: 47

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
                20                  25                  30

Gly Leu Ser Trp Val Arg Gln Ala Pro Gly Gln Gly Leu Glu Trp Met
            35                  40                  45

Gly Trp Ile Asn Asp Ala Thr Gly Asp Thr Gln Tyr Gly Gln Glu Phe
    50                  55                  60
```

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
            85                  90                  95

Ala Arg Asp Ser Ser Ser Ser Trp Ala Arg Trp Phe Phe Asp Leu Trp
            100                 105                 110

Gly Arg Gly Thr Leu Val Thr Val Ser Ser
        115                 120

<210> SEQ ID NO 48
<211> LENGTH: 108
<212> TYPE: PRT
<213> ORGANISM: Homo sapiens

<400> SEQUENCE: 48

Ser Tyr Val Leu Thr Gln Pro Pro Ser Val Ser Val Ala Pro Gly Lys
1               5                   10                  15

Thr Ala Arg Ile Thr Cys Gly Gly Asn Ile Ile Gly Ser Lys Leu Val
            20                  25                  30

His Trp Tyr Gln Gln Lys Pro Gly Gln Ala Pro Val Leu Val Ile Tyr
        35                  40                  45

Asp Asp Gly Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Thr Gly Ser Asp Pro
            85                  90                  95

Val Val Phe Gly Gly Gly Thr Lys Leu Thr Val Leu
            100                 105

<210> SEQ ID NO 49
<211> LENGTH: 122
<212> TYPE: PRT
<213> ORGANISM: Homo sapiens

<400> SEQUENCE: 49

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Gly Leu Ser Trp Val Arg Gln Ala Pro Gly Gln Gly Leu Glu Trp Met
        35                  40                  45

Gly Trp Ile Arg Asn Ile Asp Gly Tyr Thr Ile Tyr Gly Gln Glu Phe
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
            85                  90                  95

Ala Arg Asp Ser Ser Ser Ser Trp Ala Arg Trp Phe Phe Asp Leu Trp
            100                 105                 110

Gly Arg Gly Thr Leu Val Thr Val Ser Ser
        115                 120

<210> SEQ ID NO 50
<211> LENGTH: 108
<212> TYPE: PRT
<213> ORGANISM: Homo sapiens -continued

<400> SEQUENCE: 50

Ser Tyr Val Leu Thr Gln Pro Pro Ser Val Ser Val Ala Pro Gly Lys
1               5                   10                  15

Thr Ala Arg Ile Thr Cys Gly Gly Asn Ile Ile Gly Ser Lys Leu Val
            20                  25                  30

His Trp Tyr Gln Gln Lys Pro Gly Gln Ala Pro Val Leu Val Ile Tyr
        35                  40                  45

Asp Asp Gly Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Thr Gly Ser Asp Pro
                85                  90                  95

Val Val Phe Gly Gly Gly Thr Lys Leu Thr Val Leu
            100                 105

<210> SEQ ID NO 51
<211> LENGTH: 122
<212> TYPE: PRT
<213> ORGANISM: Homo sapiens

<400> SEQUENCE: 51

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Gly Leu Ser Trp Val Arg Gln Ala Pro Gly Gln Gly Leu Glu Trp Met
        35                  40                  45

Gly Trp Ile Asp Asp Asp Ser Gly Thr Thr Ile Tyr Gly Gln Glu Phe
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Ser Ser Ser Ser Trp Ala Arg Trp Phe Phe Asp Leu Trp
            100                 105                 110

Gly Arg Gly Thr Leu Val Thr Val Ser Ser
        115                 120

<210> SEQ ID NO 52
<211> LENGTH: 108
<212> TYPE: PRT
<213> ORGANISM: Homo sapiens

<400> SEQUENCE: 52

Ser Tyr Val Leu Thr Gln Pro Pro Ser Val Ser Val Ala Pro Gly Lys
1               5                   10                  15

Thr Ala Arg Ile Thr Cys Gly Gly Asn Ile Ile Gly Ser Lys Leu Val
            20                  25                  30

His Trp Tyr Gln Gln Lys Pro Gly Gln Ala Pro Val Leu Val Ile Tyr
        35                  40                  45

Asp Asp Gly Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Thr Gly Ser Asp Pro

```
                      85                  90                  95

Val Val Phe Gly Gly Gly Thr Lys Leu Thr Val Leu
                100                 105

<210> SEQ ID NO 53
<211> LENGTH: 122
<212> TYPE: PRT
<213> ORGANISM: Homo sapiens

<400> SEQUENCE: 53

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ala Asn Thr
                20                  25                  30

Gly Ile Ser Trp Val Arg Gln Ala Pro Gly Gln Gly Leu Glu Trp Met
            35                  40                  45

Gly Trp Ile Ser Ala Asn Asn Gly Asp Thr Asn Tyr Gly Gln Glu Phe
        50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Ser Ser Ser Ser Trp Ala Arg Trp Phe Phe Asp Leu Trp
                100                 105                 110

Gly Arg Gly Thr Leu Val Thr Val Ser Ser
            115                 120

<210> SEQ ID NO 54
<211> LENGTH: 108
<212> TYPE: PRT
<213> ORGANISM: Homo sapiens

<400> SEQUENCE: 54

Ser Tyr Val Leu Thr Gln Pro Pro Ser Val Ser Val Ala Pro Gly Lys
1               5                   10                  15

Thr Ala Arg Ile Thr Cys Gly Gly Asn Ile Ile Gly Ser Lys Leu Val
                20                  25                  30

His Trp Tyr Gln Gln Lys Pro Gly Gln Ala Pro Val Leu Val Ile Tyr
            35                  40                  45

Asp Asp Gly Asp Arg Pro Ser Gly Ile Pro Glu Arg Phe Ser Gly Ser
        50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Thr Gly Ser Asp Pro
                85                  90                  95

Val Val Phe Gly Gly Gly Thr Lys Leu Thr Val Leu
                100                 105

<210> SEQ ID NO 55
<211> LENGTH: 5
<212> TYPE: PRT
<213> ORGANISM: Homo sapiens

<400> SEQUENCE: 55

Ser Tyr Ala Met Ser
1               5

<210> SEQ ID NO 56
```

```
<211> LENGTH: 17
<212> TYPE: PRT
<213> ORGANISM: Homo sapiens

<400> SEQUENCE: 56

Ala Ile Ser Gly Ser Gly Gly Ser Thr Tyr Tyr Ala Asp Ser Val Lys
1               5                   10                  15

Gly

<210> SEQ ID NO 57
<211> LENGTH: 11
<212> TYPE: PRT
<213> ORGANISM: Homo sapiens

<400> SEQUENCE: 57

Val Gly Ala Ala Gly Glu Gly Tyr Tyr Gly Tyr
1               5                   10

<210> SEQ ID NO 58
<211> LENGTH: 13
<212> TYPE: PRT
<213> ORGANISM: Homo sapiens

<400> SEQUENCE: 58

Thr Arg Ser Ser Gly Ser Ile Ala Ser Asn Tyr Val Gln
1               5                   10

<210> SEQ ID NO 59
<211> LENGTH: 7
<212> TYPE: PRT
<213> ORGANISM: Homo sapiens

<400> SEQUENCE: 59

Asp Asp Asn Gln Arg Pro Ser
1               5

<210> SEQ ID NO 60
<211> LENGTH: 9
<212> TYPE: PRT
<213> ORGANISM: Homo sapiens

<400> SEQUENCE: 60

Gln Ser Tyr Asp Ser Asn Asn Asp Val
1               5

<210> SEQ ID NO 61
<211> LENGTH: 5
<212> TYPE: PRT
<213> ORGANISM: Homo sapiens

<400> SEQUENCE: 61

Gln Thr Gly Val Ser
1               5

<210> SEQ ID NO 62
<211> LENGTH: 17
<212> TYPE: PRT
<213> ORGANISM: Homo sapiens

<400> SEQUENCE: 62

Trp Ile Ser Ala Asn Asn Gly Asp Thr Asn Tyr Gly Gln Glu Phe Gln Gly
1               5                   10                  15

<210> SEQ ID NO 63
```

```
<211> LENGTH: 13
<212> TYPE: PRT
<213> ORGANISM: Homo sapiens

<400> SEQUENCE: 63

Asp Ser Ser Ser Ser Trp Ala Arg Trp Phe Phe Asp Leu
1               5                   10

<210> SEQ ID NO 64
<211> LENGTH: 11
<212> TYPE: PRT
<213> ORGANISM: Homo sapiens

<400> SEQUENCE: 64

Gly Gly Asn Ile Ile Gly Ser Lys Leu Val His
1               5                   10

<210> SEQ ID NO 65
<211> LENGTH: 7
<212> TYPE: PRT
<213> ORGANISM: Homo sapiens

<400> SEQUENCE: 65

Asp Asp Gly Asp Arg Pro Ser
1               5

<210> SEQ ID NO 66
<211> LENGTH: 11
<212> TYPE: PRT
<213> ORGANISM: Homo sapiens

<400> SEQUENCE: 66

Gln Val Trp Asp Thr Gly Ser Asp Pro Val Val
1               5                   10

<210> SEQ ID NO 67
<211> LENGTH: 5
<212> TYPE: PRT
<213> ORGANISM: Homo sapiens

<400> SEQUENCE: 67

Asn Thr Gly Ile Ser
1               5

<210> SEQ ID NO 68
<211> LENGTH: 17
<212> TYPE: PRT
<213> ORGANISM: Homo sapiens

<400> SEQUENCE: 68

Trp Ile Ser Ala Asn Asn Gly Asp Thr Asn Tyr Gly Gln Glu Phe Gln Gly
1               5                   10                  15

<210> SEQ ID NO 69
<211> LENGTH: 13
<212> TYPE: PRT
<213> ORGANISM: Homo sapiens

<400> SEQUENCE: 69

Asp Ser Ser Ser Ser Trp Ala Arg Trp Phe Phe Asp Leu
1               5                   10

<210> SEQ ID NO 70
<211> LENGTH: 11
<212> TYPE: PRT
```

<213> ORGANISM: Homo sapiens

<400> SEQUENCE: 70

Gly Gly Asn Ile Ile Gly Ser Lys Leu Val His
1               5                   10

<210> SEQ ID NO 71
<211> LENGTH: 7
<212> TYPE: PRT
<213> ORGANISM: Homo sapiens

<400> SEQUENCE: 71

Asp Asp Gly Asp Arg Pro Ser
1               5

<210> SEQ ID NO 72
<211> LENGTH: 11
<212> TYPE: PRT
<213> ORGANISM: Homo sapiens

<400> SEQUENCE: 72

Gln Val Trp Asp Thr Gly Ser Asp Pro Val Val
1               5                   10

<210> SEQ ID NO 73
<211> LENGTH: 5
<212> TYPE: PRT
<213> ORGANISM: Homo sapiens

<400> SEQUENCE: 73

Asn Tyr Gly Leu Ser
1               5

<210> SEQ ID NO 74
<211> LENGTH: 17
<212> TYPE: PRT
<213> ORGANISM: Homo sapiens

<400> SEQUENCE: 74

Trp Ile Ser Gly Ser Asn Gly Tyr Thr Ser Tyr Gly Gln Glu Phe Gln Gly
1               5                   10                  15

<210> SEQ ID NO 75
<211> LENGTH: 13
<212> TYPE: PRT
<213> ORGANISM: Homo sapiens

<400> SEQUENCE: 75

Asp Ser Ser Ser Ser Trp Ala Arg Trp Phe Phe Asp Leu
1               5                   10

<210> SEQ ID NO 76
<211> LENGTH: 11
<212> TYPE: PRT
<213> ORGANISM: Homo sapiens

<400> SEQUENCE: 76

Gly Gly Asn Ile Ile Gly Ser Lys Leu Val His
1               5                   10

<210> SEQ ID NO 77
<211> LENGTH: 7
<212> TYPE: PRT
<213> ORGANISM: Homo sapiens

```
<400> SEQUENCE: 77

Asp Asp Gly Asp Arg Pro Ser
1               5

<210> SEQ ID NO 78
<211> LENGTH: 11
<212> TYPE: PRT
<213> ORGANISM: Homo sapiens

<400> SEQUENCE: 78

Gln Val Trp Asp Thr Gly Ser Asp Pro Val Val
1               5                   10

<210> SEQ ID NO 79
<211> LENGTH: 5
<212> TYPE: PRT
<213> ORGANISM: Homo sapiens

<400> SEQUENCE: 79

Asn Tyr Gly Leu Ser
1               5

<210> SEQ ID NO 80
<211> LENGTH: 17
<212> TYPE: PRT
<213> ORGANISM: Homo sapiens

<400> SEQUENCE: 80

Trp Ile Asn Asp Ala Thr Gly Asp Thr Gln Tyr Gly Gln Glu Phe Gln Gly
1               5                   10                  15

<210> SEQ ID NO 81
<211> LENGTH: 13
<212> TYPE: PRT
<213> ORGANISM: Homo sapiens

<400> SEQUENCE: 81

Asp Ser Ser Ser Ser Trp Ala Arg Trp Phe Phe Asp Leu
1               5                   10

<210> SEQ ID NO 82
<211> LENGTH: 11
<212> TYPE: PRT
<213> ORGANISM: Homo sapiens

<400> SEQUENCE: 82

Gly Gly Asn Ile Ile Gly Ser Lys Leu Val His
1               5                   10

<210> SEQ ID NO 83
<211> LENGTH: 7
<212> TYPE: PRT
<213> ORGANISM: Homo sapiens

<400> SEQUENCE: 83

Asp Asp Gly Asp Arg Pro Ser
1               5

<210> SEQ ID NO 84
<211> LENGTH: 11
<212> TYPE: PRT
<213> ORGANISM: Homo sapiens

<400> SEQUENCE: 84
```

Gln Val Trp Asp Thr Gly Ser Asp Pro Val Val
1               5                   10

<210> SEQ ID NO 85
<211> LENGTH: 5
<212> TYPE: PRT
<213> ORGANISM: Homo sapiens

<400> SEQUENCE: 85

Asp Thr Gly Val Ser
1               5

<210> SEQ ID NO 86
<211> LENGTH: 17
<212> TYPE: PRT
<213> ORGANISM: Homo sapiens

<400> SEQUENCE: 86

Trp Ile Ser Ala Asn Asn Gly Asp Thr Asn Tyr Gly Gln Glu Phe Gln Gly
1               5                   10                  15

<210> SEQ ID NO 87
<211> LENGTH: 13
<212> TYPE: PRT
<213> ORGANISM: Homo sapiens

<400> SEQUENCE: 87

Asp Ser Ser Ser Ser Trp Ala Arg Trp Phe Phe Asp Leu
1               5                   10

<210> SEQ ID NO 88
<211> LENGTH: 11
<212> TYPE: PRT
<213> ORGANISM: Homo sapiens

<400> SEQUENCE: 88

Gly Gly Asn Ile Ile Gly Ser Lys Leu Val His
1               5                   10

<210> SEQ ID NO 89
<211> LENGTH: 7
<212> TYPE: PRT
<213> ORGANISM: Homo sapiens

<400> SEQUENCE: 89

Asp Asp Gly Asp Arg Pro Ser
1               5

<210> SEQ ID NO 90
<211> LENGTH: 11
<212> TYPE: PRT
<213> ORGANISM: Homo sapiens

<400> SEQUENCE: 90

Gln Val Trp Asp Thr Gly Ser Asp Pro Val Val
1               5                   10

<210> SEQ ID NO 91
<211> LENGTH: 5
<212> TYPE: PRT
<213> ORGANISM: Homo sapiens

<400> SEQUENCE: 91

Asn Tyr Gly Leu Ser
1               5

```
<210> SEQ ID NO 92
<211> LENGTH: 17
<212> TYPE: PRT
<213> ORGANISM: Homo sapiens

<400> SEQUENCE: 92

Trp Ile Ala Thr Pro Asp Gly Gln Thr Ser Tyr Gly Gln Glu Phe Gln Gly
1               5                   10                  15

<210> SEQ ID NO 93
<211> LENGTH: 13
<212> TYPE: PRT
<213> ORGANISM: Homo sapiens

<400> SEQUENCE: 93

Asp Ser Asn Ser Ser Trp Ala Arg Trp Phe Phe Asp Leu
1               5                   10

<210> SEQ ID NO 94
<211> LENGTH: 11
<212> TYPE: PRT
<213> ORGANISM: Homo sapiens

<400> SEQUENCE: 94

Gly Gly Asn Ile Ile Gly Ser Lys Leu Val His
1               5                   10

<210> SEQ ID NO 95
<211> LENGTH: 7
<212> TYPE: PRT
<213> ORGANISM: Homo sapiens

<400> SEQUENCE: 95

Asp Asp Gly Asp Arg Pro Ser
1               5

<210> SEQ ID NO 96
<211> LENGTH: 11
<212> TYPE: PRT
<213> ORGANISM: Homo sapiens

<400> SEQUENCE: 96

Gln Val Trp Asp Thr Gly Ser Asp Pro Val Val
1               5                   10

<210> SEQ ID NO 97
<211> LENGTH: 5
<212> TYPE: PRT
<213> ORGANISM: Homo sapiens

<400> SEQUENCE: 97

Asn Tyr Gly Leu Ser
1               5

<210> SEQ ID NO 98
<211> LENGTH: 17
<212> TYPE: PRT
<213> ORGANISM: Homo sapiens

<400> SEQUENCE: 98

Trp Ile Asn Tyr Asp Gly Gly Asn Thr Gln Tyr Gly Gln Glu Phe Gln Gly
1               5                   10                  15
```

```
<210> SEQ ID NO 99
<211> LENGTH: 13
<212> TYPE: PRT
<213> ORGANISM: Homo sapiens

<400> SEQUENCE: 99

Asp Ser Ser Ser Ser Trp Ala Arg Trp Phe Phe Asp Leu
1               5                   10

<210> SEQ ID NO 100
<211> LENGTH: 11
<212> TYPE: PRT
<213> ORGANISM: Homo sapiens

<400> SEQUENCE: 100

Gly Gly Asn Ile Ile Gly Ser Lys Leu Val His
1               5                   10

<210> SEQ ID NO 101
<211> LENGTH: 7
<212> TYPE: PRT
<213> ORGANISM: Homo sapiens

<400> SEQUENCE: 101

Asp Asp Gly Asp Arg Pro Ser
1               5

<210> SEQ ID NO 102
<211> LENGTH: 11
<212> TYPE: PRT
<213> ORGANISM: Homo sapiens

<400> SEQUENCE: 102

Gln Val Trp Asp Thr Gly Ser Asp Pro Val Val
1               5                   10

<210> SEQ ID NO 103
<211> LENGTH: 5
<212> TYPE: PRT
<213> ORGANISM: Homo sapiens

<400> SEQUENCE: 103

Asp Tyr Gly Leu Ser
1               5

<210> SEQ ID NO 104
<211> LENGTH: 16
<212> TYPE: PRT
<213> ORGANISM: Homo sapiens

<400> SEQUENCE: 104

Trp Arg Ile Asn Asp Gly Tyr Thr Ile Tyr Gly Gln Glu Phe Gln Gly
1               5                   10                  15

<210> SEQ ID NO 105
<211> LENGTH: 13
<212> TYPE: PRT
<213> ORGANISM: Homo sapiens

<400> SEQUENCE: 105

Asp Ser Ser Ser Ser Trp Ala Arg Trp Phe Phe Asp Leu
1               5                   10

<210> SEQ ID NO 106
<211> LENGTH: 11
```

-continued

<212> TYPE: PRT
<213> ORGANISM: Homo sapiens

<400> SEQUENCE: 106

Gly Gly Asn Ile Ile Gly Ser Lys Leu Val His
1               5                   10

<210> SEQ ID NO 107
<211> LENGTH: 7
<212> TYPE: PRT
<213> ORGANISM: Homo sapiens

<400> SEQUENCE: 107

Asp Asp Gly Asp Arg Pro Ser
1               5

<210> SEQ ID NO 108
<211> LENGTH: 11
<212> TYPE: PRT
<213> ORGANISM: Homo sapiens

<400> SEQUENCE: 108

Gln Val Trp Asp Thr Gly Ser Asp Pro Val Val
1               5                   10

<210> SEQ ID NO 109
<211> LENGTH: 366
<212> TYPE: DNA
<213> ORGANISM: Homo sapiens

<400> SEQUENCE: 109

```
caggtgcagc tggtgcagtc tggggctgag gtgaagaagc ctggggcctc agtgaaggtc      60
tcctgcaagg cttctggtta cacctttaca aattatggtc tcagctgggt gcgacaggcc     120
cctggacaag gcttgagtg gatgggatgg atcagcgcta ataatggcga cacaaattat      180
ggacaggaat ccagggcag agtcaccatg accacagata catccacgag cacagcctac      240
atggagttga ggagcctgag atctgacgac acggccgttt attactgtgc gagagactcc     300
agcagcaact gggcccgctg gttttttcgat ctctggggcc gggggacact ggtcaccgtc    360
tcctca                                                               366
```

<210> SEQ ID NO 110
<211> LENGTH: 327
<212> TYPE: DNA
<213> ORGANISM: Homo sapiens

<400> SEQUENCE: 110

```
tcctatgtgc tgactcagcc accctcggtg tcagtggccc caggtaagac ggccaggatt      60
acctgtgggg gaaacaacat tggaagtaaa cttgtacact ggtaccagca gaagccaggc     120
caggcccctg tgctggtcat ctatgatgat ggcgaccggc cctcagggat ccctgagcga     180
ttctctggct ccaactctgg gaacacggcc accctgacca tcagcagggt cgaggccggg     240
gatgaggccg actattattg tcaggtgtgg gatactggta gtgatcccgt ggtattcggc     300
ggagggacca agctgaccgt cctaggt                                        327
```

<210> SEQ ID NO 111
<211> LENGTH: 366
<212> TYPE: DNA
<213> ORGANISM: Homo sapiens

<400> SEQUENCE: 111

```
caggtccagc tggtgcagtc tggggctgag gtgaagaagc ctggggcctc agtgaaggtc     60
tcctgcaagg cttctggtta cacctttaca aattatggtc tcagctgggt gcgacaggcc    120
cctggacaag ggcttgagtg gatgggatgg atcagcgcta ataatggcga cacaaattat    180
ggacaggaat tccagggcag agtcaccatg accacagata catccacgag cacagcctac    240
atggagttga ggagcctgag atctgacgac acggccgttt attactgtgc gagagactcc    300
agcagcagct gggcccgctg ttttttcgat ctctggggcc ggggggacact ggtcaccgtc    360 tcctca                                                                366
```

<210> SEQ ID NO 112
<211> LENGTH: 327
<212> TYPE: DNA
<213> ORGANISM: Homo sapiens

<400> SEQUENCE: 112

```
tcctatgtgc tgactcagcc accctcggtg tcagtggccc caggaaagac ggccaggatt     60
acctgtgggg gaaacatcat tggaagtaaa cttgtacact ggtaccagca gaagccaggc    120
caggcccctg tgctggtcat ctatgatgat ggcgaccggc cctcagggat ccctgagcga    180
ttctctggct ccaactctgg gaacacggcc accctgacca tcagcagggt cgaggccggg    240
gatgaggccg actattattg tcaggtgtgg gatactggta gtgatcccgt ggtattcggc    300
ggagggacca agctgaccgt cctaggt                                          327
```

<210> SEQ ID NO 113
<211> LENGTH: 366
<212> TYPE: DNA
<213> ORGANISM: Homo sapiens

<400> SEQUENCE: 113

```
caggtccagc tggtgcagtc tggggctgag gtgaagaagc ctggggcctc agtgaaggtc     60
tcctgcaagg cttctggtta cacctttaca aattatggtc tcagctgggt gcgacaggcc    120
cctggacaag ggcttgagtg gatgggatgg atctccggct tgaacggcga gacattgtat    180
ggacaggaat tccagggcag agtcaccatg accacagata catccacgag cacagcctac    240
atggagttga ggagcctgag atctgacgac acggccgttt attactgtgc gagagactcc    300
agcagcagct gggcccgctg ttttttcgat ctctggggcc ggggggacact ggtcaccgtc    360 tcctca                                                                366
```

<210> SEQ ID NO 114
<211> LENGTH: 327
<212> TYPE: DNA
<213> ORGANISM: Homo sapiens

<400> SEQUENCE: 114

```
tcctatgtgc tgactcagcc accctcggtg tcagtggccc caggaaagac ggccaggatt     60
acctgtgggg gaaacatcat tggaagtaaa cttgtacact ggtaccagca gaagccaggc    120
caggcccctg tgctggtcat ctatgatgat ggcgaccggc cctcagggat ccctgagcga    180
ttctctggct ccaactctgg gaacacggcc accctgacca tcagcagggt cgaggccggg    240
gatgaggccg actattattg tcaggtgtgg gatactggta gtgatcccgt ggtattcggc    300
ggagggacca agctgaccgt cctaggt                                          327
```

<210> SEQ ID NO 115

```
<211> LENGTH: 366
<212> TYPE: DNA
<213> ORGANISM: Homo sapiens

<400> SEQUENCE: 115
caggtgcagc tggtgcagtc tggggctgag gtgaagaagc ctggggcctc agtgaaggtc      60
tcctgcaagg cttctggtta caccttaca aattatggtc tcagctgggt gcgacaggcc     120
cctggacaag ggcttgagtg gatgggatgg atcgcaaccc cagacggcca gacaagctat    180
ggacaggaat tccagggcag agtcaccatg accacagata catccacgag cacagcctac    240
atggagttga ggagcctgag atctgacgac acggccgttt attactgtgc gagagactcc    300
aacagcagct gggcccgctg gttttttcgat ctctggggcc ggggggacact ggtcaccgtc    360 tcctca                                                                 366

<210> SEQ ID NO 116
<211> LENGTH: 327
<212> TYPE: DNA
<213> ORGANISM: Homo sapiens

<400> SEQUENCE: 116
tcctatgtgc tgactcagcc accctcggtg tcagtggccc caggaaagac ggccaggatt      60
acctgtgggg gaaacatcat tggaagtaaa cttgtacact ggtaccagca gaagccaggc     120
caggcccctg tgctggtcat ctatgatgat ggcgaccggc cctcagggat ccctgagcga    180
ttctctggct ccaactctgg gaacacggcc accctgacca tcagcagggt cgaggccggg    240
gatgaggccg actattattg tcaggtgtgg gatactggta gtgatccgt ggtattcggc      300 ggagggacca agctgaccgt cctaggt                                          327

<210> SEQ ID NO 117
<211> LENGTH: 366
<212> TYPE: DNA
<213> ORGANISM: Homo sapiens

<400> SEQUENCE: 117
caagtgcagc tggtgcagtc tggggctgag gtgaagaagc ctggggcctc agtgaaggtc      60
tcctgcaagg cttctggtta cacctttgag cagaccggcg tctcctgggt gcgacaggcc     120
cctggacaag ggcttgagtg gatgggatgg atcagcgcta ataatggcga cacaaattat    180
ggacaggaat tccagggcag agtcaccatg accacagata catccacgag cacagcctac    240
atggagttga ggagcctgag atctgacgac acggccgttt attactgtgc gagagactcc    300
agcagcagct gggcccgctg gttttttcgat ctctggggcc ggggggacact ggtcaccgtc    360 tcctca                                                                 366

<210> SEQ ID NO 118
<211> LENGTH: 327
<212> TYPE: DNA
<213> ORGANISM: Homo sapiens

<400> SEQUENCE: 118
tcctatgtgc tgactcagcc accctcggtg tcagtggccc caggaaagac ggccaggatt      60
acctgtgggg gaaacatcat tggaagtaaa cttgtacact ggtaccagca gaagccaggc     120
caggcccctg tgctggtcat ctatgatgat ggcgaccggc cctcagggat ccctgagcga    180
ttctctggct ccaactctgg gaacacggcc accctgacca tcagcagggt cgaggccggg    240
gatgaggccg actattattg tcaggtgtgg gatactggta gtgatccgt ggtattcggc      300
```

```
ggagggacca agctgaccgt cctaggt                                           327
```

<210> SEQ ID NO 119
<211> LENGTH: 366
<212> TYPE: DNA
<213> ORGANISM: Homo sapiens

<400> SEQUENCE: 119

```
caggtgcagc tggtgcagtc tggggctgag gtgaagaagc ctggggcctc agtgaaggtc        60
tcctgcaagg cttctggtta cacctttatc gacaccgggg tctcctgggt gcgacaggcc       120
cctggacaag gcttgagtg gatgggatgg atcagcgcta ataatggcga cacaaattat        180
ggacaggaat ccagggcag agtcaccatg accacagata catccacgag cacagcctac        240
atggagttga ggagcctgag atctgacgac acggccgttt attactgtgc gagagactcc       300
agcagcagct gggcccgctg gttttttcgat ctctggggcc ggggacact ggtcaccgtc       360
tcctca                                                                  366
```

<210> SEQ ID NO 120
<211> LENGTH: 327
<212> TYPE: DNA
<213> ORGANISM: Homo sapiens

<400> SEQUENCE: 120

```
tcctatgtgc tgactcagcc accctcggtg tcagtggccc caggaaagac ggccaggatt        60
acctgtgggg gaaacatcat tggaagtaaa cttgtacact ggtaccagca gaagccaggc       120
caggcccctg tgctggtcat ctatgatgat ggcgaccggc cctcagggat ccctgagcga       180
ttctctggct ccaactctgg gaacacggcc accctgacca tcagcagggt cgaggccggg       240
gatgaggccg actattattg tcaggtgtgg gatactggta gtgatcccgt ggtattcggc       300
ggagggacca agctgaccgt cctaggt                                           327
```

<210> SEQ ID NO 121
<211> LENGTH: 366
<212> TYPE: DNA
<213> ORGANISM: Homo sapiens

<400> SEQUENCE: 121

```
caggtgcagc tggtgcagtc tggggctgag gtgaagaagc ctggggcctc agtgaaggtc        60
tcctgcaagg cttctggtta ccctttaca aattatggtc tcagctgggt gcgacaggcc        120
cctggacaag gcttgagtg gatgggatgg atcaactacg acggcggcaa cacacagtat        180
ggacaggaat ccagggcag agtcaccatg accacagata catccacgag cacagcctac        240
atggagttga ggagcctgag atctgacgac acggccgttt attactgtgc gagagactcc       300
agcagcagct gggcccgctg gttttttcgat ctctggggcc ggggacact ggtcaccgtc       360
tcctca                                                                  366
```

<210> SEQ ID NO 122
<211> LENGTH: 327
<212> TYPE: DNA
<213> ORGANISM: Homo sapiens

<400> SEQUENCE: 122

```
tcctatgtgc tgactcagcc accctcggtg tcagtggccc caggaaagac ggccaggatt        60
acctgtgggg gaaacatcat tggaagtaaa cttgtacact ggtaccagca gaagccaggc       120
```

```
caggcccctg tgctggtcat ctatgatgat ggcgaccggc cctcagggat ccctgagcga    180
ttctctggct ccaactctgg gaacacggcc accctgacca tcagcagggt cgaggccggg    240
gatgaggccg actattattg tcaggtgtgg gatactggta gtgatcccgt ggtattcggc    300
ggagggacca agctgaccgt cctaggt                                        327
```

<210> SEQ ID NO 123
<211> LENGTH: 366
<212> TYPE: DNA
<213> ORGANISM: Homo sapiens

<400> SEQUENCE: 123

```
caggtgcagc tggtgcagtc tggggctgag gtgaagaagc ctggggcctc agtgaaggtc     60
tcctgcaagg cttctggtta cacctttaca aattatggtc tcagctgggt gcgacaggcc    120
cctggacaag gcttgagtg gatgggatgg atcagcggga gcaacggcta cacatcttat    180
ggacaggaat tccagggcag agtcaccatg accacagata cgtccacgag cacagcctac    240
atggagttga ggagcctgag atctgacgac acggccgttt attactgtgc gagagactcc    300
agcagcagct gggcccgctg ttttttcgat ctctggggcc gggggacact ggtcaccgtc    360
tcctca                                                               366
```

<210> SEQ ID NO 124
<211> LENGTH: 327
<212> TYPE: DNA
<213> ORGANISM: Homo sapiens

<400> SEQUENCE: 124

```
tcctatgtgc tgactcagcc accctcggtg tcagtggccc caggaaagac ggccaggatt     60
acctgtgggg gaaacatcat tggaagtaaa cttgtacact ggtaccagca gaagccaggc    120
caggcccctg tgctggtcat ctatgatgat ggcgaccggc cctcagggat ccctgagcga    180
ttctctggct ccaactctgg gaacacggcc accctgacca tcagcagggt cgaggccggg    240
gatgaggccg actattattg tcaggtgtgg gatactggta gtgatcccgt ggtattcggc    300
ggagggacca agctgaccgt cctaggt                                        327
```

<210> SEQ ID NO 125
<211> LENGTH: 366
<212> TYPE: DNA
<213> ORGANISM: Homo sapiens

<400> SEQUENCE: 125

```
caggtgcagc tggtgcagtc tggggctgag gtgaagaagc ctggggcctc agtgaaggtc     60
tcctgcaagg cttctggtta cacctttaca aattatggtc tcagctgggt gcgacaggcc    120
cctggacaag gcttgagtg gatgggatgg atcaacgacg ccaccggcga cacacagtat    180
ggacaggaat tccagggcag agtcaccatg accacagata catccacgag cacagcctac    240
atggagttga ggagcctgag atctgacgac acggccgttt attactgtgc gagagactcc    300
agcagcagct gggcccgctg ttttttcgat ctctggggcc gggggacact ggtcaccgtc    360
tcctca                                                               366
```

<210> SEQ ID NO 126
<211> LENGTH: 327
<212> TYPE: DNA
<213> ORGANISM: Homo sapiens

<400> SEQUENCE: 126

```
tcctatgtgc tgactcagcc accctcggtg tcagtggccc caggaaagac ggccaggatt    60
acctgtgggg gaaacatcat tggaagtaaa cttgtacact ggtaccagca gaagccaggc   120
caggcccctg tgctggtcat ctatgatgat ggcgaccggc cctcagggat ccctgagcga   180
ttctctggct ccaactctgg gaacacggcc accctgacca tcagcagggt cgaggccggg   240
gatgaggccg actattattg tcaggtgtgg gatactggta gtgatcccgt ggtattcggc   300
ggagggacca agctgaccgt cctaggt                                       327
```

<210> SEQ ID NO 127
<211> LENGTH: 366
<212> TYPE: DNA
<213> ORGANISM: Homo sapiens

<400> SEQUENCE: 127

```
caggtgcagc tggtgcagtc tggggctgag gtgaagaagc ctggggcctc agtgaaggtc    60
tcctgcaagg cttctggtta ccctttaca gattatggtc tcagctgggt gcgacaggcc   120
cctggacaag gctagagtg atgggatgg atccgcaaca tcgacggcta cacaatttat    180
ggacaggaat tccagggcag agtcaccatg accacagata catccacgag cacagcctac   240
atggagttga ggagcctgag atctgacgac acggccgttt attactgtgc gagagactcc   300
agcagcagct gggcccgctg gttttttcgat ctctggggcc ggggggacact ggtcaccgtc   360 tcctca                                                              366
```

<210> SEQ ID NO 128
<211> LENGTH: 327
<212> TYPE: DNA
<213> ORGANISM: Homo sapiens

<400> SEQUENCE: 128

```
tcctatgtgc tgactcagcc accctcggtg tcagtggccc caggaaagac ggccaggatt    60
acctgtgggg gaaacatcat tggaagtaaa cttgtacact ggtaccagca gaagccaggc   120
caggcccctg tgctggtcat ctatgatgat ggcgaccggc cctcagggat ccctgagcga   180
ttctctggct ccaactctgg gaacacggcc accctgacca tcagcagggt cgaggccggg   240
gatgaggccg actattattg tcaggtgtgg gatactggta gtgatcccgt ggtattcggc   300
ggagggacca agctgaccgt cctaggt                                       327
```

<210> SEQ ID NO 129
<211> LENGTH: 366
<212> TYPE: DNA
<213> ORGANISM: Homo sapiens

<400> SEQUENCE: 129

```
caggtccagc tggtgcagtc tggggctgag gtgaagaagc ctggggcctc agtgaaggtc    60
tcctgcaagg cttctggtta ccctttaca aattatggtc tcagctgggt gcgacaggcc   120
cctggacaag gcttgagtg atgggatgg atcgacgacg acagcggcac gacaatatat    180
ggacaggaat tccagggcag agtcaccatg accacagata catccacgag cacagcctac   240
atggagttga ggagcctgag atctgacgac acggccgttt attactgtgc gagagactcc   300
agcagcagct gggcccgctg gttttttcgat ctctggggcc ggggggacact ggtcaccgtc   360 tcctca                                                              366
```

<210> SEQ ID NO 130

<210> SEQ ID NO 130
<211> LENGTH: 327
<212> TYPE: DNA
<213> ORGANISM: Homo sapiens

<400> SEQUENCE: 130

```
tcctatgtgc tgactcagcc accctcggtg tcagtggccc caggaaagac ggccaggatt      60
acctgtgggg gaaacatcat tggaagtaaa cttgtacact ggtaccagca gaagccaggc     120
caggcccctg tgctggtcat ctatgatgat ggcgaccggc cctcagggat ccctgagcga     180
ttctctggct ccaactctgg gaacacggcc accctgacca tcagcagggt cgaggccggg     240
gatgaggccg actattattg tcaggtgtgg gatactggta gtgatcccgt ggtattcggc     300
ggagggacca agctgaccgt cctaggt                                         327
```

<210> SEQ ID NO 131
<211> LENGTH: 366
<212> TYPE: DNA
<213> ORGANISM: Homo sapiens

<400> SEQUENCE: 131

```
caagtgcagt tggtgcagtc tggggctgag gtgaagaagc ctggggcctc agtgaaggtc      60
tcctgcaagg cttctggtta caccttttgcg aacaccggga tctcgtgggt gcgacaggcc    120
cctggacaag gcttgagtg gatgggatgg atcagcgcta ataatggcga cacaaattat      180
ggacaggaat tccagggcag agtcaccatg accacagata catccacgag cacagcctac     240
atggagttga ggagcctgag atctgacgac acggccgttt attactgtgc gagagactcc     300
agcagcagct gggcccgctg ttttttcgat ctctggggtc gggggacact ggtcaccgtc     360
tcctca                                                                366
```

<210> SEQ ID NO 132
<211> LENGTH: 327
<212> TYPE: DNA
<213> ORGANISM: Homo sapiens

<400> SEQUENCE: 132

```
tcctatgtgc tgactcagcc accctcggtg tcagtggccc caggaaagac ggccaggatt      60
acctgtgggg gaaacatcat tggaagtaaa cttgtacact ggtaccagca gaagccaggc     120
caggcccctg tgctggtcat ctatgatgat ggcgaccggc cctcagggat ccctgagcga     180
ttctctggct ccaactctgg gaacacggcc accctgacca tcagcagggt cgaggccggg     240
gatgaggccg actattattg tcaggtgtgg gatactggta gtgatcccgt ggtattcggc     300
ggagggacca agctgaccgt cctaggt                                         327
```

<210> SEQ ID NO 133
<211> LENGTH: 122
<212> TYPE: PRT
<213> ORGANISM: Homo sapiens

<400> SEQUENCE: 133

```
Glu Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Asn Tyr
             20                  25                  30

Gly Leu Ser Trp Val Arg Gln Ala Pro Gly Gln Gly Leu Glu Trp Met
         35                  40                  45

Gly Trp Ile Ser Ala Asn Asn Gly Glu Thr Asn Tyr Gly Gln Glu Phe
     50                  55                  60
```

Gln Gly Arg Val Thr Met Thr Thr Glu Thr Pro Asn Thr Ala His
65                  70                  75                  80

Met Glu Leu Arg Ser Leu Thr Ser Asp Asp Thr Ala Val Tyr Tyr Cys
                85                  90                  95

Val Arg Asp Ser Ser Ser Asn Trp Ala Arg Trp Tyr Phe Asp Leu Trp
            100                 105                 110

Gly Gln Gly Thr Leu Val Thr Val Ser Ser
        115                 120

<210> SEQ ID NO 134
<211> LENGTH: 109
<212> TYPE: PRT
<213> ORGANISM: Homo sapiens

<400> SEQUENCE: 134

Ser Tyr Val Leu Thr Gln Pro Pro Ser Val Ser Val Ala Pro Gly Gln
1               5                   10                  15

Thr Ala Arg Ile Pro Cys Gly Gly Asn Asn Ile Gly Ser Lys Leu Val
            20                  25                  30

His Trp Tyr Gln Gln Lys Pro Gly Gln Ala Pro Val Leu Val Val Tyr
        35                  40                  45

Asp Asp Gly Asp Arg Pro Ser Gly Ile Pro Glu Arg Phe Ser Gly Ser
    50                  55                  60

Asn Ser Gly Asn Thr Ala Thr Leu Thr Ile Ser Arg Ile Asp Ala Gly
65                  70                  75                  80

Asp Glu Ala Asp Tyr Tyr Cys Gln Val Trp Asp Thr Gly Ser Asp Pro
                85                  90                  95

Val Val Phe Gly Gly Gly Thr Lys Leu Thr Val Leu Gly
            100                 105

<210> SEQ ID NO 135
<211> LENGTH: 5
<212> TYPE: PRT
<213> ORGANISM: Homo sapiens

<400> SEQUENCE: 135

Asn Tyr Gly Leu Ser
1               5

<210> SEQ ID NO 136
<211> LENGTH: 17
<212> TYPE: PRT
<213> ORGANISM: Homo sapiens

<400> SEQUENCE: 136

Trp Ile Ser Ala Asn Asn Gly Glu Thr Asn Tyr Gly Gln Glu Phe Gln
1               5                   10                  15

Gly

<210> SEQ ID NO 137
<211> LENGTH: 13
<212> TYPE: PRT
<213> ORGANISM: Homo sapiens

<400> SEQUENCE: 137

Asp Ser Ser Ser Asn Trp Ala Arg Trp Tyr Phe Asp Leu
1               5                   10

<210> SEQ ID NO 138

```
<211> LENGTH: 11
<212> TYPE: PRT
<213> ORGANISM: Homo sapiens

<400> SEQUENCE: 138

Gly Gly Asn Asn Ile Gly Ser Lys Leu Val His
1               5                   10

<210> SEQ ID NO 139
<211> LENGTH: 7
<212> TYPE: PRT
<213> ORGANISM: Homo sapiens

<400> SEQUENCE: 139

Asp Asp Gly Asp Arg Pro Ser
1               5

<210> SEQ ID NO 140
<211> LENGTH: 11
<212> TYPE: PRT
<213> ORGANISM: Homo sapiens

<400> SEQUENCE: 140

Gln Val Trp Asp Thr Gly Ser Asp Pro Val Val
1               5                   10

<210> SEQ ID NO 141
<211> LENGTH: 5
<212> TYPE: PRT
<213> ORGANISM: Homo sapiens

<400> SEQUENCE: 141

Ser Tyr Ala Met Ser
1               5

<210> SEQ ID NO 142
<211> LENGTH: 17
<212> TYPE: PRT
<213> ORGANISM: Homo sapiens

<400> SEQUENCE: 142

Ala Ile Ser Gly Ser Gly Gly Ser Thr Tyr Tyr Ala Asp Ser Val Lys
1               5                   10                  15

Gly

<210> SEQ ID NO 143
<211> LENGTH: 11
<212> TYPE: PRT
<213> ORGANISM: Homo sapiens

<400> SEQUENCE: 143

Val Gly Ala Ala Gly Glu Gly Tyr Tyr Gly Tyr
1               5                   10

<210> SEQ ID NO 144
<211> LENGTH: 13
<212> TYPE: PRT
<213> ORGANISM: Homo sapiens

<400> SEQUENCE: 144

Thr Arg Ser Ser Gly Ser Ile Ala Ser Asn Tyr Val Glu
1               5                   10

<210> SEQ ID NO 145
```

```
<211> LENGTH: 7
<212> TYPE: PRT
<213> ORGANISM: Homo sapiens

<400> SEQUENCE: 145

Asp Asp Asn Gln Arg Pro Ser
1               5

<210> SEQ ID NO 146
<211> LENGTH: 9
<212> TYPE: PRT
<213> ORGANISM: Homo sapiens

<400> SEQUENCE: 146

Gln Ser Tyr Asp Ser Asn Asn Asp Val
1               5

<210> SEQ ID NO 147
<211> LENGTH: 5
<212> TYPE: PRT
<213> ORGANISM: Homo sapiens

<400> SEQUENCE: 147

Ser Tyr Ala Met Ser
1               5

<210> SEQ ID NO 148
<211> LENGTH: 17
<212> TYPE: PRT
<213> ORGANISM: Homo sapiens

<400> SEQUENCE: 148

Ala Ile Ser Gly Ser Gly Gly Ser Thr Tyr Tyr Ala Asp Ser Val Lys
1               5                   10                  15

Gly

<210> SEQ ID NO 149
<211> LENGTH: 13
<212> TYPE: PRT
<213> ORGANISM: Homo sapiens

<400> SEQUENCE: 149

Val Gly Arg Ala Thr Thr Asp Glu Gly Tyr Tyr Gly Tyr
1               5                   10

<210> SEQ ID NO 150
<211> LENGTH: 13
<212> TYPE: PRT
<213> ORGANISM: Homo sapiens

<400> SEQUENCE: 150

Thr Arg Ser Ser Gly Ser Ile Ala Ser Asn Tyr Val Gln
1               5                   10

<210> SEQ ID NO 151
<211> LENGTH: 7
<212> TYPE: PRT
<213> ORGANISM: Homo sapiens

<400> SEQUENCE: 151

Asp Asp Asn Gln Arg Pro Ser
1               5

<210> SEQ ID NO 152
```

<211> LENGTH: 9
<212> TYPE: PRT
<213> ORGANISM: Homo sapiens

<400> SEQUENCE: 152

Gln Ser Tyr Asp Ser Asn Asn Asp Val
1               5

<210> SEQ ID NO 153
<211> LENGTH: 5
<212> TYPE: PRT
<213> ORGANISM: Homo sapiens

<400> SEQUENCE: 153

Ser Tyr Ala Met Ser
1               5

<210> SEQ ID NO 154
<211> LENGTH: 17
<212> TYPE: PRT
<213> ORGANISM: Homo sapiens

<400> SEQUENCE: 154

Ala Ile Ser Gly Ser Gly Gly Ser Thr Tyr Tyr Ala Asp Ser Val Lys
1               5                   10                  15

Gly

<210> SEQ ID NO 155
<211> LENGTH: 11
<212> TYPE: PRT
<213> ORGANISM: Homo sapiens

<400> SEQUENCE: 155

Val Gly Lys Ala Thr Thr Glu Glu Gly Tyr Tyr
1               5                   10

<210> SEQ ID NO 156
<211> LENGTH: 13
<212> TYPE: PRT
<213> ORGANISM: Homo sapiens

<400> SEQUENCE: 156

Thr Arg Ser Ser Gly Ser Ile Ala Ser Asn Tyr Val Gln
1               5                   10

<210> SEQ ID NO 157
<211> LENGTH: 7
<212> TYPE: PRT
<213> ORGANISM: Homo sapiens

<400> SEQUENCE: 157

Asp Asp Asn Gln Arg Pro Ser
1               5

<210> SEQ ID NO 158
<211> LENGTH: 9
<212> TYPE: PRT
<213> ORGANISM: Homo sapiens

<400> SEQUENCE: 158

Gln Ser Tyr Asp Ser Asn Asn Asp Val
1               5

<210> SEQ ID NO 159

```
<211> LENGTH: 15
<212> TYPE: DNA
<213> ORGANISM: Homo sapiens

<400> SEQUENCE: 159
aattatggtc tcagc                                                      15

<210> SEQ ID NO 160
<211> LENGTH: 51
<212> TYPE: DNA
<213> ORGANISM: Homo sapiens

<400> SEQUENCE: 160
tggatcagcg ctaataatgg cgacacaaat tatggacagg aattccaggg c              51

<210> SEQ ID NO 161
<211> LENGTH: 39
<212> TYPE: DNA
<213> ORGANISM: Homo sapiens

<400> SEQUENCE: 161
gactccagca gcaactgggc ccgctggttt ttcgatctc                            39

<210> SEQ ID NO 162
<211> LENGTH: 33
<212> TYPE: DNA
<213> ORGANISM: Homo sapiens

<400> SEQUENCE: 162
gggggaaaca acattggaag taaacttgta cac                                  33

<210> SEQ ID NO 163
<211> LENGTH: 21
<212> TYPE: DNA
<213> ORGANISM: Homo sapiens

<400> SEQUENCE: 163
gatgatggcg accggccctc a                                               21

<210> SEQ ID NO 164
<211> LENGTH: 33
<212> TYPE: DNA
<213> ORGANISM: Homo sapiens

<400> SEQUENCE: 164
caggtgtggg atactggtag tgatcccgtg gta                                  33

<210> SEQ ID NO 165
<211> LENGTH: 15
<212> TYPE: DNA
<213> ORGANISM: Homo sapiens

<400> SEQUENCE: 165
aattatggtc tcagc                                                      15

<210> SEQ ID NO 166
<211> LENGTH: 51
<212> TYPE: DNA
<213> ORGANISM: Homo sapiens

<400> SEQUENCE: 166
tggatcagcg ctaataatgg cgacacaaat tatggacagg aattccaggg c              51
```

```
<210> SEQ ID NO 167
<211> LENGTH: 39
<212> TYPE: DNA
<213> ORGANISM: Homo sapiens

<400> SEQUENCE: 167
gactccagca gcagctgggc ccgctggttt ttcgatctc                              39

<210> SEQ ID NO 168
<211> LENGTH: 33
<212> TYPE: DNA
<213> ORGANISM: Homo sapiens

<400> SEQUENCE: 168
gggggaaaca tcattggaag taaacttgta cac                                   33

<210> SEQ ID NO 169
<211> LENGTH: 21
<212> TYPE: DNA
<213> ORGANISM: Homo sapiens

<400> SEQUENCE: 169
gatgatggcg accggccctc a                                                21

<210> SEQ ID NO 170
<211> LENGTH: 33
<212> TYPE: DNA
<213> ORGANISM: Homo sapiens

<400> SEQUENCE: 170
caggtgtggg atactggtag tgatcccgtg gta                                   33

<210> SEQ ID NO 171
<211> LENGTH: 327
<212> TYPE: PRT
<213> ORGANISM: Homo sapiens

<400> SEQUENCE: 171
```

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 172
<211> LENGTH: 105
<212> TYPE: PRT
<213> ORGANISM: Homo sapiens

<400> SEQUENCE: 172

Gln Pro Lys Ala Ala Pro Ser Val Thr Leu Phe Pro Pro Ser Ser Glu
1               5                   10                  15

Glu Leu Gln Ala Asn Lys Ala Thr Leu Val Cys Leu Ile Ser Asp Phe
            20                  25                  30

Tyr Pro Gly Ala Val Thr Val Ala Trp Lys Ala Asp Ser Ser Pro Val
        35                  40                  45

Lys Ala Gly Val Glu Thr Thr Thr Pro Ser Lys Gln Ser Asn Asn Lys
    50                  55                  60

Tyr Ala Ala Ser Ser Tyr Leu Ser Leu Thr Pro Glu Gln Trp Lys Ser
65                  70                  75                  80

His Arg Ser Tyr Ser Cys Gln Val Thr His Glu Gly Ser Thr Val Glu
                85                  90                  95

Lys Thr Val Ala Pro Thr Glu Cys Ser
            100                 105

<210> SEQ ID NO 173
<211> LENGTH: 132
<212> TYPE: PRT
<213> ORGANISM: Homo sapiens

<400> SEQUENCE: 173

Met Ala Leu Leu Leu Thr Thr Val Ile Ala Leu Thr Cys Leu Gly Gly
1               5                   10                  15

Phe Ala Ser Pro Gly Pro Val Pro Pro Ser Thr Ala Leu Arg Glu Leu
            20                  25                  30

Ile Glu Glu Leu Val Asn Ile Thr Gln Asn Gln Lys Ala Pro Leu Cys
        35                  40                  45

Asn Gly Ser Met Val Trp Ser Ile Asn Leu Thr Ala Gly Met Tyr Cys
    50                  55                  60

```
Ala Ala Leu Glu Ser Leu Ile Asn Val Ser Gly Cys Ser Ala Ile Glu
 65                  70                  75                  80

Lys Thr Gln Arg Met Leu Ser Gly Phe Cys Pro His Lys Val Ser Ala
                 85                  90                  95

Gly Gln Phe Ser Ser Leu His Val Arg Asp Thr Lys Ile Glu Val Ala
                100                 105                 110

Gln Phe Val Lys Asp Leu Leu Leu His Leu Lys Lys Leu Phe Arg Glu
            115                 120                 125

Gly Arg Phe Asn
        130

<210> SEQ ID NO 174
<211> LENGTH: 132
<212> TYPE: PRT
<213> ORGANISM: Macaca fascicularis

<400> SEQUENCE: 174

Met Ala Leu Leu Leu Thr Thr Val Ile Ala Leu Thr Cys Leu Gly Gly
  1               5                  10                  15

Phe Ala Ser Pro Ser Pro Val Pro Pro Ser Thr Ala Leu Lys Glu Leu
                 20                  25                  30

Ile Glu Glu Leu Val Asn Ile Thr Gln Asn Gln Lys Ala Pro Leu Cys
             35                  40                  45

Asn Gly Ser Met Val Trp Ser Ile Asn Leu Thr Ala Gly Val Tyr Cys
 50                  55                  60

Ala Ala Leu Glu Ser Leu Ile Asn Val Ser Gly Cys Ser Ala Ile Glu
 65                  70                  75                  80

Lys Thr Gln Arg Met Leu Asn Gly Phe Cys Pro His Lys Val Ser Ala
                 85                  90                  95

Gly Gln Phe Ser Ser Leu Arg Val Arg Asp Thr Lys Ile Glu Val Ala
                100                 105                 110

Gln Phe Val Lys Asp Leu Leu Val His Leu Lys Lys Leu Phe Arg Glu
            115                 120                 125

Gly Gln Phe Asn
        130

<210> SEQ ID NO 175
<211> LENGTH: 131
<212> TYPE: PRT
<213> ORGANISM: Mus sp.

<400> SEQUENCE: 175

Met Ala Leu Trp Val Thr Ala Val Leu Ala Leu Ala Cys Leu Gly Gly
  1               5                  10                  15

Leu Ala Ala Pro Gly Pro Val Pro Arg Ser Val Ser Leu Pro Leu Thr
                 20                  25                  30

Leu Lys Glu Leu Ile Glu Glu Leu Ser Asn Ile Thr Gln Asp Gln Thr
             35                  40                  45

Pro Leu Cys Asn Gly Ser Met Val Trp Ser Val Asp Leu Ala Ala Gly
 50                  55                  60

Gly Phe Cys Val Ala Leu Asp Ser Leu Thr Asn Ile Ser Asn Cys Asn
 65                  70                  75                  80

Ala Ile Tyr Arg Thr Gln Arg Ile Leu His Gly Leu Cys Asn Arg Lys
                 85                  90                  95

Ala Pro Thr Thr Val Ser Ser Leu Pro Asp Thr Lys Ile Glu Val Ala
                100                 105                 110
```

```
His Phe Ile Thr Lys Leu Leu Ser Tyr Thr Lys Gln Leu Phe Arg His
        115                 120                 125

Gly Pro Phe
    130

<210> SEQ ID NO 176
<211> LENGTH: 5
<212> TYPE: PRT
<213> ORGANISM: Artificial sequence
<220> FEATURE:
<223> OTHER INFORMATION: HCDR1 formula
<220> FEATURE:
<221> NAME/KEY: MISC_FEATURE
<222> LOCATION: (1)..(1)
<223> OTHER INFORMATION: Xaa = Asn, Gln, Asp, Leu, Gly or Glu
<220> FEATURE:
<221> NAME/KEY: MISC_FEATURE
<222> LOCATION: (2)..(2)
<223> OTHER INFORMATION: Xaa = Tyr or Thr
<220> FEATURE:
<221> NAME/KEY: MISC_FEATURE
<222> LOCATION: (4)..(4)
<223> OTHER INFORMATION: Xaa = Val, Ile, Phe or Leu

<400> SEQUENCE: 176

Xaa Xaa Gly Xaa Ser
1               5

<210> SEQ ID NO 177
<211> LENGTH: 17
<212> TYPE: PRT
<213> ORGANISM: Artificial sequence
<220> FEATURE:
<223> OTHER INFORMATION: HCDR2 formula
<220> FEATURE:
<221> NAME/KEY: MISC_FEATURE
<222> LOCATION: (3)..(3)
<223> OTHER INFORMATION: Xaa = Ser, Asp, Asn, Ala, Arg, Gly or Glu
<220> FEATURE:
<221> NAME/KEY: MISC_FEATURE
<222> LOCATION: (4)..(4)
<223> OTHER INFORMATION: Xaa = Ala, Asp, Gly, Thr, Pro, Asn or Tyr
<220> FEATURE:
<221> NAME/KEY: MISC_FEATURE
<222> LOCATION: (5)..(5)
<223> OTHER INFORMATION: Xaa = Asn, Asp, Leu, Ala, Pro, Thr, Ser, Ile or
      Arg
<220> FEATURE:
<221> NAME/KEY: MISC_FEATURE
<222> LOCATION: (6)..(6)
<223> OTHER INFORMATION: Xaa = Asn, Ser, Thr, Asp, Gly, Lys or Ile
<220> FEATURE:
<221> NAME/KEY: MISC_FEATURE
<222> LOCATION: (8)..(8)
<223> OTHER INFORMATION: Xaa = Asp, Thr, Glu, Gln, Leu, Tyr, Asn, Val,
      Ala, Met or Gly
<220> FEATURE:
<221> NAME/KEY: MISC_FEATURE
<222> LOCATION: (10)..(10)
<223> OTHER INFORMATION: Xaa = Asn, Ile, Leu, Gln, Ser, Met, His, Asp or
      Lys
<220> FEATURE:
<221> NAME/KEY: MISC_FEATURE
<222> LOCATION: (12)..(12)
<223> OTHER INFORMATION: Xaa = Gly or Arg
<220> FEATURE:
<221> NAME/KEY: MISC_FEATURE
<222> LOCATION: (13)..(13)
<223> OTHER INFORMATION: Xaa = Gln or Arg
<220> FEATURE:
<221> NAME/KEY: MISC_FEATURE
<222> LOCATION: (14)..(14)
<223> OTHER INFORMATION: Xaa = Glu, Lys or Gly
<220> FEATURE:
```

```
<221> NAME/KEY: MISC_FEATURE
<222> LOCATION: (16)..(16)
<223> OTHER INFORMATION: Xaa = Gln or Arg
<220> FEATURE:
<221> NAME/KEY: MISC_FEATURE
<222> LOCATION: (17)..(17)
<223> OTHER INFORMATION: Xaa = Gly or Lys

<400> SEQUENCE: 177

Trp Ile Xaa Xaa Xaa Xaa Gly Xaa Thr Xaa Tyr Xaa Xaa Xaa Phe Xaa
1               5                   10                  15

Xaa

<210> SEQ ID NO 178
<211> LENGTH: 13
<212> TYPE: PRT
<213> ORGANISM: Artificial sequence
<220> FEATURE:
<223> OTHER INFORMATION: HCDR3 formula
<220> FEATURE:
<221> NAME/KEY: MISC_FEATURE
<222> LOCATION: (2)..(2)
<223> OTHER INFORMATION: Xaa = Ser, Arg or Asp
<220> FEATURE:
<221> NAME/KEY: MISC_FEATURE
<222> LOCATION: (3)..(3)
<223> OTHER INFORMATION: Xaa = Ser, Asn, Asp, Thr or Pro
<220> FEATURE:
<221> NAME/KEY: MISC_FEATURE
<222> LOCATION: (4)..(4)
<223> OTHER INFORMATION: Xaa = Ser or Arg
<220> FEATURE:
<221> NAME/KEY: MISC_FEATURE
<222> LOCATION: (5)..(5)
<223> OTHER INFORMATION: Xaa = Ser, Asn, Ala, Ile, Arg, Pro or Lys
<220> FEATURE:
<221> NAME/KEY: MISC_FEATURE
<222> LOCATION: (10)..(10)
<223> OTHER INFORMATION: Xaa = Phe or Tyr
<220> FEATURE:
<221> NAME/KEY: MISC_FEATURE
<222> LOCATION: (12)..(12)
<223> OTHER INFORMATION: Xaa = Asp or Tyr

<400> SEQUENCE: 178

Asp Xaa Xaa Xaa Xaa Trp Ala Arg Trp Xaa Phe Xaa Leu
1               5                   10

<210> SEQ ID NO 179
<211> LENGTH: 11
<212> TYPE: PRT
<213> ORGANISM: Artificial sequence
<220> FEATURE:
<223> OTHER INFORMATION: LCDR1 formula
<220> FEATURE:
<221> NAME/KEY: MISC_FEATURE
<222> LOCATION: (3)..(3)
<223> OTHER INFORMATION: Xaa = Asn, Asp or Ser
<220> FEATURE:
<221> NAME/KEY: MISC_FEATURE
<222> LOCATION: (4)..(4)
<223> OTHER INFORMATION: Xaa = Asn, Ile, Leu, Met, Cys, Val, Lys, Tyr,
      Phe, Arg, Thr, Ser, Ala, His or Gly
<220> FEATURE:
<221> NAME/KEY: MISC_FEATURE
<222> LOCATION: (5)..(5)
<223> OTHER INFORMATION: Xaa = Ile or Val
<220> FEATURE:
<221> NAME/KEY: MISC_FEATURE
<222> LOCATION: (7)..(7)
<223> OTHER INFORMATION: Xaa = Ser or Gly
<220> FEATURE:
<221> NAME/KEY: MISC_FEATURE
<222> LOCATION: (8)..(8)
```

```
<223> OTHER INFORMATION: Xaa = Lys or Arg

<400> SEQUENCE: 179

Gly Gly Xaa Xaa Xaa Gly Xaa Xaa Leu Val His
1               5                   10

<210> SEQ ID NO 180
<211> LENGTH: 7
<212> TYPE: PRT
<213> ORGANISM: Artificial sequence
<220> FEATURE:
<223> OTHER INFORMATION: LCDR2 formula
<220> FEATURE:
<221> NAME/KEY: MISC_FEATURE
<222> LOCATION: (7)..(7)
<223> OTHER INFORMATION: Xaa = Ser or Thr

<400> SEQUENCE: 180

Asp Asp Gly Asp Arg Pro Xaa
1               5

<210> SEQ ID NO 181
<211> LENGTH: 11
<212> TYPE: PRT
<213> ORGANISM: Artificial sequence
<220> FEATURE:
<223> OTHER INFORMATION: LCDR3 formula
<220> FEATURE:
<221> NAME/KEY: MISC_FEATURE
<222> LOCATION: (8)..(8)
<223> OTHER INFORMATION: Xaa = Asp or Asn
<220> FEATURE:
<221> NAME/KEY: MISC_FEATURE
<222> LOCATION: (11)..(11)
<223> OTHER INFORMATION: Xaa = Val or Ile

<400> SEQUENCE: 181

Gln Val Trp Asp Thr Gly Ser Xaa Pro Val Xaa
1               5                   10

<210> SEQ ID NO 182
<211> LENGTH: 5
<212> TYPE: PRT
<213> ORGANISM: Homo sapiens

<400> SEQUENCE: 182

Leu Thr Gly Val Ser
1               5

<210> SEQ ID NO 183
<211> LENGTH: 5
<212> TYPE: PRT
<213> ORGANISM: Homo sapiens

<400> SEQUENCE: 183

Gly Thr Gly Val Ser
1               5

<210> SEQ ID NO 184
<211> LENGTH: 5
<212> TYPE: PRT
<213> ORGANISM: Homo sapiens

<400> SEQUENCE: 184

Glu Thr Gly Ile Ser
1               5
```

<210> SEQ ID NO 185
<211> LENGTH: 5
<212> TYPE: PRT
<213> ORGANISM: Homo sapiens

<400> SEQUENCE: 185

Asp Thr Gly Ile Ser
1               5

<210> SEQ ID NO 186
<211> LENGTH: 5
<212> TYPE: PRT
<213> ORGANISM: Homo sapiens

<400> SEQUENCE: 186

Gly Thr Gly Ile Ser
1               5

<210> SEQ ID NO 187
<211> LENGTH: 5
<212> TYPE: PRT
<213> ORGANISM: Homo sapiens

<400> SEQUENCE: 187

Asn Tyr Gly Phe Ser
1               5

<210> SEQ ID NO 188
<211> LENGTH: 17
<212> TYPE: PRT
<213> ORGANISM: Homo sapiens

<400> SEQUENCE: 188

Trp Ile Arg Pro Thr Asp Gly Leu Thr Met Tyr Gly Gln Glu Phe Gln
1               5                   10                  15

Gly

<210> SEQ ID NO 189
<211> LENGTH: 17
<212> TYPE: PRT
<213> ORGANISM: Homo sapiens

<400> SEQUENCE: 189

Trp Ile Asp Asp Arg Thr Gly Thr Gln Tyr Gly Gln Glu Phe Gln
1               5                   10                  15

Gly

<210> SEQ ID NO 190
<211> LENGTH: 17
<212> TYPE: PRT
<213> ORGANISM: Homo sapiens

<400> SEQUENCE: 190

Trp Ile Arg Ala Ser Asp Gly Gln Thr Ile Tyr Gly Gln Glu Phe Gln
1               5                   10                  15

Gly

<210> SEQ ID NO 191
<211> LENGTH: 17
<212> TYPE: PRT
<213> ORGANISM: Homo sapiens

<400> SEQUENCE: 191

Trp Ile Ser Gly Ile Asp Gly Val Thr Leu Tyr Gly Gln Glu Phe Gln
1               5                   10                  15

Gly

<210> SEQ ID NO 192
<211> LENGTH: 17
<212> TYPE: PRT
<213> ORGANISM: Homo sapiens

<400> SEQUENCE: 192

Trp Ile Arg Ala Ala Asp Gly Glu Thr His Tyr Gly Gln Glu Phe Gln
1               5                   10                  15

Gly

<210> SEQ ID NO 193
<211> LENGTH: 17
<212> TYPE: PRT
<213> ORGANISM: Homo sapiens

<400> SEQUENCE: 193

Trp Ile Gly Asn Asn Asn Gly Asp Thr Leu Tyr Gly Gln Glu Phe Gln
1               5                   10                  15

Gly

<210> SEQ ID NO 194
<211> LENGTH: 17
<212> TYPE: PRT
<213> ORGANISM: Homo sapiens

<400> SEQUENCE: 194

Trp Ile Gly Pro Ser Lys Gly Glu Thr Ser Tyr Gly Gln Glu Phe Gln
1               5                   10                  15

Gly

<210> SEQ ID NO 195
<211> LENGTH: 17
<212> TYPE: PRT
<213> ORGANISM: Homo sapiens

<400> SEQUENCE: 195

Trp Ile Arg Pro Arg Asp Gly Thr Thr His Tyr Gly Gln Glu Phe Gln
1               5                   10                  15

Gly

<210> SEQ ID NO 196
<211> LENGTH: 17
<212> TYPE: PRT
<213> ORGANISM: Homo sapiens

<400> SEQUENCE: 196

Trp Ile Ser Gly Arg Ser Gly Ala Thr Leu Tyr Gly Gln Glu Phe Gln
1               5                   10                  15

Gly

<210> SEQ ID NO 197
<211> LENGTH: 17
<212> TYPE: PRT
<213> ORGANISM: Homo sapiens

<400> SEQUENCE: 197

Trp Ile Glu Gly Ser Thr Gly Asn Thr Ile Tyr Gly Gln Glu Phe Gln

-continued

```
                1               5                  10                  15

Gly

<210> SEQ ID NO 198
<211> LENGTH: 17
<212> TYPE: PRT
<213> ORGANISM: Homo sapiens

<400> SEQUENCE: 198

Trp Ile Gly Pro Ile Asn Gly Met Thr His Tyr Gly Gln Glu Phe Gln
1               5                   10                  15

Gly

<210> SEQ ID NO 199
<211> LENGTH: 17
<212> TYPE: PRT
<213> ORGANISM: Homo sapiens

<400> SEQUENCE: 199

Trp Ile Ser Ala Asn Asn Gly Asp Thr Asn Tyr Gly Gln Lys Phe Gln
1               5                   10                  15

Gly

<210> SEQ ID NO 200
<211> LENGTH: 17
<212> TYPE: PRT
<213> ORGANISM: Homo sapiens

<400> SEQUENCE: 200

Trp Ile Ser Ala Asn Asn Gly Asp Thr Asp Tyr Gly Gln Glu Phe Gln
1               5                   10                  15

Gly

<210> SEQ ID NO 201
<211> LENGTH: 17
<212> TYPE: PRT
<213> ORGANISM: Homo sapiens

<400> SEQUENCE: 201

Trp Ile Ser Ala Asn Asn Gly Gly Thr Asn Tyr Gly Gln Glu Phe Gln
1               5                   10                  15

Gly

<210> SEQ ID NO 202
<211> LENGTH: 17
<212> TYPE: PRT
<213> ORGANISM: Homo sapiens

<400> SEQUENCE: 202

Trp Ile Ser Ala Asn Asn Gly Asp Thr Asn Tyr Arg Gln Glu Phe Gln
1               5                   10                  15

Gly

<210> SEQ ID NO 203
<211> LENGTH: 17
<212> TYPE: PRT
<213> ORGANISM: Homo sapiens

<400> SEQUENCE: 203

Trp Ile Gly Ala Asn Asn Gly Asp Thr Asn Tyr Gly Gln Glu Phe Gln
1               5                   10                  15
```

Gly

<210> SEQ ID NO 204
<211> LENGTH: 17
<212> TYPE: PRT
<213> ORGANISM: Homo sapiens

<400> SEQUENCE: 204

Trp Ile Ser Ala Asn Asn Gly Asp Thr Asn Tyr Gly Gln Glu Phe Arg
1               5                   10                  15

Gly

<210> SEQ ID NO 205
<211> LENGTH: 17
<212> TYPE: PRT
<213> ORGANISM: Homo sapiens

<400> SEQUENCE: 205

Trp Ile Ser Ala Asn Asn Gly Asp Thr Ile Tyr Gly Gln Glu Phe Gln
1               5                   10                  15

Gly

<210> SEQ ID NO 206
<211> LENGTH: 17
<212> TYPE: PRT
<213> ORGANISM: Homo sapiens

<400> SEQUENCE: 206

Trp Ile Ser Thr Asn Asn Gly Asp Thr Asn Tyr Gly Gln Glu Phe Gln
1               5                   10                  15

Gly

<210> SEQ ID NO 207
<211> LENGTH: 17
<212> TYPE: PRT
<213> ORGANISM: Homo sapiens

<400> SEQUENCE: 207

Trp Ile Ser Ala Asn Asn Gly Asp Thr Ile Tyr Arg Gln Glu Phe Gln
1               5                   10                  15

Gly

<210> SEQ ID NO 208
<211> LENGTH: 17
<212> TYPE: PRT
<213> ORGANISM: Homo sapiens

<400> SEQUENCE: 208

Trp Ile Ser Ala Asn Asn Gly Asp Thr Ser Tyr Gly Gln Glu Phe Gln
1               5                   10                  15

Gly

<210> SEQ ID NO 209
<211> LENGTH: 17
<212> TYPE: PRT
<213> ORGANISM: Homo sapiens

<400> SEQUENCE: 209

Trp Ile Ser Ala Asn Asn Gly Asp Thr Lys Tyr Gly Gln Glu Phe Gln
1               5                   10                  15

Gly

```
<210> SEQ ID NO 210
<211> LENGTH: 17
<212> TYPE: PRT
<213> ORGANISM: Homo sapiens

<400> SEQUENCE: 210

Trp Ile Gly Ala Asn Asn Gly Asp Thr Asp Tyr Gly Gln Glu Phe Gln
1               5                   10                  15

Gly

<210> SEQ ID NO 211
<211> LENGTH: 17
<212> TYPE: PRT
<213> ORGANISM: Homo sapiens

<400> SEQUENCE: 211

Trp Ile Ser Ala Asn Ile Gly Asp Thr Asn Tyr Gly Gln Glu Phe Gln
1               5                   10                  15

Gly

<210> SEQ ID NO 212
<211> LENGTH: 17
<212> TYPE: PRT
<213> ORGANISM: Homo sapiens

<400> SEQUENCE: 212

Trp Ile Ser Ala Asn Asn Gly Asp Thr Asn Tyr Gly Gln Gly Phe Gln
1               5                   10                  15

Gly

<210> SEQ ID NO 213
<211> LENGTH: 17
<212> TYPE: PRT
<213> ORGANISM: Homo sapiens

<400> SEQUENCE: 213

Trp Ile Ser Thr Asn Asn Gly Asp Thr Asn Tyr Gly Arg Glu Phe Gln
1               5                   10                  15

Gly

<210> SEQ ID NO 214
<211> LENGTH: 17
<212> TYPE: PRT
<213> ORGANISM: Homo sapiens

<400> SEQUENCE: 214

Trp Ile Ser Ala Asn Asn Gly Asp Thr Asn Tyr Gly Gln Glu Phe Gln
1               5                   10                  15

Lys

<210> SEQ ID NO 215
<211> LENGTH: 13
<212> TYPE: PRT
<213> ORGANISM: Homo sapiens

<400> SEQUENCE: 215

Asp Ser Asp Ser Ser Trp Ala Arg Trp Phe Phe Asp Leu
1               5                   10
```

```
<210> SEQ ID NO 216
<211> LENGTH: 13
<212> TYPE: PRT
<213> ORGANISM: Homo sapiens

<400> SEQUENCE: 216

Asp Ser Thr Ser Ala Trp Ala Arg Trp Phe Phe Asp Leu
1               5                   10

<210> SEQ ID NO 217
<211> LENGTH: 13
<212> TYPE: PRT
<213> ORGANISM: Homo sapiens

<400> SEQUENCE: 217

Asp Ser Asn Ser Ala Trp Ala Arg Trp Phe Phe Asp Leu
1               5                   10

<210> SEQ ID NO 218
<211> LENGTH: 13
<212> TYPE: PRT
<213> ORGANISM: Homo sapiens

<400> SEQUENCE: 218

Asp Ser Ser Ser Ile Trp Ala Arg Trp Phe Phe Asp Leu
1               5                   10

<210> SEQ ID NO 219
<211> LENGTH: 13
<212> TYPE: PRT
<213> ORGANISM: Homo sapiens

<400> SEQUENCE: 219

Asp Ser Thr Ser Arg Trp Ala Arg Trp Phe Phe Asp Leu
1               5                   10

<210> SEQ ID NO 220
<211> LENGTH: 13
<212> TYPE: PRT
<213> ORGANISM: Homo sapiens

<400> SEQUENCE: 220

Asp Asp Pro Arg Pro Trp Ala Arg Trp Phe Phe Asp Leu
1               5                   10

<210> SEQ ID NO 221
<211> LENGTH: 13
<212> TYPE: PRT
<213> ORGANISM: Homo sapiens

<400> SEQUENCE: 221

Asp Ser Ser Ser Lys Trp Ala Arg Trp Phe Phe Asp Leu
1               5                   10

<210> SEQ ID NO 222
<211> LENGTH: 13
<212> TYPE: PRT
<213> ORGANISM: Homo sapiens

<400> SEQUENCE: 222

Asp Ser Asn Ser Asn Trp Ala Arg Trp Phe Phe Tyr Leu
1               5                   10

<210> SEQ ID NO 223
<211> LENGTH: 13
```

```
<212> TYPE: PRT
<213> ORGANISM: Homo sapiens

<400> SEQUENCE: 223

Asp Ser Asn Ser Ser Trp Ala Arg Trp Phe Phe Asp Leu
1               5                   10

<210> SEQ ID NO 224
<211> LENGTH: 13
<212> TYPE: PRT
<213> ORGANISM: Homo sapiens

<400> SEQUENCE: 224

Asp Arg Asp Ser Ser Trp Ala Arg Trp Phe Phe Asp Leu
1               5                   10

<210> SEQ ID NO 225
<211> LENGTH: 11
<212> TYPE: PRT
<213> ORGANISM: Homo sapiens

<400> SEQUENCE: 225

Gly Gly Asn Leu Ile Gly Ser Lys Leu Val His
1               5                   10

<210> SEQ ID NO 226
<211> LENGTH: 11
<212> TYPE: PRT
<213> ORGANISM: Homo sapiens

<400> SEQUENCE: 226

Gly Gly Asn Met Ile Gly Ser Lys Leu Val His
1               5                   10

<210> SEQ ID NO 227
<211> LENGTH: 11
<212> TYPE: PRT
<213> ORGANISM: Homo sapiens

<400> SEQUENCE: 227

Gly Gly Asn Cys Ile Gly Ser Lys Leu Val His
1               5                   10

<210> SEQ ID NO 228
<211> LENGTH: 11
<212> TYPE: PRT
<213> ORGANISM: Homo sapiens

<400> SEQUENCE: 228

Gly Gly Asn Val Ile Gly Ser Lys Leu Val His
1               5                   10

<210> SEQ ID NO 229
<211> LENGTH: 11
<212> TYPE: PRT
<213> ORGANISM: Homo sapiens

<400> SEQUENCE: 229

Gly Gly Asn Lys Ile Gly Ser Lys Leu Val His
1               5                   10

<210> SEQ ID NO 230
<211> LENGTH: 11
<212> TYPE: PRT
<213> ORGANISM: Homo sapiens
```

<400> SEQUENCE: 230

Gly Gly Asn Tyr Ile Gly Ser Lys Leu Val His
1               5                   10

<210> SEQ ID NO 231
<211> LENGTH: 11
<212> TYPE: PRT
<213> ORGANISM: Homo sapiens

<400> SEQUENCE: 231

Gly Gly Asn Phe Ile Gly Ser Lys Leu Val His
1               5                   10

<210> SEQ ID NO 232
<211> LENGTH: 11
<212> TYPE: PRT
<213> ORGANISM: Homo sapiens

<400> SEQUENCE: 232

Gly Gly Asn Arg Ile Gly Ser Lys Leu Val His
1               5                   10

<210> SEQ ID NO 233
<211> LENGTH: 11
<212> TYPE: PRT
<213> ORGANISM: Homo sapiens

<400> SEQUENCE: 233

Gly Gly Asn Thr Ile Gly Ser Lys Leu Val His
1               5                   10

<210> SEQ ID NO 234
<211> LENGTH: 11
<212> TYPE: PRT
<213> ORGANISM: Homo sapiens

<400> SEQUENCE: 234

Gly Gly Asn Asn Ile Gly Gly Lys Leu Val His
1               5                   10

<210> SEQ ID NO 235
<211> LENGTH: 11
<212> TYPE: PRT
<213> ORGANISM: Homo sapiens

<400> SEQUENCE: 235

Gly Gly Asn Ser Ile Gly Ser Arg Leu Val His
1               5                   10

<210> SEQ ID NO 236
<211> LENGTH: 11
<212> TYPE: PRT
<213> ORGANISM: Homo sapiens

<400> SEQUENCE: 236

Gly Gly Asp Asn Ile Gly Gly Lys Leu Val His
1               5                   10

<210> SEQ ID NO 237
<211> LENGTH: 11
<212> TYPE: PRT
<213> ORGANISM: Homo sapiens

<400> SEQUENCE: 237

Gly Gly Asn Ser Ile Gly Gly Lys Leu Val His
1               5                   10

<210> SEQ ID NO 238
<211> LENGTH: 11
<212> TYPE: PRT
<213> ORGANISM: Homo sapiens

<400> SEQUENCE: 238

Gly Gly Asn Ala Ile Gly Ser Lys Leu Val His
1               5                   10

<210> SEQ ID NO 239
<211> LENGTH: 11
<212> TYPE: PRT
<213> ORGANISM: Homo sapiens

<400> SEQUENCE: 239

Gly Gly Asn Ser Ile Gly Ser Lys Leu Val His
1               5                   10

<210> SEQ ID NO 240
<211> LENGTH: 11
<212> TYPE: PRT
<213> ORGANISM: Homo sapiens

<400> SEQUENCE: 240

Gly Gly Asn His Ile Gly Ser Lys Leu Val His
1               5                   10

<210> SEQ ID NO 241
<211> LENGTH: 11
<212> TYPE: PRT
<213> ORGANISM: Homo sapiens

<400> SEQUENCE: 241

Gly Gly Asn Gly Ile Gly Ser Lys Leu Val His
1               5                   10

<210> SEQ ID NO 242
<211> LENGTH: 11
<212> TYPE: PRT
<213> ORGANISM: Homo sapiens

<400> SEQUENCE: 242

Gly Gly Ser Asn Ile Gly Gly Lys Leu Val His
1               5                   10

<210> SEQ ID NO 243
<211> LENGTH: 11
<212> TYPE: PRT
<213> ORGANISM: Homo sapiens

<400> SEQUENCE: 243

Gly Gly Asn Asn Val Gly Lys Leu Val His
1               5                   10

<210> SEQ ID NO 244
<211> LENGTH: 11
<212> TYPE: PRT
<213> ORGANISM: Homo sapiens

<400> SEQUENCE: 244

Gly Gly Asn Asn Ile Gly Ser Arg Leu Val His

```
1               5                  10
```

<210> SEQ ID NO 245
<211> LENGTH: 7
<212> TYPE: PRT
<213> ORGANISM: Homo sapiens

<400> SEQUENCE: 245

Asp Asp Gly Asp Arg Pro Thr
1               5

<210> SEQ ID NO 246
<211> LENGTH: 11
<212> TYPE: PRT
<213> ORGANISM: Homo sapiens

<400> SEQUENCE: 246

Gln Val Trp Asp Thr Gly Ser Asn Pro Val Val
1               5                  10

<210> SEQ ID NO 247
<211> LENGTH: 11
<212> TYPE: PRT
<213> ORGANISM: Homo sapiens

<400> SEQUENCE: 247

Gln Val Trp Asp Thr Gly Ser Asp Pro Val Ile
1               5                  10

<210> SEQ ID NO 248
<211> LENGTH: 132
<212> TYPE: PRT
<213> ORGANISM: Artificial sequence
<220> FEATURE:
<223> OTHER INFORMATION: Consensus between human IL-3 and Cynomolgus
      IL-3
<220> FEATURE:
<221> NAME/KEY: MISC_FEATURE
<222> LOCATION: (21, 30, 62, 87, 103, 120, 130)
<223> OTHER INFORMATION: Xaa = Any amino acid

<400> SEQUENCE: 248

Met Ala Leu Leu Leu Thr Thr Val Ile Ala Leu Thr Cys Leu Gly Gly
1               5                  10                  15

Phe Ala Ser Pro Xaa Pro Val Pro Pro Ser Thr Ala Leu Xaa Glu Leu
            20                  25                  30

Ile Glu Glu Leu Val Asn Ile Thr Gln Asn Gln Lys Ala Pro Leu Cys
        35                  40                  45

Asn Gly Ser Met Val Trp Ser Ile Asn Leu Thr Ala Gly Xaa Tyr Cys
    50                  55                  60

Ala Ala Leu Glu Ser Leu Ile Asn Val Ser Gly Cys Ser Ala Ile Glu
65                  70                  75                  80

Lys Thr Gln Arg Met Leu Xaa Gly Phe Cys Pro His Lys Val Ser Ala
                85                  90                  95

Gly Gln Phe Ser Ser Leu Xaa Val Arg Asp Thr Lys Ile Glu Val Ala
            100                 105                 110

Gln Phe Val Lys Asp Leu Leu Xaa His Leu Lys Lys Leu Phe Arg Glu
        115                 120                 125

Gly Xaa Phe Asn
    130

<210> SEQ ID NO 249

```
<211> LENGTH: 136
<212> TYPE: PRT
<213> ORGANISM: Artificial sequence
<220> FEATURE:
<223> OTHER INFORMATION: Consensus between human IL-3 and murine IL-3
<220> FEATURE:
<221> NAME/KEY: MISC_FEATURE
<222> LOCATION: (4, 5, 7, 9, 12, 17, 19, 25, 27..32, 34, 41, 46, 48)
<223> OTHER INFORMATION: Xaa = Any amino acid
<220> FEATURE:
<221> NAME/KEY: MISC_FEATURE
<222> LOCATION: (49, 60, 61, 63, 66, 67, 69, 72, 75, 77, 79, 81, 84)
<223> OTHER INFORMATION: Xaa = Any amino acid
<220> FEATURE:
<221> NAME/KEY: MISC_FEATURE
<222> LOCATION: (85, 89, 91, 93, 95, 96, 98..103, 107..109, 117)
<223> OTHER INFORMATION: Xaa = Any amino acid
<220> FEATURE:
<221> NAME/KEY: MISC_FEATURE
<222> LOCATION: (119..121, 124..126, 128, 132, 134, 136)
<223> OTHER INFORMATION: Xaa = Any amino acid

<400> SEQUENCE: 249

Met Ala Leu Xaa Xaa Thr Xaa Val Xaa Ala Leu Xaa Cys Leu Gly Gly
1               5                   10                  15

Xaa Ala Xaa Pro Gly Pro Val Pro Xaa Ser Xaa Xaa Xaa Xaa Xaa Xaa
            20                  25                  30

Leu Xaa Glu Leu Ile Glu Glu Leu Xaa Asn Ile Thr Gln Xaa Gln Xaa
        35                  40                  45

Xaa Pro Leu Cys Asn Gly Ser Met Val Trp Ser Xaa Xaa Leu Xaa Ala
    50                  55                  60

Gly Xaa Xaa Cys Xaa Ala Leu Xaa Ser Leu Xaa Asn Xaa Ser Xaa Cys
65                  70                  75                  80

Xaa Ala Ile Xaa Xaa Thr Gln Arg Xaa Leu Xaa Gly Xaa Cys Xaa Xaa
                85                  90                  95

Lys Xaa Xaa Xaa Xaa Xaa Ser Ser Leu Xaa Xaa Xaa Asp Thr Lys
                100                 105                 110

Ile Glu Val Ala Xaa Phe Xaa Xaa Xaa Leu Leu Xaa Xaa Xaa Lys Xaa
            115                 120                 125

Leu Phe Arg Xaa Gly Xaa Phe Xaa
            130             135
```

METHODS OF TREATMENT USING HUMAN ANTIBODY MOLECULES FOR IL-13

REFERENCE TO RELATED APPLICATIONS

This application is a divisional of U.S. application Ser. No. 10/564,647 (now U.S. Pat. No. 7,829,090, issued Nov. 9, 2010); said application Ser. No. 10/564,647 is a National Stage application of PCT/GB2004/003059, filed on Jul. 15, 2004 and published in English as WO 2005/007699; said application Ser. Nos. PCT/GB2004/003059 claims benefit under 35 U.S.C. §119(e) and §365(b) of U.S. Provisional Application No. 60/573,791, filed on May 24, 2004, 60/558,216, filed on Mar. 31, 2004, 60/487,512, filed on Jul. 15, 2003 and GB Application No. 0407315.1, filed on Mar. 31, 2004. Each of the above-listed applications is incorporated by reference herein in its entirety for all purposes.

The present invention relates to specific binding members, in particular human anti-IL-13 antibody molecules and especially those which neutralise IL-13 activity. It further relates to methods for using anti-IL-13 antibody molecules in diagnosis or treatment of IL-13 related disorders, including asthma, atopic dermatitis, allergic rhinitis, fibrosis, inflammatory bowel disease and Hodgkin's lymphoma.

Preferred embodiments of the present invention employ the antibody VH and/or VL domain of the antibody molecule herein termed BAK502G9 and other antibody molecules of the BAK502G9 lineage and of the BAK278D6 lineage, as herein defined. Further preferred embodiments employ complementarity determining regions (CDRs) of the BAK278D6 lineage, and preferably BAK502G9, especially VH CDR3 in other antibody framework regions. Further aspects of the present invention provide for compositions containing specific binding members of the invention, and their use in methods of inhibiting or neutralising IL-13, including methods of treatment of the human or animal body by therapy.

The present invention provides antibody molecules of particular value in binding and neutralising IL-13, and thus of use in any of a variety of therapeutic treatments, as indicated by the experimentation contained herein and further by the supporting technical literature.

Interleukin (IL)-13 is a 114 amino acid cytokine with an unmodified molecular mass of approximately 12 kDa [1,2]. IL-13 is most closely related to IL-4 with which it shares 30% sequence similarity at the amino acid level. The human IL-13 gene is located on chromosome 5q31 adjacent to the IL-4 gene [1][2]. This region of chromosome 5q contains gene sequences for other Th2 lymphocyte derived cytokines including GM-CSF and IL-5, whose levels together with IL-4 have been shown to correlate with disease severity in asthmatics and rodent models of allergic inflammation [3][4][5][6][7][8].

Although initially identified as a Th2 CD4+ lymphocyte derived cytokine, IL-13 is also produced by Th1 CD4+ T-cells, CD8+ T lymphocytes NK cells, and non-T-cell populations such as mast cells, basophils, eosinophils, macrophages, monocytes and airway smooth muscle cells.

IL-13 is reported to mediate its effects through a receptor system that includes the IL-4 receptor a chain (IL-4Rα), which itself can bind IL-4 but not IL-13, and at least two other cell surface proteins, IL-13Rα1 and IL-13Rα2 [9][10]. IL-13Rα1 can bind IL-13 with low affinity, subsequently recruiting IL-4Rα to form a high affinity functional receptor that signals [11][12]. The Genbank database lists the amino acid sequence and the nucleic acid sequence of IL-13Rα1 as NP_001551 and Y10659 respectively. Studies in STAT6 (signal transducer and activator of transcription 6)-deficient mice have revealed that IL-13, in a manner similar to IL-4, signals by utilising the JAK-STAT6 pathway [13][14]. IL-13Rα2 shares 37% sequence identity with IL-13Rα1 at the amino acid level and binds IL-13 with high affinity [15][16]. However, IL-13Rα2 has a shorter cytoplasmic tail that lacks known signalling motifs. Cells expressing IL-13Rα2 are not responsive to IL-13 even in the presence of IL-4Rα [17]. It is postulated, therefore, that IL-13Rα2 acts as a decoy receptor regulating IL-13 but not IL-4 function. This is supported by studies in IL-13Rα2 deficient mice whose phenotype was consistent with increased responsiveness to IL-13 [18][19]. The Genbank database lists the amino acid sequence and the nucleic acid sequence of IL-13Rα2 as NP_000631 and Y08768 respectively.

The signalling IL-13Rα1/IL-4Rα receptor complex is expressed on human B-cells, mast cells, monocyte/macrophages, dendritic cells, eosinophils, basophils, fibroblasts, endothelial cells, airway epithelial cells and airway smooth muscle cells.

Bronchial asthma is a common persistent inflammatory disease of the lung characterised by airways hyper-responsiveness, mucus overproduction, fibrosis and raised serum IgE levels. Airways hyper-responsiveness (AHR) is the exaggerated constriction of the airways to non-specific stimuli such as cold air. Both AHR and mucus overproduction are thought to be responsible for the variable airway obstruction that leads to the shortness of breath characteristic of asthma attacks (exacerbations) and which is responsible for the mortality associated with this disease (around 2000 deaths/year in the United Kingdom).

The incidence of asthma, along with other allergic diseases, has increased significantly in recent years [20][21]. For example, currently, around 10% of the population of the United Kingdom (UK) has been diagnosed as asthmatic.

Current British Thoracic Society (BTS) and Global Initiative for Asthma (GINA) guidelines suggest a stepwise approach to the treatment of asthma [22, 23]. Mild to moderate asthma can usually be controlled by the use of inhaled corticosteroids, in combination with beta-agonists or leukotriene inhibitors. However, due to the documented side effects of corticosteroids, patients tend not to comply with the treatment regime which reduces the effectiveness of treatment [24-26].

There is a clear need for new treatments for subjects with more severe disease, who often gain very limited benefit from either higher doses of inhaled or oral corticosteroids recommended by asthma guidelines. Long term treatment with oral corticosteroids is associated with side effects such as osteoporosis, slowed growth rates in children, diabetes and oral candidiasis [88]. As both beneficial and adverse effects of corticosteroids are mediated via the same receptor, treatment is a balance between safety and efficacy. Hospitalisation of these patients, who represent around 6% of the UK asthma population, as a result of severe exacerbations accounts for the majority of the significant economic burden of asthma on healthcare authorities [89].

It is believed that the pathology of asthma is caused by ongoing Th2 lymphocyte mediated inflammation that results from inappropriate responses of the immune system to harmless antigens. Evidence has been accrued which implicates IL-13, rather than the classical Th2 derived cytokine IL-4, as the key mediator in the pathogenesis of established airway disease.

Administration of recombinant IL-13 to the airways of naïve non-sensitised rodents caused many aspects of the asthma phenotype including airway inflammation, mucus production and AHR [27][28][29][30]. A similar phenotype was observed in a transgenic mouse in which IL-13 was specifically overexpressed in the lung. In this model more chronic exposure to IL-13 also resulted in fibrosis [31].

Further, in rodent models of allergic disease many aspects of the asthma phenotype have been associated with IL-13. Soluble murine IL-13Rα2, a potent IL-13 neutraliser, has been shown to inhibit AHR, mucus hypersecretion and the influx of inflammatory cells which are characteristics of this rodent model [27][28][30]. In complementary studies, mice in which the IL-13 gene had been deleted, failed to develop allergen-induced AHR. AHR could be restored in these IL-13 deficient mice by the administration of recombinant IL-13. In contrast, IL-4 deficient mice developed airway disease in this model [32][33].

Using a longer-term allergen-induced pulmonary inflammation model, Taube at al. demonstrated the efficacy of soluble murine IL-13Rα2 against established airway disease [34]. Soluble murine IL-13Rα2 inhibited AHR, mucus overproduction and to a lesser extent airway inflammation. In contrast, soluble IL-4Rα, which binds and antagonises IL-4, had little effect on AHR or airway inflammation in this system [35]. These findings were supported by Blease et al. who developed a chronic fungal model of asthma in which polyclonal antibodies against IL-13 but not IL-4 were able to reduce mucus overproduction, AHR and subepithelial fibrosis [36].

A number of genetic polymorphisms in the IL-13 gene have also been linked to allergic disease. In particular, a variant of the IL-13 gene in which the arginine residue at amino acid 130 is substituted with glutamine (Q130R) has been associated with bronchial asthma, atopic dermatitis and raised serum IgE levels [37][38][39][40]. This particular IL-13 variant is also referred to as the Q110R variant (arginine residue at amino acid 110 is substituted with glutamine) by some groups who exclude the 20 amino acid signal sequence from the amino acid count. Arima et al, [41] report that this variant is associated with raised levels of IL-13 in serum. The IL-13 variant (Q130R) and antibodies to this variant are discussed in WO 01/62933. An IL-13 promoter polymorphism, which alters IL-13 production, has also been associated with allergic asthma [42].

Raised levels of IL-13 have also been measured in human subjects with asthma, atopic rhinitis (hay fever), allergic dermatitis (eczema) and chronic sinusitis. For example levels of IL-13 were found to be higher in bronchial biopsies, sputum and broncho-alveolar lavage (BAL) cells from asthmatics compared to control subjects [43][44][45][46]. Further, levels of IL-13 in BAL samples increased in asthmatic individuals upon challenge with allergen [47][48]. The IL-13 production capacity of CD4(+) T cells has further been shown to be useful marker of risk for subsequent development of allergic disease in newborns [49].

Li et al [114] have recently reported affects of a neutralising anti-mouse IL-13 antibody in a chronic mouse model of asthma. Chronic asthma-like response (such as AHR, severe airway inflammation, hyper mucus productions) was induced in OVA sensitised mice. Li et al report that administration of an IL-13 antibody at the time of each OVA challenge suppresses AHR, eosinophil infiltration, serum IgE levels, proinflammatory cytokine/chemokine levels and airway remodelling [14].

In summary, these data provide indication that IL-13 rather than IL-4 is a more attractive target for the treatment of human allergic disease.

IL-13 may play a role in the pathogenesis of inflammatory bowel disease. Heller et al.[116] report that neutralisation of IL-13 by administration of soluble IL-13Rα2 ameliorated colonic inflammation in a murine model of human ulcerative colitis [116]. Correspondingly, IL-13 expression was higher in rectal biopsy specimens from ulcerative colitis patients when compared to controls [117].

Aside from asthma, IL-13 has been associated with other fibrotic conditions. Increased levels of IL-13, up to a 1000 fold higher than IL-4, have been measured in the serum of patients with systemic sclerosis [50] and in BAL samples from patients affected with other forms of pulmonary fibrosis [51]. Correspondingly, overexpression of IL-13 but not IL-4 in the mouse lung resulted in pronounced fibrosis [52][53]. The contribution of IL-13 to fibrosis in tissues other than the lung has been extensively studied in a mouse model of parasite-induced liver fibrosis. Specific inhibition of IL-13 by administration of soluble IL-13Rα2 or IL-13 gene disruption, but not ablation of IL-4 production prevented fibrogenesis in the liver [54][55][56].

Chronic Obstructive Pulmonary Disease (COPD) includes patient populations with varying degrees of chronic bronchitis, small airway disease and emphysema and is characterised by progressive irreversible lung function decline that responds poorly to current asthma based therapy [90]. The incidence of COPD has risen dramatically in recent years to become the fourth leading cause of death worldwide (World Health Organisation). COPD therefore represents a large unmet medical need.

The underlying causes of COPD remain poorly understood. The "Dutch hypothesis" proposes that there is a common susceptibility to COPD and asthma and therefore, that similar mechanisms may contribute to the pathogenesis of both disorders [57].

Zheng et al [58] have demonstrated that overexpression of IL-13 in the mouse lung caused emphysema, elevated mucus production and inflammation, reflecting aspects of human COPD. Furthermore, AHR, an IL-13 dependent response in murine models of allergic inflammation, has been shown to be predictive of lung function decline in smokers [59]. A link has also been established between an IL-13 promoter polymorphism and susceptibility to develop COPD [60].

The signs are therefore that IL-13 plays an important role in the pathogenesis of COPD, particularly in patients with asthma-like features including AHR and eosinophilia. mRNA levels of IL-13 have been shown to be higher in autopsy tissue samples from subjects with a history of COPD when compared to lung samples from subjects with no reported lung disease (J. Elias, Oral communication at American Thoracic Society Annual Meeting 2002). In another study, raised levels of IL-13 were demonstrated by immunohistochemistry in peripheral lung sections from COPD patients [91].

Hodgkin's disease is a common type of lymphoma, which accounts for approximately 7,500 cases per year in the United States. Hodgkin's disease is unusual among malignancies in that the neoplastic Reed-Sternberg cell, often derived from B-cells, make up only a small proportion of the clinically detectable mass. Hodgkin's disease-derived cell lines and primary Reed-Sternberg cells frequently express IL-13 and its receptor [61]. As IL-13 promotes cell survival and proliferation in normal B-cells, it was proposed that IL-13 could act as a growth factor for Reed-Sternberg cells. Skinnider et al. have demonstrated that neutralising antibodies against IL-13 can inhibit the growth of Hodgkin's disease-derived cell lines in vitro [62]. This finding suggested that Reed-Sternberg cells might enhance their own survival by an IL-13 autocrine and paracrine cytokine loop. Consistent with this hypothesis, raised levels of IL-13 have been detected in the serum of some Hodgkin's disease patients when compared to normal controls [63]. IL-13 inhibitors may therefore prevent disease progression by inhibiting proliferation of malignant Reed-Sternberg cells.

Many human cancer cells express immunogenic tumour specific antigens. However, although many tumours spontaneously regress, a number evade the immune system (immunosurveillance) by suppressing T-cell mediated immunity. Terabe et al. (64) have demonstrated a role of IL-13 in immunosuppression in a mouse model in which tumours spontaneously regress after initial growth and then recur. Specific inhibition of IL-13, with soluble IL-13Rα2, protected these mice from tumour recurrence. Terabe et al [64] went on to show that IL-13 suppresses the differentiation of tumour specific CD8+ cytotoxic lymphocytes that mediate anti-tumour immune responses.

IL-13 inhibitors may, therefore, be used therapeutically to prevent tumour recurrence or metastasis. Inhibition of IL-13 has been shown to enhance anti-viral vaccines in animal models and may be beneficial in the treatment of HIV and other infectious diseases [65].

It should be noted that generally herein reference to interleukin-13 or IL-13 is, except where context dictates otherwise, reference to human IL-13. This is also referred to in places as "the antigen". The present invention provides antibodies to human IL-13, especially human antibodies, that are cross-reactive with non-human primate IL-13, including cynomolgus and rhesus monkey IL-13. Antibodies in accordance with some embodiments of the present invention recognise a variant of IL-13 in which the arginine residue at amino acid position 130 is replaced by glutamine. In other aspects and embodiments the present invention provides specific binding members against murine IL-13, specifically mouse IL-13.

BRIEF DESCRIPTION OF FIGURES

FIG. 4 shows the neutralisation potency (% inhibition) of BAK278D6 (closed squares) as a scFv against IL-13 in the TF-1 cell proliferation assay. The triangles represent an irrelevant scFv. Data represent the mean with standard error bars of triplicate determinations within the same experiment.

FIG. 6 shows the neutralisation potency (% inhibition) of BAK502G9 (closed squares), BAK1167F2 (closed triangles) and BAK1183H4 (closed inverted triangles) as human IgG4 against tagged IL-13 in the TF-1 cell proliferation assay. Open triangles represent an irrelevant IgG4. Data represent the mean with standard error bars of three separate experiments.

FIG. 19 shows an sequence alignment of cynomolgus IL-13 against human IL-13 amino acid sequences. The seven amino acid residues that differ between human and cynomolgus IL-13 are shaded. Rhesus and cynomolgus IL-13 have an identical amino acid sequence.

FIG. 20 illustrates the effects of single 10 mg/kg i.v bolus dose of BAK502G9 as human IgG4 on serum IgE levels in 4 allergic but non-challenged cynomolgus primates (2 male/2 female) over 29 days. Serum IgE concentration is significantly reduced from 100% (predose) to 66±10% of control values (p<0.05), at 4 and 5 days after dosing. This lowering of serum IgE concentration recovers to 88±8% of control levels by day 22. *=p<0.05 as compared to predose IgE levels, repeated measures ANOVA followed by Dunnett's multiple comparisons test (n=4 animals).

FIG. 21 illustrates the effects of intraperitoneal administration of BAK209B11 in different amounts (H=237 µg/day, M=23.7 µg/day and L=2.37 µg/day) compared with an isotype matched IgG1 irrelevant control antibody on the lung function of ovalbumin sensitised and challenged mice. In FIG. 21A lung function is represented by log $PC_{50}$s (log methacholine concentration required to increase baseline PenH by 50%) before any treatment (day 0) and post sensitisation, challenge and drug treatment (day 25). FIG. 21A shows the raw data used to calculate the study endpoint, shown in FIG. 21B (Delta log $PC_{50}$). Data represent the mean with standard error bars of n=8.

In FIG. 21B changing lung function is shown by a change in an individual mouse's log $PC_{50}$ (delta log $PC_{50}$). Delta log $PC_{50}$ is defined as an individuals change in log $PC_{50}$ at day 25 verus day 0. Data represent group mean delta log $PC_{50}$ (individual changes averaged within treatment groups) with standard error bars. The effect of antibody treatment was statistically evaluated by performing one way ANOVA with Dunnett's test using delta log $PC_{50}$ data. **p<0.01 compared to ovalbumin sensitised and challenged control animals (n=8 mice).

FIG. 22 illustrates the effects of local (i.po.) and systemic (i.v.) administration of BAK502G9 as human IgG4 in different amounts compared to an isotype matched IgG4 irrelevant control antibody on the total leukocyte recruitment (FIG. 22A) and eosinophil recruitment (FIG. 22B) into the air pouch of BALB/C mice. Data represent the mean with standard error bars of n=10. The effect of antibody treatment was statistically evaluated by performing one way ANOVA with Dunnett's test using log-transformed data. *p<0.05, **p<0.01 compared to huIL-13 challenged mice (n=10).

FIG. 26A shows effect on AHR as measured by change in area under the histamine dose response curve (n=14).

FIG. 26B shows effect on AHR as measured by change in $PC_{30}$ (n=18).

FIG. 26C shows effect on antigen priming (n=20).

FIG. 26D shows effect on BAL inflammation (n=21).

FIG. 29A shows effect of BAK502G9 on NHLF eotaxin=1 production induced by 48 h culture with IL-13/TNF-α/TGF-β1 containing media. Data are shown as an arithmetic mean±SEM from triplicate determinations of the media used in this study to induce leukocyte shape change.

FIG. 29B shows effect of BAK502G9 on shape change of human eosinophils induced by 1:16 dilution of conditioned media. Data points represented are mean±SEM % blank media shape change from separate experiments from four individual donors.

FIG. 30 shows alignment of human IL-13 against murine IL13 highlighting the mutations that were introduced into human IL-13 to produce the first panel of IL-13 chimaeras. The four alpha helices are highlighted in boxes and loop 1 and loop 3 are labelled. Five chimeric proteins were produced where helices B, C and D, and loops 1 and loop 3 were replaced with the murine sequence. Four further chimeric proteins were produced and numbered according to the amino acid in the human pre-protein (not to the numbering of the multiple alignment above) where arginine at residue 30 (position 34 above) was mutated, residues 33 and 34 (position 37 and 38 above) were mutated, residues 37 and 38 (VH) were mutated (position 41 and 42 above), and residues 40 and 41 (TQ) were mutated (position 44 and 45 above).

FIG. 31 shows alignment of human IL-13 against murine IL-13 highlighting the mutations that were introduced into human IL-13 to produce the second panel of IL-13 chimaeras. Six chimaeras were produced where the human residue(s) were substituted for the murine residue(s) (highlighted with boxes). Four further chimeric proteins were produced (numbering is according to the amino acid position in the human pre-protein) where leucine at residue 58 (62 in above figure) was mutated, leucine at residue 119 (residue 123 above) was mutated, lysine at position 123 (residue 127 above) was mutated, and arginine at residue 127 (residue 132 above was mutated.

FIG. 32 shows mutations made to human IL-13. Mutations that are double-underlined and in bold reduced binding to BAK502G9, mutations that are single-underlined did not alter binding. Linear sequence of pre-human IL-13 with the mutated residues indicated.

Figure 1:
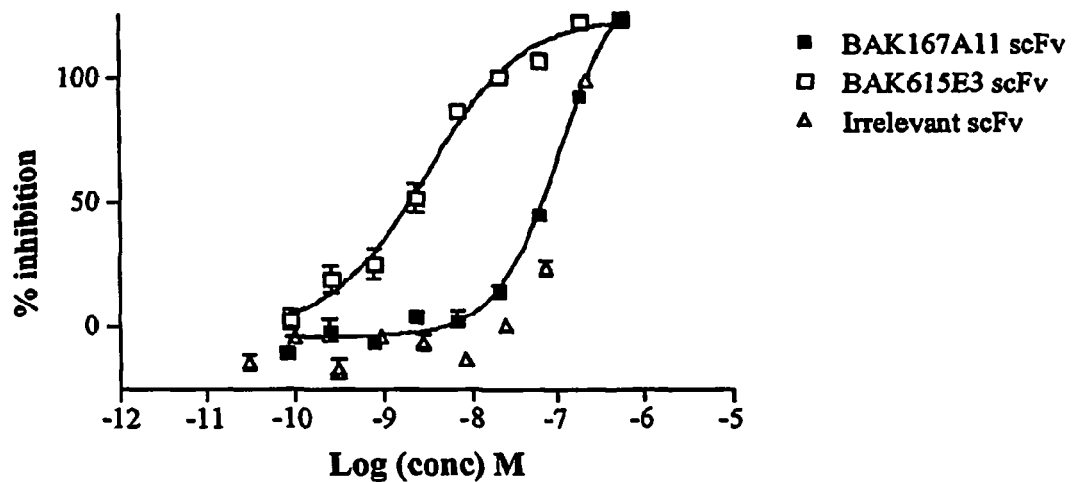
FIG. 1 shows neutralisation potency (% inhibition) of BAK167A11 (closed squares) and its derivative BAK615E3 (open squares) as scFv against 25 ng/ml human IL-13 in the TF-1 cell proliferation assay. The triangles represent an irrelevant scFv. Data represent the mean with standard error bars of triplicate determinations within the same experiment.

In various aspects and embodiments of the invention there is provided the subject-matter of the claims included below.

The present invention provides specific binding members for IL-13, in particular human and/or primate IL-13 and/or variant IL-13 (Q130R), and murine IL-13. Preferred embodiments within the present invention are antibody molecules, whether whole antibody (e.g. IgG, such as IgG4) or antibody fragments (e.g. scFv, Fab, dAb). Antibody antigen binding regions are provided, as are antibody VH and VL domains. Within VH and VL domains are provided complementarity determining regions, CDR's, which may be provided within different framework regions, FR's, to form VH or VL domains as the case may be. An antigen binding site may consist of an antibody VH domain and/or a VL domain.

An antigen binding site may be provided by means of arrangement of CDR's on non-antibody protein scaffolds such as fibronectin or cytochrome B etc. [115, 116]. Scaffolds for engineering novel binding sites in proteins have been reviewed in detail by Nygren et al [116]. Protein scaffolds for antibody mimics are disclosed in WO/0034784 in which the inventors describe proteins (antibody mimics) which include a fibronectin type III domain having at least one randomised loop. A suitable scaffold into which to graft one or more CDR's, e.g. a set of HCDR's, may be provided by any domain member of the immunoglobulin gene superfamily.

Preferred embodiments of the present invention are in what is termed herein the "BAK278D6 lineage". This is defined with reference to a set of six CDR sequences of BAK278D6 as follows: HCDR1 (SEQ ID NO: 1), HCDR2 (SEQ ID NO: 2), HCDR3 (SEQ ID NO: 3), LCDR1 (SEQ ID NO: 4), LCDR2 (SEQ ID NO: 5) and LCDR3 (SEQ ID NO: 6). In one aspect, the present invention provides a specific binding member for human IL-13, comprising an antibody antigen-binding site which is composed of a human antibody VH domain and a human antibody VL domain and which comprises a set of CDR's, wherein the VH domain comprises HCDR 1, HCDR2 and HCDR3 and the VL domain comprises LCDR1, LCDR2 and LCDR3, wherein the HCDR1 has the amino acid sequence of SEQ ID NO: 1, the HCDR2 has the amino acid sequence of SEQ ID NO: 2, the HCDR3 has the amino acid sequence of SEQ ID NO: 3, the LCDR1 has the amino acid sequence of SEQ ID NO: 4, the LCDR2 has the amino acid sequence of SEQ ID NO: 5, and the LCDR3 has the amino acid sequence of SEQ ID NO: 6; or wherein the set of CDR's contains one or two amino acid substitutions compared with the set of CDR's, wherein the HCDR1 has the amino acid sequence of SEQ ID NO: 1, the HCDR2 has the amino acid sequence of SEQ ID NO: 2, the HCDR3 has the amino acid sequence of SEQ ID NO: 3, the LCDR1 has the amino acid sequence of SEQ ID NO: 4, the LCDR2 has the amino acid sequence of SEQ ID NO: 5, and the LCDR3 has the amino acid sequence of SEQ ID NO: 6.

The set of CDR's wherein the HCDR1 has the amino acid sequence of SEQ ID NO: 1, the HCDR2 has the amino acid sequence of SEQ ID NO: 2, the HCDR3 has the amino acid sequence of SEQ ID NO: 3, the LCDR1 has the amino acid sequence of SEQ ID NO: 4, the LCDR2 has the amino acid sequence of SEQ ID NO: 5, and the LCDR3 has the amino acid sequence of SEQ ID NO: 6, are herein referred to as the "BAK278D6 set of CDR's". The HCDR1, HCDR2 and HCDR3 within the BAK278D6 set of CDR's are referred to as the "BAK278D6 set of HCDR's" and the LCDR1, LCDR2 and LCDR3 within the BAK278D6 set of CDR's are referred to as the "BAK278D6 set of LCDR's". A set of CDR's with the BAK278D6 set of CDR's, BAK278D6 set of HCDR's or BAK278D6 LCDR's, or one or two substitutions therein, is said to be of the BAK278D6 lineage.

As noted, in one aspect the invention provides a specific binding member for human IL-13, comprising an antibody antigen-binding site which is composed of a human antibody VH domain and a human antibody VL domain and which comprises a set of CDR's, wherein the set of CDR's is the BAK278D6 set of CDR's or a set of CDR's containing one or two substitutions compared with the BAK278D6 set of CDR's.

In preferred embodiments, the one or two substitutions are at one or two of the following residues within the CDRs of the VH and/or VL domains, using the standard numbering of Kabat [107].

31, 32, 34 in HCDR1
52, 52A, 53, 54, 56, 58, 60, 61, 62, 64, 65 in HCDR2
96, 97, 98, 99, 101 in HCDR3
26, 27, 28, 30, 31 in LCDR1
56 in LCDR2
95A, 97 in LCDR3

Preferred embodiments have two substitutions compared with the BAK278D6 set of CDR's, at HCDR3 residue 99 and LCDR1 residue 27. Of these embodiments, preferred embodiments have S substituted for N at HCDR3 residue 99 and/or I substituted for N at LCDR 1 residue 27. Still further embodiments have a substitution at HCDR3 residue 99 selected from the group consisting of S, A, I, R, P and K, and/or a substitution at LCDR1 residue 27 selected from the group consisting of I, L, M, C, V, K, Y, F, R, T, S, A, H and G.

In preferred embodiments one or two substitutions are made at one or two of the following residues within the BAK278D6 set of CDR's in accordance with the identified groups of possible substitute residues:

| Position of substitution | Substitute Residue selected from the group consisting of |
|---|---|
| 31 in HCDR1: | Q, D, L, G and E |
| 32 in HCDR1: | T |
| 34 in HCDR1: | V, I and F |
| 52 in HCDR2: | D, N, A, R, G and E |
| 52A in HCDR2: | D, G, T, P, N and Y |
| 53 in HCDR2: | D, L, A, P, T, S, I and R |
| 54 in HCDR2: | S, T, D, G, K and I |
| 56 in HCDR2: | T, E, Q, L, Y, N, V, A, M and G |
| 58 in HCDR2: | I, L, Q, S, M, H, D and K |
| 60 in HCDR2: | R |
| 61 in HCDR2: | R |
| 62 in HCDR2: | K and G |
| 64 in HCDR2: | R |
| 65 in HCDR2: | K |
| 96 in HCDR3: | R and D |
| 97 in HCDR3: | N, D, T and P |
| 98 in HCDR3: | R |
| 99 in HCDR3: | S, A, I, R, P and K |
| 101 in HCDR3: | Y |
| 26 in LCDR1: | D and S |
| 27 in LCDR1: | I, L, M, C, V, K, Y, F, R, T, S, A, H and G |
| 28 in LCDR1: | V |
| 30 in LCDR1: | G |
| 31 in LCDR1: | R |
| 56 in LCDR2: | T |
| 95A in LCDR3: | N |
| 97 in LCDR3: | I |

Preferred embodiments have the BAK278D6 set of CDR's with a substitution of S for N at residue 99 within HCDR3 and I for N at residue 27 within LCDR 1. The set of CDR's thus defined is as follows: HCDR1—SEQ ID NO: 7; HCDR2—SEQ ID NO: 8, HCDR3—SEQ ID NO: 9; LCDR1—SEQ ID NO: 10, LCDR2—SEQ ID NO: 11; LCDR3—SEQ ID NO: 12. This set of CDR's is herein referred to as the "BAK502G9 set of CDR's".

Further preferred embodiments have the BAK278D6 set of CDR's with one or two substitutions within the CDR's, with the proviso that the pair of substitutions of S for N at residue 99 within HCDR3 and I for N at residue 27 within LCDR 1 is excluded.

Other preferred embodiments are as follows: BAK 1166G2: HCDR1—SEQ ID NO: 67, HCDR2—SEQ ID NO: 68, HCDR3—SEQ ID NO: 69, LCDR1—SEQ ID NO: 70, LCDR2—SEQ ID NO: 71; LCDR3—SEQ ID NO: 72.

BAK1167F2 HCDR1—SEQ ID NO: 61, HCDR2—SEQ ID NO:62, HCDR3—SEQ ID NO:63, LCDR1—SEQ ID NO: 64, LCDR2—SEQ ID NO: 65; LCDR3—SEQ ID NO: 66.

BAK1184C8: HCDR1—SEQ ID NO:73, HCDR2: SEQ ID NO:74, HCDR3—SEQ ID NO:75. LCDR1—SEQ ID NO: 76, LCDR2—SEQ ID NO: 77; LCDR3—SEQ ID NO: 78.

BAK1185E1: HCDR1—SEQ ID NO:79, HCDR2—SEQ ID NO:80, HCDR3—SEQ ID NO: 81. LCDR1—SEQ ID NO: 82, LCDR2—SEQ ID NO: 83; LCDR3—SEQ ID NO: 84.

BAK1167F4: HCDR1—SEQ ID NO: 85, HCDR2—SEQ ID NO:86, HCDR3—SEQ ID NO:87. LCDR1—SEQ ID NO: 88, LCDR2—SEQ ID NO: 89; LCDR3—SEQ ID NO: 90.

BAK1111D10: HCDR1—SEQ ID NO: 91, HCDR2—SEQ ID NO: 92, HCDR3—SEQ ID NO: 93. LCDR1—SEQ ID NO: 94, LCDR2—SEQ ID NO: 95; LCDR3—SEQ ID NO: 96.

BAK1183H4: HCDR1—SEQ ID NO: 97, HCDR2—SEQ ID NO: 98, HCDR3—SEQ ID NO: 99. LCDR1—SEQ ID NO: 100, LCDR2—SEQ ID NO: 101; LCDR3—SEQ ID NO: 102.

BAK1185F8: HCDR1—SEQ ID NO: 103, HCDR2—SEQ ID NO: 104, HCDR3—SEQ ID NO: 105. LCDR1—SEQ ID NO: 106, LCDR2—SEQ ID NO: 107; LCDR3—SEQ ID NO: 108. All of these were derived from BAK502G9 by heavy chain CDR1 and CDR2 randomisation and are thus of the BAK502G9 lineage.

A VH domain comprising a set of CDR's HCDR1, HCDR2 and HCDR3 of any clone as shown in Table 1. Table 1 is also provided by the present invention, as is separately a VL domain comprising a set of CDR's LCDR1, LCDR2 and LCDR3 of the clones shown in Table 1. Preferably such a VH domain is paired with such a VL domain, and most preferably the VH and VL domain pairings are the same as in the clones as set out in Table 1.

Further provided by the present invention is a VH domain comprising a set of CDR's HCDR1, HCDR2 and HCDR3 wherein the set of CDR's corresponds to that for any clone shown in Table 1 with one or two amino acid substitutions.

Further provided by the present invention is a VL domain comprising a set of CDR's LCDR1, LCDR2 and LCDR3 wherein the set of CDR's corresponds to that for any clone shown in Table 1 with one or two amino acid substitutions.

A specific binding member comprising an antibody antigen-binding domain comprising such a VH and/or VL domain is also provided by the present invention.

The present inventors have identified the BAK278D6 lineage as providing human antibody antigen-binding domains against IL-13 which are of particular value. Within the lineage, BAK502G9 has been identified to be of special value. The BAK278D6 and BAK502G9 sets of CDR's have been identified already above.

Following the lead of computational chemistry in applying multivariate data analysis techniques to the structure/property-activity relationships [94], quantitative activity-property relationships of antibodies can be derived using well-known mathematical techniques such as statistical regression, pattern recognition and classification [95-100]. The properties of antibodies can be derived from empirical and theoretical models (for example, analysis of likely contact residues or calculated physicochemical property) of antibody sequence, functional and three-dimensional structures and these properties can be considered singly and in combination.

An antibody antigen-binding site composed of a VH domain and a VL domain is formed by six loops of polypeptide: three from the light chain variable domain (VL) and three from the heavy chain variable domain (VH). Analysis of antibodies of known atomic structure has elucidated relationships between the sequence and three-dimensional structure of antibody combining sites[101,102]. These relationships imply that, except for the third region (loop) in VH domains, binding site loops have one of a small number of main-chain conformations: canonical structures. The canonical structure formed in a particular loop has been shown to be determined by its size and the presence of certain residues at key sites in both the loop and in framework regions [101,102].

This study of sequence-structure relationship can be used for prediction of those residues in an antibody of known sequence, but of an unknown three-dimensional structure, which are important in maintaining the three-dimensional structure of its CDR loops and hence maintain binding specificity. These predictions can be backed up by comparison of the predictions to the output from lead optimization experiments.

In a structural approach, a model can be created of the antibody molecule [103] using an freely available or commercial package such as WAM [104]. A protein visualisation and analysis software package such as Insight II [105] or Deep View [106] may then be used to evaluate possible substitutions at each position in the CDR. This information may then be used to make substitutions likely to have a minimal or beneficial effect on activity.

The present inventors analysed sequence data of the panel of clones for which the sets of CDR's are shown in Table 1.

The analysis tested the hypothesis that any binary combinations of listed amino acid variations in the CDR's from the presented set of scFv variants leads to a scFv variant with at least the starting potency of the parent scFv BAK278D6.

All scFv variants in the panel shown in Table 1 have been selected for improved affinity and have been confirmed to display higher potency.

The observed amino acid variations can either be favourable, non-favourable or neutral in their effect on the starting potency of scFv BAK278D6 in the TF-1 assay of 44 nM.

No linkage was observed between any two amino acid variations confirming that there was no synergy, either "positive" or "negative", between any two selected amino acid variations.

There are four scenarios where such binary combination will fulfil the hypothesis and three scenarios where the hypothesis will not be valid. Synergistic amino acid variants are not considered as no linkage was observed.

The hypothesis is valid where:
A1: mutation 1 is favourable and mutation 2 is favourable
A2: mutation 1 is favourable and mutation 2 is neutral
A3: mutation 1 is neutral and mutation 2 is neutral
A4: mutation 1 is favourable and mutation 2 is non-favourable (with the effect of 1 outweighing the effect of 2).

The hypothesis is not valid where:
B1: mutation 1 is non-favourable and mutation 2 is neutral
B2: mutation 1 is non-favourable and mutation 2 is non-favourable
B3: mutation 1 is favourable and mutation 2 is non-favourable (with the effect of 2 outweighing the effect of 1).

For A4 to be possible, mutation 1 needs to be highly favourable to counterbalance the negative effect of mutation 2 on potency. Since such highly favourable mutation would be present in the library of variants used for selection, it would be selected for and would therefore appear frequently in the panel of variants. Since synergy can be excluded, such mutation would be beneficial in any kind of sequence context and should therefore reappear in different scFv variants. An example for such frequent amino acid change is the change in the light chain CDR1 Asn27Ile. However, this mutation on its own (in clone BAK531E2) has only a modest 2-fold effect on potency (final IC50 of 23.2 nM). On its own this mutation would not allow the scenario depicted in A4, as it is not a highly favourable mutation. This suggests that every clone in the presented set of IL-13 binding clones (Table 1) which has a light chain CDR1 Asn27Ile change along with one or more further mutations is at least as potent as the variant having the single light chain CDR1 Asn27Ile mutation. The other mutations are either neutral or positive but do not have a negative or detrimental affect.

A further example is in the heavy chain CDR3 Asn99Ser (see Table 1). As a clone carrying this particular single amino acid variation is not observed, the potency of such a clone has been estimated to be approximately 12.0 nM by the following rationale:

BAK278D6 potency is 44 nM. Alterations of VL CDR1 N27I+VH CDR3 N99S lead to BAK502G9 with potency 8 nM, i.e. 5.5 fold improvement.

BAK278D6 potency is 44 nM. Alteration of VL CDR1 N27I leads to BAK531E2 with potency 23 nM, i.e. 1.9 fold improvement BAK278D6 potency is 44 nM. Alteration VH CDR3 N99S to provide a possible clone with potency 12.2 nM, i.e. 2.9 fold improvement (5.5/1.9=2.9).

The binary combination of heavy chain CDR3 Asn99Ser with light chain CDR1 Asn27Ile gives a scFv BAK0502G9 with a potency of 8 nM. As synergy is excluded, the contribution of heavy chain CDR3 Asn99Ser change in BAK502G9 is therefore additive.

Therefore every clone in the presented set of IL-13 binding clones (Table 1) which has a heavy chain CDR3 AsnH99Ser change along with one or more further mutations would have a potency of at least 12 nM or greater, within a permissive assay window of 2.5-fold for n=1-2.

Thus, the inventors note that a highly favourable amino acid variation which would be selected preferentially is not observed. As discussed above, two variations which were prominently represented in Table 1 of scFv variants were analysed closer. Any scFv variant in Table 1 with either of these mutations along with one or more further mutations displayed a potency which was at least as improved as a clone containing any one of these two single amino acid variations in the parent BAK278D6. There is therefore no evidence that a highly favourable amino acid variation, that would allow scenario A4, is present in the panel.

This observation led the inventors to conclude that there were no non-favourable mutations present in this set of scFv variants. This means scenarios A4 and B1 to B3 are not relevant and the hypothesis is valid.

Accordingly, as noted already, the present invention provides specific binding members comprising the defined sets of CDR's, in particular the set of CDR's of BAK278D6, and sets of CDR's of the BAK278D6 lineage, with one or two substitutions within the set of CDR's, e.g. the BAK502G9 set of CDR's.

The relevant set of CDR's is provided within antibody framework regions or other protein scaffold, e.g. fibronectin or cytochrome B [115, 116]. Preferably antibody framework regions are employed, and where they are employed they are preferably germline, more preferably the antibody framework region for the heavy chain may be DP14 from the VH1 family. The preferred framework region for the light chain may be λ3-3H. For the BAK502G9 set of CDR's it is preferred that the antibody framework regions are for VH FR1, SEQ ID NO: 27, for VH FR2, SEQ ID NO: 28, for VH FR3, SEQ ID NO 29, for light chain FR1, SEQ ID NO: 30, for light chain FR2, SEQ ID NO: 31, for light chain FR3, SEQ ID NO: 32. In a highly preferred embodiment, a VH domain is provided with the amino acid sequence of SEQ ID NO: 15, this being termed "BAK502G9 VH domain". In a further highly preferred embodiment, a VL domain is provided with the amino acid sequence of SEQ ID NO: 16, this being termed "BAK502G9 VL domain". A highly preferred antibody antigen-binding site provided in accordance with the present invention is composed of the BAK502G9 VH domain, SEQ ID NO: 15, and the BAK502G9 VL domain, SEQ ID NO: 16. This antibody antigen-binding site may be provided within any desired antibody molecule format, e.g. scFv, Fab, IgG, IgG4, dAb etc., as is discussed further elsewhere herein.

In a further highly preferred embodiment, the present invention provides an IgG4 antibody molecule comprising the BAK502G9 VH domain, SEQ ID NO: 15, and the BAK502G9 VL domain, SEQ ID NO: 16. This is termed herein "BAK502G9 IgG4".

Other IgG4 or other antibody molecules comprising the BAK502G9 VH domain, SEQ ID NO: 15, and/or the BAK502G9 VL domain, SEQ ID NO: 16, are provided by the present invention, as are other antibody molecules comprising the BAK502G9 set of HCDR's (SEQ ID NO: 7, 8 and 9) within an antibody VH domain, and/or the BAK502G9 set of LCDR's (SEQ ID NO: 10, 11 and 12) within an antibody VL domain.

It is convenient to point out here that "and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

As noted, the present invention provides a specific binding member which binds human IL-13 and which comprises the BAK502G9 VH domain (SEQ ID NO: 15) and/or the BAK502G9 VL domain (SEQ ID NO: 16).

Generally, a VH domain is paired with a VL domain to provide an antibody antigen binding site, although as discussed further below a VH domain alone may be used to bind antigen. In one preferred embodiment, the BAK502G9 VH domain (SEQ ID NO: 15) is paired with the BAK502G9 VL domain (SEQ ID NO: 16), so that an antibody antigen binding site is formed comprising both the BAK502G9 VH and VL domains. In other embodiments, the BAK502G9 VH is paired with a VL domain other than the BAK502G9 VL. Light-chain promiscuity is well established in the art.

Similarly, any set of HCDR's of the BAK278D6 lineage can be provided in a VH domain that is used as a specific binding member alone or in combination with a VL domain. A VH domain may be provided with a set of HCDR's of a BAK278D6 lineage antibody, e.g. as shown in Table 1, and if such a VH domain is paired with a VL domain, then the VL domain may be provided with a set of LCDR's of a BAK278D6 lineage antibody, e.g. as shown in Table 1. A pairing of a set of HCDR's and a set of LCDR's may be as shown in Table 1, providing an antibody antigen-binding site comprising a set of CDR's as shown in Table 1. The framework regions of the VH and/or VL domains may be germline frameworks. Frameworks regions of the heavy chain domain may be selected from the VH-1 family, and a preferred VH-1 framework is DP-14 framework. Framework regions of the light chain may be selected from the λ3 family, and a preferred such framework is λ3 3H.

One or more CDRs may be taken from the BAK502G9 VH or VL domain and incorporated into a suitable framework. This is discussed further herein. BAK502G9 HCDR's 1, 2 and 3 are shown in SEQ ID NO: 7, 8 and 9, respectively. BAK502G9 LCDR's 1, 2 and 3 are shown in SEQ ID NO: 10, 11 and 12, respectively.

The same applies for other BAK278D6 lineage CDR's and sets of CDR's as shown in Table 1.

Further embodiments of the invention relate to a specific binding member comprising the VH and/or VL domain, or an antigen binding site comprising CDRs of the VH and/or VL domain of the antibody molecule disclosed herein as 167A11 (VH: SEQ ID NO: 23 and VL: SEQ ID NO: 24) and its derivatives 615E3 (VH: SEQ ID NO: 33 and VL: SEQ ID NO: 34) BAK582F7 (VH CDR's SEQ ID's 141-143) and BAK612B5 (VH CDR's SEQ ID's 147-149). These recognise human IL-13. The derivatives of 167A11 from VH CDR3 randomisation are potent scFv molecules (5-6 nM). The 167A11 lineage may be employed in any aspect and embodiment of the present invention as disclosed herein for other molecules, for instance methods of mutation and selection of antigen binding sites with improved potency.

Variants of the VH and VL domains and CDRs of the present invention, including those for which amino acid sequences are set out herein, and which can be employed in specific binding members for IL-13 can be obtained by means of methods of sequence alteration or mutation and screening. Such methods are also provided by the present invention.

Variable domain amino acid sequence variants of any of the VH and VL domains whose sequences are specifically disclosed herein may be employed in accordance with the present invention, as discussed. Particular variants may include one or more amino acid sequence alterations (addition, deletion, substitution and/or insertion of an amino acid residue), may be less than about 20 alterations, less than about 15 alterations, less than about 10 alterations or less than about 5 alterations, 4, 3, 2 or 1. Alterations may be made in one or more framework regions and/or one or more CDR's.

In accordance with further aspects of the present invention there is provided a specific binding member which competes for binding to antigen with any specific binding member which both binds the antigen and comprises a specific binding member, VH and/or VL domain disclosed herein, or HCDR3 disclosed herein, or variant of any of these. Competition between binding members may be assayed easily in vitro, for example using ELISA and/or by tagging a specific reporter molecule to one binding member which can be detected in the presence of other untagged binding member(s), to enable identification of specific binding members which bind the same epitope or an overlapping epitope.

Thus, a further aspect of the present invention provides a specific binding member comprising a human antibody antigen-binding site which competes with a BAK502G9 antibody molecule, in particular BAK502G9 scFv and/or IgG4, for binding to IL-13. In further aspects the present invention provides a specific binding member comprising a human antibody antigen-binding site which competes with an antibody antigen-binding site for binding to IL-13, wherein the antibody antigen-binding site is composed of a VH domain and a VL domain, and wherein the VH and VL domains comprise a set of CDR's of the BAK278D6 lineage.

Various methods are available in the art for obtaining antibodies against IL-13 and which may compete with a BAK502G9 antibody molecule, an antibody molecule with a BAK502G9 set of CDR's, or an antibody molecule with a set of CDR's of BAK278D6 lineage, for binding to IL-13.

In a further aspect, the present invention provides a method of obtaining one or more specific binding members able to bind the antigen, the method including bringing into contact a library of specific binding members according to the invention and said antigen, and selecting one or more specific binding members of the library able to bind said antigen.

The library may be displayed on the surface of bacteriophage particles, each particle containing nucleic acid encoding the antibody VH variable domain displayed on its surface, and optionally also a displayed VL domain if present.

Following selection of specific binding members able to bind the antigen and displayed on bacteriophage particles, nucleic acid may be taken from a bacteriophage particle displaying a said selected specific binding member. Such nucleic acid may be used in subsequent production of a specific binding member or an antibody VH variable domain (optionally an antibody VL variable domain) by expression from nucleic acid with the sequence of nucleic acid taken from a bacteriophage particle displaying a said selected specific binding member.

An antibody VH variable domain with the amino acid sequence of an antibody VH variable domain of a said selected specific binding member may be provided in isolated form, as may a specific binding member comprising such a VH domain. Ability to bind IL-13 may be further tested, also ability to compete with BAK502G9 (e.g. in scFv format and/or IgG format, e.g. IgG4) for binding to IL-13. Ability to neutralise IL-13 may be tested, as discussed further below.

A specific binding member according to the present invention may bind IL-13 with the affinity of a BAK502G9 antibody molecule, e.g. scFv, or preferably BAK502G9 IgG4, or with an affinity that is better.

A specific binding member according to the present invention may neutralise IL-13 with the potency of a BAK502G9 antibody molecule, e.g. scFv, or preferably BAK502G9 IgG4, or with a potency that is better.

A specific binding member according to the present invention may neutralise naturally occurring IL-13 with the potency of a BAK502G9 antibody molecule, e.g. scFv, or preferably BAK502G9 IgG4, or with a potency that is better.

Binding affinity and neutralisation potency of different specific binding members can be compared under appropriate conditions.

The antibodies of the present invention have a number of advantages over existing commercial anti-IL-13 antibodies, in particular three commercial rodent anti-human IL-13 antibodies namely, JES10-5A2 (BioSource), B-B13 (Euroclone) and clone 321166 (R&D Systems). The potency of the antibodies of the present invention was compared with commercial antibodies JES10-A2 and B-B13. Clone 321166 was not evaluated as previous experiments revealed that this clone was considerably less potent than other known commercial antibodies.

The efficacy and use of the rodent commercial IL-13 antibodies in man is likely to be limited, because of their increased potential to induce immunogenic responses and therefore more rapid clearance from the body. Kinetic analysis of the antibodies of the present invention in non-human primates suggests that these antibodies have a clearance rate which is similar to that of other known human or humanised antibodies.

Antibodies provided by various embodiments of the present invention recognize non-human primate IL-13, including rhesus and cynomolgus IL-13. Determining efficacy and safety profiles of an antibody in non-human primates is extremely valuable as it provides a means for predicting the antibody's safety, pharmacokinetic and pharmacodynamic profile in humans.

Moreover, antibodies of various embodiments of the present invention further recognize the human IL-13 variant, Q130R, which is associated with asthma. Cross reactivity with variant IL-13 allows antibodies of the present invention and compositions comprising antibodies of the present invention to be used for the treatment of patients with wild-type and variant IL-13.

Figure 7:
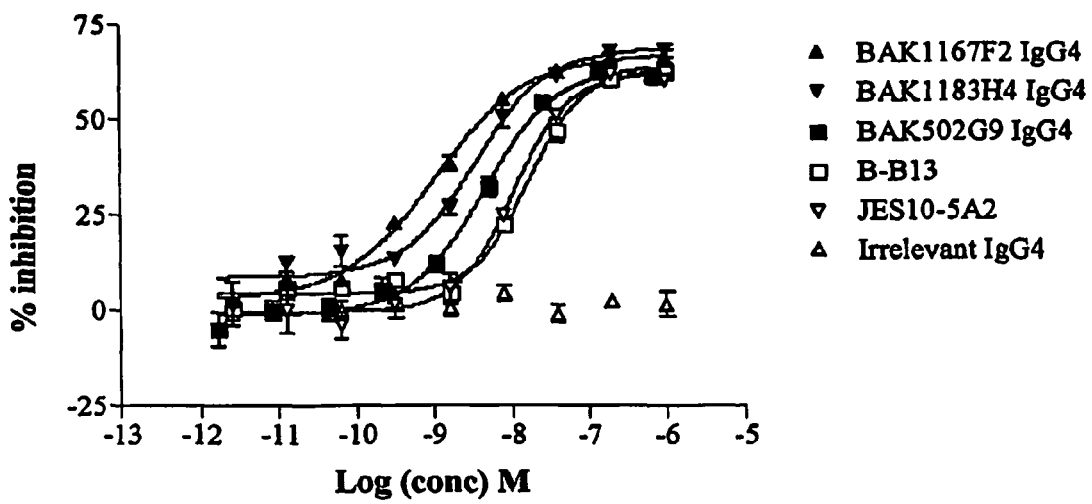
FIG. 7 shows the neutralisation potency (% inhibition) of BAK502G9 (closed squares), BAK1167F2 (closed triangles), BAK1183H4 (closed inverted triangles) as human IgG4 and commercial anti-human IL-13 antibodies (B-B13—open squares; JES10-5A2—open inverted triangles) in the native IL-13 dependent HDLM-2 cell proliferation assay. Open triangles represent an irrelevant IgG4. Data represent the mean with standard error bars of triplicate determinations within the same experiment.

A preferred embodiment of the present invention comprises antibodies that neutralise naturally occurring IL-13 with a potency that is equal to or better than the potency of a IL-13 antigen binding site formed by BAK502G9 VH domain (SEQ ID NO:15) and the BAK502G9 VL domain (SEQ ID NO: 16). For example, the inventors have demonstrated that representative clones such as BAK502G9, 1167F2 and 1183H4 are significantly more potent against naturally occurring IL-13 than known commercial antibodies (FIG. 7).

In addition to antibody sequences, a specific binding member according to the present invention may comprise other amino acids, e.g. forming a peptide or polypeptide, such as a folded domain, or to impart to the molecule another functional characteristic in addition to ability to bind antigen. Specific binding members of the invention may carry a detectable label, or may be conjugated to a toxin or a targeting moiety or enzyme (e.g. via a peptidyl bond or linker).

In further aspects, the invention provides an isolated nucleic acid which comprises a sequence encoding a specific binding member, VH domain and/or VL domains according to the present invention, and methods of preparing a specific binding member, a VH domain and/or a VL domain of the invention, which comprise expressing said nucleic acid under conditions to bring about production of said specific binding member, VH domain and/or VL domain, and recovering it.

Specific binding members according to the invention may be used in a method of treatment or diagnosis of the human or animal body, such as a method of treatment (which may include prophylactic treatment) of a disease or disorder in a human patient which comprises administering to said patient an effective amount of a specific binding member of the invention. Conditions treatable in accordance with the present invention include any in which IL-13 plays a role, especially asthma, atopic dermatitis, allergic rhinitis, fibrosis, chronic obstructive pulmonary disease, scleroderma, inflammatory bowel disease and Hodgkin's lymphoma. Further, the antibodies of the present invention may also be used in treating tumours and viral infections as these antibodies will inhibit IL-13 mediated immunosupression [64, 65].

A further aspect of the present invention provides nucleic acid, generally isolated, encoding an antibody VH variable domain and/or VL variable domain disclosed herein.

Another aspect of the present invention provides nucleic acid, generally isolated, encoding a VH CDR or VL CDR sequence disclosed herein, especially a VH CDR selected from SEQ ID NO's: 7, 8 and 9 or a VL CDR selected from SEQ ID NO's: 10, 11 and 12, most preferably BAK502G9

VH CDR3 (SEQ ID NO: 9). Nucleic acid encoding the BAK502G9 set of CDR's, nucleic acid encoding the BAK502G9 set of HCDR's and nucleic acid encoding the BAK502G9 set of LCDR's are also provided by the present invention, as are nucleic acids encoding individual CDR's, HCDR's, LCDR's and sets of CDR's, HCDR's, LCDR's of the BAK278D6 lineage.

A further aspect provides a host cell transformed with nucleic acid of the invention.

A yet further aspect provides a method of production of an antibody VH variable domain, the method including causing expression from encoding nucleic acid. Such a method may comprise culturing host cells under conditions for production of said antibody VH variable domain.

Analogous methods for production of VL variable domains and specific binding members comprising a VH and/or VL domain are provided as further aspects of the present invention.

A method of production may comprise a step of isolation and/or purification of the product.

A method of production may comprise formulating the product into a composition including at least one additional component, such as a pharmaceutically acceptable excipient.

These and other aspects of the invention are described in further detail below.

Terminology

Specific Binding Member

This describes a member of a pair of molecules which have binding specificity for one another. The members of a specific binding pair may be naturally derived or wholly or partially synthetically produced. One member of the pair of molecules has an area on its surface, or a cavity, which specifically binds to and is therefore complementary to a particular spatial and polar organisation of the other member of the pair of molecules. Thus the members of the pair have the property of binding specifically to each other. Examples of types of specific binding pairs are antigen-antibody, biotin-avidin, hormone-hormone receptor, receptor-ligand, enzyme-substrate. The present invention is concerned with antigen-antibody type reactions.

Antibody Molecule

This describes an immunoglobulin whether natural or partly or wholly synthetically produced. The term also covers any polypeptide or protein comprising an antibody binding domain. Antibody fragments which comprise an antigen binding domain are molecules such as Fab, scFv, Fv, dAb, Fd; and diabodies.

It is possible to take monoclonal and other antibodies and use techniques of recombinant DNA technology to produce other antibodies or chimeric molecules which retain the specificity of the original antibody. Such techniques may involve introducing DNA encoding the immunoglobulin variable region, or the complementarity determining regions (CDRs), of an antibody to the constant regions, or constant regions plus framework regions, of a different immunoglobulin. See, for instance, EP-A-184187, GB 2188638A or EP-A-239400, and a large body of subsequent literature. A hybridoma or other cell producing an antibody may be subject to genetic mutation or other changes, which may or may not alter the binding specificity of antibodies produced.

As antibodies can be modified in a number of ways, the term "antibody molecule" should be construed as covering any specific binding member or substance having an antibody antigen-binding domain with the required specificity. Thus, this term covers antibody fragments and derivatives, including any polypeptide comprising an immunoglobulin binding domain, whether natural or wholly or partially synthetic. Chimeric molecules comprising an immunoglobulin binding domain, or equivalent, fused to another polypeptide are therefore included. Cloning and expression of chimeric antibodies are described in EP-A-0120694 and EP-A-0125023, and a large body of subsequent literature.

Further techniques available in the art of antibody engineering have made it possible to isolate human and humanised antibodies. For example, human hybridomas can be made as described by Kontermann et al [107]. Phage display, another established technique for generating specific binding members has been described in detail in many publications such as Kontermann et al [107] and WO92/01047 (discussed further below). Transgenic mice in which the mouse antibody genes are inactivated and functionally replaced with human antibody genes while leaving intact other components of the mouse immune system, can be used for isolating human antibodies to human antigens [108].

Synthetic antibody molecules may be created by expression from genes generated by means of oligonucleotides synthesized and assembled within suitable expression vectors, for example as described by Knappik et al. J. Mol. Biol. (2000) 296, 57-86 or Krebs et al. Journal of Immunological Methods 254 2001 67-84.

It has been shown that fragments of a whole antibody can perform the function of binding antigens. Examples of binding fragments are (i) the Fab fragment consisting of VL, VH, CL and CH1 domains; (ii) the Fd fragment consisting of the VH and CH1 domains; (iii) the Fv fragment consisting of the VL and VH domains of a single antibody; (iv) the dAb fragment (Ward, E. S. et al., Nature 341, 544-546 (1989), McCafferty et al (1990) Nature, 348, 552-554) which consists of a VH domain; (v) isolated CDR regions; (vi) F(ab')$_2$ fragments, a bivalent fragment comprising two linked Fab fragments (vii) single chain Fv molecules (scFv), wherein a VH domain and a VL domain are linked by a peptide linker which allows the two domains to associate to form an antigen binding site (Bird et al, Science, 242, 423-426, 1988; Huston et al, PNAS USA, 85, 5879-5883, 1988); (viii) bispecific single chain Fv dimers (PCT/US92/09965) and (ix) "diabodies", multivalent or multispecific fragments constructed by gene fusion (WO94/13804; P. Holliger et al, Proc. Natl. Acad. Sci. USA 90 6444-6448, 1993). Fv, scFv or diabody molecules may be stabilised by the incorporation of disulphide bridges linking the VH and VL domains (Y. Reiter et al, Nature Biotech, 14, 1239-1245, 1996). Minibodies comprising a scFv joined to a CH3 domain may also be made (S. Hu et al, Cancer Res., 56, 3055-3061, 1996).

Where bispecific antibodies are to be used, these may be conventional bispecific antibodies, which can be manufactured in a variety of ways (Holliger, P. and Winter G. Current Opinion Biotechnol. 4, 446-449 (1993)), e.g. prepared chemically or from hybrid hybridomas, or may be any of the bispecific antibody fragments mentioned above. Examples of bispecific antibodies include those of the BiTE™ technology in which the binding domains of two antibodies with different specificity can be used and directly linked via short flexible peptides. This combines two antibodies on a short single polypeptide chain. Diabodies and scFv can be constructed without an Fc region, using only variable domains, potentially reducing the effects of anti-idiotypic reaction.

Bispecific diabodies, as opposed to bispecific whole antibodies, may also be particularly useful because they can be readily constructed and expressed in E. coli. Diabodies (and many other polypeptides such as antibody fragments) of appropriate binding specificities can be readily selected using phage display (WO94/13804) from libraries. If one arm of the diabody is to be kept constant, for instance, with a specificity directed against IL-13, then a library can be made where the other arm is varied and an antibody of appropriate specificity selected. Bispecific whole antibodies may be made by knobs-into-holes engineering (J. B. B. Ridgeway et al, Protein Eng., 9, 616-621, 1996).

Antigen-Binding Domain

This describes the part of an antibody molecule which comprises the area which specifically binds to and is complementary to part or all of an antigen. Where an antigen is large, an antibody may only bind to a particular part of the antigen, which part is termed an epitope. An antigen binding domain may be provided by one or more antibody variable domains (e.g. a so-called Fd antibody fragment consisting of a VH domain). Preferably, an antigen binding domain comprises an antibody light chain variable region (VL) and an antibody heavy chain variable region (VH).

Specific

This may be used to refer to the situation in which one member of a specific binding pair will not show any significant binding to molecules other than its specific binding partner(s). The term is also applicable where e.g. an antigen binding domain is specific for a particular epitope which is carried by a number of antigens, in which case the specific binding member carrying the antigen binding domain will be able to bind to the various antigens carrying the epitope.

Comprise

This is generally used in the sense of include, that is to say permitting the presence of one or more features or components.

Isolated

This refers to the state in which specific binding members of the invention, or nucleic acid encoding such binding members, will generally be in accordance with the present invention. Isolated members and isolated nucleic acid will be free or substantially free of material with which they are naturally associated such as other polypeptides or nucleic acids with which they are found in their natural environment, or the environment in which they are prepared (e.g. cell culture) when such preparation is by recombinant DNA technology practised in vitro or in vivo. Members and nucleic acid may be formulated with diluents or adjuvants and still for practical purposes be isolated—for example the members will normally be mixed with gelatin or other carriers if used to coat microtitre plates for use in immunoassays, or will be mixed with pharmaceutically acceptable carriers or diluents when used in diagnosis or therapy. Specific binding members may be glycosylated, either naturally or by systems of heterologous eukaryotic cells (e.g. CHO or NS0 (ECACC 85110503) cells, or they may be (for example if produced by expression in a prokaryotic cell) unglycosylated.

Naturally Occurring IL-13

This generally refers to a state in which the IL-13 protein or fragments thereof may occur. Naturally occurring IL-13 means IL-13 protein which is naturally produced by a cell, without prior introduction of encoding nucleic acid using recombinant technology. Thus, naturally occurring IL-13 may be as produced naturally by for example CD4+ T cells and/or as isolated from a mammal, e.g. human, non-human primate, rodent such as rat or mouse.

Recombinant IL-13

This refers to a state in which the IL-13 protein or fragments thereof may occur. Recombinant IL-13 means IL-13 protein or fragments thereof produced by recombinant DNA in a heterologous host. Recombinant IL-13 may differ from naturally occurring IL-13 by glycosylation.

Recombinant proteins expressed in prokaryotic bacterial expression systems are not glycosylated while those expressed in eukaryotic systems such as mammalian or insect cells are glycosylated. Proteins expressed in insect cells however differ in glycosylation from proteins expressed in mammalian cells.

By "substantially as set out" it is meant that the relevant CDR or VH or VL domain of the invention will be either identical or highly similar to the specified regions of which the sequence is set out herein. By "highly similar" it is contemplated that from 1 to 5, preferably from 1 to 4 such as 1 to 3 or 1 or 2, or 3 or 4, amino acid substitutions may be made in the CDR and/or VH or VL domain.

The structure for carrying a CDR or a set of CDR's of the invention will generally be of an antibody heavy or light chain sequence or substantial portion thereof in which the CDR or set of CDR's is located at a location corresponding to the CDR or set of CDR's of naturally occurring VH and VL antibody variable domains encoded by rearranged immunoglobulin genes. The structures and locations of immunoglobulin variable domains may be determined by reference to (Kabat, E. A. et al, Sequences of Proteins of Immunological Interest. 4th Edition. US Department of Health and Human Services. 1987, and updates thereof, now available on the Internet (http://immuno.bme.nwu.edu or find "Kabat" using any search engine).

CDR's can also be carried by other scaffolds such as fibronectin or cytochrome B [115, 116].

Preferably, a CDR amino acid sequence substantially as set out herein is carried as a CDR in a human variable domain or a substantial portion thereof. The HCDR3 sequences substantially as set out herein represent preferred embodiments of the present invention and it is preferred that each of these is carried as a HCDR3 in a human heavy chain variable domain or a substantial portion thereof.

Variable domains employed in the invention may be obtained from any germ-line or rearranged human variable domain, or may be a synthetic variable domain based on consensus sequences of known human variable domains. A CDR sequence of the invention (e.g. CDR3) may be introduced into a repertoire of variable domains lacking a CDR (e.g. CDR3), using recombinant DNA technology.

For example, Marks et al (Bio/Technology, 1992, 10:779-783) describe methods of producing repertoires of antibody variable domains in which consensus primers directed at or adjacent to the 5' end of the variable domain area are used in conjunction with consensus primers to the third framework region of human VH genes to provide a repertoire of VH variable domains lacking a CDR3. Marks et al further describe how this repertoire may be combined with a CDR3 of a particular antibody. Using analogous techniques, the CDR3-derived sequences of the present invention may be shuffled with repertoires of VH or VL domains lacking a CDR3, and the shuffled complete VH or VL domains combined with a cognate VL or VH domain to provide specific binding members of the invention. The repertoire may then be displayed in a suitable host system such as the phage display system of WO92/01047 or any of a subsequent large body of literature, including Kay, B. K., Winter, J., and McCafferty, J. (1996) Phage Display of Peptides and Proteins: A Laboratory Manual, San Diego: Academic Press, so that suitable specific binding members may be selected. A repertoire may consist of from anything from $10^4$ individual members upwards, for example from $10^6$ to $10^8$ or $10^{10}$ members. Other suitable host systems include yeast display, bacterial display, T7 display, ribosome display and so on. For a review of ribosome display for see Lowe D and Jermutus L, 2004, Curr. Pharm, Biotech, 517-27, also WO92/01047.

Analogous shuffling or combinatorial techniques are also disclosed by Stemmer (*Nature,* 1994, 370:389-391), who describes the technique in relation to a β-lactamase gene but observes that the approach may be used for the generation of antibodies.

A further alternative is to generate novel VH or VL regions carrying CDR-derived sequences of the invention using random mutagenesis of one or more selected VH and/or VL genes to generate mutations within the entire variable domain. Such a technique is described by Gram et al (1992, *Proc. Natl. Acad. Sci., USA,* 89:3576-3580), who used error-prone PCR. In preferred embodiments one or two amino acid substitutions are made within a set of HCDR's and/or LCDR's.

Another method which may be used is to direct mutagenesis to CDR regions of VH or VL genes. Such techniques are disclosed by Barbas et al, (1994, *Proc. Natl. Acad. Sci., USA,* 91:3809-3813) and Schier et al (1996, *J. Mol. Biol.* 263:551-567).

All the above described techniques are known as such in the art and in themselves do not form part of the present invention. The skilled person will be able to use such techniques to provide specific binding members of the invention using routine methodology in the art.

A further aspect of the invention provides a method for obtaining an antibody antigen binding domain specific for IL-13 antigen, the method comprising providing by way of addition, deletion, substitution or insertion of one or more amino acids in the amino acid sequence of a VH domain set out herein a VH domain which is an amino acid sequence variant of the VH domain, optionally combining the VH domain thus provided with one or more VL domains, and testing the VH domain or VH/VL combination or combinations to identify a specific binding member or an antibody antigen binding domain specific for IL-13 antigen and optionally with one or more preferred properties, preferably ability to neutralise IL-13 activity. Said VL domain may have an amino acid sequence which is substantially as set out herein.

An analogous method may be employed in which one or more sequence variants of a VL domain disclosed herein are combined with one or more VH domains.

In a preferred embodiment, BAK502G9 VH domain (SEQ ID NO: 15) may be subject to mutation to provide one or more VH domain amino acid sequence variants, and/or BAK502G9 VL (SEQ ID NO: 16).

A further aspect of the invention provides a method of preparing a specific binding member specific for IL-13 antigen, which method comprises:
  (a) providing a starting repertoire of nucleic acids encoding a VH domain which either include a CDR3 to be replaced or lack a CDR3 encoding region;
  (b) combining said repertoire with a donor nucleic acid encoding an amino acid sequence substantially as set out herein for a VH CDR3 such that said donor nucleic acid is inserted into the CDR3 region in the repertoire, so as to provide a product repertoire of nucleic acids encoding a VH domain;
  (c) expressing the nucleic acids of said product repertoire;
  (d) selecting a specific binding member specific for a IL-13; and
  (e) recovering said specific binding member or nucleic acid encoding it.

Again, an analogous method may be employed in which a VL CDR3 of the invention is combined with a repertoire of nucleic acids encoding a VL domain which either include a CDR3 to be replaced or lack a CDR3 encoding region.

Similarly, one or more, or all three CDRs may be grafted into a repertoire of VH or VL domains which are then screened for a specific binding member or specific binding members specific for IL-13.

In a preferred embodiment, one or more of BAK502G9 HCDR1 (SEQ ID NO: 7), HCDR2 (SEQ ID NO: 8) and HCDR3 (SEQ ID NO: 9), or the BAK502G9 set of HCDR's, may be employed, and/or one or more of BAK502G9 LCDR1 (SEQ ID NO: 10), LCDR2 (SEQ ID NO: 11), or the BAK502G9 set of LCDR's.

A substantial portion of an immunoglobulin variable domain will comprise at least the three CDR regions, together with their intervening framework regions. Preferably, the portion will also include at least about 50% of either or both of the first and fourth framework regions, the 50% being the C-terminal 50% of the first framework region and the N-terminal 50% of the fourth framework region. Additional residues at the N-terminal or C-terminal end of the substantial part of the variable domain may be those not normally associated with naturally occurring variable domain regions. For example, construction of specific binding members of the present invention made by recombinant DNA techniques may result in the introduction of N- or C-terminal residues encoded by linkers introduced to facilitate cloning or other manipulation steps. Other manipulation steps include the introduction of linkers to join variable domains of the invention to further protein sequences including immunoglobulin heavy chains, other variable domains (for example in the production of diabodies) or protein labels as discussed in more detail elsewhere herein.

Although in a preferred aspect of the invention specific binding members comprising a pair of VH and VL domains are preferred, single binding domains based on either VH or VL domain sequences form further aspects of the invention. It is known that single immunoglobulin domains, especially VH domains, are capable of binding target antigens in a specific manner.

In the case of either of the single specific binding domains, these domains may be used to screen for complementary domains capable of forming a two-domain specific binding member able to bind IL-13.

This may be achieved by phage display screening methods using the so-called hierarchical dual combinatorial approach as disclosed in WO92/01047, in which an individual colony containing either an H or L chain clone is used to infect a complete library of clones encoding the other chain (L or H) and the resulting two-chain specific binding member is selected in accordance with phage display techniques such as those described in that reference. This technique is also disclosed in Marks et al, ibid.

Specific binding members of the present invention may further comprise antibody constant regions or parts thereof. For example, a VL domain may be attached at its C-terminal end to antibody light chain constant domains including human Cκ or Cλ chains, preferably Cλ chains. Similarly, a specific binding member based on a VH domain may be attached at its C-terminal end to all or part (e.g. a CH1 domain) of an immunoglobulin heavy chain derived from any antibody isotype, e.g. IgG, IgA, IgE and IgM and any of the isotype sub-classes, particularly IgG1 and IgG4. IgG4 is preferred. IgG4 is preferred because it does not bind complement and does not create effector functions. Any synthetic or other constant region variant that has these properties and stabilizes variable regions is also preferred for use in embodiments of the present invention.

Specific binding members of the invention may be labelled with a detectable or functional label. Detectable labels include radiolabels such as $^{131}$I or $^{99}$Tc, which may be attached to antibodies of the invention using conventional chemistry known in the art of antibody imaging. Labels also include enzyme labels such as horseradish peroxidase. Labels further include chemical moieties such as biotin which may be detected via binding to a specific cognate detectable moiety, e.g. labelled avidin.

Specific binding members of the present invention are designed to be used in methods of diagnosis or treatment in human or animal subjects, preferably human.

Accordingly, further aspects of the invention provide methods of treatment comprising administration of a specific binding member as provided, pharmaceutical compositions comprising such a specific binding member, and use of such a specific binding member in the manufacture of a medicament for administration, for example in a method of making a medicament or pharmaceutical composition comprising formulating the specific binding member with a pharmaceutically acceptable excipient.

Clinical indications in which an anti-IL-13 antibody may be used to provide therapeutic benefit include asthma, atopic dermatitis, allergic rhinitis, fibrosis, chronic obstructive pulmonary disease, inflammatory bowel disease, scleroderma and Hodgkin's lymphoma. As already explained, anti-IL-13 treatment is effective for all these diseases.

Anti-IL-13 treatment may be given orally, by injection (for example, subcutaneously, intravenously, intraperitoneal or intramuscularly), by inhalation, or topically (for example intraocular, intranasal, rectal, into wounds, on skin). The route of administration can be determined by the physicochemical characteristics of the treatment, by special considerations for the disease or by the requirement to optimise efficacy or to minimise side-effects.

It is envisaged that anti-IL-13 treatment will not be restricted to use in the clinic. Therefore, subcutaneous injection using a needle free device is also preferred.

Combination treatments may be used to provide significant synergistic effects, particularly the combination of an anti-IL-13 specific binding member with one or more other drugs. A specific binding member according to the present invention may be provided in combination or addition to short or long acting beta agonists, corticosteroids, cromoglycate, leukotriene (receptor) antagonists, methyl xanthines and their derivatives, IL-4 inhibitors, muscarinic receptor antagonists, IgE inhibitors, histaminic inhibitors, IL-5 inhibitors, eotaxin/CCR3 inhibitors, PDE4 inhibitors, TGF-beta antagonists, interferon-gamma, perfenidone, chemotherapeutic agents and immunotherapeutic agents.

Combination treatment with one or more short or long acting beta agonists, corticosteroids, cromoglycate, leukotriene (receptor) antagonists, xanthines, IgE inhibitors, IL-4 inhibitors, IL-5 inhibitors, eotaxin/CCR3 inhibitors, PDE4 inhibitors may be employed for treatment of asthma. Antibodies of the present invention can also be used in combination with corticosteroids, anti-metabolites, antagonists of TGF-beta and its downstream signalling pathway, for treatment of fibrosis. Combination therapy of these antibodies with PDE4 inhibitors, xanthines and their derivatives, muscarinic receptor antagonists, short and long beta antagonists can be useful for treating chronic obstructive pulmonary disease. Similar consideration of combinations apply to the use of anti-IL-13 treatment for atopic dermatitis, allergic rhinitis, chronic obstructive pulmonary disease, inflammatory bowel disease, scleroderma and Hodgkin's lymphoma.

In accordance with the present invention, compositions provided may be administered to individuals. Administration is preferably in a "therapeutically effective amount", this being sufficient to show benefit to a patient. Such benefit may be at least amelioration of at least one symptom. The actual amount administered, and rate and time-course of administration, will depend on the nature and severity of what is being treated. Prescription of treatment, e.g. decisions on dosage etc, is within the responsibility of general practitioners and other medical doctors. Appropriate doses of antibody are well known in the art; see Ledermann J. A. et al. (1991) Int. J. Cancer 47: 659-664; Bagshawe K. D. et al. (1991) Antibody, Immunoconjugates and Radiopharmaceuticals 4: 915-922.

The precise dose will depend upon a number of factors, including whether the antibody is for diagnosis or for treatment, the size and location of the area to be treated, the precise nature of the antibody (e.g. whole antibody, fragment or diabody), and the nature of any detectable label or other molecule attached to the antibody. A typical antibody dose will be in the range 100 µg to 1 gm for systemic applications, and 1 µg to 1 mg for topical applications. Typically, the antibody will be a whole antibody, preferably the IgG4 isotype. This is a dose for a single treatment of an adult patient, which may be proportionally adjusted for children and infants, and also adjusted for other antibody formats in proportion to molecular weight. Treatments may be repeated at daily, twice-weekly, weekly or monthly intervals, at the discretion of the physician. In preferred embodiments of the present invention, treatment is periodic, and the period between administrations is about two weeks or more, preferably about three weeks or more, more preferably about four weeks or more, or about once a month.

Specific binding members of the present invention will usually be administered in the form of a pharmaceutical composition, which may comprise at least one component in addition to the specific binding member.

Thus pharmaceutical compositions according to the present invention, and for use in accordance with the present invention, may comprise, in addition to active ingredient, a pharmaceutically acceptable excipient, carrier, buffer, stabiliser or other materials well known to those skilled in the art. Such materials should be non-toxic and should not interfere with the efficacy of the active ingredient. The precise nature of the carrier or other material will depend on the route of administration, which may be oral, or by injection, e.g. intravenous.

Pharmaceutical compositions for oral administration may be in tablet, capsule, powder or liquid form. A tablet may comprise a solid carrier such as gelatin or an adjuvant. Liquid pharmaceutical compositions generally comprise a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

For intravenous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required.

A composition may be administered alone or in combination with other treatments, either simultaneously or sequentially dependent upon the condition to be treated.

Specific binding members of the present invention may be formulated in liquid or solid forms depending on the physicochemical properties of the molecule and the route of delivery. Formulations may include excipients, or combinations of excipients, for example: sugars, amino acids and surfactants. Liquid formulations may include a wide range of antibody concentrations and pH. Solid formulations may be produced by lyophilisation, spray drying, or drying by supercritical fluid technology, for example. Formulations of anti-IL-13 will depend upon the intended route of delivery: for example, formulations for pulmonary delivery may consist of particles with physical properties that ensure penetration into the deep lung upon inhalation; topical formulations may include viscosity modifying agents, which prolong the time that the drug is resident at the site of action.

The present invention provides a method comprising causing or allowing binding of a specific binding member as provided herein to IL-13. As noted, such binding may take place in vivo, e.g. following administration of a specific binding member, or nucleic acid encoding a specific binding member, or it may take place in vitro, for example in ELISA, Western blotting, immunocytochemistry, immuno-precipitation, affinity chromatography, or cell based assays such as a TF-1 assay.

The amount of binding of specific binding member to IL-13 may be determined. Quantitation may be related to the amount of the antigen in a test sample, which may be of diagnostic interest.

A kit comprising a specific binding member or antibody molecule according to any aspect or embodiment of the present invention is also provided as an aspect of the present invention. In a kit of the invention, the specific binding member or antibody molecule may be labelled to allow its reactivity in a sample to be determined, e.g. as described further below. Components of a kit are generally sterile and in sealed vials or other containers. Kits may be employed in diagnostic analysis or other methods for which antibody molecules are useful. A kit may contain instructions for use of the components in a method, e.g. a method in accordance with the present invention. Ancillary materials to assist in or to enable performing such a method may be included within a kit of the invention.

The reactivities of antibodies in a sample may be determined by any appropriate means. Radioimmunoassay (RIA) is one possibility. Radioactive labelled antigen is mixed with unlabelled antigen (the test sample) and allowed to bind to the antibody. Bound antigen is physically separated from unbound antigen and the amount of radioactive antigen bound to the antibody determined. The more antigen there is in the test sample the less radioactive antigen will bind to the antibody. A competitive binding assay may also be used with non-radioactive antigen, using antigen or an analogue linked to a reporter molecule. The reporter molecule may be a fluorochrome, phosphor or laser dye with spectrally isolated absorption or emission characteristics. Suitable fluorochromes include fluorescein, rhodamine, phycoerythrin and Texas Red. Suitable chromogenic dyes include diaminobenzidine.

Other reporters include macromolecular colloidal particles or particulate material such as latex beads that are coloured, magnetic or paramagnetic, and biologically or chemically active agents that can directly or indirectly cause detectable signals to be visually observed, electronically detected or otherwise recorded. These molecules may be enzymes which catalyse reactions that develop or change colours or cause changes in electrical properties, for example. They may be molecularly excitable, such that electronic transitions between energy states result in characteristic spectral absorptions or emissions. They may include chemical entities used in conjunction with biosensors. Biotin/avidin or biotin/streptavidin and alkaline phosphatase detection systems may be employed.

The signals generated by individual antibody-reporter conjugates may be used to derive quantifiable absolute or relative data of the relevant antibody binding in samples (normal and test).

The present invention also provides the use of a specific binding member as above for measuring antigen levels in a competition assay, that is to say a method of measuring the level of antigen in a sample by employing a specific binding member as provided by the present invention in a competition assay. This may be where the physical separation of bound from unbound antigen is not required. Linking a reporter molecule to the specific binding member so that a physical or optical change occurs on binding is one possibility. The reporter molecule may directly or indirectly generate detectable, and preferably measurable, signals. The linkage of reporter molecules may be directly or indirectly, covalently, e.g. via a peptide bond or non-covalently. Linkage via a peptide bond may be as a result of recombinant expression of a gene fusion encoding antibody and reporter molecule.

The present invention also provides for measuring levels of antigen directly, by employing a specific binding member according to the invention for example in a biosensor system.

The mode of determining binding is not a feature of the present invention and those skilled in the art are able to choose a suitable mode according to their preference and general knowledge.

As noted, in various aspects and embodiments, the present invention extends to a specific binding member which competes for binding to IL-13 with any specific binding member defined herein, e.g. BAK502G9 IgG4. Competition between binding members may be assayed easily in vitro, for example by tagging a specific reporter molecule to one binding member which can be detected in the presence of other untagged binding member(s), to enable identification of specific binding members which bind the same epitope or an overlapping epitope.

Competition may be determined for example using ELISA in which IL-13 is immobilised to a plate and a first tagged binding member along with one or more other untagged binding members is added to the plate. Presence of an untagged binding member that competes with the tagged binding member is observed by a decrease in the signal emitted by the tagged binding member.

In testing for competition a peptide fragment of the antigen may be employed, especially a peptide including an epitope of interest. A peptide having the epitope sequence plus one or more amino acids at either end may be used. Such a peptide may be said to "consist essentially" of the specified sequence. Specific binding members according to the present invention may be such that their binding for antigen is inhibited by a peptide with or including the sequence given. In testing for this, a peptide with either sequence plus one or more amino acids may be used.

Specific binding members which bind a specific peptide may be isolated for example from a phage display library by panning with the peptide(s).

The present invention further provides an isolated nucleic acid encoding a specific binding member of the present invention. Nucleic acid may include DNA and/or RNA. In a preferred aspect, the present invention provides a nucleic acid which codes for a CDR or set of CDR's or VH domain or VL domain or antibody antigen-binding site or antibody molecule, e.g. scFv or IgG4, of the invention as defined above.

The present invention also provides constructs in the form of plasmids, vectors, transcription or expression cassettes which comprise at least one polynucleotide as above.

The present invention also provides a recombinant host cell which comprises one or more constructs as above. A nucleic acid encoding any CDR or set of CDR's or VH domain or VL domain or antibody antigen-binding site or antibody molecule, e.g. scFv or IgG4 as provided, itself forms an aspect of the present invention, as does a method of production of the encoded product, which method comprises expression from encoding nucleic acid therefor. Expression may conveniently be achieved by culturing under appropriate conditions recombinant host cells containing the nucleic acid. Following production by expression a VH or VL domain, or specific binding member may be isolated and/or purified using any suitable technique, then used as appropriate.

Specific binding members, VH and/or VL domains, and encoding nucleic acid molecules and vectors according to the present invention may be provided isolated and/or purified, e.g. from their natural environment, in substantially pure or homogeneous form, or, in the case of nucleic acid, free or substantially free of nucleic acid or genes origin other than the sequence encoding a polypeptide with the required function. Nucleic acid according to the present invention may comprise DNA or RNA and may be wholly or partially synthetic. Reference to a nucleotide sequence as set out herein encompasses a DNA molecule with the specified sequence, and encompasses a RNA molecule with the specified sequence in which U is substituted for T, unless context requires otherwise.

Systems for cloning and expression of a polypeptide in a variety of different host cells are well known. Suitable host cells include bacteria, mammalian cells, plant cells, yeast and baculovirus systems and transgenic plants and animals. Mammalian cell lines available in the art for expression of a heterologous polypeptide include Chinese hamster ovary (CHO) cells, HeLa cells, baby hamster kidney cells, NS0 mouse melanoma cells, YB2/0 rat myeloma cells, human embryonic kidney cells, human embryonic retina cells and many others. A common, preferred bacterial host is *E. coli*.

The expression of antibodies and antibody fragments in prokaryotic cells such as *E. coli* is well established in the art. For a review, see for example PlUckthun, A. Bio/Technology 9: 545-551 (1991). Expression in eukaryotic cells in culture is also available to those skilled in the art as an option for production of a specific binding member for example Chadd H E and Chamow S M (2001) 110 Current Opinion in Biotechnology 12: 188-194, Andersen D C and Krummen L (2002) Current Opinion in Biotechnology 13: 117, Larrick J W and Thomas D W (2001) Current opinion in Biotechnology 12:411-418.

Suitable vectors can be chosen or constructed, containing appropriate regulatory sequences, including promoter sequences, terminator sequences, polyadenylation sequences, enhancer sequences, marker genes and other sequences as appropriate. Vectors may be plasmids, viral e.g. 'phage, or phagemid, as appropriate. For further details see, for example, *Molecular Cloning: a Laboratory Manual:* 3rd edition, Sambrook and Russell, 2001, Cold Spring Harbor Laboratory Press. Many known techniques and protocols for manipulation of nucleic acid, for example in preparation of nucleic acid constructs, mutagenesis, sequencing, introduction of DNA into cells and gene expression, and analysis of proteins, are described in detail in *Current Protocols in Molecular Biology*, Second Edition, Ausubel et al. eds., John Wiley & Sons, 1988, *Short Protocols in Molecular Biology: A Compendium of Methods from Current Protocols in Molecular Biology*, Ausubel et al. eds., John Wiley & Sons, 4$^{th}$ edition 1999. The disclosures of Sambrook et al. and Ausubel et al. (both) are incorporated herein by reference.

Thus, a further aspect of the present invention provides a host cell containing nucleic acid as disclosed herein. Such a host cell may be in vitro and may be in culture. Such a host cell may be in vivo. In vivo presence of the host cell may allow intracellular expression of the specific binding members of the present invention as "intrabodies" or intracellular antibodies. Intrabodies may be used for gene therapy [112].

A still further aspect provides a method comprising introducing such nucleic acid into a host cell. The introduction may employ any available technique. For eukaryotic cells, suitable techniques may include calcium phosphate transfection, DEAE-Dextran, electroporation, liposome-mediated transfection and transduction using retrovirus or other virus, e.g. vaccinia or, for insect cells, baculovirus. Introducing nucleic acid in the host cell, in particular a eukaryotic cell may use a viral or a plasmid based system. The plasmid system may be maintained episomally or may incorporated into the host cell or into an artificial chromosome [110,111]. Incorporation may be either by random or targeted integration of one or more copies at single or multiple loci. For bacterial cells, suitable techniques may include calcium chloride transformation, electroporation and transfection using bacteriophage.

The introduction may be followed by causing or allowing expression from the nucleic acid, e.g. by culturing host cells under conditions for expression of the gene.

In one embodiment, the nucleic acid of the invention is integrated into the genome (e.g. chromosome) of the host cell. Integration may be promoted by inclusion of sequences which promote recombination with the genome, in accordance with standard techniques.

The present invention also provides a method which comprises using a construct as stated above in an expression system in order to express a specific binding member or polypeptide as above.

Aspects and embodiments of the present invention will now be illustrated by way of example with reference to the following experimentation.

EXAMPLE 1

Isolation of Anti-IL-13 scFv

ScFv Antibody Repertoire

A large single chain Fv (scFv) human antibody library derived from spleen lymphocytes from 20 donors and cloned into a phagemid vector was used for selections [66].

Selection of scFv

ScFv which recognised IL-13 were isolated from phage display libraries in a series of repeated selection cycles on recombinant bacterially derived human or murine IL-13 (Peprotech) essentially as described in [67]. In brief, following incubation with the library, the immobilised antigen, which had been pre-coupled to paramagnetic beads, and bound phage were recovered by magnetic separation whilst unbound phage were washed away. Bound phage was then rescued as described by Vaughan et al [67] and the selection process repeated. Different solid surfaces and capture methods were used at different rounds of selection to reduce non-specific binding. Antigen was either covalently coupled to beads (Dynabeads M-270 carboxylic acid) or modified by biotinylation prior to secondary capture by streptavidin-coated beads (Dynabeads M-280) according to manufacturer's protocols (Dynal). A representative proportion of clones from the output of selection rounds were subjected to DNA sequencing as described in Vaughan et al [67] and Osbourn et al [70]. Unique clones were assessed for their ability to neutralise IL-13 as purified scFv preparations in IL-13 dependent cell proliferation assays.

Ribosome display libraries were created and screened for scFv that specifically recognised recombinant, bacterially derived human or murine IL-13 (Peprotech), essentially as described in Hanes et al [113]. Initially the BAK278D6 lead clone from the initial selections was converted to ribosome display format, and this template was subsequently used for library creation. On the DNA level, a T7 promoter was added at the 5'-end for efficient transcription to mRNA. On the mRNA level, the construct contained a prokaryotic ribosome-binding site (Shine-Dalgarno sequence). At the 3' end of the single chain, the stop codon was removed and a portion of gIII (gene III) was added to act as a spacer [113].

Ribosome display libraries derived from BAK278D6 were created by mutagenesis of antibody complementarity determining regions (CDRs) where PCR reactions were performed with non-proof reading Taq polymerase. Affinity-based selections were performed whereby, following incubation with the library, the biotinylated human-IL-13 was captured by streptavidin-coated paramagnetic beads (Dynal M280) and bound tertiary complexes (mRNA-ribosome-scFv-IL-13) were recovered by magnetic separation whilst unbound complexes were washed away. The mRNA encoding the bound scFvs were then recovered by RT-PCR as described in Hanes et al [113] and the selection process repeated with decreasing concentrations (100 nM-100 pM over 5 rounds) of biotinylated human IL-13 present during the selection.

Error-prone PCR was also used to further increase library size. Three intensities of error were employed (2.0, 3.5 and 7.2 mutations per 1,000 by after a standard PCR reaction, as described in manufacturer's protocol (Clontech)) during the selection regime. Initial error prone PCR reactions took place before round one selections commenced at 100 nM. A subsequent round of error prone PCR was performed before round three selections at 10 nM biotinylated human-IL-13. As above, a representative proportion of clones from the output of selection rounds were subjected to DNA sequencing as described in Vaughan et al [67] and Osbourn et al [70]. Unique clones were assessed for their ability to neutralise IL-13 as purified scFv preparations in IL-13 dependent cell proliferation assays.

EXAMPLE 2

Neutralisation Potency of Anti-IL-13 scFv in the IL-13 Dependent TF-1 Cell Proliferation Assay The neutralisation potency of purified scFv preparations against human and murine IL-13 bioactivity was assessed using TF-1 cell proliferation assay. Purified scFv preparations were prepared as described in Example 3 of WO01/66754. Protein concentrations of purified scFv preparations were determined using the BCA method (Pierce). TF-1 is a human premyeloid cell line established from a patient with erythroleukemia [68]. The TF-1 cell line is factor dependent for survival and proliferation. In this respect TF-1 cells responded to either human or murine IL-13 [69] and were maintained in media containing human GM-CSF (4 ng/ml, R&D Systems). Inhibition of IL-13 dependent proliferation was determined by measuring the reduction in incorporation of tritiated thymidine into the newly synthesized DNA of dividing cells.

TF-1 Cell Assay Protocol

TF-1 cells were obtained from R&D Systems and maintained according to supplied protocols. Assay media comprised RPMI-1640 with GLUTAMAX I (Invitrogen) containing 5% foetal bovine serum (JRH) and 1% sodium pyruvate (Sigma). Prior to each assay, TF-1 cells were pelleted by centrifugation at 300×g for 5 mins, the media removed by aspiration and the cells resuspended in assay media. This process was repeated twice with cells resuspended at a final concentration of $10^5$ cells/ml in assay media. Test solutions of antibody (in triplicate) were diluted to the desired concentration in assay media. An irrelevant antibody not directed at IL-13 was used as a negative control. Recombinant bacterially derived human or murine IL-13 (Peprotech) was added to a final concentration of 50 ng/ml when mixed with the appropriate test antibody in a total volume of 100 μl/well in a 96 well assay plate. The concentration of IL-13 used in the assay was selected as the dose that at final assay concentration gave approximately 80% of the maximal proliferative response. All samples were incubated for 30 minutes at room temperature. 100 μl of resuspended cells were then added to each assay point to give a total assay volume of 200 μl/well. Assay plates were incubated for 72 hours at 37° C. under 5% $CO_2$. 25 μl of tritiated thymidine (10 μCi/ml, NEN) was then added to each assay point and assay plates were returned to the incubator for a further 4 hours. Cells were harvested on glass fibre filter plates (Perkin Elmer) using a cell harvester. Thymidine incorporation was determined using a Packard Top-Count microplate liquid scintillation counter. Data were analysed using Graphpad Prism software.

Results

Despite alternating selection cycles between human and murine antigen no cross-reactive neutralising antibodies were obtained. Two distinct anti-human and one anti-murine IL-13 neutralising scFvs were obtained from selections. BAK278D6 (VH SEQ ID NO: 13; VL SEQ ID NO: 14) and BAK167A11 (VH SEQ ID NO: 23; VL SEQ ID NO: 24) recognised human IL-13 whilst BAK209B11 (VH SEQ ID NO: 25; VL SEQ ID NO: 26) recognised murine IL-13. BAK278D6 (FIG. 2) and BAK167A11 (FIG. 1) as scFv neutralised 25 ng/ml human IL-13 with an $IC_{50}$ of 44 nM and 111 nM respectively. BAK209B11 (FIG. 3) as a scFv neutralised 25 ng/ml murine IL-13 with an $IC_{50}$ of 185 nM.

EXAMPLE 3

Neutralisation Potency of Lead Clones from Targeted Optimisation of Heavy Chain CDR3 of Parental Clones in the IL-13 Dependent TF-1 Cell Proliferation Assay Osbourn et al. [70] have demonstrated that targeted mutagenesis of residues within heavy chain CDR3 can significantly improve the affinity of antibodies. Selections were performed as described in Example 1, on scFv repertoires in which residues within the heavy chain CDR3 of BAK278D6 (SEQ ID NO: 6) BAK167A11 (SEQ ID NO: 57) had been randomised by mutagenesis. Unique clones from the selection output were identified by DNA sequencing and their neutralising potency assessed as scFv in the TF-1 cell proliferation assay, as described in Example 2.

Results

Figure 2:
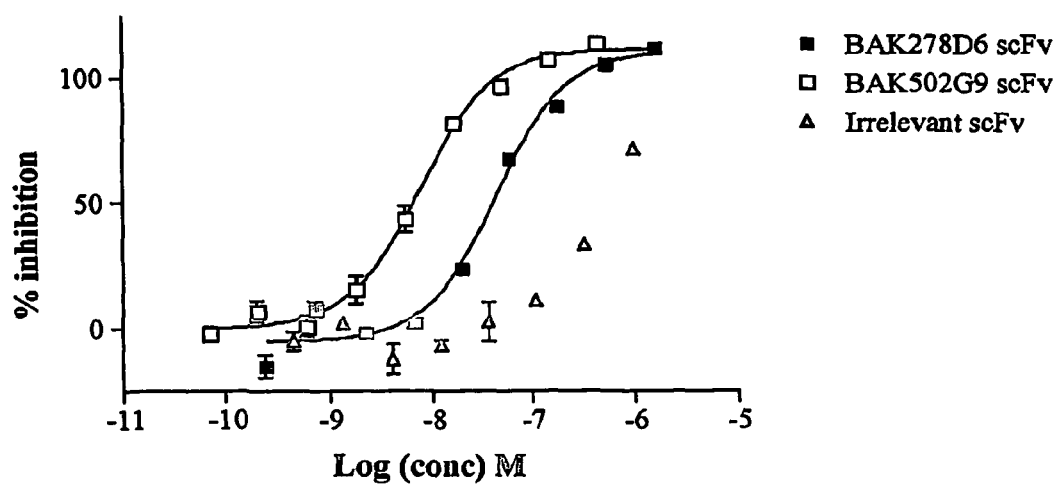
FIG. 2 shows the neutralisation potency (% inhibition) of BAK278D6 (closed squares) and its derivative BAK502G9 (open squares) as scFv against 25 ng/ml human IL-13 in the TF-1 cell proliferation assay. The triangles represent an irrelevant scFv. Data represent the mean with standard error bars of triplicate determinations within the same experiment.
Figure 3:
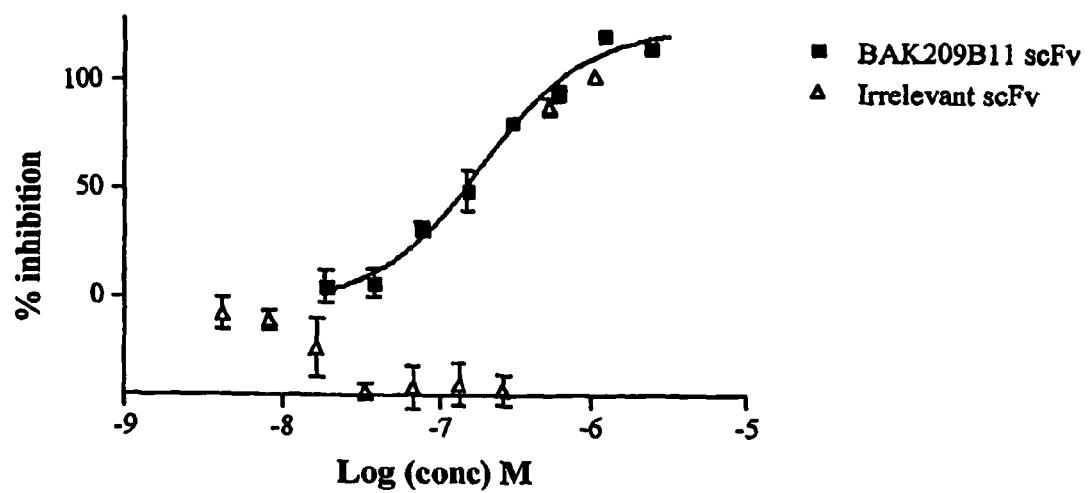
FIG. 3 shows the neutralisation potency (% inhibition) of BAK209B11 (closed squares) as a scFv against 25 ng/ml murine IL-13 in the TF-1 cell proliferation assay. The triangles represent an irrelevant scFv. Data represent the mean with standard error bars of triplicate determinations within the same experiment.

Significant gains in potency were achieved for both lineages. The most potent clones from the BAK167A11 lineage were BAK615E3, BAK612B5 and BAK582F7 which as scFv had $IC_{50}$ of 3 nM (FIG. 1), 6.6 nM, 6.65 nM respectively against 25 ng/ml human IL-13 in TF-1 cell proliferation assay. From the BAK278D6 lineage, the most potent clone was BAK502G9, which as scFv had $IC_{50}$ of 8 nM against 25 ng/ml human IL-13 in the TF-1 cell proliferation assay (FIG. 2).

EXAMPLE 4

Neutralisation Potency of BAK167A11 and BAK278D6 Lineages Against Non-Human Primate IL-13 and an IL-13 Variant Associated with Asthma in the TF-1 Factor Dependent Cell Proliferation Assay Neither of the BAK167A11 and BAK278D6 human IL-13 neutralising lineages were murine cross-reactive. The inventors therefore decided on the following criteria for the lineage selected for further optimisation and clinical development: should preferably be cross-reactive with non-human primate IL-13 and should recognise a variant of IL-13, in which arginine at amino acid at position 130 is substituted for by glutamine (Q130R). This variant has been genetically associated with asthma and other allergic diseases [37, 39, 41, 71]. Cross-reactivity was determined by the ability of purified scFv preparations to bind non-human primate IL-13 and IL-13 variant by surface plasmon resonance (BIAcore) analysis. Functional activity was determined using the TF-1 cell proliferation assay.

Production of Wild-Type, Variant and Non-Human Primate IL-13

A cDNA for wild-type human IL-13 was obtained from InvivoGen and modified by site-directed mutagenesis (Stratagene Quikchange® kit) to yield a cDNA encoding variant IL-13. The coding sequence for both rhesus and cynomolgus monkey IL-13 was obtained by PCR on genomic DNA template using degenerate primers based on the human IL-13 sequence. Both non-human primate (rhesus and cynomolgus) sequences were identical to each other but differed from human IL-13 by seven amino acids (FIG. 19). Recombinant wild type, variant and non-human primate IL-13 were subsequently expressed using the baculovirus expression system (Invitrogen). Expression constructs added a carboxyl terminus affinity tag to the expressed protein that allowed purification from insect cell conditioned media to near homogeneity.

Qualitative Binding Assay Using BIAcore

The binding affinity of purified scFv preparations to non-human primate, variant and wild type IL-13 was determined by surface plasmon resonance measurements using a BIAcore 2000 Biosensor (BIAcore AB) as described in Karlsson et al [72]. In brief, IL-13 was coupled to CM5 sensorchips using an amine coupling kit (BIAcore) at a surface density of approximately 200Ru and three concentrations of test scFv (approximately 350 nM, 175 nM and 88 nM) in HBS-EP buffer passed over the sensor chip surface. The resulting sensorgrams were evaluated using BIA evaluation 3.1 software to provide relative binding data.

TF-1 Assay Protocol

The assay was performed essentially as described in Example 2 with the following modifications: non-human primate IL-13, human variant IL-13 (Q130R) and wild type human IL-13 were used at concentrations of 50 ng/ml, 25 ng/ml and 25 ng/ml respectively.

Results

Figure 4A:
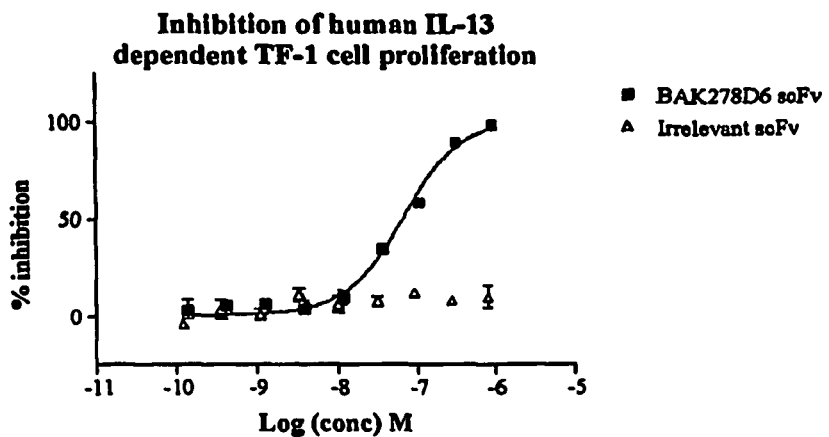
FIG. 4A show potency against 25 ng/ml human IL-13.
Figure 4B:
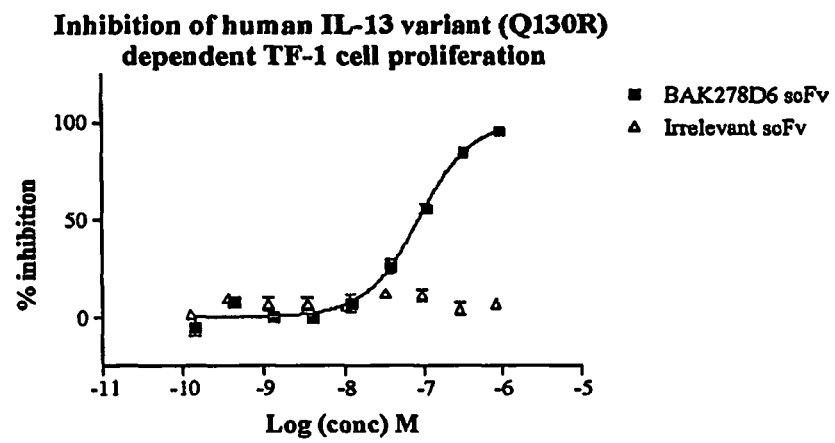
FIG. 4B shows potency against 25 ng/ml human variant IL-13.
Figure 4C:
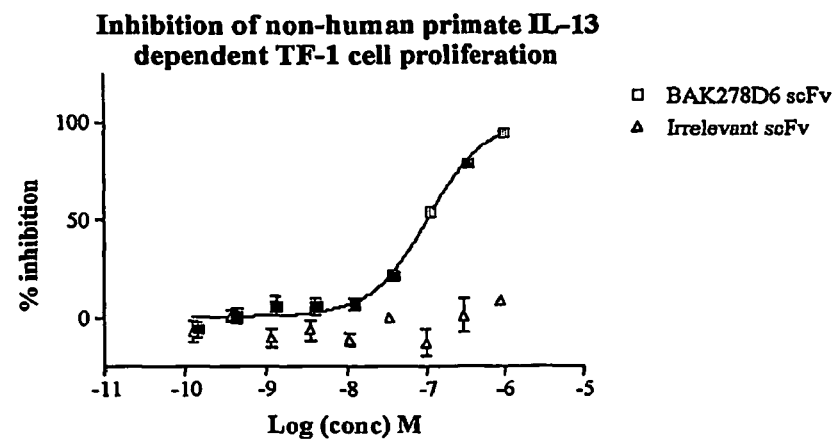
FIG. 4C shows potency against 50 ng/ml non-human primate IL-13.

BIAcore binding assay data suggested that BAK278D6 but not BAK167A11 lineage had the required cross-reactivity profile for further therapeutic development (Table 2). This finding was supported by bioassay data demonstrating that BAK278D6 (FIG. 4) and BAK502G9 (FIG. 6) were able to neutralise human IL-13, the human IL-13 (Q130R) variant and non-human primate IL-13 in the TF-1 cell proliferation assay with near equivalent potency. In contrast, although BAK615E3 (VH SEQ ID NO: 33; VL SEQ ID NO: 34) had a significantly increased potency against human IL-13 over its parent BAK167A11 (VH SEQ ID NO: 23; VL SEQ ID NO: 24) in the TF-1 cell proliferation assay (FIG. 1), neither clone bound non-human primate or variant IL-13 in the BIAcore binding assay.

Germlining Framework Regions of BAK278D6 and BAK502G9

The derived amino acid sequence of BAK278D6 VH (SEQ ID NO: 13) and VL (SEQ ID NO: 14) were aligned to the known human germline sequences in the VBASE database [73] and the closest germline identified by sequence similarity. The closest germline for the VH domain of BAK278D6 (SEQ ID NO: 14) and its derivatives, was identified as DP14, a member of the VH1 family. The BAK278D6 VH has 9 changes from the DP14 germline within framework regions. The closest germline for the VL of BAK278D6 was identified as $V_\lambda 3$ h. The BAK278D6 VL domain (SEQ ID NO: 14) has only 5 changes from the germline within framework regions. Framework regions of BAK278D6 and its derivatives were returned to germline by site directed mutagenesis (Stratagene Quikchange kit) to identically match native human antibodies.

EXAMPLE 5

Neutralisation Potency of Lead Clones from Targeted Optimisation of Heavy Chain CDR1 and Heavy Chain CDR2 Sequences of BAK502G9 in the Human IL-13 Dependent TF-1 Cell Proliferation Assay A second phase of optimisation was performed using BAK502G9 sequence, with germlined framework regions, as a template. Selections were performed essentially as described in Example 1 on scFv repertoires in which either residues within the heavy chain CDR1 or heavy chain CDR2 of BAK502G9 had been randomised by mutagenesis. Unique clones from the selection output were identified by DNA sequencing and their neutralising potency assessed as purified scFv preparations in the TF-1 cell proliferation assay as described in Example 2. Vectors were constructed for the most potent scFv clones to allow re-expression as whole human IgG4 antibody as described by Persic et al. (1997 Gene 187; 9-18) with a few modifications. An oriP fragment was included in the vectors to facilitate use with HEK-EBNA 293 cells and to allow episomal replication. The VH variable domain was cloned into the polylinker between the secretion leader sequence and the human gamma 4 constant domain of the expression vector pEU8.1(+). The VL variable domain was cloned into the polylinker between the secretion leader sequence and the human lambda constant domain of the expression vector pEU4.1(−).

Whole antibody was purified from conditioned media from EBNA-293 cells co-transfected with constructs expressing heavy and light chains by protein A affinity chromatography (Amersham Pharmacia). The purified antibody preparations were sterile filtered and stored at 4° C. in phosphate buffered saline (PBS) prior to evaluation. Protein concentration was determined by measuring absorbance at 280 nm using the BCA method (Pierce). Reformatted human IgG4 whole antibodies were compared to commercially available anti-human IL-13 antibodies in the TF-1 proliferation assay described in Example 2.

Results

Figure 5:
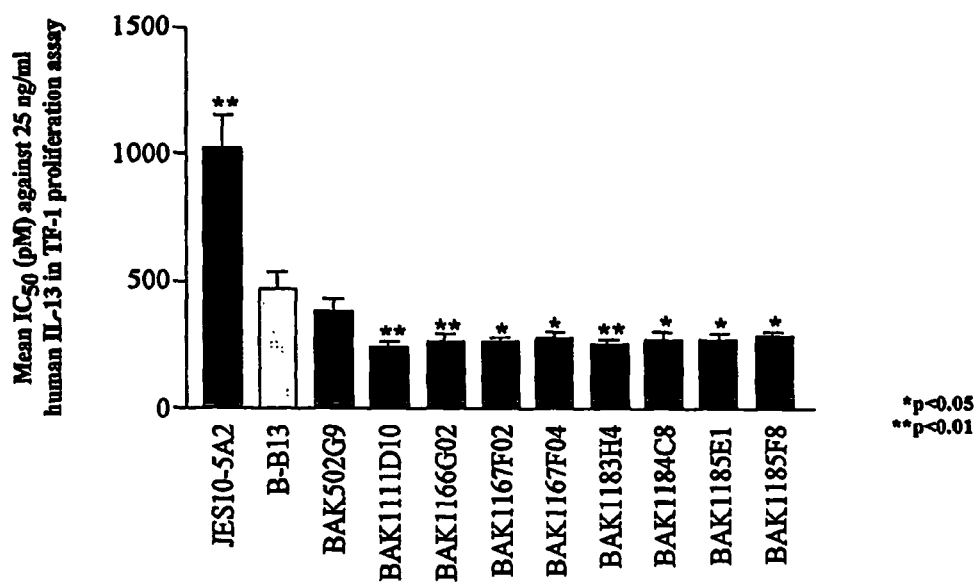
FIG. 5 shows a comparison of the potency of anti-human IL-13 antibodies in the TF-1 proliferation assay. Data represent the mean neutralisation potency with standard error bars over 5-7 experiments against 25 ng/ml human IL-13. The performance relative to the commercially available antibody, B-B13, was evaluated statistically by performing a one-way ANOVA with Dunnett's test. * $P<0.05$, ** $P<0.01$ compared to B-B13.

As demonstrated in FIG. 5, the commercial antibody B-B13, (mouse IgG1-Euroclone 5) was shown to be significantly more potent against human IL-13 than the commercial antibody JES10-5A2 (rat IgG1-Biosource) with $IC_{50}$ of 1021 pM and 471 pM respectively. Eight clones, namely, BAK1111D10, BAK1166G02, BAK1167F02, BAK1167F04, BAK1183H4, BAK1184C8, BAK1185E1, BAK1185F8, derived from BAK502G9 (and so "BAK502G9 lineage"), in which the heavy chain CDR1 or CDR2 had been targeted, showed improved potency as scFv over the commercial antibodies. These improvements were maintained on conversion to whole antibody human IgG4. Each of these VH and VL domains individually and in the respective pairings of these claims represents an aspect or embodiment of the present invention, as do specific binding members for IL-13 that comprise one or more of them, also specific binding members comprising one or more CDR's from the BAK502G9 lineage clones, preferably a VH domain comprising a BAK502G9 lineage set of HCDR's and/or a VL domain comprising a BAK502G9 lineage set of LCDR's. These may be employed in any and all aspects of the invention as disclosed elsewhere herein. Derivatives of BAK502G9 as whole antibodies (IgG4) had an $IC_{50}$ ranging from 244 pM to 283 pM. BAK502G9 as a whole antibody IgG4 had an $IC_{50}$ of 384 pM. In summary, major improvements in potency could be obtained by targeting heavy chain CDR1 (SEQ ID NO:7) or CDR2 (SEQ ID NO: 8) of BAK502G9. Statistical comparisons to B-B13 were made using an ANOVA followed by a Dunnett's post test analysis (InStat software).

Further Characterisation

Selected anti-human antibodies from the BAK278D6 lineage underwent further characterisation to determine their specificity. These included BAK502G9 (VH SEQ ID NO: 15; VL SEQ ID NO: 16) and its derivatives BAK1167F2 (VH SEQ ID NO: 35; VL SEQ ID NO: 36) and BAK1183H4 (VH SEQ ID NO: 37; VL SEQ ID NO: 38), which are representative examples of clones with modifications to heavy chain CDR1 and heavy chain CDR2 of BAK502G9 respectively.

EXAMPLE 6

Neutralisation Potency of Lead Clones from Targeted Optimisation of Heavy Chain CDR1 and Heavy Chain CDR2 Sequences of BAK5D2G9 Against Non-Human Primate IL-13 and an IL-13 Variant Associated with Asthma in the TF-1 Factor Dependent Cell Proliferation Assay Cross-reactivity of anti-human IL-13 antibodies was determined by their ability to inhibit non-human primate IL-13 and IL-13 variant mediated TF-1 cell proliferation as described in Example 4.

Results

Figure 6A:
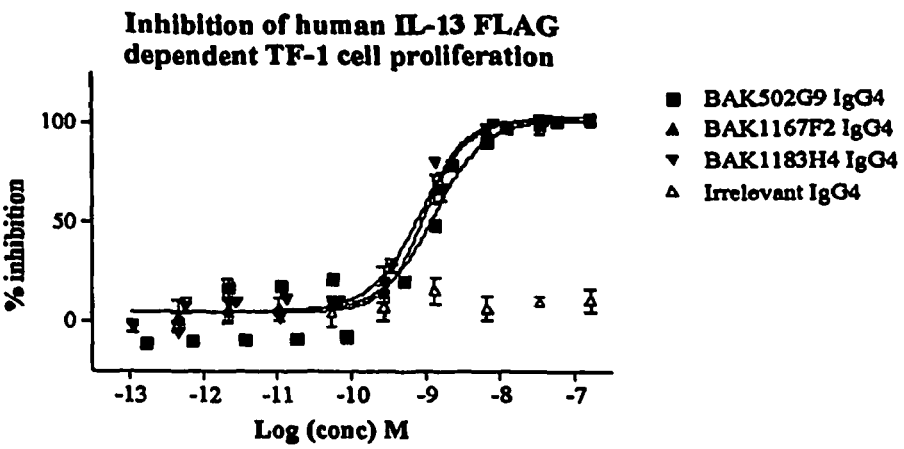
FIG. 6A shows potency against 25 ng/ml human IL-13.
Figure 6B:
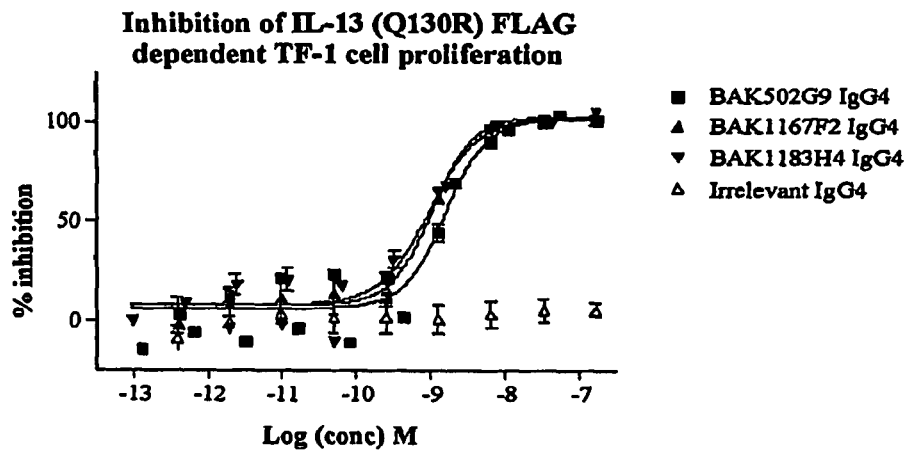
FIG. 6B shows potency against 25 ng/ml human variant IL-13.
Figure 6C:
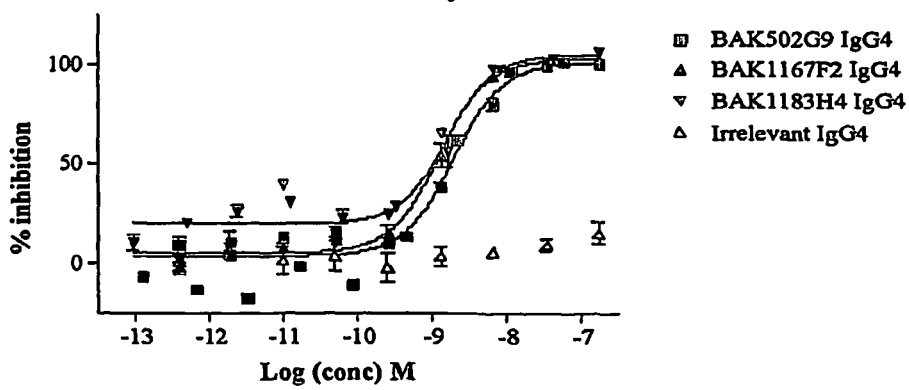
FIG. 6C shows potency against 50 ng/ml non-human primate IL-13.

Optimised anti-human IL-13 antibodies BAK1167F2 (VH SEQ ID NO: 35; VL SEQ ID NO: 36) and BAK1183H4 (VH SEQ ID NO: 37; VL SEQ ID NO: 38) maintained the specificity of their parent BAK502G9 (VH SEQ ID NO: 15; VL SEQ ID NO: 16) (FIG. 6). Potency gains against wild type IL-13 were reflected in their ability to neutralise non-human primate IL-13 and an IL-13 variant with substantially equivalent potency. The $IC_{50}$ for BAK502G9 against human, human variant and non-human primate IL-13 were 1.4 nM, 1.9 nM and 2.0 nM respectively. The $IC_{50}$ for BAK1167F2 against human, human variant and non-human primate IL-13 were 1.0 nM, 1.1 nM and 1.3 nM respectively. The $IC_{50}$ for BAK1183H4 against human, human variant and non-human primate IL-13 were 0.9 nM, 1.0 nM and 1.6 nM respectively. These clone's are suitable for therapeutic use.

EXAMPLE 7

Neutralising Potency of Lead Anti-Human IL-13 Antibodies Against Native Human IL-13 in HDLM-2 Cell Proliferation Assay The human IL-13 sequence has four potential N-glycosylation sites. The inventors have demonstrated the ability of BAK278D6 and its derivatives to neutralise recombinant IL-13 expressed either in bacterial or baculovirus expression systems. Although, there is evidence that many processing events known in mammalian systems do also occur in insects there are key differences in protein glycosylation, particularly N-glycosylation [74].

The inventors investigated the ability of BAK278D6 derivatives to neutralise native IL-13 released from human cells.

HDLM-2 cells were isolated by Drexler et al [75] from a patient with Hodgkin's disease. Skinnider et al [76] demonstrated that HDLM-2 cell proliferation was in part dependent on autocrine and paracrine release of IL-13. Lead anti-human IL-13 antibodies were assessed for their ability to inhibit HDLM-2 cell proliferation mediated by the release of native (or naturally occurring) IL-13.

HDLM-2 Cell Assay Protocol

HDLM-2 cells were obtained from the Deutsche Sammlung von Mikroorganismen and Zellkulturen (DSMZ) and maintained according to supplied protocols. Assay media comprised RPI-1640 with Glutamax I (Invitrogen) containing 20% foetal bovine serum. Prior to each assay, the cells were pelleted by centrifugation at 300×g for 5 min, the media removed by aspiration and the cells resuspended in fresh media. This process was repeated three times and the cells were finally resuspended to a final concentration of $2\times10^5$ cells/ml in assay media. 50 µl of resuspended cells were added to each assay point in a 96 well assay plate. Test solutions of antibodies (in triplicate) were diluted to the desired concentration in assay media. An irrelevant isotype antibody not directed at IL-13 was used as a negative control. The appropriate test antibody in a total volume of 50 µl/well were added to the cells, each assay point giving a total assay volume of 100 µl/well. Assay plates were incubated for 72 hours at 37° C. under 5% $CO_2$. 25 µl of tritiated thymidine (10 µCi/ml, NEN) was then added to each assay point and assay plates were returned to the incubator for a further 4 hours. Cells were harvested on glass fibre filter plates (Perkin Elmer) using a cell harvester. Thymidine incorporation was determined using a Packard TopCount microplate liquid scintillation counter. Data were analysed using Graphpad Prism software.

Results

As demonstrated in FIG. 7, BAK502G9 (VH SEQ ID NO: 15; VL SEQ ID NO: 16), and its derivatives BAK1183H4 (VH SEQ ID NO: 37; VL SEQ ID NO: 38) and BAK1167F2 (VH SEQ ID NO: 35; VL SEQ ID NO: 36) were able to cause a dose dependent inhibition of cell proliferation with relative potencies similar to those observed in other bioassays. $IC_{50}$ for BAK502G9, BAK1183H4, BAK1167F2 as human IgG4 were 4.6 nM, 3.5 nM and 1.1 nM respectively. $IC_{50}$ for the commercial antibodies JES10-5A2 and B-B13 were 10.7 nM and 16.7 nM respectively.

EXAMPLE 8

Neutralising Potency of Lead Anti-Human IL-13 Antibodies Against IL-13 Dependent Responses in Disease Relevant Primary Cells Secondary bioassays were performed using primary cells and readouts more relevant to airway disease. These included eotaxin release from normal human lung fibroblasts (NHLF) and vascular adhesion molecule 1 (VCAM-1) upregulation on the surface of human umbilical vein endothelial cells (HUVEC). Both IL-13 dependent responses could contribute to eosinophil recruitment, a feature of the asthma phenotype [92].
NHLF Assay Protocol IL-13 has been shown to cause eotaxin release from lung fibroblasts[77] [78] [79]. Factor dependent eotaxin release from NHLF was determined by ELISA.

Figure 8:
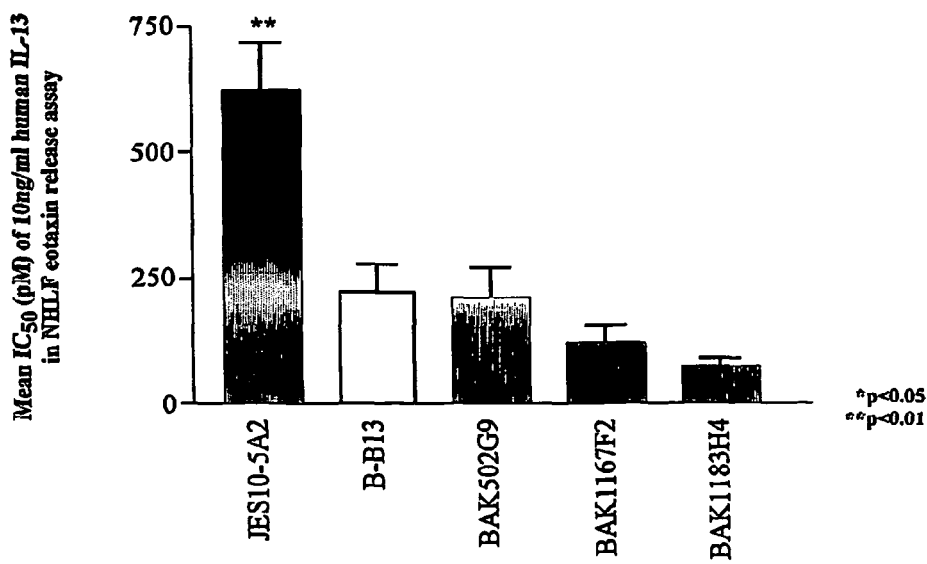
FIG. 8 shows a comparison of the potency of anti-human IL-13 antibodies in the NHLF assay. Data represent the mean neutralisation potency ($IC_{50}$ pM) with standard error bars over 4-5 experiments against 10 ng/ml human IL-13 in the NHLF eotaxin release assay. The performance relative to the commercially available antibody, B-B13, was evaluated statistically by performing a one-way ANOVA with Dunnett's test. * $P<0.05$, ** $P<0.01$ compared to B-B13.

NHLF were obtained from Biowhittaker and maintained according to supplied protocols. Assay media was FGM-2 (Biowhittaker). Test solutions of antibody (in triplicate) were diluted to the desired concentration in assay media. An irrelevant antibody not directed at IL-13 was used as a negative control. Recombinant bacterially-derived human IL-13 (Peprotech) was subsequently added to a final concentration of 10 ng/ml when mixed with the appropriate test antibody in a total volume of 200 µl. The concentration of IL-13 used in the assay was selected as the dose that gave an approximately 80% of the maximal response. All samples were incubated for 30 minutes at room temperature. Assay samples were then added to NHLF that had been preseeded at a density of $1\times10^4$ cells per well in 96-well assay plates. Assay plates were incubated at 37° C. for 16-24 hours at 37° C. under 5% $CO_2$. Assay plates were centrifuged at 300×g for 5 minutes to pellet detached cells. Eotaxin levels in the supernatant were determined by ELISA using reagents and methods described by the manufacturer (R&D Systems). Data were analysed using Graphpad Prism software.
Results BAK278D6 lineage clones were able to inhibit human IL-13 dependent eotaxin release from NHLF. Relative potency was similar to that observed in the TF-1 cell proliferation assay (FIG. 8). BAK502G9 (VH SEQ ID NO: 15; VL SEQ ID NO: 16), BAK1183H4 (VH SEQ ID NO: 37; VL SEQ ID NO: 38), BAK1167F2 (VH SEQ ID NO: 35; VL SEQ ID NO: 36) had $IC_{50}$ of 207 pM, 118 pM and 69 pM respectively against 10 ng/ml human IL-13. Commercial antibodies JES10-5A2 and B-B13 had $IC_{50}$ of 623 pM and 219 pM respectively.
HUVEC Assay Protocol IL-13 has been shown to upregulate expression of VCAM-1 on cell surface of HUVECs [80, 81]. Factor dependent VCAM-1 expression was determined by detection of upregulation of VCAM-1 receptor cellular expression using a time-resolved fluorescence read out.

Figure 9:
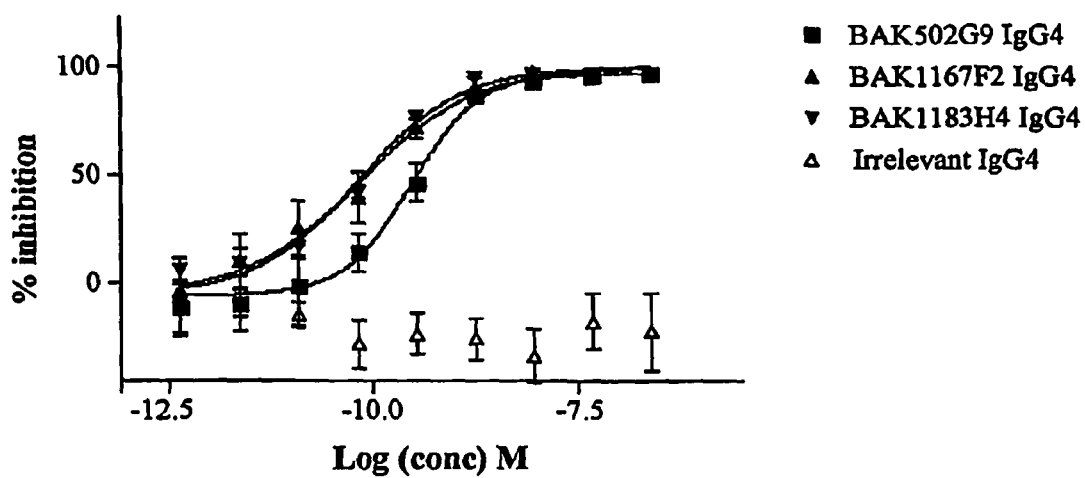
FIG. 9 shows the neutralisation potency (% inhibition) of BAK502G9 (closed squares), BAK1167F2 (closed triangles), BAK1183H4 (closed inverted triangles) as human IgG4 against VCAM-1 upregulation on the surface of HUVEC in response to 10 ng/ml human IL-13. Open triangles represent irrelevant IgG4. Data represent the mean with standard error bars of triplicate determinations within the same experiment.

HUVEC were obtained from Biowhittaker and maintained according to supplied protocols. Assay media was EGM-2 (Biowhittaker). Test solutions of antibody (in triplicate) were diluted to the desired concentration in assay media. An irrelevant antibody not directed at IL-13 was used as a negative control. Recombinant bacterially derived human IL-13 (Peprotech) was added to a final concentration of 10 ng/ml when mixed with the appropriate test antibody in a total volume of 200 µl. The concentration of IL-13 used in the assay was selected as the dose that gave approximately 80% of the maximal response. All samples were incubated for 30 minutes at room temperature. Assay samples were then added to HUVEC that had been preseeded at $4\times10^4$ cells per well in 96-well assay plates. Assay plates were incubated at 37° C. for 16-20 hours under 5% $CO_2$. Assay media was then removed by aspiration and replaced with blocking solution (PBS containing 4% dried Marvel® milk powder). Assay plates were incubated at room temperature for 1 hour at room temperature. Wells were washed three times with PBST Tween before 100 µl (1:500 dilution in PBST/1% Marvel® of biotinylated anti-VCAM-1 antibody (Serotec) was added to each well. Assay plates were incubated at room temperature for 1 hour. Wells were washed three times with Delfia wash buffer (Perkin Elmer) before 100 µl of Europium-labelled Streptavidin or anti-murine IgG1(1:1000 dilution in Delfia assay buffer, Perkin Elmer) was added to each well. Assay plates were then incubated at RT for 1 hour. Wells were washed 7 times with Delfia wash buffer (Perkin Elmer). Finally, 100 µl of enhancement solution (Perkin Elmer) was added to each well and fluorescence intensity was determined using the Wallac 1420 VICTOR2 plate reader (Standard Europium protocol). Data were analysed using Graphpad Prism software.
Results Typical data for BAK502G9 (VH SEQ ID NO: 15; VL SEQ ID NO: 16), BAK1183H4 (VH SEQ ID NO: 37; VL SEQ ID NO: 38), BAK1167F2 (VH SEQ ID NO: 35; VL SEQ ID NO: 36) as whole antibody human IgG4 are shown in FIG. 9. Relative potency was similar to the observed in the TF-1 cell proliferation assay. $IC_{50}$ for BAK502G9, BAK1183H4 and BAK1167F2 were 235 pM, 58 pM and 55 pM respectively against 10 ng/ml human IL-13.

EXAMPLE 9

Figure 10A:
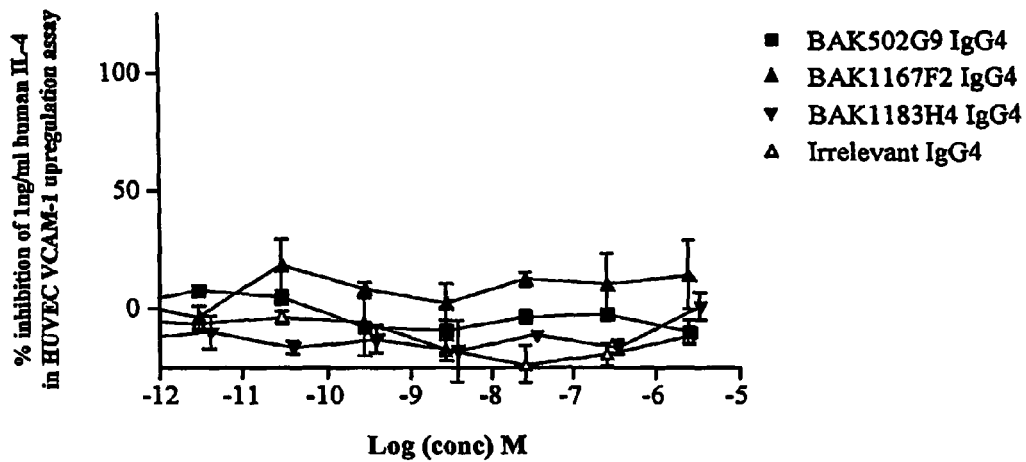
FIG. 10 shows the neutralisation potency (% inhibition) of BAK502G9 (closed squares), BAK1167F2 (closed triangles), BAK1183H4 (closed inverted triangles) as human IgG4 against eotaxin release from VCAM-1 upregulation on the surface of HUVEC in response to either 1 ng/ml human IL-4 (FIG. 10A) or 0.5 ng/ml human IL-1β (FIG. 10B). Open triangles represent an irrelevant IgG4. Data represent the mean with standard error bars of triplicate determinations within the same experiment.
Figure 10B:
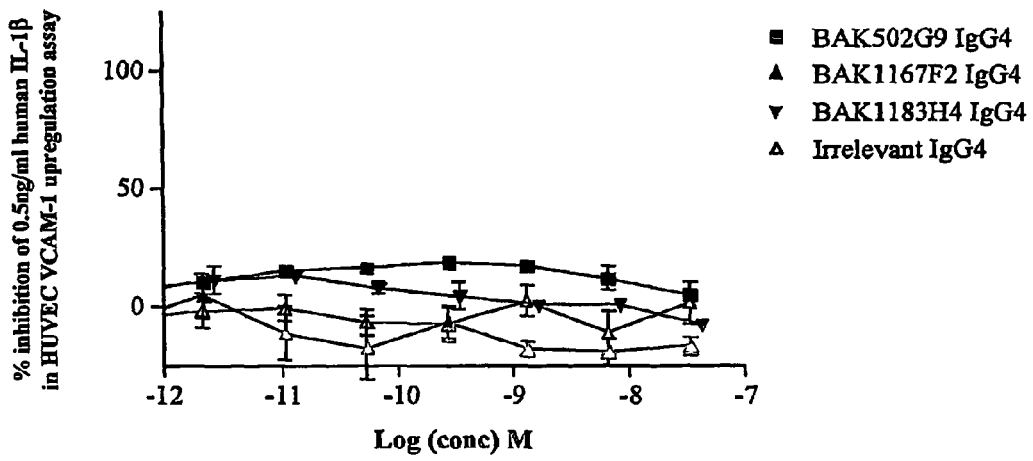

Neutralisation Potency of Anti-IL-13 Antibodies Against IL-1β and IL-4 Dependent VCAM-1 Upregulation The specificity of the BAK278D6 lineage of clones was assessed in a modification of the HUVEC bioassay. Together with IL-13, both IL-4 and IL-10 have been shown to upregulate expression of VCAM-1 on cell surface of HUVECs [80, 81].
HUVEC Assay Protocol The assay was performed essentially as described in Example 5 with the following modifications. Recombinant human IL-1β and IL-4 (R&D Systems) were used in place of human IL-13 at 0.5 ng/ml and 1 ng/ml respectively and represented the dose that gave approximately 80% of the maximal response.
Results None of the clones evaluated from the BAK278D6 lineage neutralised VCAM-1 upregulation in response to either human IL-1β or IL-4 and thus demonstrated specificity for IL-13 (FIG. 10). IL-4 is most closely related to IL-13, sharing 30% sequence identity at the amino acid level [82].

EXAMPLE 10

Neutralisation Potency of BAK209B11 as a Human IgG4 in a Murine IL-13 Dependent Murine B9 Cell Proliferation Assay BAK209B11, identified as an anti-murine IL-13 neutralising clone as a scFv as described in Example 1, was reformatted as a whole antibody human IgG4 as described in Example 5 and its potency evaluated in the murine IL-13 dependent B9 cell proliferation assay. B9 is a murine B-cell hybridoma cell line [83]. B9 is factor dependent for survival and proliferation. In this respect B cells respond to murine IL-13 and are maintained in media containing human IL-6 (50 pg/ml, R&D Systems). Inhibition of murine IL-13 dependent proliferation was determined by measuring the reduction in incorporation of tritiated thymidine into the newly synthesized DNA of dividing cells.

B9 Cell Assay Protocol

B9 cells were obtained from European Collection of Animal Cell Culture ECACC and maintained according to supplied protocols. The assay was performed essentially as described for the TF-1 assay in Example 2 but with the following modifications. Assay media comprised RPMI-1640 with GLUTAMAX I (Invitrogen) containing 5% foetal bovine serum (Hyclone) and 50 μM 2-mercaptoethanol (Invitrogen). Recombinant bacterially derived murine IL-13 (Peprotech) replaced human IL-13 with a final assay concentration of 1 ng/ml.

Results

Figure 11:
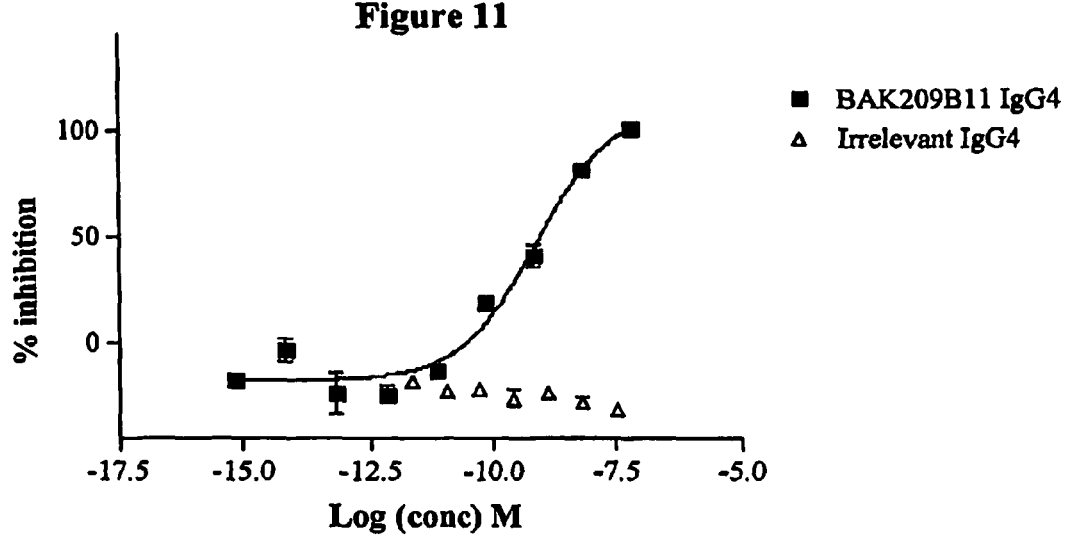
FIG. 11 shows the neutralisation potency (% inhibition) of BAK209B11 (squares) as a human IgG4 against 1 ng/ml murine IL-13 in the factor dependent B9 cell proliferation assay. Open triangles represent an irrelevant IgG4. Data represent the mean with standard error bars of triplicate determinations within the same experiment.

BAK209B11 (VH SEQ ID NO: 25; VL SEQ ID NO: 26) as a human IgG4 neutralised 1 ng/ml murine IL-13 with an $IC_{50}$ of 776 pM in the B9 assay (FIG. 11). BAK209B11 therefore represents a useful tool to investigate the role of IL-13 in murine models of disease. This is clearly demonstrated in Example 12, which demonstrates the efficacy of BAK209B11 in a murine model of acute pulmonary inflammation.

EXAMPLE 11

Affinity Determination of Anti-IL-13 Antibodies by BIAcore Analysis

The affinity of BAK502G9 (VH SEQ ID NO: 15; VL SEQ ID NO: 16), BAK1167F2 (VH SEQ ID NO: 35; VL SEQ ID NO: 36) and BAK1183H4 (VH SEQ ID NO: 37; VL SEQ ID NO: 38) for human IL-13 and BAK209B11 (VH SEQ ID NO: 25; VL SEQ ID NO: 26) for murine IL-13 as human IgG4 were determined by surface plasmon resonance measurements using a BIAcore 2000 Biosensor (BIAcore AB) essentially as described in [72]. In brief, antibodies were coupled to CM5 sensorchips using an amine coupling kit (BIAcore) at a surface density of approximately 500 Ru and a serial dilution of IL-13 (between 50 nM to 0.78 nM) in HBS-EP buffer was passed over the sensorchip surface. The resulting sensorgrams were evaluated using BIA evaluation 3.1 software to provide kinetic data.

Results

BAK502G9, BAK1167F2 and BAK1183H4 IgG4 bound human IL-13 with high affinity with Kd of 178 pM, 136 pM and 81 pM respectively corresponding to their relative potency in cell based assays. BAK209B11 bound murine IL-13 with affinity of 5.1 nM (Table 3).

EXAMPLE 12

Figure 12:
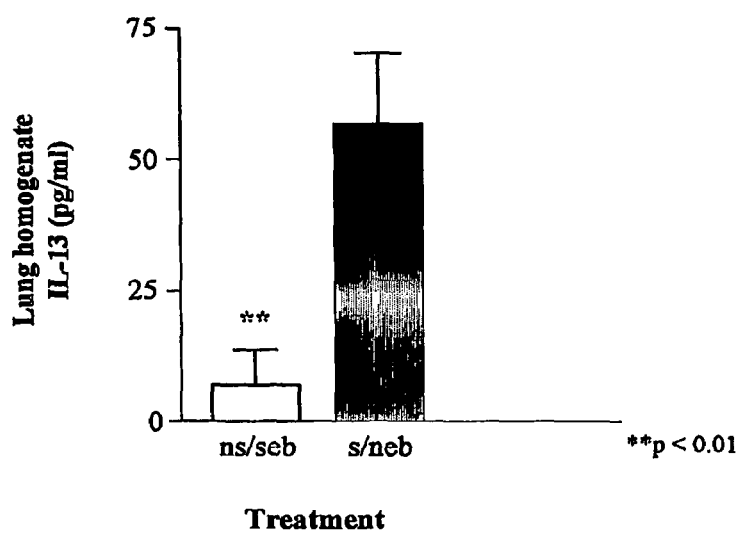
FIG. 12 shows the relative level of IL-13 in lung homogenates from sensitised (s)(right-hand bar) and non-sensitised (ns)(left-hand bar) mice post challenge in a murine model of acute pulmonary allergic inflammation. The effect of sensitisation was statistically evaluated by performing Student's t-test using quantity of IL-13 data. * $<0.05$. ** $<0.01$ compared to non-sensitised control animals (n=5-6 mice). Data represent the mean with standard error bars.

Efficacy of BAK209B11 in a Murine Model of Acute Allergic Pulmonary Inflammation Murine model of acute allergic pulmonary Inflammation
The effect of BAK209B11 (VH SEQ ID NO: 25; VL SEQ ID NO: 26), an anti-murine IL-13 neutralising human IgG4 antibody, was investigated in a murine of acute allergic pulmonary inflammation. This model was performed essentially as described by Riffo-Vasquez et al [84] and is characterised at its endpoint by increased bronchial alveolar lavage (BAL) IL-13 (FIG. 12), cellular infiltration into the lung and BAL (FIG. 13), increased serum IgE levels and airways hyperresponsiveness (AHR).

Model Protocol

Female Balb/C mice (Charles River UK) were treated with either anti-murine IL-13 antibody BAK209B11 (at 12, 36, 119 or 357 μg doses) or an isotype matched control antibody (357 μg dose). On days 0 and 7, mice in each group were sensitised by intraperitoneal injection of 10 μg of ovalbumin (Ova) in 0.2 ml of the vehicle (saline containing 2% $Al_2O_3$ (Rehydragel) as an adjuvant). A separate control group of non-sensitised mice received an equal volume of the vehicle. Mice were challenged with ovalbumin on days 14, 15 and 16. Ovalbumin was diluted to 1% (w/v) in sterile saline prior to nebulisation. All inhalation challenges were administered in a Plexiglas exposure chamber. Ova was aerosolised using a deVilbiss Ultraneb 2000 nebuliser (Sunrise Medical) in a series of three exposures of 20 minutes separated by 1 hour intervals.

BAK209B11 or an irrelevant human IgG4 were administered intravenously, 1 day prior to first challenge and then 2 hours prior to each subsequent challenge (4 doses in total). The model ended at day 17, 24 hours post final challenge. Blood (serum) and BAL were collected. Serum was assayed for total IgE. BAL was obtained by injecting 3 aliquots of saline (0.3 ml, 0.3 ml and 0.4 ml) and pooling samples. Total leukocytes and differential cell counts were obtained from BAL cells.

Results

Figure 13:
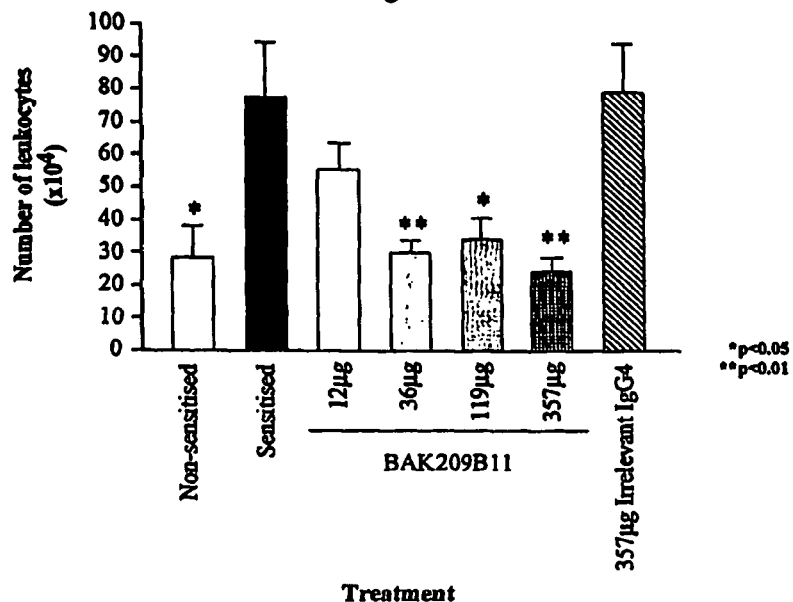
FIG. 13 illustrates the effects of i.v. administration of BAK209B11 as human IgG4 in different amounts compared to an isotype matched IgG4 irrelevant control antibody on ovalbumin induced leukocyte recruitment to the lung in ovalbumin sensitised mice. The number of leukocytes is shown ($\times 10^4$). The effect of antibody treatment was statistically evaluated by performing one way ANOVA with Dunnett's test using differential cell count data. *<0.05. **<0.01 compared to ovalbumin challenged PBS control animals (=0% inhibition; n=5-8 mice). Data represent the mean with standard error bars.
Figure 14:
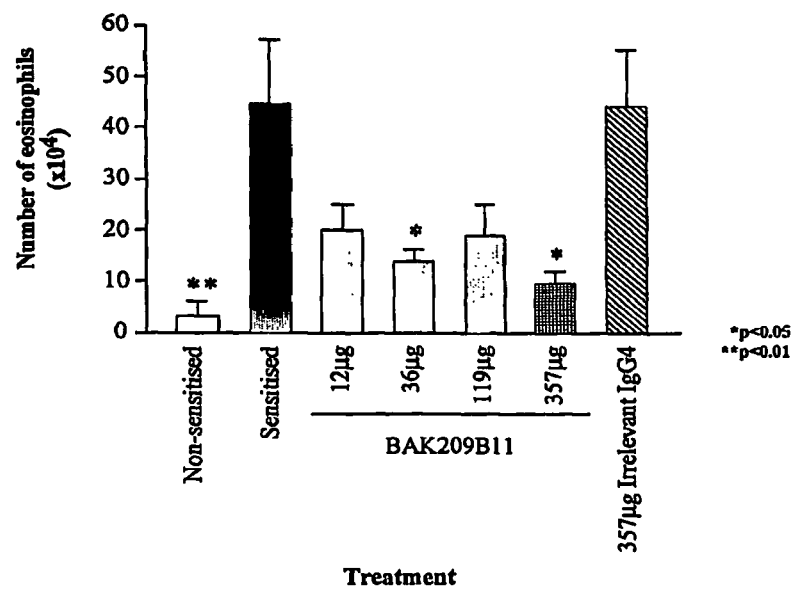
FIG. 14 illustrates the effects of i.v. administration of BAK209B11 as human IgG4 in different amounts compared to an isotype matched IgG4 irrelevant control antibody on ovalbumin induced eosinophil recruitment to the lung in ovalbumin sensitised mice. The number of eosinophils is shown ($\times 10^4$). The effect of antibody treatment was statistically evaluated by performing one way ANOVA with Dunnett's test using differential cell count data. *<0.05. **<0.01 compared to ovalbumin challenged PBS control animals (=0% inhibition; n=5-8 mice). Data represent the mean with standard error bars.
Figure 15:
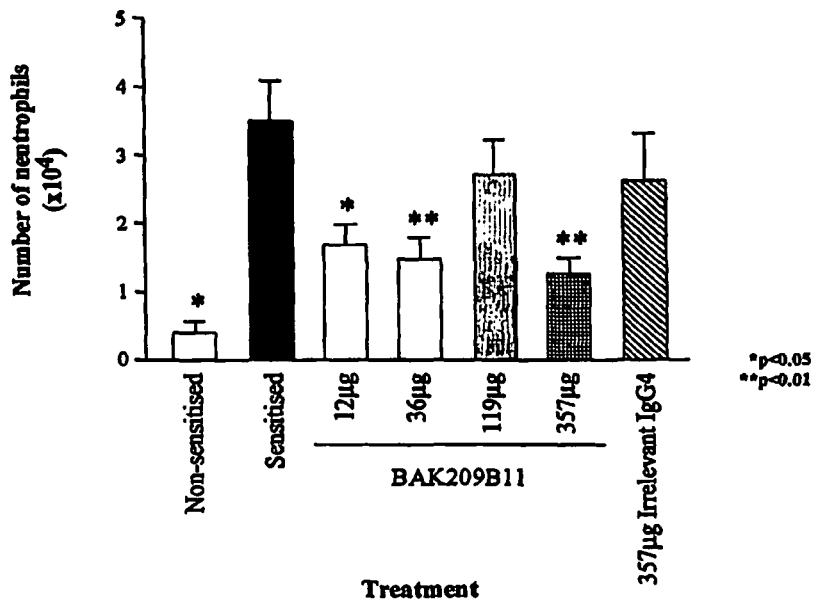
FIG. 15 illustrates the effects of i.v. administration of BAK209B11 as human IgG4 in different amounts compared to an isotype matched IgG4 irrelevant control antibody on ovalbumin induced neutrophil recruitment to the lung in ovalbumin sensitised mice. The number of neutrophils is shown ($\times 10^4$). The effect of antibody treatment was statistically evaluated by performing one way ANOVA with Dunnett's test using differential cell count data. *<0.05. **<0.01 compared to ovalbumin challenged PBS control animals (=0% inhibition; n=5-8 mice). Data represent the mean with standard error bars.
Figure 16:
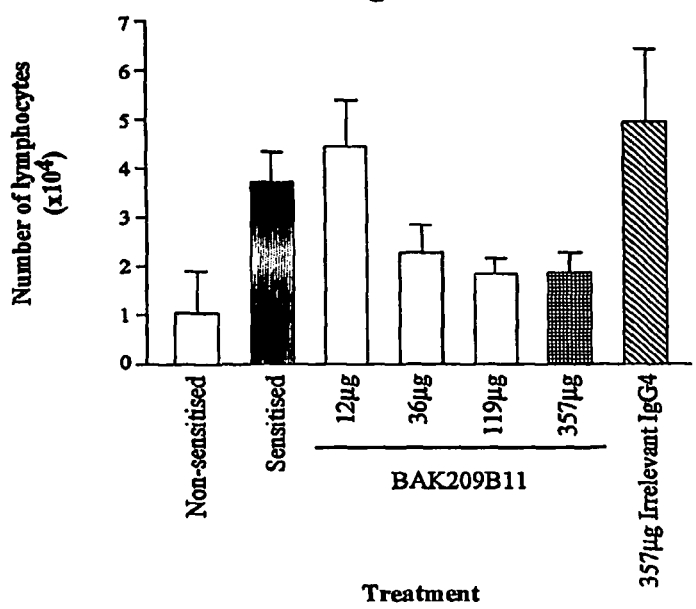
FIG. 16 illustrates the effects of i.v. administration of BAK209B11 as human IgG4 in different amounts compared to an isotype matched IgG4 irrelevant control antibody on ovalbumin induced lymphocyte recruitment to the lung in ovalbumin sensitised mice. The induction of lymphocytes was dose dependently inhibited by BAK209B11 with maximal inhibition at 3 µg/ml of BAK209B11. The effect of antibody treatment was statistically evaluated by performing one way ANOVA with Dunnett's test using differential cell count data. *<0.05. <0.01 compared to ovalbumin challenged PBS control animals (=0% inhibition; n=5-8 mice). Data represent the mean with standard error bars.
Figure 17:
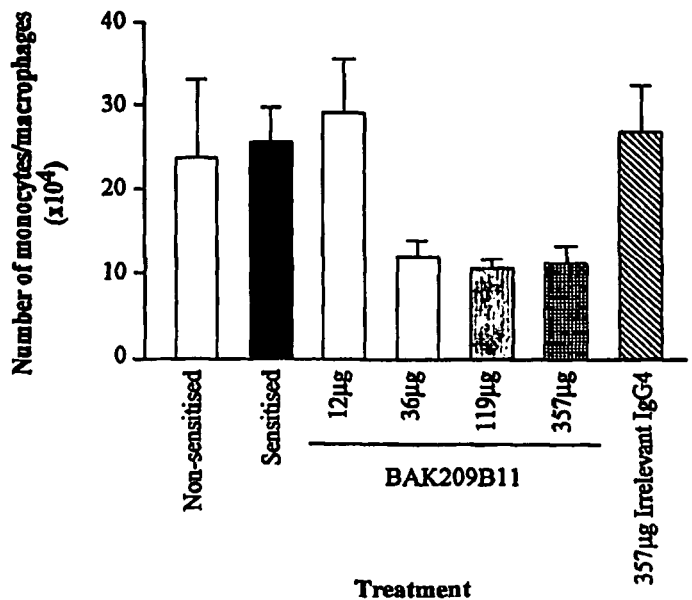
FIG. 17 illustrates the effects of i.v. administration of BAK209B11 as human IgG4 in different amounts compared to an isotype matched IgG4 irrelevant control antibody on ovalbumin induced monocyte/macrophage recruitment to the lung in ovalbumin sensitised mice. There was no significant increase in the levels of monocytes/macrophages of sensitised animals when compared with control animals. However, such background levels of these cells were depressed by ≥36 µg/ml BAK209B11 in sensitised animals. The effect of antibody treatment was statistically evaluated by performing one way ANOVA with Dunnett's test using differential cell count data. *<0.05.**<0.01 compared to ovalbumin challenged PBS control animals (=0% inhibition; n=5-8 mice). Data represent the mean with standard error bars.

Ovalbumin challenge of sensitised mice caused a significant (p<0.05) increase in total BAL cell recruitment over non-sensitised but challenged animals. This recruitment was dose-dependently inhibited by BAK209B11; significant (p<0.05) inhibition was seen with ≥36 μg BAK209B11, but not control antibody (FIG. 13). Similar effects were also seen on eosinophils (FIG. 14) and neutrophils (FIG. 15) with significant (p<0.05) inhibition of cellular influx at a minimum BAK209B11 dose of 36 μg. This inhibition was not seen with the control antibody. Lymphocytes were also induced in sensitised but not non-sensitised mice upon challenge. This induction was dose-dependently inhibited by BAK209B11, with maximal inhibition seen with 36 μg BAK209B11. Control antibody had no effect (FIG. 16). Although monocyte/macrophages were not induced in sensitised animals when compared to non-sensitised animals, background levels were depressed by 236 μg BAK209B11, but not by control antibody (FIG. 17). Serum IgE levels were significantly increased in sensitised animals when compared to non-sensitised after challenge (p<0.05). This increase was decreased after treatment with 36 μg BAK209B11 but not by the control antibody.

In summary, systemic administration of BAK209B11, a murine IL-13 neutralising antibody, but not control antibody inhibited inflammatory cell influx and the upregulation of serum IgE levels caused by sensitisation and subsequent challenge with ovalbumin in a murine model of allergic inflammation.

Examples 13 to 20 are prophetic.

EXAMPLE 13

Efficacy of BAK209B11 in the Lloyd Murine Model of Acute Pulmonary Inflammation

Murine Model of Acute Allergic Pulmonary Inflammation
The effect of BAK209B11 (VH SEQ ID NO: 25; VL SEQ ID NO: 26), an anti murine IL-13 neutralising antibody, was investigated in a second murine model of acute allergic pulmonary inflammation. This model was performed essentially as described by McMillan et al. [85] and is characterised at its endpoint by increased BAL and lung tissue IL-13, cellular infiltration into the lung and BAL, increased serum IgE levels and airways hyperresponsiveness (AHR).
Model Protocol Female Balb/C mice (Charles River UK) were administered with various doses of anti-murine IL-13 antibody BAK209B11 or an isotype matched control antibody, as follows. On days 0 and 12, mice in each group were sensitised (SN) by intraperitoneal injection of 10 µg of ovalbumin (Ova) in 0.2 ml of the vehicle (saline containing 2 mg Al(OH)$_3$ as an adjuvant [calculated as described in Example 12]). A separate control group of non-sensitised mice (NS) received an equal volume of the vehicle. Mice were challenged with ovalbumin for 20 minutes on days 19, 20, 21, 22, 23 and 24. Ovalbumin was diluted to 5% (w/v) in saline prior to nebulisation. All inhalation challenges were administered in a Plexiglas exposure chamber. Ova was aerosolised using a deVilbiss Ultraneb 2000 nebuliser (Sunrise Medical). On days 18, 19, 20, 21, 22, 23 and 24 mice were administered with various intraperitoneal doses (237 µg, 23.7 µg or 2.37 µg; denoted in FIG. 21 by H, M and L) of anti-murine IL-13 antibody BAK209B11 muIgG1 or an isotype matched control antibody (237 µg). Airway function was assessed on days 0 and 25 by increasing methacholine challenges and monitored using conscious plethysmography (Buxco). $PC_{50}$ (concentration of methacholine required to increase baseline PenH by 50%) was estimated for individual mice at both day 0 and day 25 from 4 parameter unfixed curve fitting of methacholine dose-response curves.

The model ended at day 25, 24 hours post final challenge. Blood, serum, BAL and lung tissue were collected.
Results Lung function was evaluated for individual animals at day 0 (pre-treatment) and at day 25 (post-challenge) and was quantitated by calculating $PC_{50}$ values (concentration of methacholine required to increase baseline PenH by 50%) (FIG. 21A). An individuals airways hyperresponsiveness (AHR) was determined by the change in log $PC_{50}$ at day 25 versus day 0 (log day 25 $PC_{50}$-log day 0 $PC_{50}$). This delta log$PC_{50}$ was the primary endpoint of the study; $PC_{50}$ data log-transformed because of requirements of endpoint ANOVA. Individual changes were averaged within groups to generate group average delta log $PC_{50}$ (as shown in FIG. 21B).

Ovalbumin challenge of sensitised mice caused a significant AHR compared to non-sensitised and challenged mice (p<0.01). BAK209B11 caused a clear and dose-dependent decrease in AHR whereas the control antibody had no effect.

EXAMPLE 14

Efficacy of BAK209B11 in the Gerard Murine Model of Acute Pulmonary Inflammation Murine Model Of Acute Allergic Pulmonary Inflammation The effect of BAK209B11 (VH SEQ ID NO: 25; VL SEQ ID NO: 26), an anti-murine IL-13 neutralising human IgG4 antibody, was investigated in a third murine model of acute allergic pulmonary inflammation. This model was performed essentially as described by Humbles et al. [86] and is characterised at its endpoint by increased BAL and lung tissue IL-13, cellular infiltration into the lung and BAL, increased serum IgE levels and airways hyperresponsiveness (AHR).
Model Protocol Female Balb/C mice (Charles River UK) were administered with various doses of anti-murine IL-13 antibody BAK209B11 or an isotype matched control antibody. On days 0, 7 and 14, mice in each group were sensitised (SN) by intraperitoneal injection of 10 µg of ovalbumin (Ova) in 0.2 ml of the vehicle (saline containing 1.125 mg Al(OH)$_3$ as an adjuvant [calculated as described in Example 12]). A separate control group of non-sensitised mice (NS) received an equal volume of the vehicle. Mice were challenged with ovalbumin for 20 minutes on days 21, 22, 23 and 24. Ovalbumin was diluted to 5% (w/v) in saline prior to nebulisation. All inhalation challenges were administered in a Plexiglas exposure chamber. Ova was aerosolised using a deVilbiss Ultraneb 2000 nebuliser (Sunrise Medical).

The model ended at day 25, 24 hours post challenge. Blood, serum, BAL and lung tissue were collected.

EXAMPLE 15

Efficacy of BAX209B11 in the Lloyd Chronic Model of Pulmonary Inflammation

Murine Model of Chronic Allergic Pulmonary Inflammation

The effect of BAK209B11 (VH SEQ ID NO: 25; VL SEQ ID NO: 26), an anti murine IL-13 neutralising human IgG4 antibody, was investigated in a model of chronic allergic pulmonary inflammation. This model was performed essentially as described by Temelkovski et al. [87] and is characterised at its endpoint by cellular infiltration into the lung and BAL, increased serum IgE levels and airways hyperresponsiveness (AHR).
Model Protocol Female Balb/C mice (Charles River UK) were dosed with various doses of anti-murine IL-13 antibody BAK209B11 or an isotype matched control antibody. On days 0 and 11, mice in each group were sensitised (SN) by intraperitoneal injection of 10 µg of ovalbumin (Ova) in 0.2 ml of the vehicle (saline containing 2 mg Al(OH)$_3$ as an adjuvant [calculated as described in Example 12]). A separate control group of non-sensitised mice (NS) received an equal volume of the vehicle. Mice were challenged with ovalbumin for 20 minutes on days 18, 19, 20, 21, 22, 23, 28, 30, 32, 35, 37, 39, 42, 44, 46, 49 and 51. Ovalbumin was diluted to 5% (w/v) in saline prior to nebulisation. All inhalation challenges were administered in a Plexiglas exposure chamber. Ova was aerosolised using a deVilbiss Ultraneb 2000 nebuliser (Sunrise Medical).

The model ended at day 52, 24 hours post challenge. Blood, serum, BAL and lung tissue were collected.

EXAMPLE 16

Efficacy of Anti-Human IL-13 Antibodies Against Exogenous Human IL-13 Administered to the Murine Air Pouch Model The effect of anti-human IL-13 antibodies on the pro-inflammatory action of human IL-13 was investigated in a basic murine model. This model was performed essentially as described by Edwards et al [93] and was characterised at its endpoint by cellular infiltration into the airpouch.
Model Protocol An air pouch was created on the back of female Balb/C mice by subcutaneous injection of 2.5 mL of sterile air at day 0. The air pouch was reinflated with another 2.5 mL sterile air at day 3. 2 µg huIL-13 in 0.75% CMC was injected directly into the pouch at day 6. 24 hours later the mice were killed and the air pouch lavaged with 1 mL heparinised saline. Antibody treatments were either given with the huIL-13 (into the pouch) or given systemically.
Results Human IL-13, injected into the airpouch (i.po.), caused a significantly increased infiltration of total leukocytes (p<0.01) and eosinophils (p<0.01) at 24 hours post-challenge versus vehicle (0.75% carboxymethyl cellulose (CMC) in saline i.po.) treated mice.

Locally administered BAK502G9 (200 mg, 20 mg or 2 mg intrapouch) significantly and dose-dependently inhibited the total leukocyte (p<0.01) and eosinophil (p<0.01) infiltration into the air pouch caused by 2 µg huIL-13 in 0.75% CMC.

Systemically administered BAK209B11 (30 mg/kg, 10 mg/kg and 1 mg/kg) also significantly and dose-dependently inhibited the total leukocyte (p<0.01) and eosinophil (p<0.01) infiltration into the air pouch caused by 2 µg huIL-13 in 0.75% CMC.

EXAMPLE 17

Figure 18:
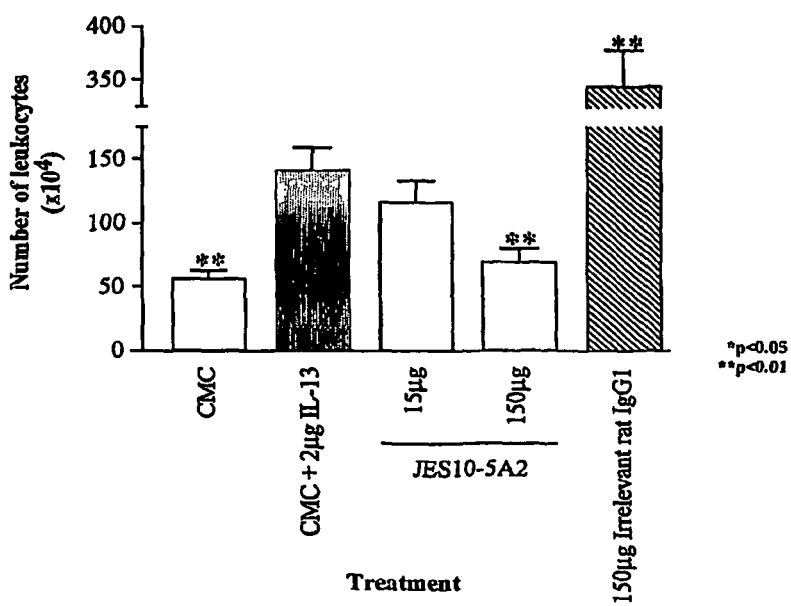
FIG. 18 shows the effects of a commercial anti-IL-13 neutralising antibody JES10-5A2 on the influx of cells (number of leukocytes is shown ($\times 10^4$)) into the murine airpouch elicited by administration of bacterially derived recombinant human IL-13. The effect of antibody treatment was statistically evaluated by performing one way ANOVA with Dunnett's test using differential cell count data. *<0.05.**<0.01 compared to CMC control animals (=0% inhibition; n=11-13 mice). Data represent the mean with standard error bars.

Generation of Human IL-13 Knock-in/Murine IL-13 Knock Out Transgenic Mice for the Purposes of Evaluating the Efficacy of Anti-Human IL-13 Antibodies in Models of Pulmonary Allergic Inflammation The present inventors have generated mice which express human, rather than murine IL-13 by gene targeting. The mouse IL-13 gene has been replaced from start to stop codon with the relevant portion of the human IL-13 gene. This mouse strain expresses human IL-13, rather than mouse IL-13, in response to the same stimuli as in the wild-type mouse, as the endogenous IL-13 promoter and IL-13 pA tail remaining unchanged. It has been shown that human IL-13 can bind to and signal through mouse IL-13 receptors to generate the same physiological consequences as signalling caused by mouse IL-13 ligating mouse IL-13 receptors. For example exogenous human IL-13 caused inflammatory cell recruitment into the murine air pouch (FIG. 18). These transgenic animals allow us to evaluate non-murine cross reactive anti-human IL-13 antibodies in established murine models of disease.

This mouse has been used in the acute allergic airway inflammation models (as described in examples 18 and 19) and chronic allergic airway inflammation models (as described in Example 20) allowing the evaluation of anti-human IL-13 antibody pharmacology in allergic airway disease.

EXAMPLE 18

Efficacy of Anti-Human IL-13 Antibodies in the huIL-13-Transgenic Lloyd Murine Model of Acute Pulmonary Inflammation Murine Model of Acute Allergic Pulmonary Inflammation The effect of anti human IL-13 neutralising human IgG4 antibodies were investigated in a murine model of acute allergic pulmonary inflammation using the transgenic mice generated in example 17. This model was performed essentially as described by McMillan et al. [85] and example 13. The model was characterised at its endpoint by increased BAL and lung tissue IL-13, cellular infiltration into the lung and BAL, increased serum IgE levels and airways hyperresponsiveness (AHR).

Model Protocol

The protocol for this model was as described in Example 13 except that anti-human IL-13 antibodies were dosed instead of BAK209B11.

EXAMPLE 19

Efficacy of Anti-Human IL-13 Antibodies in the huIL-13-Transgenic Gerard Murine Model of Acute Pulmonary Inflammation Murine Model of Acute Allergic Pulmonary Inflammation The effect of anti human IL-13 neutralising human IgG4 antibodies were investigated in another murine model of acute allergic pulmonary inflammation using the transgenic mice generated in example 17. This model was performed essentially as described by Humbles et al, [86] and in example 14. The model is characterised at its endpoint by increased BAL and lung tissue IL-13, cellular infiltration into the lung and BAL, increased serum IgE levels and airways hyperresponsiveness (AHR).

Model Protocol

The protocol for this model was as described in Example 14 except that anti-human IL-13 antibodies were dosed instead of BAK209B11.

EXAMPLE 20

Efficacy of Anti-Human IL-13 Antibodies in the huIL-13-Transgenic Lloyd Chronic Model of Pulmonary Inflammation The effect of anti human IL-13 neutralising human IgG4 antibodies were investigated in a model of chronic allergic pulmonary inflammation using the transgenic mice generated in example 17. This model was performed essentially as described by Temelkovski et al. [87] and in Example 15 and is characterised at its endpoint by cellular infiltration into the lung and BAL, increased serum IgE levels and airways hyper-responsiveness (AHR).

Model Protocol

The protocol for this model was as described in Example 15 except that anti-human IL-13 antibodies were dosed instead of BAK209B11

EXAMPLE 21

Pharmacokinetics and Pharmacodynamics of Anti-Human IL-13 Antibodies in *Ascaris. suum*-Allergic Cynomolgus Monkeys The pharmacokinetics and pharmacodynamics of 502G9 were evaluated in 4 allergic but non-challenged cynomolgus primates (2 male/2 female) after a single 10 mg/kg i.v bolus dose. The experiment ran for 29 days. The antibody's pharmacokinetic parameters were determined from a geomean average serum-drug concentration curve and are detailed below in Table 4.

In the same study serum IgE concentrations were also followed using a human IgE ELISA kit (Bethyl laboratories, USA).

Results

Serum IgE concentrations were significantly reduced after a single 10 mg/kg i.v bolus dose of BAK502G9, from 100% control levels (predose) to 66±10% of control values (p<0.05), at 4 and 5 days after dosing. This lowering of serum IgE concentration recovered to 88±8% of control levels by day 22 (see FIG. 20). Again these data were derived by normalising each animals serum IgE concentration to predose levels, where predose concentrations was 100%, and then averaging the curves from the 4 animals tested.

Figure 20B:
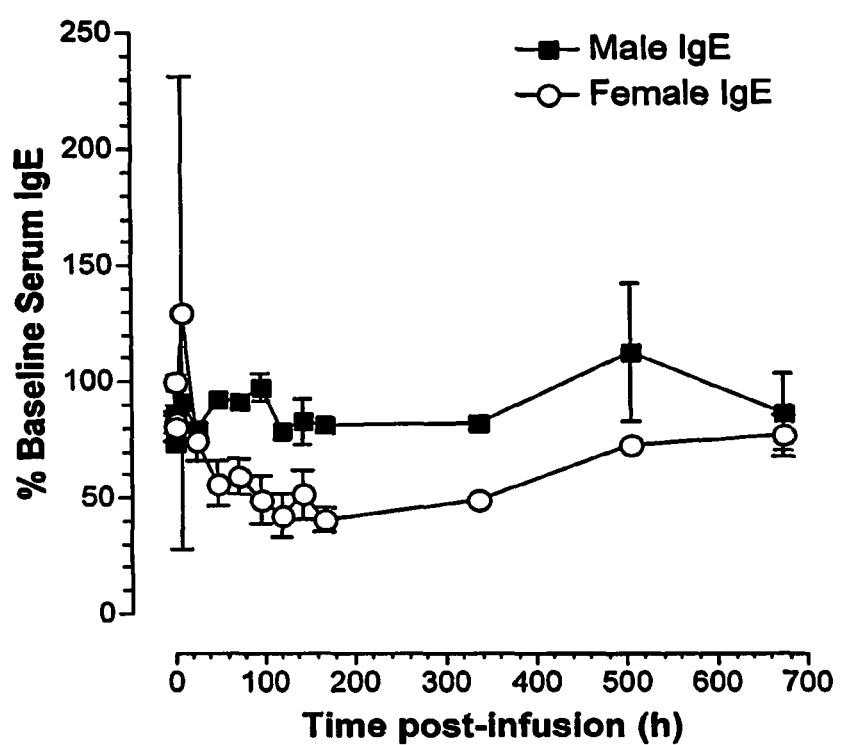
FIG. 20B shows relative serum IgE levels of male and female cynomolgus primates versus time following a single 10 mg/kg intravenous dose of BAK502G9. Relative serum IgE data are expressed as arithmetic mean±SEM percentage of baseline value.

The two male monkeys had relatively low predose total serum IgE (60 ng/mL and 67 ng/mL). These IgE levels did not change in a fashion suggesting a trend following treatment with BAK502G9 (FIG. 20B). The two female monkeys had relatively high predose total serum IgE (1209 ng/mL and 449 ng/mL). These IgE levels were decreased following treatment with BAK502G9, maximally by 60% at 7 days, and returning to approximately predose levels by 28 days post-administration (FIG. 20B). These data provide indication that BAK502G9 lowers serum IgE concentrations in animals with relatively high circulating IgE of IgE.

EXAMPLE 22

Efficacy of Anti-Human IL-13 Antibodies in Cynomolgus Models of Dermal Allergy

The effects of anti-human IL-13 neutralising human IgG4 antibodies were investigated in a primate model of acute allergic dermal inflammation. This model was performed by injecting human IL-13 and *A. suum* antigen intradermally into cynomolgus monkeys. 24-96 h later, dermal biopsies and serum samples were taken. The model was characterised at its endpoint by cellular infiltration into the skin.

EXAMPLE 23

Efficacy of Anti-Human IL-13 Antibodies in Cynomolgus Models of Pulmonary Allergy The effect of anti human IL-13 neutralising human IgG4 antibodies were investigated in a primate model of acute allergic pulmonary inflammation. This model was performed by exposing *a. suum*-allergic cynomolgus primates to nebulised *a. suum* antigen, thereby generating an allergic reaction. This allergy was characterized at its end point by cellular infiltration into the lung and BAL, increased serum IgE levels and airways hyper-responsiveness.

Pharmacodynamics were additionally evaluated ex vivo using a flow cytometric method. CD23 is the high affinity IgE receptor and can be expressed on peripheral human blood mononuclear cells. CD23 expression can be induced, in terms of the number of cells expressing CD23 and also in how much CD23 each cell expresses by both IL-13 and IL-4. The IL-13, but not IL-4, mediated response can be inhibited by anti-human IL-13 antibodies.

Animals were preselected for entry into this 2-phase study on the basis of previously established AHR following nebulised antigen (*ascaris suum* extract) challenge. In phase I airway function was assessed during intravenous histamine challenge on days 1 and 11. $PC_{30}$, the histamine dose required to generate a 30% increase in lung resistance ($R_L$) above baseline, was determined from each histamine dose-response curve. On days 9 and 10, animals were challenged with individually tailored doses of nebulised antigen previously shown to generate a 40% increase in $R_L$ as well as a 35% decrease in dynamic compliance ($C_{DYN}$). Historically in this model, a greater $R_L$ has been observed following the second challenge with a given allergen dose than the first; this is antigen priming. The two antigen challenges caused AHR, as measured by an increased area under the histamine dose-response curve and/or a fall in $PC_{30}$, and BAL, as well as eosinophilia at day 11 compared to day 1. Animals displaying an AHR-phenotype were selected to enter phase II.

Phase II was run exactly as phase I except that all animals received a 30 mg/kg BAK502G9 infusion on days 1, 5 and 9. The effects of BAK502G9 were assessed by comparing the changes seen in phase II with changes seen in phase I for individual animals.

Blood, serum, BAL and lung tissue were collected. Serum IgE levels were monitored by ELISA. Serum from BAK502G9 treated cynomolgus monkeys was shown to inhibit the expression of CD23 on human peripheral blood mononuclear cells induced by IL-13 but not IL-4. The magnitude of this inhibition was consistent with the serum BAK502G9 levels predicted by PK ELISA.

Results

Figure 26:
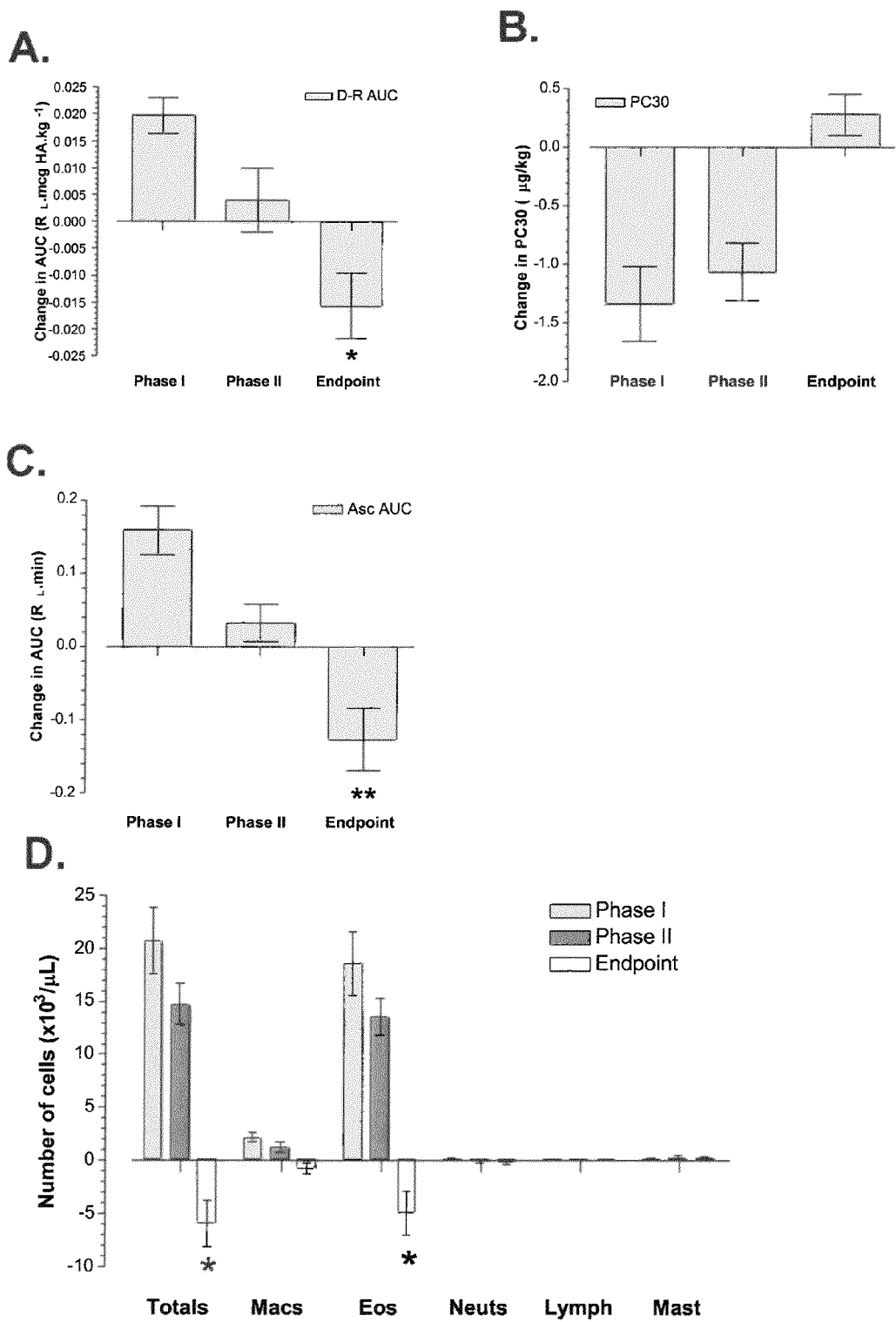
FIG. 26 shows effects of phase II administered BAK502G9.

BAK502G9 significantly inhibited AHR as measured by $R_L$ AUC (p<0.05) (FIG. 26A; Table 7). An inhibitory effect of BAK502G9 on AHR, as measured by $PC_{30}$, was observed but did not reach statistical significance (FIG. 26B; Table 7). BAK502G9 also significantly inhibited both antigen priming (p<0.01) (FIG. 26C; Table 7) and BAL inflammation. BAK502G9 significantly inhibited total cell (p<0.05) and eosinophil (p<0.05) but not macrophage, lymphocyte or mast cell influx into the BAL (FIG. 26D; Table 7).

EXAMPLE 24

Efficacy of Anti-Human IL-13 Antibodies Against the Asthmatic Phenotype that Develops when Human IL-13 is Administered to the Mouse Lung Murine Model of Airways Hyperresponsiveness The efficacy of the anti-human IL-13 neutralising antibody BAK502G9, against the development of airways hyper-responsiveness (AHR) following administration of human IL-13 to the mouse lung was investigated. This model was performed essentially as described by Yang et al [119] with the exception that human IL-13 was used in place of murine IL-13.

Model Protocol

To develop the phenotype, male BALB/c mice were exposed to two doses of human IL-13 separated by a 48-hour interval. In brief, mice were anaesthetised with an intravenous injection of 100 µl saffan solution (1:4 diluted in water). Mice were intubated with a 22-gauge catheter needle, through which human recombinant IL-13 (25 µg dissolved in 20 µl phosphate-buffered saline (PBS)) or vehicle control (PBS) was instilled. Airway function was assessed 24 hours after the last administration of IL-13 by increasing methacholine challenges and monitored using conscious plethysmography (Buxco). $PC_{200}$ (concentration of methacholine required to increase baseline penH by 200%) was determined from 4 parameter unfixed curve fitting of methacholine dose-response curves. Antibody treatments were administered by intra-peritoneal injection 24 hours prior to the each dose of IL-13.

Results

Figure 23:
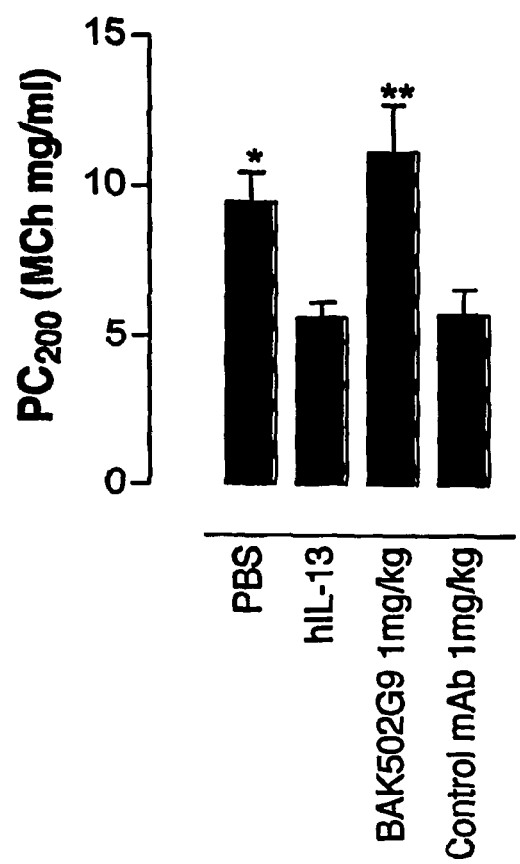
FIG. 23: illustrates the effects of i.p. administration of BAK502G9 as human IgG4 compared to an isotype matched IgG4 irrelevant control antibody on the development of AHR following intratracheal administration of human IL-13 to the airways of mice. The effect of antibody treatment was statistically evaluated by performing one way ANOVA with Dunnett's test using $PC_{200}$ Methacholine data. *<0.05. **<0.01 compared to the human IL-13 positive control group (n=6-8 mice). Data represent the mean with standard error bars.

Intratracheal installation of human IL-13 into naïve wild-type mice resulted in development of significant (p<0.05) airways hyperresponsiveness relative to control animals as determined by $PC_{200}$ methacholine concentrations. Systemically administered BAK502G9 (1 mg/kg) significantly (p<0.01) inhibited the development of AHR whereas the null control antibody had no effect (FIG. 23).

EXAMPLE 25

Neutralisation Potency of BAK502G9 as a Human IgG4 Against Human IL-13 Dependent IgE Release from Human B Cells B Cell Switching Assay Protocol IL-13 has been shown to induce IgE synthesis in human B cells in vitro [120]. Factor dependent IgE release from human B cells was determined by ELISA. The neutralisation potency of BAK502G9 as a human IgG4 was assessed against human IL-13 dependent IgE release from human B cells.

Peripheral blood mononuclear cells (PBMC) were purified from human buffy coat (Blood Transfusion Service) by centrifugation over a 1.077 g/L density gradient. B cells were purified from PBMC with a B cell isolation kit II (Miltenyi Biotec), using reagents and methods described by the manufacturer. Assay media comprised Iscoves modified dulbeccos medium (Life Technologies) containing 10% foetal bovine serum and 20 µg/mL human transferrin (Serologicals Proteins Inc). Following purification, B cells were resuspended to a final concentration of $10^6$/mL in assay media. 50 µl of resuspended cells were added to each assay point in a 96 well assay plate. 50 µl of 4 µg/mL of the anti-CD40 antibody EA5 (Biosource) was added to assay wells as appropriate. Test solutions of antibodies (six replicates) were diluted to the desired concentration in assay media. An irrelevant antibody not directed at IL-13 was used as a negative control. 50 µl/well of the appropriate test antibody were added to the cells. Recombinant bacterially derived human IL-13 (Peprotech) was subsequently added to a final concentration of 30 ng/ml to give a total assay volume of 200 µl/well. The concentration of IL-13 used in the assay was selected to give a maximal response. Assay plates were incubated for 14 days at 37° C. under 5% $CO_2$. IgE levels in the supernatant were determined by ELISA using reagents and protocols supplied by the manufacturer (BD Biosciences, Bethyl Laboratories). Data were analysed using Graphpad prism software.

Results

Figure 24:
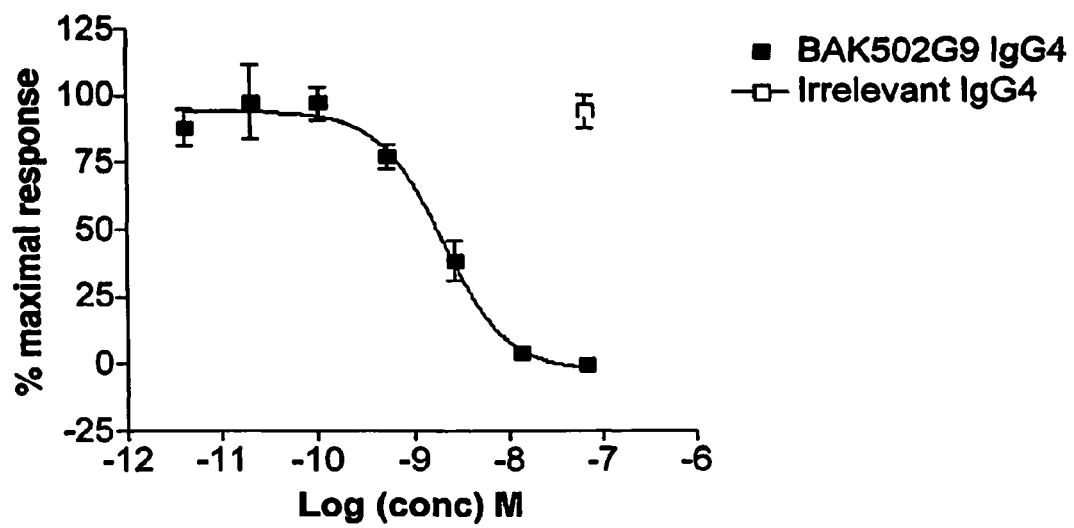
FIG. 24 shows the neutralisation potency (% maximal response) of BAK502G9 (closed squares) as IgG4 against 30 ng/ml IL-13 in a human B cell IgE production assay. Open squares represent an irrelevant IgG4. Data represent the mean with standard error bars of six donors from separate experiments.

As demonstrated in FIG. 24, BAK502G9 (VH SEQ ID NO: 15; VL SEQ ID NO: 16) was able to inhibit human IL-13 dependant IgE production by human B cells. BAK502G9 as human IgG4 had an $IC_{50}$ of 1.8 nM against 30 ng/ml human IL-13.

EXAMPLE 26

Efficacy of BAK502G9 Against IL-13 Mediated Potentiation of Histamine Induced $Ca^{2+}$ Signalling in Primary Human Bronchial Smooth Muscle Cells IL-13 has been shown to directly modulate the contractility of airway smooth muscle [121, 122]. Intracellular calcium mobilization is a prerequisite for smooth muscle contraction. Recent studies have shown that IL-13's ability to alter smooth muscle contractility is mediated in part through modulation of contractile agonist induced $Ca^{2+}$ signaling [123, 124].

The efficacy of BAK502G9, an anti-human IL-13 antibody formatted as an IgG4, against IL-13 mediated alterations in primary human bronchial smooth muscle cells (BSMC) signalling responses to the contractile agonist, histamine, was investigated in a $Ca^{2+}$ signalling assay.

BSMC $Ca^{2+}$ Signalling Assay Protocol

Human primary BSMC, Smooth Muscle Growth Medium-2 (SmGM-2) and Smooth Muscle Basal Medium (SmBM) were obtained from Bio Whittaker. The BSMC were maintained in SmGM-2 according to supplier's recommendations. BSMC were plated at $2 \times 10^4$ cells/well in a 96-well microtitre cell culture plate and were allowed to attach for 24 hours, then re-fed and incubated for a further 24 hours. Prior to the $Ca^{2+}$ signalling experiment, the BSMC were stimulated with IL-13 (Peprotech) at 50 ng/ml final concentration with or without antibody and incubated for 18-24 hours. BAK502G9 and an isotype matched irrelevant control monoclonal antibody, CAT-001, were evaluated at a final concentration of 10 µg/ml. Changes in intracellular $Ca^{2+}$ concentrations in response to histamine (Calbiochem), titrated from 20 µM, were measured using standard techniques with the $Ca^{2+}$ sensitive dye Fluo-4 (Molecular Probes) and a 96-well Fluorescence Imaging Plate Reader (FLIPR) (Molecular Devices). The area under the curve (AUC) of the $Ca^{2+}$ signalling response to histamine was determined for each cell pre-treatment condition. Data analyses were performed using Graph-Pad Prism version 4 for Windows (GraphPad Software).

Results

Figure 25:
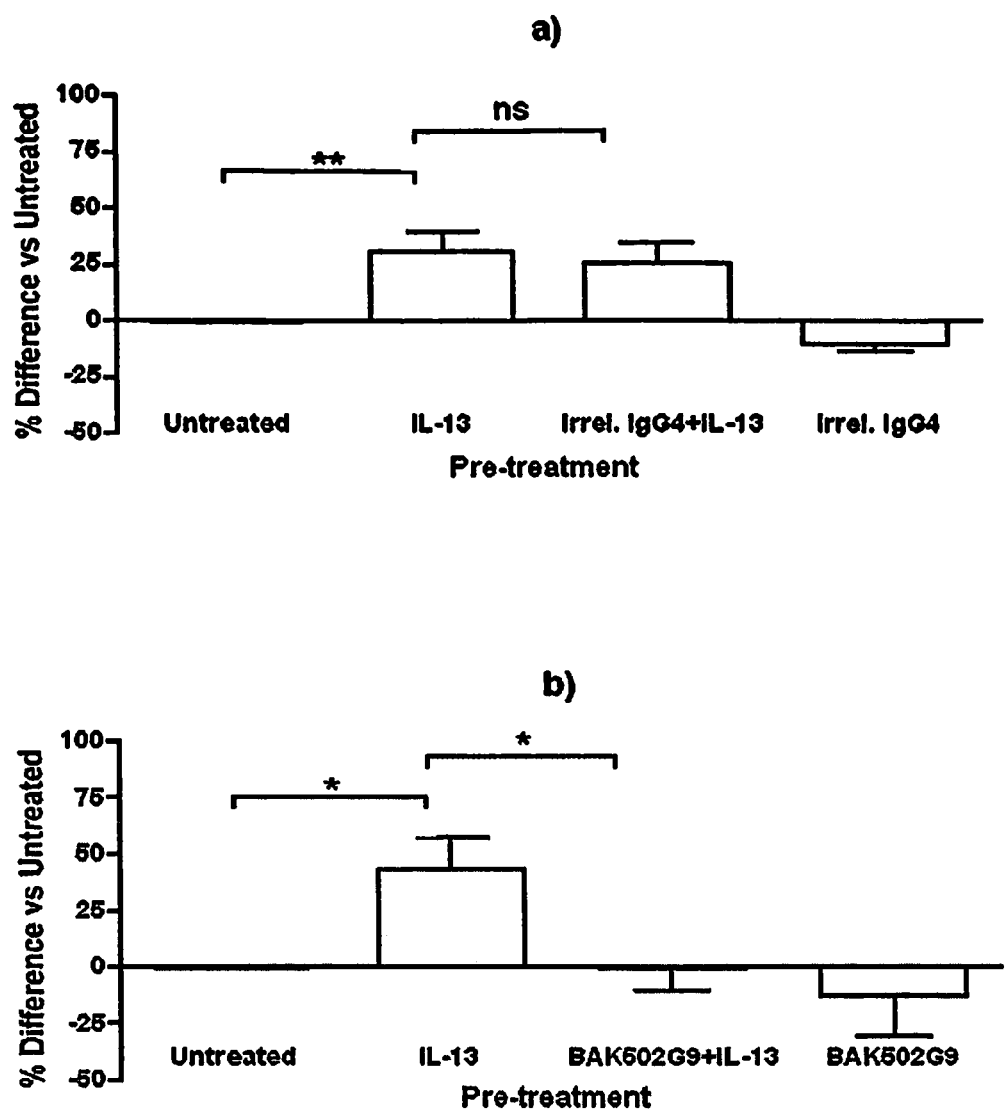
FIG. 25 shows the effects of BAK502G9 on IL-13 induced potentiation of agonist induced $Ca^{2+}$ signalling in bronchial smooth muscle cells. The area under the curve (AUC) of the $Ca^2$+ signalling response to histamine was determined for each antibody+/−IL-13 pre-treatment condition. Combined data from three independent experiments are shown for irrelevant antibody CAT-001 (a) and BAK502G9 (b) as the percentage difference versus untreated cells of AUC±SD (ns=not significant (p>0.05), *p<0.05, **p<0.01). The results were statistically evaluated utilising a one-way analysis of variance (ANOVA) with Bonferroni's multiple comparisons post-test.

Pre-incubation of BSMC with IL-13 significantly enhanced $Ca^{2+}$ signalling in response to histamine. Pre-incubation of BAK502G9 (FIG. 25B) (but not an irrelevant isotype control antibody (FIG. 25A)) with IL-13 significantly inhibited the potentiation of $Ca^{2+}$ signalling in response to histamine (FIG. 25).

EXAMPLE 27

Neutralisation Potency of Anti-IL-13 Antibodies in a Human IL-13 Dependent PBMC CD23 Expression Assay The potency of a representative IL-13 antibody was evaluated in the human IL-13 dependent peripheral blood mononuclear cell (PBMC) CD23 expression assay. PBMC respond to both IL-13 and IL-4 by increasing cell surface expression of CD23 [120]. CD23 (FceRII) is the low-affinity receptor for IgE and is expressed on a variety of inflammatory cells, including monocytes. Inhibition of human IL-13 dependent CD23 expression upregulation was determined by measuring the reduction in binding of fluorescently labelled CD23 monoclonal antibody to PBMCs by flow cytometry.

Assay Protocol

Human blood was obtained from the Blood Transfusion Service and erythrocytes depleted by 40 minute dextran-T500 (Pharmacia) sedimentation (0.6% final concentration). The leukocyte and platelet rich fraction was then separated by a 20 minute 1137 g centrifugation over a discontinuous Percoll gradient of 3 mL 64% and 5 mL 80% (100% was 9 parts Percoll and 1 part 10×PBS). PBMCs were harvested from the top of the 64% layer, washed and resuspended in assay buffer (Invitrogen RPMI 1640, 10% FCS, 2001 U/mL penicillin, 100 µg/mL streptomycin, 2 mM L-Glutamine). The assay was performed in 24 well plates with $2 \times 10^6$ cells, ±80 pM recombinant human IL-13 (Peprotech) or 21 pM recombinant human IL-4 (R&D Systems), ±BAK502G9 or irrelevant IgG4, in a final volume of 500 mcL. Cells were cultured for 48 h at 37 C before being harvested and stained with CD23-PE (BD Pharmingen) for 20 minutes at 4 C. Finally, cells were read on a flow cytometer. CD23 expression was determined by CD23 'score'; percent of CD23 positive cells multiplied by the 'brightness' of the stain (geomean fluorescence). No stimulant CD23 'score' was subtracted and data presented as a percentage of the response to IL-13 alone (100%). Data has been expressed as the mean±SEM drawn from 4-6 separate experiments, using cells from 4-6 individual donors, performed in triplicate for each point.

Figure 27:
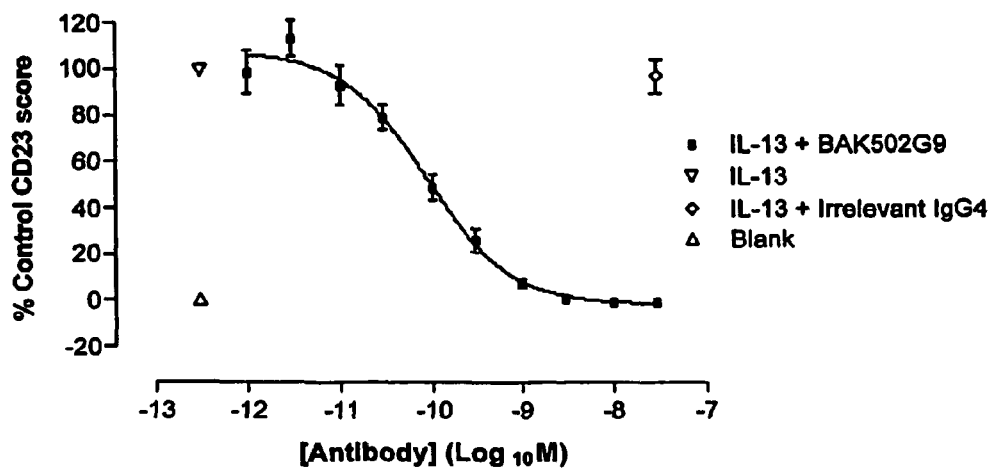
FIG. 27 shows effect of BAK502G9 on IL-13-induced CD23 expression. Data are presented as a percentage of the response to IL-13 alone (100%) and expressed as mean±SEM % control of 6 separate experiments from 6 individual donors (performed in triplicate).
Figure 28:
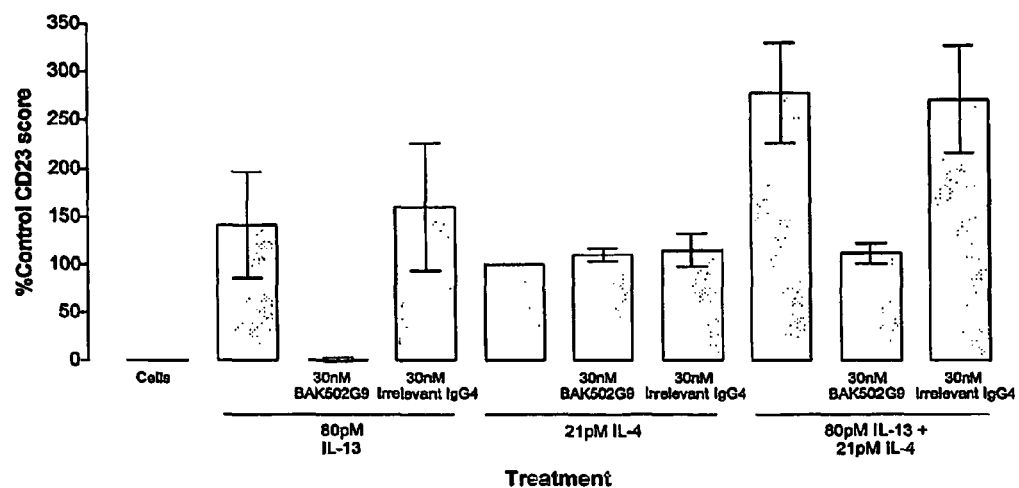
FIG. 28 shows effect of BAK502G9 and irrelevant IgG4 on IL-13 and/or IL-4 induced PBMC CD23 expression. Data are presented as a percentage of the response to IL-4 alone (100%) and expressed as mean±SEM % control of 4 separate experiments from 4 individual donors (performed in triplicate).

Results
Incubation of PBMC with 80 pM IL-13 or 21 pM IL-4 for 48 hours resulted in clear CD23 expression (FIG. 27 and FIG. 28). BAK502G9 dose-dependently inhibited IL-13-induced CD23 expression with a geometric mean of 120.2 pM (FIG. 27). In contrast, BAK502G9 was unable to inhibit the CD23 expression induced by 21.4 pM IL-4 (n=4 from individual donors, FIG. 28). Irrelevant IgG4 did not inhibit either IL-13 or IL-4 dependent CD23 expression on PBMC (FIG. 27 and FIG. 28). Co-stimulation of PBMC with 80 pM IL-13 and 21.4 pM IL-4, produced an additive CD23 response. BAK502G9, but not CAT-001, reduced CD23 expression levels to those seen with IL-4 stimulation alone (FIG. 28).

EXAMPLE 28

Neutralisation Potency of a Human IL-13 Antibody in a Human IL-13 Dependent Eosinophil Shape Change Assay The aims of this study were to evaluate the effect of IL-13 antibodies on eosinophil shape change induced by mediators released from NHLF following stimulation with factors found in the lungs of asthmatics such as IL-13 [125,126], TNF-α[127], TGF-β1 [128]. IL-13 synergises with TNF-α [129] or TGF-β1 [130] to induce fibroblasts to produce eotaxin=1, which can then act to directly chemoattract eosinophils. Leukocyte shape change responses are mediated through rearrangements of the cellular cytoskeleton and are essential to the processes of leukocyte migration from the microcirculation into sites of inflammation. Inhibition of IL-13-dependent shape-change-inducing factor release by NHLFs was determined by measuring the reduction in eotaxin-1 secretion by ELISA and reduction in eosinophil shape change by flow cytometry.
Assay Protocol
NHLF cells were cocultured with media alone or media containing stimulants (9.6 nM IL-13, 285.7 pM TNF-α(R&D Systems) and 160 pM TGF-β1 (R&D Systems) in the absence or presence of BAK502G9 (concentration range 875 nM-6.84 nM). Cells were then cultured for a further 48 h at 37° C. before the resulting conditioned media was aspirated and stored at −80° C. The concentration of eotaxin=1 in conditioned media was assessed using the R&D systems Duoset ELISA system (R&D Systems).

Human blood was obtained from the Blood Transfusion Service and erythrocytes depleted by 40 minute dextran-T500 (Pharmacia) sedimentation (0.6% final concentration). The leukocyte and platelet rich fraction was then separated by a 20 minute 1137 g centrifugation over a discontinuous Percoll gradient of 3 mL 64% and 5 mL 80% (100% was 9 parts Percoll and 1 part 10×PBS). Granulocytes were harvested from the 64%:80% interface, washed and resuspended in assay buffer (Sigma PBS, 1 mM CaCl2, 1 mM MgCl2, 10 mM HEPES, 10 mM D-glucose, 0.1% Sigma BSA, pH 7.3). The assay was performed in FACS tubes with $5 \times 10^5$ cells, ±3 nM recombinant human eotaxin=1 (R&D Systems) or conditioned media, in a final volume of 400 µL. Cells were incubated for 8.5 minutes at 37 C before being transferred to 4° C. and fixed with a fixing agent (CeilFix, BD Biosciences) and finally read on a flow cytometer. Eosinophils were identified by their FL-2 autofluorescence and the forward scatter (FSC) parameter read. Eosinophil FSC changed in response to both eotaxin=1 and conditioned media providing measurement of shape change. Tubes were sampled at high flow rate and acquisition was terminated after 1000 eosinophil events or 1 minute, whichever was the sooner. Shape change was calculated as a percentage of the FSC caused by shape change buffer alone (100% blank shape change). Data have been expressed as the mean % blank shape change ±SEM drawn from 4 separate experiments. Each experiment used cells from an individual buffy coat (and hence individual donor), performed in duplicate for each point.
Results
NHLF cells co-stimulated with 9.6 nM IL-13, 285.7 pM TNF-α and 160 pM TGF-β1 and cultured for 48 h secreted 9.6 nM eotaxin=1 into the culture media. In contrast, NHLF cells cultured only with maintenance media secreted 0.1 nM eotaxin=1 into the culture media. This eotaxin=1 production was IL-13 dependent as IL-13/TNF-α/TGF-β1 co-stimulated NHLF cell eotaxin=1 production was dose-dependently inhibited by BAK502G9 with an $IC_{50}$ of 32.4 nM (FIG. 29A).

The primary aim of this part of the study was to examine eosinophil shape change. The magnitude of eosinophil shape change in response to 3 nM eotaxin (positive control) was 122.2±2.1% (n=4). Eotaxin=1 induced shape change was completely inhibited by 100 nM of an anti-eotaxin antibody CAT-213, mean shape change 101.0±1.0% (n=4).

Media from NHLF cells co-stimulated with 9.6 nM IL-13, 285.7 pM TNF-α and 160 pM TGF-β1 and cultured for 48 h (conditioned media), induced a clear eosinophil and shape change (FIG. 29B). In contrast, media from NHLF cultured for 48 h in NHLF maintenance media alone did not induce eosinophil shape change (FIG. 29B).

The addition of anti-IL-13 antibody BAK502G9 to co-stimulated media prior to NHLF culture, resulted in a dose-dependent inhibition of eosinophil shape change, with a geometric mean $IC_{50}$ of 16.8 nM when assayed at 1:16 dilution (FIG. 29B).

The ability of stimulants (IL-13, TNF-α and TGF-β1) not cultured with NHLF cells to induce eosinophil and neutrophil shape change was also investigated. 9.6 nM IL-13, 285.7 pM TNF-α and 160 pM TGF-β1 did not induce a clear eosinophil shape change. This suggests that the eosinophil shape change ability of conditioned media develops during NHLF cell culture with the stimulants is not due to any of the stimulants alone or in combination (FIG. 29B).

EXAMPLE 29

Mapping of Anti-IL-13 Antibodies on Human IL-13

The epitope mapping of a representative IL-13 antibody BAK502G9 was performed using a molecular approach and standard peptide excision.
Molecular Approach
IL-13 chimaeras were engineered, where parts of the human IL-13 sequence were replaced with murine sequence. These chimeras were used in binding studies with representative IL-13 antibodies to help identify the specific epitope.

Two panels of IL-13 chimaeras were produced. The first panel contained nine chimaeras (FIG. 30) and was used to locate the general position of the epitope. The second panel contained ten chimaeras (FIG. 31) and was used to fine map the epitope.

The chimeric IL-13 sequences were assembled using PCR and cloned into a Gateway® entry vector, which were then recombined with a destination vector pDEST8 (modified to code for a detection and affinity tag at the C-terminus of the recombinant protein). These expression vectors were used to transform DH10Bac™ chemically competent *E coli* allowing site-specific transposition of tagged chimeric IL-13, into the baculovirus shuttle vector (bacmid). Recombinant bacmid DNA was isolated for each IL-13 chimera and transfected into Sf9 (*Spodoptera frugiperda*) insect cells using Cellfectin® Reagent. Recombinant baculovirus was harvested 72 hours post-transfection and passaged through Sf9 insect cells twice more.

Insect 2000-500 ml culture supernatant was purified on an affinity column and eluted material was concentrated from 16 to 1 ml and loaded on a size exclusion Superdex 200 HR10/300GL column for final polishing and buffer exchange.

A homogenous competition assay using biotinylated human IL-13, streptavidin-anthophyocynate and Europium labelled BAK502G9 was developed. The assay is as follows: Eu-BAK502G9 binds biotinylated-human IL-13, the complex is then recognised by the streptavidin APC conjugate and when a flash of light is applied the energy is transferred from the APC label to the Europium by proximity, and time resolved florescence can be measured. Competition for this binding is introduced by way of the un-labelled human IL-13 (as control) and the chimeric constructs. This competition is quantified to calculate the relative affinities of the IL-13 mutants for IL-13 antibodies enabling mutations altering binding to be identified.

Results

Chimeric construct IL13-Helix D (Table 5) was found to be the weakest competitor against biotinylated human IL-13 for binding BAK502G9, indicating that helixD within the IL-13 molecule was involved with BAK502G9 epitope binding (Table 5) Reduced activity was also seen for the 4041 and 3334 mutants where residues 40, 41, and 33, 34 of the parent sequence respectively were changed indicating potential involvement of helixA in the recognition of BAK502G9. The reduced activities of loop3 was discounted as this loop has a reduced number of amino acids in the mutant as compared to the human molecule and is likely to alter the overall structure of the protein. Other reductions in the ability of the chimeric IL-13 molecules to compete for BAK502G9 binding were not considered significant for such amino acid changes.

A more targeted set of mutations within helix D (FIG. 26) were then tested. Results obtained are demonstrated in Table 6 and are as follows:

Results show that chimeric constructs 116117TK (where lysine at position 116 was replaced with threonine and the aspartate at position 117 was replaced with lysine), 123KA (where lysine at position 123 was replaced) and 127RA (where arginine at position 127 was replaced) are least able to compete for binding to BAK502G9 (123KA and 127RA do not compete at 1 μM). Other residues implicated in binding to BAK502G9 due to their reduced effectiveness in the competition assay include the helixD residues 124Q (here lysine has been replaced with glutamine) and 120121SY (a leucine histidine pair has been changed to a serine tyrosine pair). Mutation of leucine at position 58L also reduces binding and analysis of the 3D structures revealed that this residue packs against helixD and may either be directly contacted by BAK502G9 or may affect the alignment of helixD.

These experiments demonstrate that residues within helixD are critical for the binding of BAK502G9 to IL-13. In particular the lysine at position 123 and the arginine at position 127 are critical for this binding as mutation to either abolishes binding of BAK502G9.

Epitope Excision

The epitope mapping of BAK502G9 was also performed using the standard peptide excision procedure. Here IgG is immobilised onto solid phase and allowed to capture the IL-13 ligand. The formed complex is then subject to specific proteolytic digestion, during which accessible peptide bonds are cleaved, however those protected by the IgG: ligand interface remain intact. Thus, a peptide containing the epitope remains bound to the IgG. This can then be desorbed, collected and identified by mass spectrometry (ms).

Two complementary techniques were used, the first made use of the Ciphergen ProteinChip Reader MALDI-TOF mass spectrometer, where it was possible to covalently link the IgG to a mass spectrometer chip and then perform the digestion and extraction in-situ. The second technique used biotinylated BAK502G9 linked to streptavidin coated beads and allowed the collection of sufficient peptide for sequence confirmation by tandem mass spectrometry (ms/ms).

The two procedures although differing in absolute detail and scale involved essentially the same steps, coupling of the IgG, blocking of unreacted binding sites, washing, ligand capture, removal of unbound ligand, digestion and a final washing step.

The MALDI-TOF ms approach made use of proprietary ms chips activated with carbonyldiimidazole that covalently binds to free primary amine groups to which the IgG at 1-2 mg/ml in PBS was coupled to overnight at 4° C. The chip was subsequently blocked with an ethanolamine solution at room temperature for 1 hour and then washed extensively with PBS or HBS plus a suitable detergent. A one picomole aliquot of IL-13 was then applied to the chip in either PBS or HBS and allowed to bind to the chemically immobilized IgG for 2 hours at room temperature. This was followed by further washes in PBS or HBS with and without detergent to remove any non-specifically bound IL-13. A solution of trypsin ranging from 200 to 3.1 μg/ml in PBS or HBS was then applied to the IgG:ligand complex and digestion allowed to proceed for 30 minutes at room temperature after which the chip was washed in PBS or HBS plus detergent, PBS or HBS and finally water. After application of a suitable MALDI-TOF ms matrix the chip was then be placed directly in the mass spectrometer and analysed.

The bead based approach started with the biotinylation of the IgG, using an NHS biotin compound, at a molar ratio of 1 IgG to 4 biotin molecules. Removal of unbound biotin and the by-products of the reaction using gel filtration followed this. The biotinylated IgG was then allowed to bind to neutravidin coated agarose beads, where it was attempted to maximize the IgG capture. Aliquots of IgG coated beads were then dispensed into a concentrator spin columns and washed with Dulbecco's PBS+0.05% Tween 20 followed by resuspension in Dulbecco's PBS+0.05% Tween 20. A pulse of IL-13 was then applied to the resuspended IgG beads and binding allowed to proceed for 10 minutes after which the liquid phase was removed by centrifugation and the beads washed with Dulbecco's PBS+0.05% Tween 20 followed by resuspension in Dulbecco's PBS+0.05% Tween 20.

The bead:IgG:ligand complex was then subject to proteolysis with either trypsin or chymotrypsin with incubation at room temperature or 37° C. After which the beads were again washed in Dulbecco's PBS+0.05% Tween 20 followed by a further washes in Dulbecco's PBS without detergent. The beads were then resuspended in a water, acetonitrile, trifluoroacetic mix and the supernatant recovered. This was then variously analysed either by MALDI-TOF ms or by reverse phase HPLC mass spectrometry, including tandem (ms/ms) fragmentation using the ThermoQuest LCQ ESI ion-trap mass spectrometer. An attempt was then made to match the resulting fragmentation pattern to the human IL-13 sequence and the separate heavy and light chain sequence of BAK502G9 IgG.

During the experimental sequence a number of controls, primarily blank surfaces, IgG only and isotype controls were employed to demonstrate that the identified peptides were derived specifically from IgG captured IL-13 and not a product of BAK502G9 or non-specifically bound IL-13 digestion.
Results The experimental series consistently gave single IL-13 specific peptides for each digestion. Data from the LCQ ion trap instrument revealed that the tryptic fragment had a monoisotopic mass of 3258Da (MH+) and the chymotrypsin fragment a monoisotopic mass of 3937Da (MH+).

A search of these masses against the appropriate in silico digestion of human IL-13 gave close matches to related peptides in the C-terminal portion of the molecule.
Match for Trypsin Peptide Mass: 3258Da At a tolerance of 1000 ppm, 3258Da matches to the sequence from aspartic acid at position 106 to the C-terminal asparagine at position 132. There are no other matches at this tolerance. This region is highlighted in bold on the sequence of the precursor form of human IL-13 below.

MALLLTTVIALTCLGGFASPGPVPPSTALRELIEELVNITQNQKAPLCNG

SMVWSINLTAGMYCAALESLINVSGCSAIEKTQRMLSGFCPHKVSAGQFS

SLHVRDTKIEVAQFVKDLLLHLKKLFREGRFN

Match for Chymotrypsin Peptide Mass: 3937Da

At a tolerance of 1000 ppm, 3937Da matches to the sequence from serine at position 99 to the C-terminal asparagine at position 132. This region is highlighted in bold on the sequence of the precursor form of human IL-13 below.

MALLLTTVIALTCLGGFASPGPVPPSTALRELIEELVNITQNQKAPLCNG

SMVWSINLTAGMYCAALESLINVSGCSAIEKTQRMLSGFCPHKVSAGQFS

SLHVRDTKIEVAQFVKDLLLHLKKLFREGRFN

Both these matches show that the BAK502G9 IgG retains the C-terminal portion of the IL-13 molecule during proteolysis of the antibody:ligand complex.

The identity of both peptides was successfully confirmed by the ms/ms, neither of which showed any significant sequence parallels with BAK502G9. The ms/ms fragment map tailored to identify either Y or B ions matched 26 of 104 possible ions in one charge state for the trypsin peptide and 19 of 128 possible ions for the chymotrypsin peptide. A review of all charge states shows identification of 23 of the 27 amino acid residues for the trypsin fragment and 29 of the 33 residues for the chymotrypsin fragment. This is sufficient to confirm identity.

The experimental sequence as a whole has identified that part of the BAK502G9 epitope on human IL-13 as lying within the twenty-seven C-terminal amino acid residues. These findings corroborate the finding of the molecular approach detailed above.

REFERENCES

1. McKenzie, A. N., et al. J Immunol, 1993. 150(12): p. 5436-44.
2. Minty, A., et al. Nature, 1993. 362(6417): p. 248-50.
3. Nakamura, Y., et al. Am J Respir Cell Mol Biol, 1996. 15(5): p. 680-7.
4. Robinson, D. S., et al. N Engl J Med, 1992. 326(5): p. 298-304.
5. Walker, C., et al. Am J Respir Crit. Care Med, 1994. 150(4): p. 1038-48.
6. Humbert, M., et al. Am J Respir Crit. Care Med, 1996. 154(5): p. 1497-504.
7. Corrigan, C. J. and A. B. Kay Int Arch Allergy Appl Immunol, 1991. 94(1-4): p. 270-1.
8. Bentley, A. M., et al. Am J Respir Cell Mol Biol, 1993. 8(1): p. 35-42.
9. Murata, T., et al. Int J Hematol, 1999. 69(1): p. 13-20.
10. Andrews, A. L., et al. J Biol Chem, 2002. 277(48): p. 46073-8.
11. Miloux, B., et al. FEBS Lett, 1997. 401(2-3): p. 163-6.
12. Hilton, D. J., et al. Proc Natl Acad Sci USA, 1996. 93(1): p. 497-501.
13. Kuperman, D., et al. J Exp Med, 1998. 187(6): p. 939-48.
14. Nelms, K., et al. Annu Rev Immunol, 1999. 17: p. 701-38.
15. Zhang, J. G., et al. J Biol Chem, 1997. 272(14): p. 9474-80.
16. Caput, D., et al. J Biol Chem, 1996. 271(28): p. 16921-6.
17. Kawakami, K., et al. Blood, 2001. 97(9): p. 2673-9.
18. Wood, N., et al. J Exp Med, 2003. 197(6): p. 703-709.
19. Chiaramonte, M. G., et al. J Exp Med, 2003. 197(6): p. 687-701.
20. Beasley, R., et al. J Allergy Clin Immunol, 2000. 105(2 Pt 2): p. S466-72.
21. Peat, J. K. and J. Li J Allergy Clin Immunol, 1999. 103(1 Pt 1): p. 1-10.
22. Society, B. T., *British guideline on the management of asthma*. Thorax, 2003. 58 Suppl 1: p. i1-94.
23. GINA, *Global Strategy for Asthma Management and Prevention*. 2002, National Insitute of Health.
24. Milgrom, H. B. Bender, and F. Wamboldt. Ann Allergy Asthma Immunol, 2002. 88(5): p. 429-31.
25. Fish, L. and C. L. Lung, *Adherence to asthma therapy*. Ann Allergy Asthma Immunol, 2001. 86(6 Suppl 1): p. 24-30.
26. Bender, B. G. J Allergy Clin Immunol, 2002. 109(6 Suppl): p. S554-9.
27. Wills-Karp, M., et al. Science, 1998. 282(5397): p. 2258-61.
28. Grunig, G., et al. Science, 1998. 282(5397): p. 2261-3.
29. Venkayya, R., et al. Am J Respir Cell Mol Biol, 2002. 26(2): p. 202-8.
30. Morse, B., et al. Am J Physiol Lung Cell Mol Physiol, 2002. 282(1): p. L44-9.
31. Zhu, Z., et al. J Clin Invest, 1999. 103(6): p. 779-88.
32. Walter, D. M., et al. J Immunol, 2001. 167(8): p. 4668-75.
33. Cohn, L., J. S. Tepper, and K. Bottomly. J Immunol, 1998. 161(8): p. 3813-6.
34. Taube, C., et al. J Immunol, 2002. 169(11): p. 6482-9.
35. Yang, E. S., et al. J. Allergy Immunol., 2002. 109: p. A168.
36. Blease, K., et al. J Immunol, 2001. 166(8): p. 5219-24.
37. Heinzmann, A., et al. Hum Mol Genet, 2000. 9(4): p. 549-59.
38. Howard, T. D., et al. Am J Hum Genet, 2002. 70(1): p. 230-6.
39. Kauppi, P., et al. Genomics, 2001. 77(1-2): p. 35-42.
40. Graves, P. E., et al. J Allergy Clin Immunol, 2000. 105(3): p. 506-13.
41. Arima, K., et al. J Allergy Clin Immunol, 2002. 109(6): p. 980-7.
42. van der Pouw Kraan, T. C., et al. Genes Immun, 1999. 1(1): p. 61-5.
43. Humbert, M., et al. J Allergy Clin Immunol, 1997. 99(5): p. 657-65.
44. Kotsimbos, T. C., P. Ernst, and Q. A. Hamid, Proc Assoc Am Physicians, 1996. 108(5): p. 368-73.
45. Komai-Koma, M., F. Y. Liew, and P. C. Wilkinson, J Immunol, 1995. 155(3): p. 1110-6.
46. Naseer, T., et al. Am J Respir Crit Care Med, 1997. 155(3): p. 845-51.

47. Huang, S. K., et al. J Immunol, 1995. 155(5): p. 2688-94.
48. Kroegel, C., et al. Eur Respir J, 1996. 9(5): p. 899-904.
49. Ohshima, Y., et al. Pediatr Res, 2002. 51(2): p. 195-200.
50. Hasegawa, M., et al. J Rheumatol, 1997. 24(2): p. 328-32.
51. Hancock, A., et al. Am J Respir Cell Mol Biol, 1998. 18(1): p. 60-5.
52. Lee, C. G., et al. J Exp Med, 2001. 194(6): p. 809-21.
53. Jain-Vora, S., et al. Am J Respir Cell Mol Biol, 1997. 17(5): p. 541-51.
54. Fallon, P. G., et al. J Immunol, 2000. 164(5): p. 2585-91.
55. Chiaramonte, M. G., et al. J Clin Invest, 1999. 104(6): p. 777-85.
56. Chiaramonte, M. G., et al. Hepatology, 2001. 34(2): p. 273-82.
57. Sluiter, H. J., et al. Eur Respir J, 1991. 4(4): p. 479-89.
58. Zheng, T., et al. J Clin Invest, 2000. 106(9): p. 1081-93.
59. Tashkin, D. P., et al., *Methacholine reactivity predicts changes in lung function over time in smokers with early chronic obstructive pulmonary disease. The Lung Health Study Research Group*, Am J Respir Crit Care Med, 1996. 153(6 Pt 1): p. 1802-11.
60. Van Der Pouw Kraan, T. C., et al. Genes Immun, 2002. 3(7): p. 436-9.
61. Skinnider, B. F., et al. Blood, 2001. 97(1): p. 250-5.
62. Kapp, U., et al. J Exp Med, 1999. 189(12): p. 1939-46.
63. Fiumara, P., F. Cabanillas, and A. Younes, Blood, 2001. 98(9): p. 2877-8.
64. Terabe, M., et al. Nat Immunol, 2000. 1(6): p. 515-20.
65. Ahlers, J. D., et al. Proc Natl Acad Sci USA, 2002. 99(20): p. 13020-5.
66. Hutchings, C., *Generation of Naïve Human Antibody Libraries, in Antibody Engineering*, R. Kontermann and S. Dubel, Editors. 2001, Springer Laboratory Manuals, Berlin. p. 93-108.
67. Vaughan, T. J., et al. Nat Biotechnol, 1996. 14(3): p. 309-14.
68. Kitamura, T., et al. Blood, 1989. 73(2): p. 375-80.
69. Lefort, S., et al. FEBS Lett, 1995. 366(2-3): p. 122-6.
70. Osbourn, J. K., et al. Immunotechnology, 1996. 2(3): p. 181-96.
71. Howard, T. D., et al. Am J Respir Cell Mol Biol, 2001. 25(3): p. 377-84.
72. Karlsson, R., A. Michaelsson, and L. Mattsson, J Immunol Methods, 1991. 145(1-2): p. 229-40.
73. Tomlinson, *VBASE*. 1997, MRC Centre for Protein Engineering, Cambridge, UK.
74. Altmann, F., et al. Glycoconj J, 1999. 16(2): p. 109-23.
75. Drexler, H. G., et al. Leuk Res, 1986. 10(5): p. 487-500.
76. Skinnider, B. F., U. Kapp, and T. W. Mak, Leuk Lymphoma, 2002. 43(6): p. 1203-10.
77. Terada, N., et al. Clin Exp Allergy, 2000. 30(3): p. 348-55.
78. Wenzel, S. E., et al. J Immunol, 2002. 169(8): p. 4613-9.
79. Richter, A., et al. Am J Respir Cell Mol Biol, 2001. 25(3): p. 385-91.
80. Bochner, B. S., et al. J Immunol, 1995. 154(2): p. 799-803.
81. Kotowicz, K., et al. Int Immunol, 1996. 8(12): p. 1915-25.
82. McKenzie, A. N., et al. Journal of Immunology, 1993. 150(12): p. 5436-44.
83. Bouteiller, C. L., et al. J Immunol Methods, 1995. 181(1): p. 29-36.
84. Riffo-Vasquez, Y., et al. Clin Exp Allergy, 2000. 30(5): p. 728-38.
85. McMillan, S. J., et al. J Exp Med, 2002. 195(1): p. 51-7.
86. Humbles, A. A., et al. Proc Natl Acad Sci USA, 2002. 99(3): p. 1479-84.
87. Temelkovski, J., et al. Thorax, 1998. 53(10): p. 849-56.
88. Belvisi, M. G., et al., Pulm Pharmacol Ther, 2001. 14(3): p. 221-7.
89. Barnes, P. J., et al. Eur Respir J, 1996. 9(4): p. 636-42.
90. Barnes, P. J., Pharmacol Ther, 2003. 97(1): p. 87-94.
91. Wardlaw, A. J., Clin Med, 2001. 1(3): p. 214-8.
92. Edwards, J. C., et al. J Pathol, 1981. 134(2): p. 147-56.
93. McDonough, J. E., et al. W. M. Elliot, and J. C. Hogg. TGF-beta Isoform and IL-13 *Immunostaining on Lung Tissue from Patients with COPD*. in *ATS 99th International Conference*. 2003. Seattle.
94. Wold, et al. Multivariate data analysis in chemistry. Chemometrics—Mathematics and Statistics in Chemistry (Ed.: B. Kowalski), D. Reidel Publishing Company, Dordrecht, Holland, 1984 (ISBN 90-277-1846-6).
95. Norman et al. Applied Regression Analysis. Wiley-Interscience; 3rd edition (April 1998) ISBN: 0471170828
96. Abraham Kandel, Eric Backer. Computer-Assisted Reasoning in Cluster Analysis. Prentice Hall PTR; (May 11, 1995), ISBN: 0133418847
97. Wojtek Krzanowski. Principles of Multivariate Analysis: A User's Perspective (Oxford Statistical Science Series, No 22 (Paper)). Oxford University Press; (December 2000), ISBN: 0198507089
98. Ian H. Witten, Eibe Frank. Data Mining: Practical Machine Learning Tools and Techniques with Java Implementations. Morgan Kaufmann; (Oct. 11, 1999), ISBN: 1558605525
99. David G. T. Denison (Editor), Christopher C. Holmes, Bani K. Mallick, Adrian F. M. Smith. Bayesian Methods for Nonlinear Classification and Regression (Wiley Series in Probability and Statistics). John Wiley & Sons; (July 2002), ISBN: 0471490369
100. Arup K. Ghose, Vellarkad N. Viswanadhan. Combinatorial Library Design and Evaluation Principles, Software, Tools, and Applications in Drug Discovery. ISBN: 0-8247-0487-8
101. Chothia C. et al., *Journal Molecular Biology* (1992) 227, 799-817.
102. Al-Lazikani, et al. *Journal Molecular Biology* (1997) 273(4), 927-948.
103. Chothia, et al. *Science,* 233, 755-758 (1986).
104. Whitelegg, N. R. J. and Rees, A. R (2000). *Prot. Eng.,* 13, 819-824.
105. Available from Accelerys Inc.
106. Guex, N. and Peitsch, M. C. (1997). *Electrophoresis* (1997) 18, 2714-2723.
107. Kabat E A et al (1991): Sequences of Proteins of Immunological Interest, 5th Edition. US Department of Health and Human Services, Public Service, NIH, Washington.
108. Kontermann R and Dubel Stefan; (2001) Antibody Engineering, Springer Laboratory Manuals.
109. Mendez et al (1997); Nature Genetics Vol. 2: 146-156.
110. Csonka E et al (2000) Journal of Cell Science, 113: 3207-3216.
111. Vanderbyl S et al (2002) Molecular Therapy, 5(5): 10.
112. Marasco W A (1997) Gene Therapy, 4(1): 11.
113. Hanes J et al (2000). Methods in Enzymology, Vol 328: 24.
114. Li et al (2003). Abstract for poster [605] submitted at The American Thoracis Society Annual Meeting, 2003, Seattle.
115. Koide et al (1998). Journal of Molecular Biology, Vol 284:1141-1151.
116. Nygren et al (1997). Current Opinion in Structural Biology, Vol 7:463-469.
117. Heller, F., et al. (2002) Immunity, 17(5):629-38.

118. Inoue, S., et al. (1999) Am J Gastroenterol, 94(9):2441-6.
119. Yang, M., et al. Am J Respir Cell Mol. Biol. 2001. 25(4): p. 522-30
120. Punnonen J., et al 1993. Proc Natl Acad. Sci. 90(8):3730-4.
121. Grunstein, M., et al. Am J Physiol Lung Cell Mol Physiol 2002. 282: p. L520-L528.
122. Laporte, J., et al. Am J Respir Crit. Care Med 2001. 164: p. 141-148.
123. Tliba O., et al. Br J Pharmacol 2003. 140(7): p. 1159-62.
124. Deshpande, D., et al. Am J Respir Cell Mol Biol 2004. 31(1): p. 36-42; Epub February 5 as doi:10.1165/rcmb.2003-0313OC.
125. Humbert et al. 1997. J. Allergy Clin. Immunol., 99:657.
126. Berry, M. A., Parker, D., Neale, N., Woodman, L., Morgan, A. Monk, P. D. Submitted to J. Allergy Clin Immunol.
127. Obase et al. Ann Allergy Asthma Immunol. 2001; 86(3): 304-10.
128. Chu et al. 2000; J. Allergy Clin. Immunol. 106:1115
129. Terada et al. 2000. Clin. Exp. Allergy., 30: 348-55.
130. Wenzel et al. 2000. J. Immunol. 169: 4613-19.

TABLE 1

| Kabat numbering | | HCDR1 | | | | | | | HCDR2 | | | | | | | | | | | | | | |
|---|---|---|---|---|---|---|---|---|---|---|---|---|---|---|---|---|---|---|---|---|---|---|---|
| | | 31 | 32 | 33 | 34 | 35 | 50 | 51 | 52 | 52A | 53 | 54 | 55 | 56 | 57 | 58 | 59 | 60 | 61 | 62 | 63 | 64 | 65 |
| | | N | Y | G | L | S | W | I | S | A | N | N | G | D | T | N | Y | G | Q | E | F | Q | G |
| BAK028D6 | PD | | | | | | | | | | | | | | | | | | | | | | |
| BAK0502G9 | PD | | | | | | | | | | | | | | | | | | | | | | |
| BAK1187E4 | PD | Q | T | | | | | | D | D | D | S | | T | | I | | | | | | | |
| BAK1167F2 | PD | | | | V | | | | | | | | | | | | | | | | | | |
| BAK1105H3 | PD | | | | | | | | | | | | | | | | | | | | | | |
| BAK1185E1 | PD | | | | | | | | N | G | L | T | | E | | L | | | | | | | |
| BAK1111D10 | PD | | | | | | | | A | D | A | D | | Q | | Q | | | | | | | |
| BAK1184G5 | PD | | T | | | | | | R | P | P | | | L | | S | | | | | | | |
| BAK1166G2 | PD | | | | | | | | | | | | | | | M | | | | | | | |
| BAK1184C8 | PD | | | | I | | | | | G | S | D | | Y | | S | | | | | | | |
| BAK1185F8 | PD | D | | | | | | | R | N | I | | | Y | | I | | | | | | | |
| BAK1167F4 | PD | D | T | | V | | | | | | | | | | | | | | | | | | |
| BAK1109G06 | PD | | | | | | | | D | D | R | T | | T | | Q | | | | | | | |
| BAK1183H4 | PD | | | | | | | | N | Y | D | G | | N | | Q | | | | | | | |
| BAK1183D2 | PD | | | | | | | | R | | S | D | | Q | | I | | | | | | | |
| BAK1184F9 | PD | | | | | | | | | G | I | D | | V | | L | | | | | | | |
| BAK1103G08 | PD | L | T | | V | | | | R | | A | | | E | | H | | | | | | | |
| BAK1157D08 | PD | | | | | | | | | | | | | | | | | | | | | | |
| BAK1183B5 | PD | | | | | | | | | N | S | K | | E | | L | | | | | | | |
| BAK1097H06 | PD | | | | | | | | G | P | R | D | | T | | S | | | | | | | |
| BAK1106F04 | PD | | | | | | | | G | P | R | S | | A | | H | | | | | | | |
| BAK1183G5 | PD | | | | | | | | R | G | | | | | | L | | | | | | | |
| BAK1161H07 | PD | G | T | | V | | | | | | | | | | | | | | | | | | |
| BAK1162G04 | PD | E | T | | I | | | | | | | | | | | | | | | | | | |
| BAK1161D07 | PD | D | T | | I | | | | | | | | | | | | | | | | | | |
| BAK1162D09 | PD | G | T | | | | | | | | | | | | | | | | | | | | |
| BAK1108F05 | PD | | | | | | | | E | G | S | T | | N | | I | | | | | | | |
| BAK1107F08 | PD | | | | F | | | | G | P | I | | | M | | H | | | | | | | |
| ALA_VL26L | O | | | | | | | | | | | | | | | | | | | | | | |
| ALA_VL26M | O | | | | | | | | | | | | | | | | | | | | | | |
| ALA_VL26C | O | | | | | | | | | | | | | | | | | | | | | | |
| ALA_VL26V | O | | | | | | | | | | | | | | | | | | | | | | |
| ALA_VL26K | O | | | | | | | | | | | | | | | | | | | | | | |
| ALA_VL26Y | O | | | | | | | | | | | | | | | | | | | | | | |
| ALA_VL26F | O | | | | | | | | | | | | | | | | | | | | | | |
| ALA_VL26R | O | | | | | | | | | | | | | | | | | | | | | | |
| ALA_VL26T | O | | | | | | | | | | | | | | | | | | | | | | |
| BAK1001C10 | RD | | | | | | | | | | | | | G | | | | | | K | | | |
| BAK1018G7 | RD | | | | | | | | | | | | | | | D | | | | | | | |
| BAK1008C3 | RD | | | | | | | | | | | | | | | D | | | | | | | |
| BAK1009A4 | RD | | | | | | | | | | | | | | | | | R | | | | | |
| BAK1010D2 | RD | | | | | | | | | | | | | | | | | | | | | | |
| BAK1007F9 | RD | | | | | | | | | | | | | | | | | | | | | | |
| BAK1010H9 | RD | | | | | | | | | | | | | | | | H | | | | | | |

TABLE 1-continued

| Name | Type | | | | N | Y | G | L | S | W | I | S | | | A | N | G | | | D | T | N | Y | | | DNARGE | DGTPNY | DLAPTSIR | SIDGKI | TEQLYNVALIG | ILQSMHDK | | | | |
|---|---|---|---|---|---|---|---|---|---|---|---|---|---|---|---|---|---|---|---|---|---|---|---|---|---|---|---|---|---|---|---|---|---|---|---|
| BAK1008D2 | RD | | | | | | | | | | | | | | | | | | | | | | | | | | | | | | | | | | |
| ALA_VL26A | O | | | | | | | | | | | | | | | | | | | | | | | | | | | | | | | | | | |
| BAK1007C4 | RD | | | | | | | | | | | | | | | | | | | | | | | | | | | | | | | | | | |
| ALA_VL26H | O | | | | | | | G | | | | | | | | | | | | | | | | | | | | | | | | | | | |
| BAK1054C8 | RD | | | | | | | | | | | | | | | | | | | | | | | | | | | | | | | | | | R |
| BAK1050G7 | RD | | | D | | | | | | | | | | | | | | | | | | | | | | | | | | | | | | | |
| BAK1016F8 | RD | | | | | | | | | | | | | | | | | | | | | | | | | | | | | | | | | | |
| BAK1050D2 | RD | | | | | | | | | | | | | | | | | | | | | | | | | | | | | | | | | | |
| BAK1063D10 | RD | | | | | | | | | | | | | | | | | | | | | | | | | | | I | | | | | | | |
| BAK1060F6 | RD | | | | | | | | | T | | | | | | | | | | | | | | | | | | | | | | | | | |
| BAK1021D5 | RD | | | | | | | | | | | | | | | | | | | | | | | | | | | I/S | | R | | | | | |
| BAK1052E10 | RD | | | | | | | | | | | | | | | | | | | | | | | | | | | K/D | | | | | | | |
| ALA_VL26G | O | | | | | | | | | | | | | | | | | | | | | | | | | | | | | | | | | | |
| BAK1020C6 | RD | | | | | | | | | G | | | | | | | | | | | | | | | | | | | | | | | | | |
| BAK1022G9 | RD | | | | | | | | | | | | | | | | | | | | | | | | | | | | | | | | | | |
| BAK1063G4 | RD | | | | | | | | | | | | | | | A | I/N | | | | | | | | | | | | | | | | | | |
| BAK278D6 | | | | | N | Y | G | L | S | W | I | S | | | A | N | G | | | D | T | N | Y | | | | | | | | | | | | |
| BAK502G9 | RD | | | | | | | | | | | | | | | | | | | | | | | | | | | | | G | | | | | |
| BAK1083F1 | RD | | | | | | | | | | | | | | | | | | | | | | | | | | | | | | | | | | |
| BAK494B8 | PD | | | | | | | | | | | | | | | A | | | | | | | | | | | | | | | | | | | |
| BAK1010C5 | RD | | | | | | | | | | | | | | | | | | | | | | | | | | | | | R | | | | | |
| BAK0496H4 | PD | | | | | | | | | | | | | | | | | | | | | | | | | | | | | | | | | | |
| BAK0501B6 | PD | | | | | | | | | | | | | | | | | | | | | | | | | | | | | | | | | | |
| BAK1049O7 | RD | | | | | | | | | | | | | | | | | | | | | | | | | | | | | | | | | | |
| BAK0531E2 | PD | | | | | | | | | | | | | | | | | | | | | | | | | | | | | | | | | | |
| BAK0433C4 | PD | | | | | | | | | | | | | | | | | | | | | | | | | | | | | R | | | | | |
| BAK1000E9 | RD | | | | | | | | | T | | | | | | | | | | | | | | | | | | | | | | | | | |
| BAK0489C8 | PD | | | | | | | | | | | | | | | | | | | | | | | | | | | | | | | | | | |
| BAK0442E5 | PD | | | | | | | | | | | | | | | | | | | | | | | | | | | | | | | | | | |
| BAK1047E3 | RD | | | | | | | | | | | | | | | | | | | | | | | | | | | | | | | | | | |
| BAK0472D7 | PD | | | | | | | | | | | | | | | | | | | | | | | | | | | | | | | | | | |
| BAK1008A7 | RD | | | | | | | | | | | | | | | | | | | | | | | | | | | | | | | | | | K |
| BAK1083H4 | PD | | | | | | | | | | | | | | | | | | | | | | | | | | | | | | | | | | |
| BAK0425A4 | PD | | | | | | | | | | | | | | | | | | | | | | | | | | | | | | | | | | |
| BAK0782D5 | RD | | | | | | | | | | | | | | | | | | | | | | | | | | | | | | | | | | |
| BAK0603C3 | PD | | | | | | | | | | | | | | | | | | | | | | | | | | | | | | | | | | |
| BAK1007H6 | RD | | | | | | | | | | | | | | | | | | | | | | | | | | | | | | | | | | |
| BAK1004E8 | RD | | | | | | | | | | | | | | | | | | | | | | | | | | | | | | | | | | |
| BAK1049G1 | PD | | | D | | | | | | | | | | | | | | | | | | | | | | | | | | | | | | | |
| BAK0484B2 | PD | | | | | | | | | | | | | | | | | | | | | | | | | | | | | | | | | | |
| BAK0502D5 | PD | QDLGE | T | VIF | | | | | | | | | | | | | | | | | | | | | | | DNARGE | DGTPNY | DLAPTSIR | SIDGKI | TEQLYNVALIG | ILQSMHDK | R | R | KG | R | K |
| Phage Display | PD | | | | | | | | | | | | | | | | | | | | | | | | | | | | | | | | | | |
| Ribosome Display | RD | | | | | | | | | | | | | | | | | | | | | | | | | | | | | | | | | | |
| Point mutations | O | | | | | | | | | | | | | | | | | | | | | | | | | | | | | | | | | | |
| Germlining | GL | | | | | | | | | | | | | | | | | | | | | | | | | | | | | | | | | | |

TABLE 1-continued

| Kabat numbering | | HCDR3 | | | | | | | | | | | | | | | LCDR1 | | | | | | | | | | |
|---|---|---|---|---|---|---|---|---|---|---|---|---|---|---|---|---|---|---|---|---|---|---|---|---|---|---|---|
| | | 95 | 96 | 97 | 98 | 99 | 100 | 100A | 100B | 100C | 100D | 100E | 101 | 102 | L | linker | 24 | 25 | 26 | 27 | 28 | 29 | 30 | 31 | 32 | 33 | 34 |
| BAK0278D6 | | D | S | S | S | N | W | A | R | W | F | F | D | L | | linker | G | G | N | N | I | G | S | K | L | V | H |
| BAK0502G9 | PD | | | | | S | | | | | | | | | | | | | | | | | | | | | |
| BAK1187E4 | PD | | | | | S | | | | | | | | | | | | | | | | | | | | | |
| BAK1167F2 | PD | | | | | | | | | | | | | | | | | | | | | | | | | | |
| BAK1105H3 | PD | | | | | | | | | | | | | | | | | | | | | | | | | | |
| BAK1185E1 | PD | | | | | | | | | | | | | | | | | | | | | | | | | | |
| BAK1111D10 | PD | | | N | | | | | | | | | | | | | | | | | | | | | | | |
| BAK1184G5 | PD | | | | | S | | | | | | | | | | | | | | I | | | | | | | |
| BAK1166G2 | PD | | | | | S | | | | | | | | | | | | | | | | | | | | | |
| BAK1184C8 | PD | | | | | | | | | | | | | | | | | | | | | | | | | | |
| BAK1185F8 | PD | | | | | S | | | | | | | | | | | | | | I | | | | | | | |
| BAK1167F4 | PD | | | | | S | | | | | | | | | | | | | | I | | | | | | | |
| BAK1109G06 | PD | | | | | S | | | | | | | | | | | | | | | | | | | | | |
| BAK1183H4 | PD | | | | | S | | | | | | | | | | | | | | I | | | | | | | |
| BAK1183D2 | PD | | | | | S | | | | | | | | | | | | | | I | | | | | | | |
| BAK1184F9 | PD | | | | | S | | | | | | | | | | | | | | I | | | | | | | |
| BAK1103G08 | PD | | | | | S | | | | | | | | | | | | | | I | | | | | | | |
| BAK1157D08 | PD | | | | | S | | | | | | | | | | | | | | I | | | | | | | |
| BAK1183B5 | PD | | | | | S | | | | | | | | | | | | | | I | | | | | | | |
| BAK1097H06 | PD | | | | | S | | | | | | | | | | | | | | I | | | | | | | |
| BAK1106F04 | PD | | | | | S | | | | | | | | | | | | | | I | | | | | | | |
| BAK1183G5 | PD | | | | | S | | | | | | | | | | | | | | I | | | | | | | |
| BAK1161H07 | PD | | | | | S | | | | | | | | | | | | | | I | | | | | | | |
| BAK1162G04 | PD | | | | | S | | | | | | | | | | | | | | I | | | | | | | |
| BAK1161D07 | PD | | | | | S | | | | | | | | | | | | | | I | | | | | | | |
| BAK1162D09 | PD | | | | | S | | | | | | | | | | | | | | I | | | | | | | |
| BAK1108F05 | PD | | | | | S | | | | | | | | | | | | | | I | | | | | | | |
| BAK1107F08 | PD | | | | | S | | | | | | | | | | | | | | I | | | | | | | |
| ALA_VL26L | O | | | | | | | | | | | | | | | | | | | L | | | | | | | |
| ALA_VL26M | O | | | | | | | | | | | | | | | | | | | M | | | | | | | |
| ALA_VL26C | O | | | | | | | | | | | | | | | | | | | C | | | | | | | |
| ALA_VL26V | O | | | N | | | | | | | | | | | | | | | | V | | | | | | | |
| ALA_VL26K | O | | | | | | | | | | | | | | | | | | | K | | | | | | | |
| ALA_VL26Y | O | | | | | | | | | | | | | | | | | | | Y | | | | | | | |
| ALA_VL26F | O | | | | | | | | | | | | | | | | | | | F | | | | | | | |
| ALA_VL26R | O | | | | | | | | | | | | | | | | | | | R | | | | | | | |
| ALA_VL26T | O | | | | | | | | | | | | | | | | | | | T | | | | | | | |
| BAK1001C10 | RD | | | | | S | | | | | | | | | | | | | | I | | | | | | | |
| BAK1018G7 | RD | | | | | | | | | | | | | | | | | | | | | | G | | | | |
| BAK1008C3 | RD | | | | | | | | | | | | | | | | | | | S | | | | | | | |
| BAK1009A4 | RD | | | N | | | | | | | | | | | | | | | | | | | | | | | |
| BAK1010D2 | RD | | | | | | | | | | | | | | | | | | | | | | G | | | | |
| BAK1007F9 | RD | | | | | S | | | | | | | | | | | | | D | | | | G | | | | |
| BAK1010H9 | RD | | | | | | | | | | | | | | | | | | | S | | | | | | | |
| BAK1008D2 | RD | | | N | | | | | | | | | | | | | | | | | | | G | | | | |

TABLE 1-continued

| | Phage Display | Ribosome Display | Point mutations | | | | W | A | R | W | F | D | L | G | G | N | | | | | | | |
|---|---|---|---|---|---|---|---|---|---|---|---|---|---|---|---|---|---|---|---|---|---|---|---|
| ALA_VL26A | O | | | | | | | | | | | | | | | | A | | | | | | |
| BAK1007C4 | RD | | | | | | | | | | | | | | | | S | | | | | | |
| ALA_VL26H | O | | | | | | | | | | | | | | | | H | | | | | | |
| BAK1054C8 | RD | | | | | | | | | | | | | | | | | | | | | | |
| BAK1050G7 | RD | | | | | | | | | | | | | | | | T | | | | | | |
| BAK1016F8 | RD | | | | | S | | | | | | | | | | | I | | | | | | |
| BAK1050D2 | RD | | N | | | | | | | | | | | | | | | | | | | | |
| BAK1063D10 | RD | | | | | | | | | | | | | | | | I | | | | | | |
| BAK1060F6 | RD | | | | | | | | | | | | | | | | | | | | | | |
| BAK1021D5 | RD | | | | | S | | | | | | | | | | | | | | | | | |
| BAK1052E10 | RD | | | | | S | | | | | | | | | | | | | | | | | |
| ALA_VL26G | O | | | | | S | | | | | | | | | | | G | | | G | | | |
| BAK1020C6 | RD | | | | | | | | | | | | | | | | | | | | | | |
| BAK1022G9 | RD | | N | | | | | | | | | | | | | | | | | G | | | |
| BAK1063G4 | RD | D | S | | | | | | | | | | | | | | | | | | | | |
| BAK278D6 | | | S | S | | | | | | | | | | | | | N | I | G | S | K | L | V H |
| BAK502G9 | RD | | S | | | | | | | | | | | | | | I | | | G | | | |
| BAK1083F1 | PD | D | S | | | | | | | | | | | | | | S | | | G | | | |
| BAK0494B8 | PD | | S | | | | | | | | | | | | | | | | | G | | | |
| BAK1010C5 | PD | | S | | | | | | | | | | | | | | Y | | | | | | |
| BAK0496H4 | RD | D | S | | | | | | | | | | | | | | | | | | | | |
| BAK0501B6 | RD | | S | | | | | | | | | | | | | S | I | | | G | | | |
| BAK0531E2 | PD | | A | | | | | | | | | | | | | | | | | | | | |
| BAK0433C4 | RD | T | | | | | | | | | | | | | | | | | | G | | | |
| BAK1000E9 | PD | N | A | | | | | | | | | | | | | | | | | | | | |
| BAK0489C8 | RD | N | | | | | | | | | | | | | | | | | | | | | |
| BAK0442E5 | PD | | I | | | | | | | | | | | | | | | | | | | | |
| BAK1047E3 | RD | T | R | | | | | | | | | | | | | | | | | G | | | |
| BAK0472D7 | PD | | | R | | | | | | | | | | | | | | | | V | | | |
| BAK1008A7 | RD | D | P | | | | | | | | | | | | | | | | | G | | | |
| BAK1083H4 | RD | P | | | | | | | | | | | | | | | | | | G | | | |
| BAK0425A4 | PD | | K | | | | | | | | | | | | | | | | | | | | |
| BAK0782D5 | PD | N | | | | | | | | | | | | | | | | | | G | | | |
| BAK0603C3 | PD | | | | | | | | | | | | | | | | S | | | G | | | |
| BAK1007H6 | RD | | S | | | | | | | | | | | | | | S | | | | | | |
| BAK1004E8 | RD | | | | | | | | | Y | | | | | | | | | | | | | R |
| BAK1049G1 | RD | N | | | | | | | | | | | | | | | | | | | | | |
| BAK0484B2 | PD | N D | | | | | | | | | | | | | | | | | | | | | |
| BAK0502D5 | PD | R | | | | | | | | | | | | | | | | | | | | | |
| Phage Display | PD | RD | NDTP | SAIRPK | | | | | | Y | | | | DS | ILMCVKYFRTSAHG | V | | | | G | | | R |
| Ribosome Display | RD | | | R | | | | | | | | | | | | | | | | | | | |
| Point mutations | O | | | | | | | | | | | | | | | | | | | | | | |
| Germining | GL | | | | | | | | | | | | | | | | | | | | | | |

TABLE 1-continued

| Kabat numbering | | 50 | 51 | 52 | 53 | 54 | 55 | 56 | 89 | 90 | 91 | 92 | 93 | 94 | 95 | 95A | 95B | 96 | 97 | Mean TF1 (nM) | TF1 reps |
|---|---|---|---|---|---|---|---|---|---|---|---|---|---|---|---|---|---|---|---|---|---|
| | | | | | LCDR2 | | | | | | | | | LCDR3 | | | | | | | |
| | | | | | | | | | | | | | | | | | | | | | |
| BAK028D6 | | D | D | G | D | R | P | S | Q | V | W | D | T | G | S | D | P | V | V | 44 | |
| BAK050G9 | | | | | | | | | | | | | | | | | | | | 8 | |
| BAK1187E4 | PD | | | | | | | | | | | | | | | | | | | 0.1 | 2 |
| BAK1167F2 | PD | | | | | | | | | | | | | | | | | | | 0.2 | 2 |
| BAK1105H3 | PD | | | | | | | | | | | | | | | | | | | 0.2 | 3 |
| BAK1185E1 | PD | | | | | | | | | | | | | | | | | | | 0.2 | 2 |
| BAK1111D10 | PD | | | | | | | | | | | | | | | | | | | 0.2 | 2 |
| BAK1184G5 | PD | | | | | | | | | | | | | | | | | | | 0.2 | 2 |
| BAK1166G2 | PD | | | | | | | | | | | | | | | | | | | 0.2 | 2 |
| BAK1184C8 | PD | | | | | | | | | | | | | | | | | | | 0.2 | 2 |
| BAK1185F8 | PD | | | | | | | | | | | | | | | | | | | 0.2 | 2 |
| BAK1167F4 | PD | | | | | | | | | | | | | | | | | | | 0.2 | 2 |
| BAK1109G06 | PD | | | | | | | | | | | | | | | | | | | 0.2 | 2 |
| BAK1183H4 | PD | | | | | | | | | | | | | | | | | | | 0.2 | 2 |
| BAK1183D2 | PD | | | | | | | | | | | | | | | | | | | 0.3 | 2 |
| BAK1184F9 | PD | | | | | | | | | | | | | | | | | | | 0.3 | 2 |
| BAK1103G08 | PD | | | | | | | | | | | | | | | | | | | 0.3 | 2 |
| BAK1157D08 | PD | | | | | | | | | | | | | | | | | | | 0.3 | 2 |
| BAK1183B5 | PD | | | | | | | | | | | | | | | | | | | 0.3 | 2 |
| BAK1097H06 | PD | | | | | | | | | | | | | | | | | | | 0.4 | 2 |
| BAK1106F04 | PD | | | | | | | | | | | | | | | | | | | 0.4 | 2 |
| BAK1183G5 | PD | | | | | | | | | | | | | | | | | | | 0.5 | 2 |
| BAK1161H07 | PD | | | | | | | | | | | | | | | | | | | 0.6 | 1 |
| BAK1162G04 | PD | | | | | | | | | | | | | | | | | | | 0.6 | 1 |
| BAK1161D07 | PD | | | | | | | | | | | | | | | | | | | 0.6 | 1 |
| BAK1162D09 | PD | | | | | | | | | | | | | | | | | | | 0.8 | 1 |
| BAK1108F05 | PD | | | | | | | | | | | | | | | | | | | 0.9 | 1 |
| BAK1107F08 | PD | | | | | | | | | | | | | | | | | | | 0.9 | 1 |
| ALA_VL26L | O | | | | | | | | | | | | | | | | | | | 1.4 | 1 |
| ALA_VL26M | O | | | | | | | | | | | | | | | | | | | 1.5 | 1 |
| ALA_VL26C | O | | | | | | | | | | | | | | | | | | | 2.5 | 1 |
| ALA_VL26V | O | | | | | | | | | | | | | | | | | | | 2.5 | 1 |
| ALA_VL26K | O | | | | | | | | | | | | | | | | | | | 2.9 | 1 |
| ALA_VL26Y | O | | | | | | | | | | | | | | | | | | | 3.1 | 1 |
| ALA_VL26F | O | | | | | | | | | | | | | | | | | | | 3.5 | 1 |
| ALA_VL26R | O | | | | | | | | | | | | | | | | | | | 3.8 | 1 |
| ALA_VL26T | O | | | | | | | | | | | | | | | | | | | 3.9 | 1 |
| BAK1001C10 | RD | | | | | | | | | | | | | | | | | | | 4.3 | 1 |
| BAK1018G7 | RD | | | | | | | | | | | | | | | | | | | 4.5 | 2 |
| BAK1008C3 | RD | | | | | | | | | | | | | | | | | | | 5.2 | 2 |
| BAK1009A4 | RD | | | | | | | | | | | | | | | | | | | 5.3 | 2 |
| BAK1010D2 | RD | | | | | | | | | | | | | | | | | | | 5.4 | 2 |
| BAK1007F9 | RD | | | | | | | | | | | | | | | | | | | 6.4 | 1 |

TABLE 1-continued

| | | D | D | G | D | R | P | S | Q | V | W | D | T | G | S | D | P | V | | |
|---|---|---|---|---|---|---|---|---|---|---|---|---|---|---|---|---|---|---|---|---|
| BAK1010H9 | RD | | | | | | | | | | | | | | | | | | 6.8 | 2 |
| BAK1008D2 | RD | | | | | | | | | | | | | | | | | | 6.9 | 1 |
| ALA_VL26A | O | | | | | | | | | | | | | | | | | | 7.2 | 1 |
| BAK1007C4 | RD | | | | | | | | | | | | | | | | | | 7.6 | 2 |
| ALA_VL26H | O | | | | | | | | | | | | | | | | | | 7.7 | 1 |
| BAK1054C8 | RD | | | | | | | | | | | | | | | | | | 9.3 | 1 |
| BAK1050G7 | RD | | | | | | | | | | | | | | | | | | 9.5 | 2 |
| BAK1016F8 | RD | | | | | | | | | | | | | | N | | | | 10.0 | 1 |
| BAK1050D2 | RD | | | | | | | | | | | | | | | | | | 10.0 | 1 |
| BAK1063D10 | RD | | | | | | | | | | | | | | | | | | 10.8 | 1 |
| BAK1060F6 | RD | | | | | | | T | | | | | | | | | | | 11.7 | 1 |
| BAK1021D5 | RD | | | | | | | | | | | | | | | | | | 12.0 | 1 |
| BAK1052E10 | RD | | | | | | | | | | | | | | | | | | 14.4 | 1 |
| ALA_VL26G | O | | | | | | | | | | | | | | | | | | 14.4 | 1 |
| BAK1020C6 | RD | | | | | | | | | | | | | | | | | I | 15.0 | 1 |
| BAK1022G9 | RD | | | | | | | | | | | | | | | | | | 17.0 | 1 |
| BAK1063G4 | RD | | | | | | | | | | | | | | | | | V | 17.0 | 1 |
| BAK278D6 | | D | D | G | D | R | P | S | Q | V | W | D | T | G | S | D | P | V | 44 | |
| BAK502G9 | | | | | | | | | | | | | | | | | | | 8 | |
| BAK1083F1 | RD | | | | | | | | | | | | | | | | | | 20.0 | 1 |
| BAK0494B8 | PD | | | | | | | | | | | | | | | | | | 21.8 | 4 |
| BAK1010C5 | RD | | | | | | | | | | | | | | | | | | 22.0 | 1 |
| BAK0496H4 | PD | | | | | | | | | | | | | | | | | | 22.0 | 3 |
| BAK0501B6 | PD | | | | | | | | | | | | | | | | | | 22.8 | 2 |
| BAK1049O7 | RD | | | | | | | | | | | | | | | | | | 23.0 | 1 |
| BAK0531E2 | PD | | | | | | | | | | | | | | | | | | 23.2 | 3 |
| BAK0433C4 | RD | | | | | | | | | | | | | | | | | | 25.3 | 4 |
| BAK1000E9 | RD | | | | | | | | | | | | | | | | | | 27.0 | 1 |
| BAK0489C8 | PD | | | | | | | | | | | | | | | | | | 28.2 | 5 |
| BAK0442E5 | PD | | | | | | | | | | | | | | | | | | 29.3 | 3 |
| BAK1047E3 | RD | | | | | | | | | | | | | | | | | | 30.0 | 1 |
| BAK0472D7 | PD | | | | | | | | | | | | | | | | | | 31.0 | 4 |
| BAK1008A7 | RD | | | | | | | | | | | | | | | | | | 32.0 | 1 |
| BAK1083H4 | RD | | | | | | | | | | | | | | | | | | 34.0 | 1 |
| BAK0425A4 | PD | | | | | | | | | | | | | | | | | | 34.6 | 5 |
| BAK0782D5 | PD | | | | | | | | | | | | | | | | | | 39.0 | 1 |
| BAK0603C3 | PD | | | | | | | | | | | | | | | | | | 39.3 | 3 |
| BAK1007H6 | RD | | | | | | | | | | | | | | | | | | 40.5 | 2 |
| BAK1004E8 | RD | | | | | | | | | | | | | | | | | | 45.0 | 1 |
| BAK1049G1 | RD | | | | | | | | | | | | | | | | | | 45.0 | 1 |
| BAK0484B2 | PD | | | | | | | | | | | | | | | | | | 28.6 | 5 |
| BAK0502D5 | PD | | | | | | | T | | | | | | | | | N | | | 29.3 | 4 |
| Phage Display | PD | | | | | | | | | | | | | | | | | | | |
| Ribosome Display | RD | | | | | | | | | | | | | | | | | I | | |
| Point mutations | O | | | | | | | | | | | | | | | | | | | |
| Germining | GL | | | | | | | | | | | | | | | | | | | |

TABLE 2

Binding specificity of anti-human IL-13 antibodies

| | Human IL-13 | Human IL-13 variant | Non-human primate IL-13 |
|---|---|---|---|
| BAK278D6 | + | + | + |
| BAK502G9 | + | + | + |
| BAK615E3 | + | − | − |

TABLE 3a

Kinetic analysis of anti-human IL-13 antibodies

| IgG | Off-rate ($s^{-1}$) | On-rate ($M^{-1} s^{-1}$) | KD (pM) |
|---|---|---|---|
| BAK278D6 | $7.41e^{-3}$ | $5.49e^{5}$ | 13500 |
| BAK502G9 | $4.09e^{-4}$ | $2.49e^{6}$ | 178 |
| BAK1167F2 | $4.05e^{-4}$ | $2.99e^{6}$ | 136 |
| BAK1183H4 | $3.00e^{-4}$ | $3.7e^{6}$ | 81 |

TABLE 3b

Kinetic analysis of anti-murine IL-13 antibodies

| IgG | Off-rate ($s^{-1}$) | On-rate ($M^{-1} s^{-1}$) | KD (pM) |
|---|---|---|---|
| BAK209B11 | $1.98e^{-2}$ | $3.9e^{6}$ | 5100 |

TABLE 4

Pharmacokinetics of BAK502G9 in 4 allergic but non-challenged cynomolgus primates (2 male/2 female) after a single 10 mg/kg i.v bolus dose over 29 days.
BAK502G9 levels in serum were measured by ELISA (mean data).

| | | |
|---|---|---|
| $C_{max}$ (t = 0.25 h) (μg/mL) | 349.04 | |
| $Vd_{inf}$ (mL · $kg^{-1}$) | 75.03 | <80 mL/kg, infers no tissue binding. |
| $Cl_{inf}$ (mL · $hr^{-1}$ · $kg^{-1}$) | 0.23 | |
| $AUC_{inf}$ (mg · h · $mL^{-1}$) | 42.99 | |
| $AUC_{ext}$ (%) | 17.34 | <30% so clearance and vol. of distribution should be accurate. |
| $T_{0.5}$ (h) | 223.55 | |

$Vd_{inf}$ = volume of distribution over time 0-infinity, calculated from the extrapolated AUC.
$Cl_{inf}$ = clearance over time 0-infinity, calculated from the extrapolated AUC.
$AUC_{inf}$ = area under the curve (measure of total drug exposure) over time 0-infinity, including an extrapolated term based on the elimination rate constant (k) and the last observed serum drug concentration.
$AUC_{ext}$ = percentage of the total AUC that is extrapolated.
$T_{0.5}$ = Drug half-life in the terminal elimination phase.

TABLE 5

First set of Chimeric constructs

| Chimeric constructs | IC50 nM |
|---|---|
| BAK502G9 | 0.17 ± 0.07 |
| loop1 | 0.71 ± 0.35 |
| hum-flag | 1.30 ± 0.18 |
| 30R | 1.76 ± 0.45 |
| 3738VN | 1.89 ± 1.9 |
| helixB | 2.49 ± 0.88 |
| helixC | 4.11 ± 0.70 |
| loop3 | 5.45 ± 3.96 |
| 4041 | 12.02 ± 1.3 |
| 3334 | 12.17 ± 1.2 |
| helixD | 110.07 ± 9.9 |

TABLE 6

Second Set of Chimeric Constructs

| Chimeric Constructs | IC50 nM |
|---|---|
| BAK502G9 | 0.11 ± 0.04 |
| 113H | 1.6 ± 0.5 |
| 128H | 1.6 ± 1.0 |
| 119LA | 1.96 ± 1.0 |
| 130P | 2.22 ± 0.8 |
| 120121SY | 4.73 ± 1.5 |
| 58LA | 5.2 ± 2.0 |
| 124Q | 18.7 ± 15.9 |
| 116117T | 82 ± 11.3 |
| 123KA | none |
| 127RA | none |

TABLE 7

Effects of BAK502G9 on various predefined endpoints.

| Parameter | Phase I change | N | Phase II change | N | Endpoint |
|---|---|---|---|---|---|
| AHR ($R_L$ AUC) | 0.020 ± 0.003 | 14[a] | 0.004 ± 0.006 | 14[a] | −0.016 ± 0.006* |
| AHR ($PC_{30}$) | −1.343 ± 0.318 | 18[b] | −1.061 ± 0.244 | 18[b] | 0.282 ± 0.179 |
| Antigen priming ($R_L$ AUC) | 0.159 ± 0.033 | 20[c] | 0.033 ± 0.025 | 20[c] | −0.126 ± 0.043** |
| BAL total cells | 20.623 ± 3.160 | 21[d] | 14.597 ± 1.951 | 21[d] | −6.026 ± 2.194* |
| BAL eosinophils | 18.453 ± 3.009 | 21[d] | 13.412 ± 1.737 | 21[d] | −5.041 ± 2.090* |
| BAL mono-nuclear cells | 2.050 ± 0.438 | 21[d] | 1.176 ± 0.481 | 21[d] | −0.874 ± 0.506 |

21 animals displaying AHR ($PC_{30}$) in Phase I and an additional animal with an antigen priming phenotype were carried forward for testing in Phase II (22 in total). Not every animal had AHR as measured by both AUC and $PC_{30}$. Only animals which displayed AHR in phase I and whose AHR was assessed in both Phase I and Phase II were included in the AHR results. Statistical testing was performed using InStat. Testing was a 2-way student's t-test against the null hypothesis that the endpoint did include the number 0 (i.e. there was no change in phase II compared to phase I);
*p < 0.05,
**p < 0.01.
Data are shown as arithmetic mean ± SEM (n = 14-21).
[a]5 animals were excluded from the AUC analysis as they did not display AHR (increased AUC) in Phase I.
3 further animals were excluded due to a technical failure in Phase II airway function data collection.
[b]3 animals were excluded from $PC_{30}$ analysis due to a technical failure in Phase II airway function data collection (same animals as in [a]). The additional animal with antigen priming phenotype was excluded as it did not display $PC_{30}$ AHR in Phase I.
[c]2 animals were excluded from the antigen priming analysis as there was a technical failure in Phase I airway function data collection.
[d]1 animal was excluded from the BAL analysis due to marked BAL inflammation at study initiation.

```
BAK278D6
HEAVY CHAIN
CDR1- SEQ ID NO 1: NYGLS
WISANNGDTNYGQEFQG
CDR3- SEQ ID NO 3: DSSSNWARWFFDL
```

BAK278D6
LIGHT CHAIN
CDR1- SEQ ID NO 4: GGNNIGSKLVH
CDR2- SEQ ID NO 5: DDGDRPS
CDR3- SEQ ID NO 6: QVWDTGSDPVV

BAK502G9
HEAVY CHAIN
CDR1-SEQ ID NO 7: NYGLS
CDR2-SEQ ID NO 8: WISANNGDTNYGQEFQG
CDR3-SEQ ID NO 9: DSSSSWARWFFDL

LIGHT CHAIN
CDR1-SEQ ID NO 10: GGNIIGSKLVH
CDR2-SEQ ID NO 11: DDGDRPS
CDR3-SEQ ID NO 12: QVWDTGSDPVV

BAK278D6
HEAVY CHAIN DOMAIN
SEQ ID NO 13:
EVQLVQSGAEVKKPGASVKVSCKASGYTFRNYGLSWVRQAPGQGLEWMGW
ISANNGDTNYGQEFQGRITMTTETSTNTAHMELRSLRSDDTAVYYCVRDS
SSNWARWFFDLWGKGTMVTVSS

BAK278D6
LIGHT CHAIN DOMAIN
SEQ ID NO 14:
SYVLTQPPSVSVAPGQTARIPCGGNNIGSKLVHWYQQKPGQAPVLVVYDD
GDRPSGIPERFSGSNSGNTATLTISRIDAGDEADYYCQVWDTGSDPVVFG
GGTKLTVL

BAK502G9
HEAVY CHAIN DOMAIN
SEQ ID NO 15:
QVQLVQSGAEVKKPGASVKVSCKASGYTFTNYGLSWVRQAPGQGLEWMGW
ISANNGDTNYGQEFQGRVTMTTDTSTSTAYMELRSLRSDDTAVYYCARDS
SSSWARWFFDLWGRGTLVTVSS

BAK502G9
LIGHT CHAIN DOMAIN
SEQ ID NO 16:
SYVLTQPPSVSVAPGKTARITCGGNIIGSKLVHWYQQKPGQAPVLVIYDD
GDRPSGIPERFSGSNSGNTATLTISRVEAGDEADYYCQVWDTGSDPVVFG
GGTKLTVL

BAK278D6
HEAVY CHAIN
FR1- SEQ ID NO 17: EVQLVQSGAEVKKPGASVKVSCKASGYTFR
FR2- SEQ ID NO 18: WVRQAPGQGLEWMG
FR3- SEQ ID NO 19: RITMTTETSTNTAHMELRSLRSDDTAVYYCVR

BAK278D6
LIGHT CHAIN
FR1- SEQ ID NO 20: SYVLTQPPSVSVAPGQTARIPC
FR2- SEQ ID NO 21: WYQQKPGQAPVLVVY
FR3- SEQ ID NO 22: GIPERFSGSNSGNTATLTISRIDAGDEADYYC

BAK167A11
HEAVY CHAIN DOMAIN
SEQ ID NO 23:
EVQLLESGGGLVQPGGSLRLSCAASGFTFSSYAMSWVRQAPGKGLEWVSA
ISGSGGSTYYADSVKGRFTISRDNSKNTLYLQMNSLRAEDTAVYYCARVG
AAGEGYYGYWGRGTLVTVSS

BAK167A11
LIGHT CHAIN DOMAIN
SEQ ID NO 24:
NFMLTQPHSVSESPGKTVTISCTRSSGSIASNYVQWYQQRPGSAPTTVIY
DDNQRPSGVPDRFSGSIDSSSNSASLTISGLKTEDEADYYCQSYDSNNDV
FGGGTKVTVL

BAK209B11
HEAVY CHAIN DOMAIN
SEQ ID NO 25:
QVQLQESGGGGLVQPGGSLRLSCAASGFTFSSYGMSWVRQAPGKGLEWVS
SISASGDSTFYADSVKGRFTISRDNNKNMVFLQVNSLRADDTAVYFCAKD
WSQWLVGDAFDVWGRGTTVTVSS

BAK209B11
LIGHT CHAIN DOMAIN
SEQ ID NO 26:
DIQLTQSPSTLSASVGDRVTITCRASQSVSLWVAWYQQRPGKAPKLLIYD
GSTLQSGVPARFSGSGSGTEFTLTISSLQPDDFATYYCQQYKTFSTFGQG
TKVEIKRA

BAK502G9
HEAVY CHAIN
FR1- SEQ ID NO 27: QVQLVQSGAEVKKPGASVKVSCKASGYTFT
FR2- SEQ ID NO 28: WYRQAPGQGLEWMG
FR3- SEQ ID NO 29: RVTMTTDTSTSTAYMELRSLRSDDTAVYYCAR

BAK502G9
LIGHT CHAIN
FR1- SEQ ID NO 30: SYVLTQPPSVSVAPGKTARITC
FR2- SEQ ID NO 31: WYQQKPGQAPVLVIY
FR3- SEQ ID NO 32: GIPERFSGSNSGNTATLTISRVEAGDEADYYC

BAK615E3
HEAVY CHAIN DOMAIN
SEQ ID NO 33:
EVQLLESGGGLVQPGGSLRLSCAASGFTFSSYAMSWVRQAPGKGLEWVSA
ISGSGGSTYYADSVKGRFTISRDNSKNTLYLQMNSLRAEDTAVYYCARVG
KATTEEGYYGYWGRGTLVTVSS

BAK615E3
LIGHT CHAIN DOMAIN
SEQ ID NO 34:
NFMLTQPHSVSESPGKTVTISCTRSSGSIASNYVQWYQQRPGSAPTTVIY
DDNQRPSGVPDRFSGSIDSSSNSASLTISGLKTEDEADYYCQSYDSNNDV
FGGGTKVTVL

BAK1167F2
HEAVY CHAIN DOMAIN
SEQ ID NO 35:
QVQLVQSGAEVKKPGASVKVSCKASGYTFEQTGVSWVRQAPGQGLEWMGW
ISANNGDTNYGQEFQGRVTMTTDTSTSTAYMELRSLRSDDTAVYYCARDS
SSSWARWFFDLWGRGTLVTVSS

BAK1167F2
LIGHT CHAIN DOMAIN
SEQ ID NO 36:
SYVLTQPPSVSVAPGKTARITCGGNIIGSKLVHWYQQKPGQAPVLVIYDD
GDRPSGIPERFSGSNSGNTATLTISRVEAGDEADYYCQVWDTGSDPVVFG
GGTKLTVL

BAK1183H4
HEAVY CHAIN DOMAIN
SEQ ID NO 37:
QVQLVQSGAEVKKPGASVKVSCKASGYTFTNYGLSWVRQAPGQGLEWMGW
INYDGGNTQYGQEFQGRVTMTTDTSTSTAYMELRSLRSDDTAVYYCARDS
SSSWARWFFDLWGRGTLVTVSS

BAK1183H4
LIGHT CHAIN DOMAIN
SEQ ID NO 38:
SYVLTQPPSVSVAPGKTARITCGGNIIGSKLVHWYQQKPGQAPVLVIYDD
GDRPSGIPERFSGSNSGNTATLTISRVEAGDEADYYCQVWDTGSDPVVFG
GGTKLTVL

BAK1105H3
HEAVY CHAIN DOMAIN
SEQ ID NO 39:
QVQLVQSGAEVKKPGASVKVSCKASGYTFTNYGLSWVRQAPGQGLEWMGW
ISGLNGETLYGQEFQGRVTMTTDTSTSTAYMELRSLRSDDTAVYYCARDS
SSSWARWFFDLWGRGTLVTVSS

BAK1105H3
LIGHT CHAIN DOMAIN
SEQ ID NO 40:
SYVLTQPPSVSVAPGKTARITCGGNIIGSKLVHWYQQKPGQAPVLVIYDD
GDRPSGIPERFSGSNSGNTATLTISRVEAGDEADYYCQVWDTGSDPVVFG
GGTKLTVL

BAK1111D10
HEAVY CHAIN DOMAIN
SEQ ID NO 41:
QVQLVQSGAEVKKPGASVKVSCKASGYTFTNYGLSWVRQAPGQGLEWMGW
IATPDGQTSYGQEFQGRVTMTTDTSTSTAYMELRSLRSDDTAVYYCARDS
NSSWARWFFDLWGRGTLVTVSS

BAK1111D10
LIGHT CHAIN DOMAIN
SEQ ID NO 42:
SYVLTQPPSVSVAPGKTARITCGGNIIGSKLVHWYQQKPGQAPVLVIYDD
GDRPSGIPERFSGSNSGNTATLTISRVEAGDEADYYCQVWDTGSDPVVFG
GGTKLTVL

BAK1167F4
HEAVY CHAIN DOMAIN
SEQ ID NO 43:
QVQLVQSGAEVKKPGASVKVSCKASGYTFIDTGVSWVRQAPGQGLEWMGW
ISANNGDTNYGQEFQGRVTMTTDTSTSTAYMELRSLRSDDTAVYYCARDS
SSSWARWFFDLWGRGTLVTVSS

BAK1167F4
LIGHT CHAIN DOMAIN
SEQ ID NO 44:
SYVLTQPPSVSVAPGKTARITCGGNIIG-
SKLVHWYQQKPGQAPVLVIYDDGDRPSGIPE
RFSGSNSGNTATLTISRVEAGDEADYYCQVWDTGSDPVVFGGGTKLTVL

BAK1184C8
HEAVY CHAIN DOMAIN
SEQ ID NO 45:
QVQLVQSGAEVKKPGASVKVSCKASGYTFTNYGLSWVRQAPGQGLEWMGW
ISGSNGYTSYGQEFQGRVTMTTDTSTSTAYMELRSLRSDDTAVYYCARDS
SSSWARWFFDLWGRGTLVTVSS

BAK1184C8
LIGHT CHAIN DOMAIN
SEQ ID NO 46:
SYVLTQPPSVSVAPGKTARITCGGNIIGSKLVHWYQQKPGQAPVLVIYDD
GDRPSGIPERFSGSNSGNTATLTISRVEAGDEADYYCQVWDTGSDPVVFG
GGTKLTVL

BAK1185E1
HEAVY CHAIN DOMAIN
SEQ ID NO 47:
QVQLVQSGAEVKKPGASVKVSCKASGYTFTNYGLSWVRQAPGQGLEWMGW
INDATGDTQYGQEFQGRVTMTTDTSTSTAYMELRSLRSDDTAVYYCARDS
SSSWARWFFDLWGRGTLVTVSS

BAK1185E1
LIGHT CHAIN DOMAIN
SEQ ID NO 48:
SYVLTQPPSVSVAPGKTARITCGGNIIG-
SKLVHWYQQKPGQAPVLVIYDDGDRPSGIPE
RFSGSNSGNTATLTISRVEAGDEADYYCQVWDTGSDPVVFGGGTKLTVL

BAK1185F8
HEAVY CHAIN DOMAIN
SEQ ID NO 49:
QVQLVQSGAEVKKPGASVKVSCKASGYTFTDYGLSWVRQAPGQGLEWMGW
IRNDGYTIYGQEFQGRVTMTTDTSTSTAYMELRSLRSDDTAVYYCARDS
SSSWARWFFDLWGRGTLVTVSS

BAK1185F8
LIGHT CHAIN DOMAIN
SEQ ID NO 50:
SYVLTQPPSVSVAPGKTARITCGGNIIGSKLVHWYQQKPGQAPVLVIYDD
GDRPSGIPERFSGSNSGNTATLTISRVEAGDEADYYCQVWDTGSDPVVFG
GGTKLTVL

BAK1187B4
HEAVY CHAIN DOMAIN
SEQ ID NO 51:
QVQLVQSGAEVKKPGASVKVSCKASGYTFTNYGLSWVRQAPGQGLEWMGW
IDDDSGTTIYGQEFQGRVTMTTDTSTSTAYMELRSLRSDDTAVYYCARDS
SSSWARWFFDLWGRGTLVTVSS

BAK1187B4
LIGHT CHAIN DOMAIN
SEQ ID NO 52:
SYVLTQPPSVSVAPGKTARITCGGNIIGSKLVHWYQQKPGQAPVLVIYDD
GDRPSGIPERFSGSNSGNTATLTISRVEAGDEADYYCQVWDTGSDPVVFG
GGTKLTVL

BAK1166G2
HEAVY CHAIN DOMAIN
SEQ ID NO 53:
QVQLVQSGAEVKKPGASVKVSCKASGYTFANTGISWVRQAPGQGLEWMGW
ISANNGDTNYGQEFQGRVTMTTDTSTSTAYMELRSLRSDDTAVYYCARDS
SSSWARWFFDLWGRGTLVTVSS

BAK1166G2
LIGHT CHAIN DOMAIN
SEQ ID NO 54:
SYVLTQPPSVSVAPGKTARITCGGNIIGSKLVHWYQQKPGQAPVLVIYDD
GDRPSGIPERFSGSNSGNTATLTISRVEAGDEADYYCQVWDTGSDPVVFG
GGTKLTVL

BAK167A11
HEAVY CHAIN
CDR1- SEQ ID NO 55: SYAMS
CDR2- SEQ ID NO 56: AISGSGGSTYYADSVKG
CDR3- SEQ ID NO 57: VGAAGEGYYGY

BAK167A11
LIGHT CHAIN
CDR1- SEQ ID NO 58: TRSSGSIASNYVQ
CDR2- SEQ ID NO 59: DDNQRPS
CDR3- SEQ ID NO 60: QSYDSNNDV

BAK1167F2
HEAVY CHAIN
CDR1- SEQ ID NO 61: QTGVS
CDR2- SEQ ID NO 62: WISANNGDTNYGQEFQG
CDR3- SEQ ID NO 63: DSSSSWARWFFDL

BAK1167F2
LIGHT CHAIN
CDR1- SEQ ID NO 64: GGNIIGSKLVH
CDR2- SEQ ID NO 65: DDGDRPS
CDR3- SEQ ID NO 66: QVWDTGSDPVV

BAK1166G2
HEAVY CHAIN
CDR1- SEQ ID NO 67: NTGIS
CDR2- SEQ ID NO 68: WISANNGDTNYGQEFQG
CDR3- SEQ ID NO 69: DSSSSWARWFFDL

BAK1166G2
LIGHT CHAIN
CDR1- SEQ ID NO 70: GGNIIGSKLVH
CDR2- SEQ ID NO 71: DDGDRPS
CDR3- SEQ ID NO 72: QVWDTGSDPVV

BAK1184C8
HEAVY CHAIN
CDR1- SEQ ID NO 73: NYGLS
CDR2- SEQ ID NO 74: WISGSNGYTSYGQEFQG
CDR3- SEQ ID NO 75: DSSSSWARWFFDL

BAK1184C8
LIGHT CHAIN
CDR1- SEQ ID NO 76: GGNIIGSKLVH
CDR2- SEQ ID NO 77: DDGDRPS
CDR3- SEQ ID NO 78: QVWDTGSDPVV

BAK1185E1
HEAVY CHAIN
CDR1- SEQ ID NO 79: NYGLS
CDR2- SEQ ID NO 80: WINDATGDTQYGQEFQG
CDR3- SEQ ID NO 81: DSSSSWARWFFDL

BAK1185E1
LIGHT CHAIN
CDR1- SEQ ID NO 82: GGNIIGSKLVH
CDR2- SEQ ID NO 83: DDGDRPS
CDR3- SEQ ID NO 84: QVWDTGSDPVV

BAK1167F4
HEAVY CHAIN
CDR1- SEQ ID NO 85: DTGVS
CDR2- SEQ ID NO 86: WISANNGDTNYGQEFQG
CDR3- SEQ ID NO 87: DSSSSWARWFFDL

```
BAK1167F4
LIGHT CHAIN
CDR1- SEQ ID NO 88: GGNIIGSKLVH
CDR2- SEQ ID NO 89: DDGDRPS
CDR3- SEQ ID NO 90: QVWDTGSDPVV

BAK1111D10
HEAVY CHAIN
CDR1- SEQ ID NO 91: NYGLS
CDR2- SEQ ID NO 92: WIATPDGQTSYGQEFQG
CDR3- SEQ ID NO 93: DSNSSWARWFFDL

BAK1111D10
LIGHT CHAIN
CDR1- SEQ ID NO 94: GGNIIGSKLVH
CDR2- SEQ ID NO 95: DDGDRPS
CDR3- SEQ ID NO 96: QVWDTGSDPVV

BAK1183H4
HEAVY CHAIN
CDR1- SEQ ID NO 97: NYGLS
CDR2- SEQ ID NO 98: WINYDGGNTQYGQEFQG
CDR3- SEQ ID NO 99: DSSSSWARWFFDL

BAK1183H4
LIGHT CHAIN
CDR1- SEQ ID NO 100: GGNIIGSKLVH
CDR2- SEQ ID NO 101: DDGDRPS
CDR3- SEQ ID NO 102: QVWDTGSDPVV

BAK1185H8
HEAVY CHAIN
CDR1- SEQ ID NO 103: DYGLS
CDR2- SEQ ID NO 104: WRINDGYTIYGQEFQG
CDR3- SEQ ID NO 105: DSSSSWARWFFDL

BAK1185H8
LIGHT CHAIN
CDR1- SEQ ID NO 106: GGNIIGSKLVH
CDR2- SEQ ID NO 107: DDGDRPS
CDR3- SEQ ID NO 108: QVWDTGSDPVV

BAK278D6
HEAVY CHAIN- SEQ ID NO: 109
CAGGTGCAGCTGGTGCAGTCTGGGGCTGAGGTGAAGAAGCCTGGGGCCTC
AGTGAAGGTCTCCTGCAAGGCTTCTGGTTACACCTTTACAAATTATGGTC
TCAGCTGGGTGCGACAGGCCCCTGGACAAGGGCTTGAGTGGATGGGATGG
ATCAGCGCTAATAATGGCGACACAAATTATGGACAGGAATTCCAGGGCAG
AGTCACCATGACCACAGATACATCCACGAGCACAGCCTACATGGAGTTGA
GGAGCCTGAGATCTGACGACACGGCCGTTTATTACTGTGCGAGAGACTCC
AGCAGCAACTGGGCCCGCTGGTTTTTCGATCTCTGGGGCCGGGGGACACT
GGTCACCGTCTCCTCA

BAK278D6
LIGHT CHAIN- SEQ ID NO: 110
TCCTATGTGCTGACTCAGCCACCCTCGGTGTCAGTGGCCCCAGGTAAGAC
GGCCAGGATTACCTGTGGGGGAAACAACATTGGAAGTAAACTTGTACACT
GGTACCAGCAGAAGCCAGGCCAGGCCCCTGTGCTGGTCATCTATGATGAT
GGCGACCGGCCCTCAGGGATCCCTGAGCGATTCTCTGGCTCCAACTCTGG
GAACACGGCCACCCTGACCATCAGCAGGGTCGAGGCCGGGGATGAGGCCG
ACTATTATTGTCAGGTGTGGGATACTGGTAGTGATCCCGTGGTATTCGGC
GGAGGGACCAAGCTGACCGTCCTAGGT

BAK502G9
HEAVY CHAIN- SEQ ID NO: 111
CAGGTCCAGCTGGTGCAGTCTGGGGCTGAGGTGAAGAAGCCTGGGGCCTC
AGTGAAGGTCTCCTGCAAGGCTTCTGGTTACACCTTTACAAATTATGGTC
TCAGCTGGGTGCGACAGGCCCCTGGACAAGGGCTTGAGTGGATGGGATGG
ATCAGCGCTAATAATGGCGACACAAATTATGGACAGGAATTCCAGGGCAG
AGTCACCATGACCACAGATACATCCACGAGCACAGCCTACATGGAGTTGA
GGAGCCTGAGATCTGACGACACGGCCGTTTATTACTGTGCGAGAGACTCC
AGCAGCAGCTGGGCCCGCTGGTTTTTCGATCTCTGGGGCCGGGGGACACT
GGTCACCGTCTCCTCA

BAK502G9
LIGHT CHAIN- SEQ ID NO: 112
TCCTATGTGCTGACTCAGCCACCCTCGGTGTCAGTGGCCCCAGGAAAGAC
GGCCAGGATTACCTGTGGGGGAAACATCATTGGAAGTAAACTTGTACACT
GGTACCAGCAGAAGCCAGGCCAGGCCCCTGTGCTGGTCATCTATGATGAT
GGCGACCGGCCCTCAGGGATCCCTGAGCGATTCTCTGGCTCCAACTCTGG
GAACACGGCCACCCTGACCATCAGCAGGGTCGAGGCCGGGGATGAGGCCG
ACTATTATTGTCAGGTGTGGGATACTGGTAGTGATCCCGTGGTATTCGGC
GGAGGGACCAAGCTGACCGTCCTAGGT

BAK1105H03
HEAVY CHAIN- SEQ ID NO: 113
CAGGTCCAGCTGGTGCAGTCTGGGGCTGAGGTGAAGAAGCCTGGGGCCTC
AGTGAAGGTCTCCTGCAAGGCTTCTGGTTACACCTTTACAAATTATGGTC
TCAGCTGGGTGCGACAGGCCCCTGGACAAGGGCTTGAGTGGATGGGATGG
ATCTCCGGCTTGAACGGCGAGACATTGTATGGACAGGAATTCCAGGGCAG
AGTCACCATGACCACAGATACATCCACGAGCACAGCCTACATGGAGTTGA
GGAGCCTGAGATCTGACGACACGGCCGTTTATTACTGTGCGAGAGACTCC
AGCAGCAGCTGGGCCCGCTGGTTTTTCGATCTCTGGGGCCGGGGGACACT
GGTCACCGTCTCCTCA

BAK1105H03
LIGHT CHAIN- SEQ ID NO: 114
TCCTATGTGCTGACTCAGCCACCCTCGGTGTCAGTGGCCCCAGGAAAGAC
GGCCAGGATTACCTGTGGGGGAAACATCATTGGAAGTAAACTTGTACACT
GGTACCAGCAGAAGCCAGGCCAGGCCCCTGTGCTGGTCATCTATGATGAT
GGCGACCGGCCCTCAGGGATCCCTGAGCGATTCTCTGGCTCCAACTCTGG
GAACACGGCCACCCTGACCATCAGCAGGGTCGAGGCCGGGGATGAGGCCG
ACTATTATTGTCAGGTGTGGGATACTGGTAGTGATCCCGTGGTATTCGGC
GGAGGGACCAAGCTGACCGTCCTAGGT

BAK1111D10
HEAVY CHAIN- SEQ ID NO: 115
CAGGTGCAGCTGGTGCAGTCTGGGGCTGAGGTGAAGAAGCCTGGGGCCTC
AGTGAAGGTCTCCTGCAAGGCTTCTGGTTACACCTTTACAAATTATGGTC
TCAGCTGGGTGCGACAGGCCCCTGGACAAGGGCTTGAGTGGATGGGATGG
ATCGCAACCCCAGACGGCCAGACAAGCTATGGACAGGAATTCCAGGGCAG
AGTCACCATGACCACAGATACATCCACGAGCACAGCCTACATGGAGTTGA
GGAGCCTGAGATCTGACGACACGGCCGTTTATTACTGTGCGAGAGACTCC
AACAGCAGCTGGGCCCGCTGGTTTTTCGATCTCTGGGGCCGGGGGACACT
GGTCACCGTCTCCTCA

BAK1111D10
LIGHT CHAIN- SEQ ID NO: 116
TCCTATGTGCTGACTCAGCCACCCTCGGTGTCAGTGGCCCCAGGAAAGAC
GGCCAGGATTACCTGTGGGGGAAACATCATTGGAAGTAAACTTGTACACT
GGTACCAGCAGAAGCCAGGCCAGGCCCCTGTGCTGGTCATCTATGATGAT
GGCGACCGGCCCTCAGGGATCCCTGAGCGATTCTCTGGCTCCAACTCTGG
GAACACGGCCACCCTGACCATCAGCAGGGTCGAGGCCGGGGATGAGGCCG
ACTATTATTGTCAGGTGTGGGATACTGGTAGTGATCCCGTGGTATTCGGC
GGAGGGACCAAGCTGACCGTCCTAGGT

BAK 1167F2
HEAVY CHAIN- SEQ ID NO: 117
CAAGTGCAGCTGGTGCAGTCTGGGGCTGAGGTGAAGAAGCCTGGGGCCTC
AGTGAAGGTCTCCTGCAAGGCTTCTGGTTACACCTTTGAGCAGACCGGCG
TCTCCTGGGTGCGACAGGCCCCTGGACAAGGGCTTGAGTGGATGGGATGG
ATCAGCGCTAATAATGGCGACACAAATTATGGACAGGAATTCCAGGGCAG
AGTCACCATGACCACAGATACATCCACGAGCACAGCCTACATGGAGTTGA
GGAGCCTGAGATCTGACGACACGGCCGTTTATTACTGTGCGAGAGACTCC
AGCAGCAGCTGGGCCCGCTGGTTTTTCGATCTCTGGGGCCGGGGGACACT
GGTCACCGTCTCCTCA

BAK 1167F2
LIGHT CHAIN- SEQ ID NO: 118
TCCTATGTGCTGACTCAGCCACCCTCGGTGTCAGTGGCCCCAGGAAAGAC
GGCCAGGATTACCTGTGGGGGAAACATCATTGGAAGTAAACTTGTACACT
GGTACCAGCAGAAGCCAGGCCAGGCCCCTGTGCTGGTCATCTATGATGAT
GGCGACCGGCCCTCAGGGATCCCTGAGCGATTCTCTGGCTCCAACTCTGG
GAACACGGCCACCCTGACCATCAGCAGGGTCGAGGCCGGGGATGAGGCCG
ACTATTATTGTCAGGTGTGGGATACTGGTAGTGATCCCGTGGTATTCGGC
GGAGGGACCAAGCTGACCGTCCTAGGT

BAK 1167F04
HEAVY CHAIN- SEQ ID NO: 119
CAGGTGCAGCTGGTGCAGTCTGGGGCTGAGGTGAAGAAGCCTGGGGCCTC
AGTGAAGGTCTCCTGCAAGGCTTCTGGTTACACCTTTATCGACACCGGGG
TCTCCTGGGTGCGACAGGCCCCTGGACAAGGGCTTGAGTGGATGGGATGG
ATCAGCGCTAATAATGGCGACACAAATTATGGACAGGAATTCCAGGGCAG
AGTCACCATGACCACAGATACATCCACGAGCACAGCCTACATGGAGTTGA
GGAGCCTGAGATCTGACGACACGGCCGTTTATTACTGTGCGAGAGACTCC
AGCAGCAGCTGGGCCCGCTGGTTTTTCGATCTCTGGGGCCGGGGGACACT
GGTCACCGTCTCCTCA

BAK 1167F04
LIGHT CHAIN- SEQ ID NO: 120
TCCTATGTGCTGACTCAGCCACCCTCGGTGTCAGTGGCCCCAGGAAAGAC
GGCCAGGATTACCTGTGGGGGAAACATCATTGGAAGTAAACTTGTACACT
```

```
GGTACCAGCAGAAGCCAGGCCAGGCCCCTGTGCTGGTCATCTATGATGAT
GGCGACCGGCCCTCAGGGATCCCTGAGCGATTCTCTGGCTCCAACTCTGG
GAACACGGCCACCCTGACCATCAGCAGGGTCGAGGCCGGGGATGAGGCCG
ACTATTATTGTCAGGTGTGGGATACTGGTAGTGATCCCGTGGTATTCGGC
GGAGGGACCAAGCTGACCGTCCTAGGT

BAK 1183H4
HEAVY CHAIN- SEQ ID NO: 121
CAGGTGCAGCTGGTGCAGTCTGGGGCTGAGGTGAAGAAGCCTGGGGCCTC
AGTGAAGGTCTCCTGCAAGGCTTCTGGTTACACCTTTACAAATTATGGTC
TCAGCTGGGTGCGACAGGCCCCTGGACAAGGGCTTGAGTGGATGGGATGG
ATCAACTACGACGGCGGCAACACACAGTATGGACAGGAATTCCAGGGCAG
AGTCACCATGACCACAGATACATCCACGAGCACAGCCTACATGGAGTTGA
GGAGCCTGAGATCTGACGACACGGCCGTTTATTACTGTGCGAGAGACTCC
AGCAGCAGCTGGGCCCGCTGGTTTTTCGATCTCTGGGGCCGGGGGACACT
GGTCACCGTCTCCTCA

BAK 1183H4
LIGHT CHAIN- SEQ ID NO: 122
TCCTATGTGCTGACTCAGCCACCCTCGGTGTCAGTGGCCCCAGGAAAGAC
GGCCAGGATTACCTGTGGGGGAAACATCATTGGAAGTAAACTTGTACACT
GGTACCAGCAGAAGCCAGGCCAGGCCCCTGTGCTGGTCATCTATGATGAT
GGCGACCGGCCCTCAGGGATCCCTGAGCGATTCTCTGGCTCCAACTCTGG
GAACACGGCCACCCTGACCATCAGCAGGGTCGAGGCCGGGGATGAGGCCG
ACTATTATTGTCAGGTGTGGGATACTGGTAGTGATCCCGTGGTATTCGGC
GGAGGGACCAAGCTGACCGTCCTAGGT

BAK1184C8
HEAVY CHAIN- SEQ ID NO: 123
CAGGTGCAGCTGGTGCAGTCTGGGGCTGAGGTGAAGAAGCCTGGGGCCTC
AGTGAAGGTCTCCTGCAAGGCTTCTGGTTACACCTTTACAAATTATGGTC
TCAGCTGGGTGCGACAGGCCCCTGGACAAGGGCTTGAGTGGATGGGATGG
ATCAGCGGGAGCAACGGCTACACATCTTATGGACAGGAATTCCAGGGCAG
AGTCACCATGACCACAGATACGTCCACGAGCACAGCCTACATGGAGTTGA
GGAGCCTGAGATCTGACGACACGGCCGTTTATTACTGTGCGAGAGACTCC
AGCAGCAGCTGGGCCCGCTGGTTTTTCGATCTCTGGGGCCGGGGGACACT
GGTCACCGTCTCCTCA

BAK1184C8
LIGHT CHAIN- SEQ ID NO: 124
TCCTATGTGCTGACTCAGCCACCCTCGGTGTCAGTGGCCCCAGGAAAGAC
GGCCAGGATTACCTGTGGGGGAAACATCATTGGAAGTAAACTTGTACACT
GGTACCAGCAGAAGCCAGGCCAGGCCCCTGTGCTGGTCATCTATGATGAT
GGCGACCGGCCCTCAGGGATCCCTGAGCGATTCTCTGGCTCCAACTCTGG
GAACACGGCCACCCTGACCATCAGCAGGGTCGAGGCCGGGGATGAGGCCG
ACTATTATTGTCAGGTGTGGGATACTGGTAGTGATCCCGTGGTATTCGGC
GGAGGGACCAAGCTGACCGTCCTAGGT

BAK1185E1
HEAVY CHAIN- SEQ ID NO: 125
CAGGTGCAGCTGGTGCAGTCTGGGGCTGAGGTGAAGAAGCCTGGGGCCTC
AGTGAAGGTCTCCTGCAAGGCTTCTGGTTACACCTTTACAAATTATGGTC
TCAGCTGGGTGCGACAGGCCCCTGGACAAGGGCTTGAGTGGATGGGATGG
ATCAACGACGCCACCGGCGACACACAGTATGGACAGGAATTCCAGGGCAG
AGTCACCATGACCACAGATACATCCACGAGCACAGCCTACATGGAGTTGA
GGAGCCTGAGATCTGACGACACGGCCGTTTATTACTGTGCGAGAGACTCC
AGCAGCAGCTGGGCCCGCTGGTTTTTCGATCTCTGGGGCCGGGGGACACT
GGTCACCGTCTCCTCA

BAK1185E1
LIGHT CHAIN- SEQ ID NO: 126
TCCTATGTGCTGACTCAGCCACCCTCGGTGTCAGTGGCCCCAGGAAAGAC
GGCCAGGATTACCTGTGGGGGAAACATCATTGGAAGTAAACTTGTACACT
GGTACCAGCAGAAGCCAGGCCAGGCCCCTGTGCTGGTCATCTATGATGAT
GGCGACCGGCCCTCAGGGATCCCTGAGCGATTCTCTGGCTCCAACTCTGG
GAACACGGCCACCCTGACCATCAGCAGGGTCGAGGCCGGGGATGAGGCCG
ACTATTATTGTCAGGTGTGGGATACTGGTAGTGATCCCGTGGTATTCGGC
GGAGGGACCAAGCTGACCGTCCTAGGT

BAK1185F8
HEAVY CHAIN- SEQ ID NO: 127
CAGGTGCAGCTGGTGCAGTCTGGGGCTGAGGTGAAGAAGCCTGGGGCCTC
AGTGAAGGTCTCCTGCAAGGCTTCTGGTTACACCTTTACAGATTATGGTC
TCAGCTGGGTGCGACAGGCCCCTGGACAAGGGCTTAGAGTGGATGGGATGG
ATCCGCAACATCGACGGCTACACAATTTATGGACAGGAATTCCAGGGCAG
AGTCACCATGACCACAGATACATCCACGAGCACAGCCTACATGGAGTTGA
GGAGCCTGAGATCTGACGACACGGCCGTTTATTACTGTGCGAGAGACTCC
AGCAGCAGCTGGGCCCGCTGGTTTTTCGATCTCTGGGGCCGGGGGACACT
GGTCACCGTCTCCTCA

BAK1185F8
LIGHT CHAIN- SEQ ID NO: 128
TCCTATGTGCTGACTCAGCCACCCTCGGTGTCAGTGGCCCCAGGAAAGAC
GGCCAGGATTACCTGTGGGGGAAACATCATTGGAAGTAAACTTGTACACT
GGTACCAGCAGAAGCCAGGCCAGGCCCCTGTGCTGGTCATCTATGATGAT
GGCGACCGGCCCTCAGGGATCCCTGAGCGATTCTCTGGCTCCAACTCTGG
GAACACGGCCACCCTGACCATCAGCAGGGTCGAGGCCGGGGATGAGGCCG
ACTATTATTGTCAGGTGTGGGATACTGGTAGTGATCCCGTGGTATTCGGC
GGAGGGACCAAGCTGACCGTCCTAGGT

BAK1187B4
HEAVY CHAIN- SEQ ID. NO: 129
CAGGTCCAGCTGGTGCAGTCTGGGGCTGAGGTGAAGAAGCCTGGGGCCTC
AGTGAAGGTCTCCTGCAAGGCTTCTGGTTACACCTTTACAAATTATGGTC
TCAGCTGGGTGCGACAGGCCCCTGGACAAGGGCTTGAGTGGATGGGATGG
ATCGACGACGACAGCGGCACGACAATATATGGACAGGAATTCCAGGGCAG
AGTCACCATGACCACAGATACATCCACGAGCACAGCCTACATGGAGTTGA
GGAGCCTGAGATCTGACGACACGGCCGTTTATTACTGTGCGAGAGACTCC
AGCAGCAGCTGGGCCCGCTGGTTTTTCGATCTCTGGGGCCGGGGGACACT
GGTCACCGTCTCCTCA

BAK1187B4
LIGHT CHAIN- SEQ ID NO: 130
TCCTATGTGCTGACTCAGCCACCCTCGGTGTCAGTGGCCCCAGGAAAGAC
GGCCAGGATTACCTGTGGGGGAAACATCATTGGAAGTAAACTTGTACACT
GGTACCAGCAGAAGCCAGGCCAGGCCCCTGTGCTGGTCATCTATGATGAT
GGCGACCGGCCCTCAGGGATCCCTGAGCGATTCTCTGGCTCCAACTCTGG
GAACACGGCCACCCTGACCATCAGCAGGGTCGAGGCCGGGGATGAGGCCG
ACTATTATTGTCAGGTGTGGGATACTGGTAGTGATCCCGTGGTATTCGGC
GGAGGGACCAAGCTGACCGTCCTAGGT

BAK1166G02
HEAVY CHAIN- SEQ ID NO: 131
CAAGTGCAGTTGGTGCAGTCTGGGGCTGAGGTGAAGAAGCCTGGGGCCTC
AGTGAAGGTCTCCTGCAAGGCTTCTGGTTACACCTTTGCGAACACCGGGA
TCTCGTGGGTGCGACAGGCCCCTGGACAAGGGCTTGAGTGGATGGGATGG
ATCAGCGCTAATAATGGCGACACAAATTATGGACAGGAATTCCAGGGCAG
AGTCACCATGACCACAGATACATCCACGAGCACAGCCTACATGGAGTTGA
GGAGCCTGAGATCTGACGACACGGCCGTTTATTACTGTGCGAGAGACTCC
AGCAGCAGCTGGGCCCGCTGGTTTTTCGATCTCTGGGGTCGGGGGACACT
GGTCACCGTCTCCTCA

BAK1166G02
LIGHT CHAIN- SEQ ID NO: 132
TCCTATGTGCTGACTCAGCCACCCTCGGTGTCAGTGGCCCCAGGAAAGAC
GGCCAGGATTACCTGTGGGGGAAACATCATTGGAAGTAAACTTGTACACT
GGTACCAGCAGAAGCCAGGCCAGGCCCCTGTGCTGGTCATCTATGATGAT
GGCGACCGGCCCTCAGGGATCCCTGAGCGATTCTCTGGCTCCAACTCTGG
GAACACGGCCACCCTGACCATCAGCAGGGTCGAGGCCGGGGATGAGGCCG
ACTATTATTGTCAGGTGTGGGATACTGGTAGTGATCCCGTGGTATTCGGC
GGAGGGACCAAGCTGACCGTCCTAGGT

BAK165E7
HEAVY CHAIN- SEQ ID NO: 133
EVQLVQSGAEVKKPGASVKVSCKASGYTFTNYGLSWVRQAPGQGLEWMGW
ISANNGETNYGQEFQGRVTMTTETPTNTAHMELRSLTSDDTAVYYCVRDS
SSNWARWYFDLWGQGTLVTVSS

BAK165E7
LIGHT CHAIN- SEQ ID NO: 134
SYVLTQPPSVSVAPGQTARIPCGGNNIGSKLVHWYQQKPGQAPVLVVYDD
GDRPSGIPERFSGSNSGNTATLTISRIDAGDEADYYCQVWDTGSDPVVFG
GGTKLTVLG

BAK165E7
HEAVY CHAIN
CDR1- SEQ ID NO: 135 NYGLS
CDR2- SEQ ID NO: 136 WISANNGETNYGQEFQG
CDR3- SEQ ID NO: 137 DSSSNWARWYFDL

BAK165E7
LIGHT CHAIN
CDR1- SEQ ID NO: 138 GGNNIGSKLVH
CDR2- SEQ ID NO: 139 DDGDRPS
CDR3- SEQ ID NO: 140 QVWDTGSDPVV
```

BAK582F7
HEAVY CHAIN
CDR1- SEQ ID NO 141: SYAMS
CDR2- SEQ ID NO 142: AISGSGGSTYYADSVKG
CDR3- SEQ ID NO 143: VGAAGEGYYGY

BAK582F7
LIGHT CHAIN
CDR1- SEQ ID NO 144: TRSSGSIASNYVE
CDR2- SEQ ID NO 145: DDNQRPS
CDR3- SEQ ID NO 146: QSYDSNNDV

BAK612B5
HEAVY CHAIN
CDR1- SEQ ID NO 147: SYAMS
CDR2- SEQ ID NO 148: AISGSGGSTYYADSVKG
CDR3- SEQ ID NO 149: VGRATTDEGYYGY

BAK612B5
LIGHT CHAIN
CDR1- SEQ ID NO 150: TRSSGSIASNYVQ
CDR2- SEQ ID NO 151: DDNQRPS
CDR3- SEQ ID NO 152: QSYDSNNDV

BAK615E3
HEAVY CHAIN
CDR1- SEQ ID NO 153: SYAMS
CDR2- SEQ ID NO 154: AISGSGGSTYYADSVKG
CDR3- SEQ ID NO 155: VGKATTEEGYY

BAK615E3
LIGHT CHAIN
CDR1- SEQ ID NO 156: TRSSGSIASNYVQ
CDR2- SEQ ID NO 157: DDNQRPS
CDR3- SEQ ID NO 158: QSYDSNNDV

BAK0278D6
HEAVY CHAIN
CDR1- SEQ ID NO 159: AATTATGGTCTCAGC
CDR2- SEQ ID NO 160:
TGGATCAGCGCTAATAATGGCGACACAAATTAT
GGACAGGAATTCCAGGGC

CDR3- SEQ ID NO 161:
GACTCCAGCAGCAACTGGGCCCGCTGGTTTTTCGATCTC

BAK278D6
LIGHT CHAIN
CDR1- SEQ ID NO 162:
GGGGGAAACAACATTGGAAGTAAACTTGTACAC
CDR2- SEQ ID NO 163: GATGATGGCGACCGGCCCTCA
CDR3- SEQ ID NO 164:
CAGGTGTGGGATACTGGTAGTGATCCCGTGGTA

BAK502G9
HEAVY CHAIN
CDR1- SEQ ID NO 165: AATTATGGTCTCAGC
CDR2- SEQ ID NO 166:
TGGATCAGCGCTAATAATGGCGACACAAATTATGGACA
GGAATTCCAGGGC
CDR3- SEQ ID NO 167:
GACTCCAGCAGCAGCTGGGCCCGCTGGTTTTTCGATCTC

BAK502G9
LIGHT CHAIN
CDR1- SEQ ID NO 168:
GGGGGAAACATCATTGGAAGTAAACTTGTACAC
CDR2- SEQ ID NO 169: GATGATGGCGACCGGCCCTCA
CDR3- SEQ ID NO 170:
CAGGTGTGGGATACTGGTAGTGATCCCGTGGTA

CH Domains- SEQ ID NO: 171
ASTKGPSVFPLAPCSRSTSESTAALGCLVKDYFPEPVTVSWNSGALTSGV
HTFPAVLQSSGLYSLSSVVTVPSSSLGTKTYTCNVDHKPSNTKVDKRVES
KYGPPCPSCPAPEFLGGPSVFLFPPKPKDTLMISRTPEVTCVVVDVSQED
PEVQFNWYVDGVEVHNAKTKPREEQFNSTYRVVSVLTVLHQDWLNGKEYK
CKVSNKGLPSSIEKTISKAKGQPREPQVYTLPPSQEEMTKNQVSLTCLVK
GFYPSDIAVEWESNGQPENNYKTTPPVLDSDGSFFLYSRLTVDKSRWQEG
NVFSCSVMHEALHNHYTQKSLSLSLGK CL Domain- SEQ ID NO: 172
QPKAAPSVTLFPPSSEELQANKATLVCLISDFYPGAVTVAWKADSSPVKA
GVETTTPSKQSNNKYAASSYLSLTPEQWKSHRSYSCQVTHEGSTVEKTVA
PTECS

---

The invention claimed is:

1. A method of treatment of a disease or disorder selected from the group consisting of asthma, atopic dermatitis, allergic rhinitis, fibrosis and Hodgkin's lymphoma, the method comprising administering a specific binding member to a patient with the disease or disorder, wherein the specific binding member binds interleukin-13 (IL-13) and comprises an antibody antigen-binding site which is composed of a human antibody heavy chain variable region (VH) and a human antibody light chain variable region (VL) comprising a set of complementarity determining regions (CDRs) HCDR1, HCDR2, HCDR3, LCDR1, LCDR2 and LCDR3, wherein the VH comprises HCDR1, HCDR2 and HCDR3 and the VL comprises LCDR1, LCDR2 and LCDR3, wherein:

HCDR1 comprises SEQ ID NO:7;
HCDR2 comprises SEQ ID NO:8;
HCDR3 comprises SEQ ID NO:9;
LCDR1 comprises SEQ ID NO:10;
LCDR2 comprises SEQ ID NO:11; and
LCDR3 comprises SEQ ID NO:12.

2. The method of claim 1, wherein the specific binding member is an antibody.

3. The method of claim 2, wherein the antibody is a monoclonal antibody, a human antibody, a humanized antibody, a chimeric antibody, a synthetic antibody, a bi-specific antibody, a multi-specific antibody, or an antibody fragment thereof.

4. The method of claim 3, wherein the antibody fragment is a Fab fragment, a Fd fragment, a Fv fragment, a F(ab')$_2$ fragment, a single chain Fv molecule, or a diabody.

5. The method of claim 3, wherein the antibody further comprises a heavy chain immunoglobulin constant region selected from the group consisting of:
   (a) an IgA constant region;
   (b) an IgE constant region;
   (c) an IgG1 constant region;
   (d) an IgG2 constant region;
   (e) an IgG3 constant region;
   (f) an IgG4 constant region; and
   (g) an IgM constant region.

6. The method of claim 3, wherein the antibody further comprises a light chain immunoglobulin constant region selected from the group consisting of:
   (a) a kappa constant domain; and
   (b) a lambda constant domain.

7. The method of claim 3, wherein the antibody further comprises a human IgG4 constant region and a human lambda constant domain.

8. The method of claim 7, wherein the disease or disorder is asthma.

9. The method of claim 7, wherein the disease or disorder is atopic dermatitis.

10. The method of claim 7, wherein the disease or disorder is allergic rhinitis.

11. The method of claim 7, wherein the disease or disorder is fibrosis.

12. The method of claim 7, wherein the disease or disorder is Hodgkin's lymphoma.

13. The method of claim 1, wherein the specific binding member comprises the BAK502G9 VH domain (SEQ ID NO:15).

14. The method of claim 1, wherein the specific binding member comprises the BAK502G9 VL domain (SEQ ID NO:16).

15. The method of claim 1, wherein the specific binding member comprises the BAK502G9 VH domain (SEQ ID NO:15) and the BAK502G9 VL domain (SEQ ID NO:16).

16. The method of claim 15, wherein the specific binding member is an antibody.

17. The method of claim 16, wherein the antibody is a monoclonal antibody, a human antibody, a humanized antibody, a chimeric antibody, a synthetic antibody, a bi-specific antibody, a multi-specific antibody, or an antibody fragment thereof.

18. The method of claim 17, wherein the antibody fragment is a Fab fragment, a Fd fragment, a Fv fragment, a F(ab')$_2$ fragment, a single chain Fv molecule, or a diabody.

19. The method of claim 17, wherein the antibody further comprises a heavy chain immunoglobulin constant region selected from the group consisting of:
(a) an IgA constant region;
(b) an IgE constant region;
(c) an IgG1 constant region;
(d) an IgG2 constant region;
(e) an IgG3 constant region;
(f) an IgG4 constant region; and
(g) an IgM constant region.

20. The method of claim 17, wherein the antibody further comprises a light chain immunoglobulin constant region selected from the group consisting of:
(a) a kappa constant domain; and
(b) a lambda constant domain.

21. The method of claim 17, wherein the antibody further comprises a human IgG4 constant region and a human lambda constant domain.

22. The method of claim 21, wherein the disease or disorder is asthma.

23. The method of claim 21, wherein the disease or disorder is atopic dermatitis.

24. The method of claim 21, wherein the disease or disorder is allergic rhinitis.

25. The method of claim 21, wherein the disease or disorder is fibrosis.

26. The method of claim 21, wherein the disease or disorder is Hodgkin's lymphoma.

27. A method of treating an interleukin-13 (IL-13) related disorder in a patient comprising administering to the patient an antibody or antibody fragment thereof comprising:
(a) a set of complementarity determining regions (CDRs) HCDR1, HCDR2, HCDR3, LCDR1, LCDR2 and LCDR3, wherein HCDR1 comprises SEQ ID NO:7;
HCDR2 comprises SEQ ID NO:8;
HCDR3 comprises SEQ ID NO:9;
LCDR1 comprises SEQ ID NO:10;
LCDR2 comprises SEQ ID NO:11; and
LCDR3 comprises SEQ ID NO:12;
or
(b) a heavy chain variable region (VH) comprising SEQ ID NO:15 and a light chain variable region (VL) comprising SEQ ID NO:16:,
wherein the IL-13 related disorder is selected from the group consisting of: asthma, atopic dermatitis, allergic rhinitis, chronic obstructive pulmonary disease (COPD), fibrosis, scleroderma, and Hodgkin's lymphoma.

28. The method of claim 27, wherein the antibody is a monoclonal antibody, a human antibody, a humanized antibody, a chimeric antibody, a synthetic antibody, a bi-specific antibody, a multi-specific antibody, or an antibody fragment thereof.

29. The method of claim 27, wherein the antibody fragment is a Fab fragment, a Fd fragment, a Fv fragment, a F(ab')$_2$ fragment, a single chain Fv molecule, or a diabody.

30. The method of claim 27, wherein the antibody further comprises a heavy chain immunoglobulin constant region selected from the group consisting of:
(a) an IgA constant region;
(b) an IgE constant region;
(c) an IgG1 constant region;
(d) an IgG2 constant region;
(e) an IgG3 constant region;
(f) an IgG4 constant region; and
(g) an IgM constant region.

31. The method of claim 27, wherein the antibody or antibody fragment thereof further comprises a light chain immunoglobulin constant region selected from the group consisting of:
(a) a kappa constant domain; and
(b) a lambda constant domain.

32. The method of claim 27, wherein the antibody further comprises a human IgG4 constant region and a human lambda constant domain.

33. The method of claim 27, wherein the antibody or antibody fragment thereof comprises (a).

34. The method of claim 27, wherein the antibody or antibody fragment thereof comprises (b).

35. The method of claim 27, wherein the IL-13 related disorder is asthma.

36. The method of claim 27, wherein the IL-13 related disorder is atopic dermatitis.

37. The method of claim 27, wherein the IL-13 related disorder is allergic rhinitis.

38. The method of claim 27, wherein the IL-13 related disorder is fibrosis.

39. The method of claim 27, wherein the IL-13 related disorder is Hodgkin's lymphoma.

40. The method of claim 27, wherein the IL-13 related disorder is COPD.

41. The method of claim 27, wherein the IL-13 related disorder is scleroderma.

42. A method of inhibiting or neutralizing interleukin-13 (IL-13) in a patient comprising administering to the patient an antibody or antibody fragment thereof comprising:
(a) a set of complementarity determining regions (CDRs) HCDR1, HCDR2, HCDR3, LCDR1, LCDR2 and LCDR3, wherein
HCDR1 comprises SEQ ID NO:7;
HCDR2 comprises SEQ ID NO:8;
HCDR3 comprises SEQ ID NO:9;
LCDR1 comprises SEQ ID NO:10;

LCDR2 comprises SEQ ID NO:11; and
LCDR3 comprises SEQ ID NO:12;
or
(b) a heavy chain variable region (VH) comprising SEQ ID NO:15 and a light chain variable region (VL) comprising SEQ ID NO:16;
wherein the patient has a disease or condition selected from the group consisting of: asthma, atopic dermatitis, allergic rhinitis, chronic obstructive pulmonary disease (COPD), fibrosis, scleroderma, and Hodgkin's lymphoma.

43. The method of claim 42, wherein the antibody is a monoclonal antibody, a human antibody, a humanized antibody, a chimeric antibody, a synthetic antibody, a bi-specific antibody, a multi-specific antibody, or an antibody fragment thereof.

44. The method of claim 42, wherein the antibody fragment is a Fab fragment, a Fd fragment, a Fv fragment, a $F(ab')_2$ fragment, a single chain Fv molecule, or a diabody.

45. The method of claim 42, wherein the antibody further comprises a heavy chain immunoglobulin constant region selected from the group consisting of:
(a) an IgA constant region;
(b) an IgE constant region;
(c) an IgG1 constant region;
(d) an IgG2 constant region;
(e) an IgG3 constant region;
(f) an IgG4 constant region; and
(g) an IgM constant region.

46. The method of claim 42, wherein the antibody or antibody fragment thereof further comprises a light chain immunoglobulin constant region selected from the group consisting of:
(a) a kappa constant domain; and
(b) a lambda constant domain.

47. The method of claim 42, wherein the antibody further comprises a human IgG4 constant region and a human lambda constant domain.

48. The method of claim 42, wherein the antibody or antibody fragment thereof comprises (a).

49. The method of claim 42, wherein the antibody or antibody fragment thereof comprises (b).

50. The method of claim 42, wherein the disease or condition is asthma.

51. The method of claim 42, wherein the disease or condition is atopic dermatitis.

52. The method of claim 42, wherein the disease or condition is allergic rhinitis.

53. The method of claim 42, wherein the disease or condition is fibrosis.

54. . The method of claim 42, wherein the disease or condition is Hodgkin's lymphoma.

55. The method of claim 42, wherein the disease or condition is COPD.

56. The method of claim 42, wherein the disease or condition is scleroderma.

57. A method of treating asthma in a patient comprising administering to the patient an effective amount of an anti-IL-13 antibody or antibody fragment thereof, wherein the anti-IL-13 antibody or antibody fragment thereof comprises:
(a) a set of complementarity determining regions (CDRs) HCDR1, HCDR2, HCDR3, LCDR1, LCDR2 and LCDR3, wherein
HCDR1 comprises SEQ ID NO:7;
HCDR2 comprises SEQ ID NO:8;
HCDR3 comprises SEQ ID NO:9;
LCDR1 comprises SEQ ID NO:10;
LCDR2 comprises SEQ ID NO:11; and
LCDR3 comprises SEQ ID NO:12;
or
(b) a heavy chain variable region (VH) comprising SEQ ID NO:15 and a light chain variable region (VL) comprising SEQ ID NO:16.

58. The method of claim 57, wherein the antibody is a monoclonal antibody, a human antibody, a humanized antibody, a chimeric antibody, a synthetic antibody, a bi-specific antibody, a multi-specific antibody, or an antibody fragment thereof.

59. The method of claim 57, wherein the antibody fragment is a Fab fragment, a Fd fragment, a Fv fragment, a $F(ab')_2$ fragment, a single chain Fv molecule, or a diabody.

60. The method of claim 57, wherein the antibody further comprises a heavy chain immunoglobulin constant region selected from the group consisting of:
(a) an IgA constant region;
(b) an IgE constant region;
(c) an IgG1 constant region;
(d) an IgG2 constant region;
(e) an IgG3 constant region;
(f) an IgG4 constant region; and
(g) an IgM constant region.

61. The method of claim 57, wherein the antibody or antibody fragment thereof further comprises a light chain immunoglobulin constant region selected from the group consisting of:
(a) a kappa constant domain; and
(b) a lambda constant domain.

62. The method of claim 57, wherein the antibody further comprises a human IgG4 constant region and a human lambda constant domain.

63. The method of claim 57, wherein the antibody or antibody fragment thereof comprises (a).

64. The method of claim 57, wherein the antibody or antibody fragment thereof comprises (b).

65. A method of treating atopic dermatitis in a patient comprising administering to the patient an effective amount of an anti-IL-13 antibody or antibody fragment thereof, wherein the anti-IL-13 antibody or antibody fragment thereof comprises:
(a) a set of complementarity determining regions (CDRs) HCDR1, HCDR2, HCDR3, LCDR1, LCDR2 and LCDR3, wherein
HCDR1 comprises SEQ ID NO:7;
HCDR2 comprises SEQ ID NO:8;
HCDR3 comprises SEQ ID NO:9;
LCDR1 comprises SEQ ID NO:10;
LCDR2 comprises SEQ ID NO:11; and
LCDR3 comprises SEQ ID NO:12;
or
(b) a heavy chain variable region (VH) comprising SEQ ID NO:15 and a light chain variable region (VL) comprising SEQ ID NO:16.

66. The method of claim 65, wherein the antibody is a monoclonal antibody, a human antibody, a humanized antibody, a chimeric antibody, a synthetic antibody, a bi-specific antibody, a multi-specific antibody, or an antibody fragment thereof.

67. The method of claim 65, wherein the antibody fragment is a Fab fragment, a Fd fragment, a Fv fragment, a $F(ab')_2$ fragment, a single chain Fv molecule, or a diabody.

68. The method of claim 65, wherein the antibody further comprises a heavy chain immunoglobulin constant region selected from the group consisting of:
(a) an IgA constant region;
(b) an IgE constant region;

(c) an IgG1 constant region;
(d) an IgG2 constant region;
(e) an IgG3 constant region;
(f) an IgG4 constant region; and
(g) an IgM constant region.

69. The method of claim 65, wherein the antibody or antibody fragment thereof further comprises a light chain immunoglobulin constant region selected from the group consisting of:
(a) a kappa constant domain; and
(b) a lambda constant domain.

70. The method of claim 65, wherein the antibody further comprises a human IgG4 constant region and a human lambda constant domain.

71. The method of claim 65, wherein the antibody or antibody fragment thereof comprises (a).

72. The method of claim 65, wherein the antibody or antibody fragment thereof comprises (b).

* * * * *